(12) United States Patent
Weinzierl et al.

(10) Patent No.: US 11,987,632 B2
(45) Date of Patent: May 21, 2024

(54) ANTIBODIES BINDING TO HLA-A2/MAGE-A4

(71) Applicant: Hoffmann-La Roche Inc., Little Falls, NJ (US)

(72) Inventors: Tina Weinzierl, Remetschwil (CH); Lydia Jasmin Hanisch, Birmensdorf (CH); Alexander Bujotzek, Munich (DE); Alejandro Carpy Gutierrez Cirlos, Munich (DE); Stefan Klostermann, Neuried (DE); Christian Klein, Bonstetten (CH); Simon Patrick Keiser, Aarau (CH); Tanja Fauti, Zurich (CH); Estelle Marrer-Berger, Basel (CH); Pablo Umaña, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 517 days.

(21) Appl. No.: 17/125,500

(22) Filed: Dec. 17, 2020

(65) Prior Publication Data
US 2021/0230278 A1    Jul. 29, 2021

(30) Foreign Application Priority Data
Dec. 18, 2019 (EP) .................... 19217463

(51) Int. Cl.
*C07K 16/28* (2006.01)
*A61P 35/00* (2006.01)
*C07K 16/30* (2006.01)
*A61K 39/00* (2006.01)

(52) U.S. Cl.
CPC .......... *C07K 16/2833* (2013.01); *A61P 35/00* (2018.01); *C07K 16/2809* (2013.01); *C07K 16/30* (2013.01); *A61K 2039/505* (2013.01); *C07K 2317/31* (2013.01); *C07K 2317/55* (2013.01); *C07K 2317/73* (2013.01); *C07K 2317/92* (2013.01)

(58) Field of Classification Search
CPC .......... C07K 16/2833; C07K 16/2809; C07K 16/30; C07K 2317/31; C07K 2317/55; C07K 2317/73; C07K 2317/92; C07K 2317/32; C07K 2317/33; C07K 2317/34; C07K 2317/35; C07K 2317/64; C07K 2317/732; A61P 35/00; A61K 2039/505
See application file for complete search history.

(56) References Cited

U.S. PATENT DOCUMENTS

| | | |
|---|---|---|
| 4,676,980 A | 6/1987 | Segal et al. |
| 4,737,456 A | 4/1988 | Weng et al. |
| 5,208,020 A | 5/1993 | Chari et al. |
| 5,500,362 A | 3/1996 | Robinson et al. |
| 5,571,894 A | 11/1996 | Wels et al. |
| 5,587,458 A | 12/1996 | Richter et al. |
| 5,591,828 A | 1/1997 | Bosslet et al. |
| 5,731,168 A | 3/1998 | Carter et al. |
| 5,750,373 A | 5/1998 | Garrard et al. |
| 5,770,429 A | 6/1998 | Lonberg et al. |
| 5,821,337 A | 10/1998 | Carter et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,248,516 B1 | 6/2001 | Winter et al. |
| 6,417,429 B1 | 7/2002 | Hein et al. |
| 6,420,548 B1 | 7/2002 | Vezina et al. |
| 6,737,056 B1 | 5/2004 | Presta et al. |
| 6,982,321 B2 | 1/2006 | Winter et al. |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman et al. |
| 7,332,581 B2 | 2/2008 | Presta et al. |
| 7,521,541 B2 | 4/2009 | Eigenbrot et al. |
| 7,527,791 B2 | 5/2009 | Adams et al. |
| 7,695,936 B2 | 4/2010 | Carter et al. |
| 7,785,903 B2 | 8/2010 | Bond et al. |
| 7,855,275 B2 | 12/2010 | Eigenbrot et al. |
| 7,985,840 B2 | 7/2011 | Fuh et al. |
| 8,309,300 B2 | 11/2012 | Junutula et al. |

(Continued)

FOREIGN PATENT DOCUMENTS

| | | |
|---|---|---|
| EP | 0404097 B1 | 12/1990 |
| EP | 1870459 A1 | 12/2007 |

(Continued)

OTHER PUBLICATIONS

Almagro & Fransson, Frontiers in Bioscience 2008; 13:1619-33 (Year: 2008).*

(Continued)

*Primary Examiner* — Julie Wu
*Assistant Examiner* — John J Skoko, III
(74) *Attorney, Agent, or Firm* — Clark & Elbing LLP; Karen L. Elbing

(57) ABSTRACT

The present invention generally relates to antibodies that bind to HLA-A2/MAGE-A4, including multispecific antibodies e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

68 Claims, 25 Drawing Sheets
Specification includes a Sequence Listing.

(56) References Cited

U.S. PATENT DOCUMENTS

| | | | |
|---|---|---|---|
| 8,679,490 B2 | 3/2014 | Dennis et al. | |
| 9,000,130 B2 | 4/2015 | Bhakta et al. | |
| 2003/0157108 A1 | 8/2003 | Presta et al. | |
| 2004/0093621 A1 | 5/2004 | Shitara et al. | |
| 2004/0110282 A1 | 6/2004 | Kanda et al. | |
| 2004/0132140 A1 | 7/2004 | Satoh et al. | |
| 2004/0259150 A1 | 12/2004 | Nakamura et al. | |
| 2005/0031613 A1 | 2/2005 | Nakamura et al. | |
| 2005/0079574 A1 | 4/2005 | Bond et al. | |
| 2005/0216958 A1 | 9/2005 | Yamane et al. | |
| 2007/0061900 A1 | 3/2007 | Murphy et al. | |
| 2007/0117126 A1 | 5/2007 | Sidhu et al. | |
| 2007/0224627 A1* | 9/2007 | Horowitz | G01N 33/5088 435/7.1 |
| 2007/0237764 A1 | 10/2007 | Birtalan et al. | |
| 2007/0292936 A1 | 12/2007 | Barthelemy et al. | |
| 2008/0069820 A1 | 3/2008 | Fuh et al. | |
| 2009/0203538 A1* | 8/2009 | Sugioka | C07K 16/2803 506/18 |
| 2015/0315295 A1* | 11/2015 | Beckmann | C07K 16/243 506/17 |
| 2018/0179283 A1* | 6/2018 | Peled Kamar | C07K 16/2809 |
| 2020/0276237 A1* | 9/2020 | Shiku | A61P 35/00 |

FOREIGN PATENT DOCUMENTS

| | | | | |
|---|---|---|---|---|
| WO | 93/01161 A1 | 1/1993 | | |
| WO | 93/16185 A2 | 8/1993 | | |
| WO | 93/16185 A3 | 8/1993 | | |
| WO | 94/11026 A2 | 5/1994 | | |
| WO | 94/11026 A3 | 5/1994 | | |
| WO | 96/27011 A1 | 9/1996 | | |
| WO | 97/30087 A1 | 8/1997 | | |
| WO | 98/50431 A2 | 11/1998 | | |
| WO | 98/50431 A3 | 11/1998 | | |
| WO | 98/58964 A1 | 12/1998 | | |
| WO | 99/22764 A1 | 5/1999 | | |
| WO | 99/54342 A1 | 10/1999 | | |
| WO | 01/07611 A2 | 2/2001 | | |
| WO | 01/077342 A1 | 10/2001 | | |
| WO | 03/011878 A2 | 2/2003 | | |
| WO | 03/011878 A3 | 2/2003 | | |
| WO | 03/085107 A1 | 10/2003 | | |
| WO | 2004/056312 A2 | 7/2004 | | |
| WO | 2004/056312 A3 | 7/2004 | | |
| WO | 2004/065540 A2 | 8/2004 | | |
| WO | 2004/065540 A3 | 8/2004 | | |
| WO | 2004/106381 A1 | 12/2004 | | |
| WO | 2005/061547 A2 | 7/2005 | | |
| WO | 2005/100402 A1 | 10/2005 | | |
| WO | 2006/029879 A2 | 3/2006 | | |
| WO | 2006/029879 A3 | 3/2006 | | |
| WO | 2006/082515 A2 | 8/2006 | | |
| WO | 2007/042261 A2 | 4/2007 | | |
| WO | 2007/110205 A2 | 10/2007 | | |
| WO | 2007/147901 A1 | 12/2007 | | |
| WO | 2008/024715 A2 | 2/2008 | | |
| WO | 2008/119567 A2 | 10/2008 | | |
| WO | 2009/080251 A1 | 7/2009 | | |
| WO | 2009/080252 A1 | 7/2009 | | |
| WO | 2009/080253 A1 | 7/2009 | | |
| WO | 2009/089004 A1 | 7/2009 | | |
| WO | 2010/112193 A1 | 10/2010 | | |
| WO | 2010/115589 A1 | 10/2010 | | |
| WO | 2010/115589 A8 | 10/2010 | | |
| WO | 2010/136172 A1 | 12/2010 | | |
| WO | 2010/145792 A1 | 12/2010 | | |
| WO | 2010/129304 A2 | 2/2011 | | |
| WO | 2010/129304 A3 | 2/2011 | | |
| WO | 2011/034605 A2 | 3/2011 | | |
| WO | 2011/090754 A1 | 7/2011 | | |
| WO | 2011/090762 A1 | 7/2011 | | |
| WO | 2011/143545 A1 | 11/2011 | | |
| WO | 2012/058768 A1 | 6/2012 | | |
| WO | 2012/058768 A8 | 6/2012 | | |
| WO | 2012/130831 A1 | 10/2012 | | |
| WO | 2013/026831 A1 | 2/2013 | | |
| WO | 2013/026833 A1 | 2/2013 | | |
| WO | 2013/026839 A1 | 2/2013 | | |
| WO | 2013/096291 A2 | 6/2013 | | |
| WO | 2013/096291 A3 | 6/2013 | | |
| WO | 2013/120929 A1 | 8/2013 | | |
| WO | 2013/157953 A1 | 10/2013 | | |
| WO | 2013/157954 A1 | 10/2013 | | |
| WO | 2014/131694 A1 | 9/2014 | | |
| WO | 2015/095539 A1 | 6/2015 | | |
| WO | 2015/150447 A1 | 10/2015 | | |
| WO | 2016/016299 A1 | 2/2016 | | |
| WO | 2016/020309 A1 | 2/2016 | | |
| WO | 2016/040856 A2 | 3/2016 | | |
| WO | 2016/172485 A2 | 10/2016 | | |
| WO | 2016/199141 A2 | 12/2016 | | |
| WO | 2016/199141 A3 | 12/2016 | | |
| WO | WO-2016199141 A2 * | 12/2016 | | A61P 35/00 |
| WO | 2017/174824 A1 | 10/2017 | | |
| WO | 2017/175006 A1 | 10/2017 | | |
| WO | WO-2017175006 A1 * | 10/2017 | | A61K 35/17 |
| WO | WO-2018225732 A1 * | 12/2018 | | A61K 35/17 |

OTHER PUBLICATIONS

Wang X et al. Protein Cell. 2018 9(1): 63-73 (Year: 2018).*
Janeway, Immuno Biology the immune system in Health and Disease, 5th edition, 2001, section 7.8 (Year: 2001).*
Lydard et. al. Immunology, 2011, in Antibodies: Generation of diversity pp. 76-85 (Year: 2011).*
Chiu ML et al. Antibodies 2019, 8, 55; doi:10.3390/antib8040055 (Year: 2019).*
Almagro, J., et al., "Humanization of antibodies" Front Biosci 13:1619-1633 (Jan. 1, 2008).
Atwell, S., et al., "Stable heterodimers from remodeling the domain interface of a homodimer using a phage display library" J Mol Biol 270(1):26-35 (Jul. 4, 1997).
Baca, M., et al., "Antibody humanization using monovalent phage display" J Biol Chem 272(16):10678-10684 (Apr. 18, 1997).
Bacac, M., et al., "CEA TCB: A novel head-to-tail 2:1 T cell bispecific antibody for treatment of CEA-positive solid tumors" Oncoimmunology 5(8 Suppl e1203498):1-3 (Jun. 24, 2016).
Bazan, J., et al., "Phage display—A powerful technique for immunotherapy" Hum Vaccines Immuno 8(12):1817-1828 (Dec. 13, 2012).
Boerner, P., et al., "Production of antigen-specific human monoclonal antibodies from in vitro-primed human splenocytes" J Immunol 147(1):86-95 (Jul. 1, 1991).
Brennan, M. et al., "Preparation of bispecific antibodies by chemical recombination of monoclonal immunoglobulin G1 fragments" Science 229( Suppl 4708):81-83 (Jul. 5, 1985).
Brodeur, B. et al., "Mouse-human myeloma partners for the production of heterohybridomas" Monoclonal Antibody Production Techniques and Applications (New York: Marcel Dekker, Inc.),:51-63 ( 1987).
Bruggemann, M., et al., "Comparison of the Effector Functions of Human Immunogobulins Using a Matched set of Chimeric Antibodies" J Exp Med 166(5):1351-1361 (Oct. 1, 1987).
Carter, P., et al., "Humanization of an anti-p185 HER2 antibody for human cancer therapy" PNAS USA 89(10):4285-4289 (May 15, 1992).
Carter, Paul, "Bispecific human IgG by design" J Immunol Methods 248(1-2):7-15 (Feb. 1, 2001).
Chari, R., et al., "Immunoconjugates containing novel maytansinoids: Promising anticancer drugs" Cancer Res 52(1):127-131 (Jan. 1, 1992).
Cherf, G., et al., "Applications of yeast surface display for protein engineering" Methods Mol Biol 1319:155-175 (Jan. 1, 2015).
Clackson, T., et al., "Making antibody fragments using phage display libraries" Nature 352(6336):624-628 (Aug. 15, 1991).
Clynes, R., et al., "Fc receptors are required in passive and active immunity to melanoma" PNAS USA 95(2):652-656 (Jan. 1, 1998).

(56) References Cited

OTHER PUBLICATIONS

Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Dall'Acqua, W., et al., "Antibody humanization by framework shuffling" Methods 36(1):43-60 (Jan. 17, 2005).
Ferrara, C., et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi a-mannosidase II" Biotechnol Bioeng 93(5):851-861 (Jan. 24, 2006).
Frenzel, A., et al., "Phage display-derived human antibodies in clinical development and therapy" MABS 8(7):1177-1194 (Jul. 8, 2016).
Gazzano-Santoro, H., et al., "A non-radioactive complement-dependent cytotoxicity assay for anti-CD20 monoclonal antibody" J Immunol Methods 202(2):163-171 (Mar. 28, 1997).
Gerngross, T., "Advances in the Production of Human Therapeutic Proteins in Yeasts and Filamentous Fungi" Nat Biotechnol 22(11):1409-1414 (Nov. 22, 2004).
Graham, F., et al., "Characteristics of a Human Cell Line Transformed by DNA from Human Adenovirus Type 5" J Gen Virol 36(1):59-74 (Feb. 1, 1977).
Griffiths, A., et al., "Human anti-self antibodies with high specificity from phage display libraries" EMBO J 12(2):725-734 (Feb. 1, 1993).
Gruber, M. et al., "Efficient tumor cell lysis mediated by a bispecific single chain antibody expressed in *Escherichia coli*" J Immunol 152(11):5368-5374 (Jun. 1, 1994).
Hanes, J., et al., "In vitro selection and evolution of functional proteins by using ribosome display" PNAS 94(10):4937-4942 (May 1, 1997).
He, M., et al., "Antibody-ribosome-mRNA (ARM) complexes as efficient selection particles for in vitro display and evolution of antibody combining sites" Nucleic Acids Res 25(24):5132-5134 (Oct. 4, 1997).
Hellstrom, I et al., "Strong antitumor activities of IgG3 antibodies to a human melanoma-associated ganglioside" PNAS USA 82(5):1499-1502 (Mar. 1, 1985).
Hellstrom, I., et al., "Antitumor effects of L6, an IgG2a antibody that reacts with most human carcinomas" PNAS US 83(18):7059-7063 (Sep. 1, 1986).
Holliger, P., et al., "Specific killing of lymphoma cells by cytotoxic T-cells mediated by a bispecifc diabody" Protein Eng 9(3):299-305 (Mar. 1, 1996).
Hollinger, P., et al., "Diabodies: Small Bivalent and Bispecific Antibody Fragments" PNAS 90(14):6444-6448 (Jul. 15, 1993).
Hollinger, P., et al., "Engineered Antibody Fragments and the Rise of Single Domains" Nature Biotechnol 23(9):1126-1136 ( 2005).
Hoogenboom and Winter, "By-passing immunisation. Human antibodies from synthetic repertoires of germline VH gene segments rearranged in vitro" J Mol Biol 227(2):381-388 (Sep. 20, 1992).
Hoogenboom, H., et al., "Overview of antibody phage-display technology and its applications" Methods Mol Biol 178:1-37 ( 2002).
Hudson, P., et al., "Engineered antibodies" Nat Med 9(1):129-134 (Jan. 1, 2003).
International Search Report and Written Opinion for PCT/EP2020/086614 dated Apr. 9, 2021.
Johnson, S., et al., "Effector Cell Recruitment with Novel Fv-based Dual-affinity Re-targeting Protein Leads to Potent Tumor Cytolysis and in Vivo B-cell Depletion" J Mol Biol 399(3):436-449 (Jun. 11, 2010).
Kanda, Y. et al., "Comparison of Cell Lines for Stable Production of Fucose-Negative Antibodies with Enhanced ADCC" Biotechnol Bioeng 94(4):680-688 (Jul. 1, 2006).

Kashmiri, S., et al., "SDR grafting—a new approach to antibody humanization" Methods 36:25-34 (Jan. 1, 2005).
Kipriyanov, S., et al., "Bispecific Tandem Diabody for Tumor Therapy with Improved Antigen Binding and Pharmacokinetics" J Mol Biol 293(1):41-56 (Oct. 15, 1999).
Klein, C. et al., "The use of CrossMAb technology for the generation of bi- and multispecific antibodies" MABS 8(6):1010-1020 (Aug. 31, 2016).
Klimka, A. et al., "Human anti-CD30 recombinant antibodies by guided phage antibody selection using cell panning" Brit J Cancer 83(2):252-260 (Jun. 15, 2000).
Kostelny, S., et al., "Formation of a bispecific antibody by the use of leucine zippers" J Immunol 148(5):1547-1553 (Mar. 1, 1992).
Kozbor, D., et al., "A Human Hybrid Myeloma for Production of Human Monoclonal Antibodies" J Immunol 133(6):3001-3005 (Dec. 1, 1984).
Lerner, R., "Combinatorial antibody libraries: new advances, new immunological insights" Nat Rev Immunol 16(8):498-508 (Jul. 6, 2016).
Li, H., et al., "Optimization of humanized IgGs in glycoengineered Pichia pastoris" Nat Biotechnol 24(2):210-215 (Feb. 1, 2006).
Li, J., et al., "Human antibodies for immunotherapy development generated via a human B cell hybridoma technology" PNAS USA 103(10):3557-3562 (Mar. 7, 2006).
Lonberg, N.,, "Fully human antibodies from transgenic mouse and phage display platforms" Curr Opin Immunol 20(4):450-459 (Aug. 1, 2008).
Lonberg, N.,, "Human antibodies from transgenic animals" Nat Biotechnol 23(9):1117-1125 (Sep. 7, 2005).
Marks and Bradbury Methods Mol Biol, Antibody Engineering "Selection of human antibodies from phage display libraries" Benny K. C. Lo, Humana Press, vol. 248:161-176 ( 2004).
Mather, J., "Establishment and characterization of two distinct mouse testicular epithelial cell lines" Biol Reprod 23(1):243-252 (Aug. 1, 1980).
Mather, J., et al., "Culture of Testicular Cells in Hormone-Supplemented Serum-Free Medium" Ann NY Acad Sci 383:44-68 (Jan. 1, 1982).
Milstein, C., et al., "Hybrid hybridomas and their use in immunohistochemistry" Nature 305(5934):537-539 (Oct. 6, 1983).
Myszka, D.,, "Improving Biosensor Analysis" J Mol Recognit 12(5):279-284 (Sep. 30, 1999).
Nagorsen, D., et al., "Immunomodulatory therapy of cancer with T cell-engaging BiTE antibody blinatumomab" Exp Cell Res 317(9):1255-1260 (May 15, 2011).
Ni et al., "Research progress and future perspectives in antibodomics and antibodomic drugs" Xiandai Mianyixue ((Abstract only)), 26(4):265-268 ( 2006).
Osbourn, J. et al., "From rodent reagents to human therapeutics using antibody guided selection" Methods 36(1):61-68 (May 1, 2005).
Oshannessy, D., et al., "Determination of Rate and Equilibrium Binding Constants for Macromolecular Interactions Using Surface Plasmon Resonance: Use of Nonlinear Least Squares Analysis Methods" Anal Biochem 212(2):457-468 (Aug. 1, 1993).
Padlan, E., "A possible procedure for reducing the immunogenicity of antibody variable domains while preserving their ligand-binding properties" Mol Immunol 28(4-5):489-498 (Apr. 30, 1991).
Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).
Pluckthun, A. et al. The Pharmacology of Monoclonal Antibodies "Antibodies from *Escherichia coli*" (Antibodies from *Escherichia coli*), Rosenberg & Moore, vol. 113:269-315 ( 1994).
Polakis, P. et al., "Antibody Drug Conjugates for Cancer Therapy" Pharmacol Rev 68(1):3-19 (Jan. 1, 2016).
Portolano, S., et al., "Lack of promiscuity in autoantigen-specific H and L chain combinations as revealed by human H and L chain 'roulette'" J Immunol 150(3):880-887 (Feb. 1, 1993).
Presta, L., et al., "Humanization of an Antibody Directed Against IgE" J Immunol 151(5):2623-2632 (Sep. 1, 1993).

(56) References Cited

OTHER PUBLICATIONS

Queen, C., et al., "A humanized antibody that binds to the interleukin 2 receptor" PNAS USA 86(24):10029-10033 (Dec. 1, 1989).
Ridgway, J., et al., "Knobs-into-holes' engineering of antibody CH3 domains for heavy chain heterodimerization" Protein Eng 9(7):617-621 (Jul. 1, 1996).
Riechmann, L., et al., "Reshaping human antibodies for therapy" Nature 332:323-327 (Mar. 24, 1988).
Ripka, J., et al., "Two Chinese Hamster Ovary Glycosylation Mutants Affected in the Conversion of GDP-Mannose to GDP-Fucose" Arch Biochem Biophys 249(2):533-545 (Sep. 1, 1986).
Rosok, M., et al., "A combinatorial library strategy for the rapid humanization of anticarcinoma BR96 Fab" J Biol Chem 271(37):22611-22618 (Sep. 13, 1996).
Schaefer, W., et al., "Immunoglobulin domain crossover as a generic approach for the production of bispecific IgG antibodies" PNAS USA 108(27):11187-11192 (Jul. 5, 2011).
Scholler, N., Methods in Molecular Biology; Antibody Engineering: Methods and Protocols "Chapter 15: Selection of Antibody Fragments by Yeast Display" Chames, P., Second Edition, New York, NY:Springer—Humana Press, vol. 907:259-280 (Jan. 1, 2012).
Seimetz, D., et al., "Development and approval of the trifunctional antibody catumaxomab (anti-EpCAM x anti-CD3) as a target cancer immunotherapy" Cancer Treat Rev 36(6):458-467 (Oct. 1, 2010).
Sims, M., et al., "A Humanized CD18 Antibody Can Block Function Without Cell Destruction" J Immunol 151(4):2296-2308 (Aug. 15, 1993).
Spiess, C., et al., "Alternative molecular formats and therapeutic applications for bispecific antibodies" Mol Immunol 67( Suppl 2 Pt A):95-106 (Jan. 27, 2015).
Tutt, A., et al., "Trispecific F(ab')3 derivatives that use cooperative signaling via the TCR/CD3 complex and CD2 to activate and redirect resting cytotoxic T cells" J Immunol 147(1):60-69 (Jul. 1, 1991).
Umana, P., et al., "Engineered Glycoforms of an Antineuroblastoma IgG1 with Optimized Antibody-Dependent Cellular Cytotoxic Activity" Nat Biotechnol 17(2):176-180 (Feb. 1, 1999).
Urlaub, G., et al., "Isolation of Chinese hamster cell mutants deficient in dihydrofolate reductase activity" PNAS US 77(7):4216-4220 (Jul. 1, 1980).
Van Dijk, M., et al., "Human antibodies as next generation therapeutics" Curr Opin Chem Biol 5(4):368-374 (Aug. 1, 2001).
Vitetta, E. et al., "Redesigning nature's poisons to create anti-tumor reagents" Science 238(4830):1098-1104 (Nov. 20, 1987).
Vollmers, H., et al., "The 'early birds': Natural IgM antibodies and immune surveillance" Histol Histopathol 20(3):927-937 (Jul. 1, 2005).
Vollmers, H.,, "Death by stress: natural IgM-induced apoptosis" Methods Find Exp Clin Pharmacol 27(3):185-191 (Apr. 1, 2005).
Winter, G., et al., "Making Antibodies by Phage Display Technology" Annu Rev Immunol 12:433-455 ( 1994).
Wright, A., et al., "Effect of Glycosylation on Antibody Function: Implications for Genetic Engineering" Trends Biotechnol 15(1):26-32 (Jan. 1, 1997).
Wu, Z, et al., "T cell engaging bispecific antibody (T-BsAb): From technology to therapeutics" Pharmacol Therapeut 182:161-175 (Feb. 1, 2018).
Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki, P. J., et al. Methods in Molecular Biology "Expression of recombinant antibodies in mammalian cell lines" Lo, B.K.C. (ed.), Totowa, NJ:Humana Press, vol. 248:255-268 ( 2004).
Zhao, A., et al., "Phage antibody display libraries: a powerful antibody discovery platform for immunotherapy" Crit Rev Biotechnol 36(2):276-289 (Nov. 14, 2014).
Zhao, Q., et al. Methods in Molecular Biology: Therapeutic Proteins—Methods and Protocols "Chapter 5: Yeast Display of Engineered Antibody Domains" Voynov, Vladimir, ed., New York, NY:Springer, vol. 889:73-84 (Jan. 17, 2012).

* cited by examiner

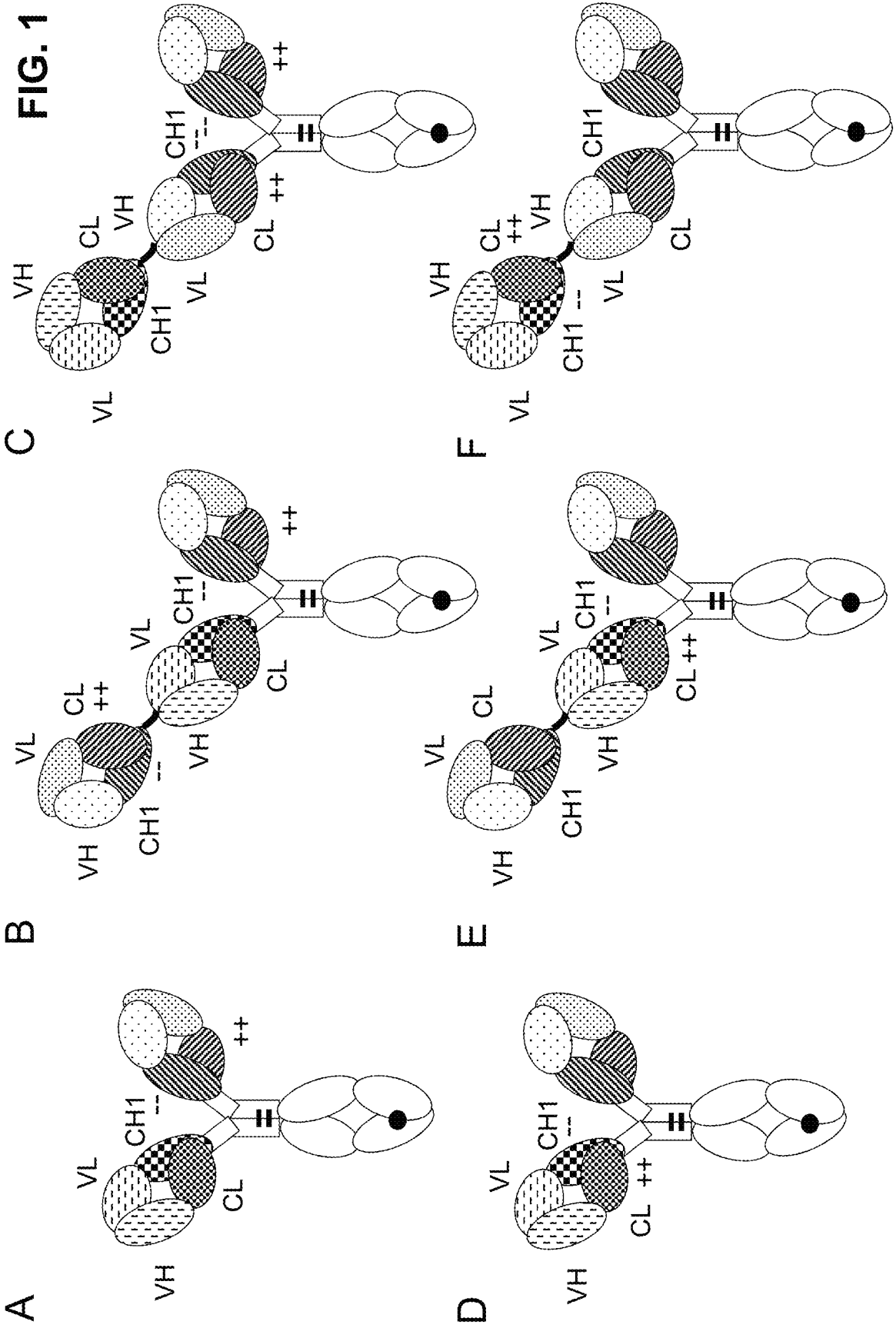

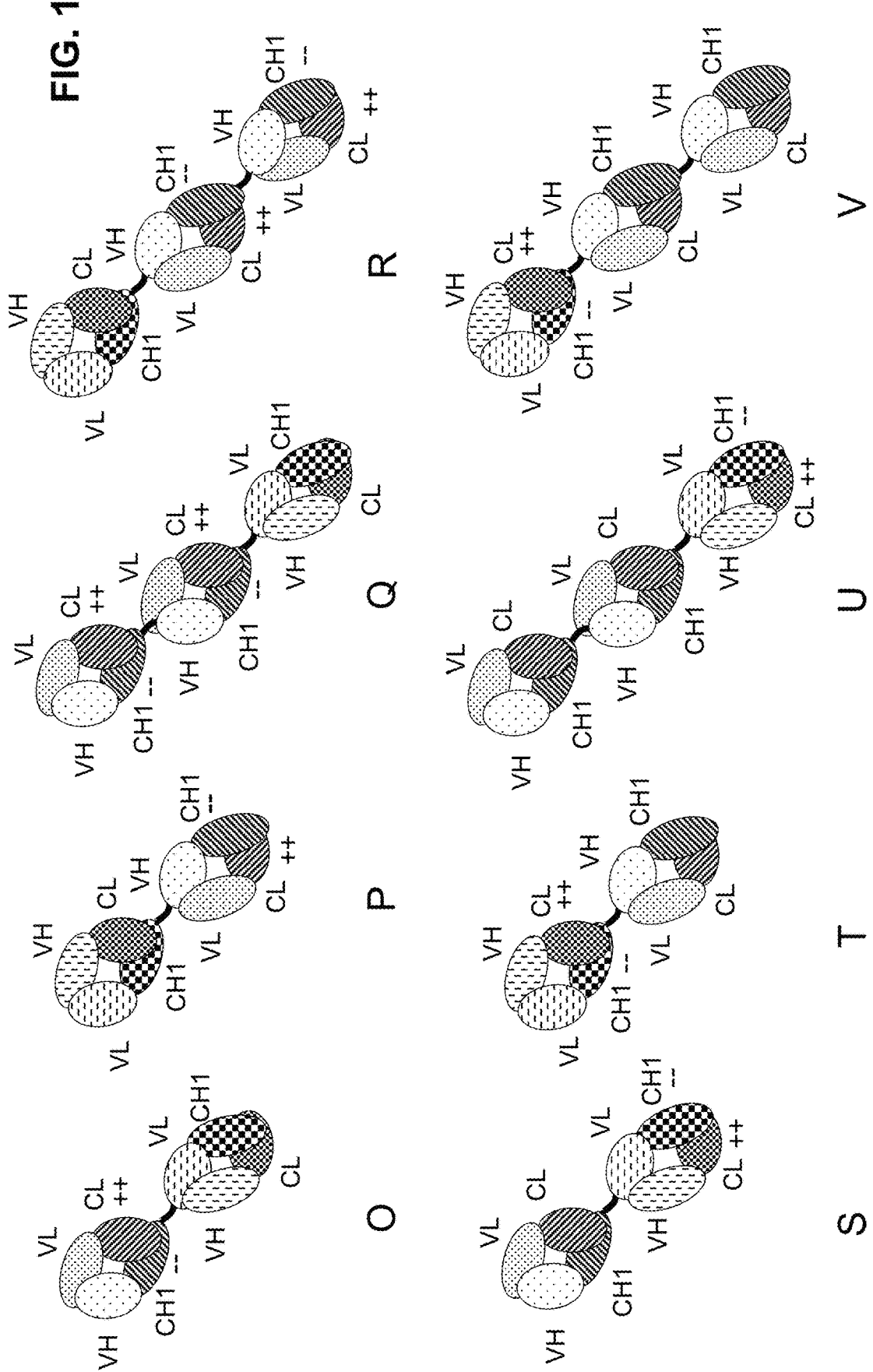

A

| EC50(pM) | Molecule A | Molecule B | Molecule C | Molecule D | Molecule E | Molecule F |
|---|---|---|---|---|---|---|
| GVYDGREHTV | 10.5 | 189.3 | 1026 | 73.2 | 1617 | 95.41 |
| G1A | 40050 | 140600 | 1441 | 2304 | 2717 | 259.3 |
| V2A | 18.4 | 257.5 | 686.8 | 9657 | 4067 | 6566 |
| Y3A | 5268 | 27920 | 626.2 | 4977 | 2065 | 14950 |
| D4A | 51600 | 191100 | 738.1 | 7782 | 22320 | 9953 |
| G5A | 5.6 | 181.2 | 16770 | 594 | 9439 | 1094 |
| R6A | 40060 | 45490 | 4338 | 6656 | 2369 | 195.7 |
| E7A | 100.3 | 3481 | 1216 | 1692 | 2979 | 332.1 |
| H8A | 44 | 716.9 | 3939 | 87.19 | 1229 | 81.3 |
| T9A | 38.3 | 426.3 | 669.7 | 130.3 | 4263 | 450.1 |
| V10A | 29 | 1005 | 12950 | 400.8 | 7463 | 790.9 |
|  | GVYDGREHTV | GVYDGREHTV | GVYDGREHTV | GVYDGREHTV | GVYDGREHTV | GVYDGREHTV |

| x-fold increase in EC50 | Molecule A | Molecule B | Molecule C | Molecule D | Molecule E | Molecule F |
|---|---|---|---|---|---|---|
| G1A | 3814 | 743 | 1 | 31 | 2 | 3 |
| V2A | 2 | 1 | 1 | 132 | 3 | 69 |
| Y3A | 502 | 147 | 1 | 68 | 1 | 157 |
| D4A | 4914 | 1010 | 1 | 106 | 14 | 104 |
| G5A | 1 | 1 | 16 | 8 | 6 | 11 |
| R6A | 3815 | 240 | 4 | 91 | 1 | 2 |
| E7A | 10 | 18 | 1 | 23 | 2 | 3 |
| H8A | 4 | 4 | 4 | 1 | 1 | 1 |
| T9A | 4 | 2 | 1 | 2 | 3 | 5 |
| V10A | 3 | 5 | 13 | 5 | 5 | 8 |
| | GVYDGREHTV | GVYDGREHTV | GVYDGREHTV | GVYDGREHTV | GVYDGREHTV | GVYD

FIG. 8

| POIP | Peptide Sequence (N' - C') | UniProtKB | A | B | C | D | E | F |
|---|---|---|---|---|---|---|---|---|
| pfkA | GLYEGRIKQL | Q8DCY1 | 0.58 | 1.10 | 0.40 | 0.43 | 0.26 | 0.80 |
| DPYSL3 | GMYDGPVFDL | Q14195 | 32.91 | 111.77 | 0.35 | 0.49 | 1.04 | 61.93 |
| gutQ | GMIESRDYML | Q8K4S5 | 0.64 | 1.11 | 0.36 | 0.55 | 0.31 | 0.73 |
| UBE2V2 | GMVDARSIPV | Q15819 | 0.75 | 1.37 | 0.52 | 0.49 | 0.40 | 0.71 |
| DPYSL4 | GLYDGPVHEV | O14531 | 1.68 | 53.08 | 0.27 | 0.63 | 0.48 | 14.32 |
| PIGG | GHEARFVYV | Q5H8A4 | 0.70 | 1.46 | 0.33 | 0.43 | 0.26 | 0.78 |
| CRMP1 | GMYDGPVYEV | Q14194 | 1.74 | 67.51 | 0.29 | 0.67 | 0.37 | 6.54 |
| ZNF624 | GLWDSRMEGL | Q9P2J8 | 0.54 | 1.22 | 0.31 | 0.59 | 0.35 | 1.05 |
| DPYSL2 | GLYDGPVCEV | Q16555 | 0.75 | 5.19 | 0.24 | 0.51 | 0.41 | 9.47 |
| WDFY4 | GLAEGPWPAA | Q6ZS81 | 0.64 | 0.95 | 0.22 | 0.64 | 0.66 | 0.64 |
| TRANK1 | GLFDGPKPTV | O15050 | 4.56 | 7.67 | 0.23 | 0.53 | 0.35 | 3.28 |
| BNRF1 | GMFESRWLNI | Q1HVJ0 | 0.47 | 1.05 | 0.36 | 0.49 | 0.45 | 0.55 |
| C19orf54 | GLVDGRYSPV | Q5BKX5 | 0.75 | 1.27 | 0.29 | 0.39 | 0.47 | 0.52 |
| MST1R | GTMDGRILQV | Q04912 | 0.77 | 0.97 | 0.38 | 0.47 | 0.36 | 1.05 |
| AGFG2 | GLFDARTSLV | O95081 | 86.52 | 13.29 | 0.31 | 0.33 | 1.69 | 76.19 |
| EDC3 | GVYQGRVSAV | Q96F86 | 0.90 | 0.63 | 0.48 | 0.41 | 0.54 | 0.89 |
| FBXO34 | GVYAGRPLSV | Q9NWN3 | 0.46 | 0.91 | 0.39 | 0.63 | 4.03 | 0.78 |
| SLC45A1 | GLLEGREGAL | Q9Y2W3 | 0.39 | 1.22 | 0.22 | 0.43 | 0.38 | 0.68 |
| KEAP1 | GVIDGHIYAV | Q14145 | 0.39 | 1.07 | 0.51 | 0.72 | 0.34 | 0.66 |
| UNC80 | GLADGVEDLL | Q8N2C7 | 0.48 | 0.98 | 0.43 | 0.57 | 0.49 | 1.05 |
| MAGEA10 | GLYDGMEHLI | P43363 | 1.59 | 10.63 | 0.21 | 9.62 | 43.18 | 145.37 |
| VPS13D | GLFDGAFVVL | Q5THJ4 | 0.67 | 1.80 | 0.39 | 1.19 | 46.96 | 177.41 |
| MAGEB2 | GVYDGEEHSV | O15479 | 0.83 | 1.58 | 0.34 | 0.49 | 108.46 | 125.51 |
| ARF1 | GLYEGLDWLS | P84077 | 0.67 | 1.14 | 0.23 | 0.51 | 0.93 | 1.58 |
| MAGEB6 | GIYDGILHSI | Q8N7X4 | 22.38 | 57.86 | 0.55 | 14.47 | 109.93 | 130.08 |
| ARF3 | GLYEGLDWLA | P61204 | 0.92 | 1.59 | 0.49 | 0.51 | 0.85 | 1.53 |
| URB1 | GVYDVRQAYV | O60287 | 80.47 | 67.38 | 0.45 | 0.59 | 1.20 | 78.40 |
| GAPDHS | GIVEGLMTTV | O14556 | 0.91 | 1.37 | 0.37 | 0.49 | 0.39 | 1.01 |
| CCS | GTIDGLEPGL | O14618 | 3.06 | 10.78 | 0.29 | 1.49* | 30.61 | 76.75 |
| KDM1A | ALAEGLDIKL | O60341 | 0.50 | 1.04 | 0.24 | 0.45 | 0.34 | 0.90 |
| DYNC1H1 | GLFEGDEYAT | Q14204 | 0.40 | 0.85 | 0.17 | 0.47 | 0.17 | 0.64 |
| MTOR | GMFEVLEPLH | P42345 | 0.41 | 0.59 | 0.26 | 0.27 | 0.29 | 0.42 |
| PKP1 | GLIDSLMAYV | 13835 | 0.50 | 0.94 | 0.49 | 0.52 | 0.43 | 0.64 |

| OTP | Peptide Sequence (N'-C') | UniProtKB | % ratio POTP/MAGE-A4 Assay 1 | % ratio POTP/MAGE-A4 Assay 2 |
|---|---|---|---|---|
| MAGE-A8 | GLYDGREHSV | P43361 | 105.38 | 136.09 |
| MAGBA | GLYDGIEHFM | Q96LZ2 | 52.28 | 44.00 |
| MAGAB | GVYAGREHFL | P43364 | 55.87 | 38.70 |
| MAGC2 | GVYAGREHFV | Q9UBF1 | 33.91 | 22.73 |
| TSHR | GVYSGPSLLV | P16473 | 7.72 | - |
| MAGEB6 | GIYDGILHSI | Q8N7X4 | 5.69 | 3.41 |
| MAGEA10 | GLYDGMEHLI | P43363 | 2.12 | - |
| HUS1B | GLHEARLWCE | | - | 3.01 |

FIG. 9

| Peptide | Sequence (N'-C') | % ratio POTP/MAGE-A4 |
|---|---|---|
| VP3_ROTHC[137:146] | ELYAGREYTL | 111.96 |
| MAGEA8 | GLYDGREHSV | 106.42 |
| TPC_HU[111:120] | SVYDAREFSV | 102.83 |
| MAGA8_HU[232:241] | GLYDGREHSV | 74.70 |
| MAGC2_HU[257:266] | GVVAGREHFV | 71.20 |
| RBBP5_HU[223:232] | RVYDGREILT | 51.67 |
| RENT1_HU[944:953] | AMYDAREAII | 50.68 |
| DYH6_HU[1555:1564] | FMFEGREIKL | 46.11 |
| MAGAB_HU[342:351] | GVVAGREHFL | 44.59 |
| HUS1B_HU[48:57] | GLHEARLWCE | 4.48 |
| R1AB_CVHN1[6624:6633] | ILFDGRDTGA | 3.06 |
| YAJC_CHLMU[81:90] | TIAEIREHTV | 2.44 |

FIG. 11

SEQUENCE LISTING

```
<160> NUMBER OF SEQ ID NOS: 589

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence

<400> SEQUENCE: 1

Leu Asp Met Ser
1

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence

<400> SEQUENCE: 2

Ser Ile Ser Pro Lys Gly Gly Ser Thr Tyr Tyr Asn Asp Asn Val Leu
1               5                   10                  15

Gly

<210> SEQ ID NO 3
<211> LENGTH: 7
```

```
<212> TYPE: PRT
<213> ORGANISM: Artificial Sequence
<220> FEATURE:
<223> OTHER INFORMATION: Synthetic sequence

<400> SEQUENCE: 3

Asp Trp Gly Phe Phe Asp Leu
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence

<400> SEQUENCE: 4

Arg Ala Ser Gln Ser Ile Ser Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence

<400> SEQUENCE: 5

Asp Ala Asn Ala His Glu Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence

<400> SEQUENCE: 6

Gln Gln Tyr Ser Ser His Pro Tyr Thr
1               5

<210> SEQ ID NO 7
<211> LENGTH: 115
<212> TYPE: PRT
<213> ORGANISM: Artificial Sequence
<220> FEATURE:
<223> OTHER INFORMATION: Synthetic sequence

<400> SEQUENCE: 7

Tyr Val Gln Leu Val Glu Ser Gly Gly Gly Leu Val Lys Pro Gly Gly
1               5                   10                  15

Ser Leu Arg Leu Ser Cys Ala Ala Pro Leu Pro Phe Thr Gly Leu Asp
            20                  25                  30

Met Ser Trp Val Arg Gln Ala Pro Gly Lys Gly Leu Glu Trp Val Gly
        35                  40                  45

Ser Ile Ser Pro Lys Gly Gly Ser Thr Tyr Tyr Asn Asp Asn Val Leu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Trp Gly Phe Phe Asp Leu Trp Gly Gln Gly Thr Leu Val Thr
            100                 105                 110
```

Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic sequence

<400> SEQUENCE: 8

Ala Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Asn Ala His Glu Asn Asp Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser His Pro Tyr
                85                  90                  95

Thr Phe Gly Gln Gly Thr Lys Leu Glu Ile Lys
            100                 105

<210> SEQ ID NO 9
<211> LENGTH: 4
<212> TYPE: PRT
<213> ORGANISM: Artificial Sequence
<220> FEATURE:
<223> OTHER INFORMATION: Synthetic sequence

<400> SEQUENCE: 9

Leu Asp Met Ser
1

<210> SEQ ID NO 10
<211> LENGTH: 17
<212> TYPE: PRT
<213> ORGANISM: Artificial Sequence
<220> FEATURE:
<223> OTHER INFORMATION: Synthetic sequence

<400> SEQUENCE: 10

Ser Ile Ser Pro Lys Gly Gly Ser Thr Tyr Tyr Asn Asp Asn Val Leu
1               5                   10                  15

Gly

<210> SEQ ID NO 11
<211> LENGTH: 7
<212> TYPE: PRT
<213> ORGANISM: Artificial Sequence
<220> FEATURE:
<223> OTHER INFORMATION: Synthetic sequence

<400> SEQUENCE: 11

Asp Trp Gly Phe Phe Asp Asn
1               5

<210> SEQ ID NO 12
<211> LENGTH: 11

```
<212> TYPE: PRT
<213> ORGANISM: Artificial Sequence
<220> FEATURE:
<223> OTHER INFORMATION: Synthetic sequence

<400> SEQUENCE: 12

Arg Ala Ser Gln Ser Ile Ser Asn Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic sequence

<400> SEQUENCE: 13

Asn Ala Ser His Pro Glu Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic sequence

<400> SEQUENCE: 14

Gln Gln Tyr Ser Ser His Pro Tyr Thr
1               5

<210> SEQ ID NO 15
<211> LENGTH: 115
<212> TYPE: PRT
<213> ORGANISM: Artificial Sequence
<220> FEATURE:
<223> OTHER INFORMATION: Synthetic sequence

<400> SEQUENCE: 15

Tyr Pro Gln Leu Val Glu Ser Gly Gly Gly Leu Val Lys Pro Gly Gly
1               5                   10                  15

Ser Leu Arg Leu Ser Cys Ala Ala Arg Tyr Pro Phe Thr Arg Leu Asp
            20                  25                  30

Met Ser Trp Val Arg Gln Ala Pro Gly Lys Gly Leu Glu Trp Val Gly
        35                  40                  45

Ser Ile Ser Pro Lys Gly Gly Ser Thr Tyr Tyr Asn Asp Asn Val Leu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Trp Gly Phe Phe Asp Asn Trp Gly Gln Gly Thr Leu Val Thr
            100                 105                 110

Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: Synthetic sequence

<400> SEQUENCE: 16
```

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asn Ala Ser His Pro Glu Tyr Asp Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser His Pro Tyr
                85                  90                  95

Thr Phe Gly Gln Gly Thr Lys Leu Glu Ile Lys
            100                 105
```

```
<210> SEQ ID NO 17
<211> LENGTH: 5
<212> TYPE: PRT
<213> ORGANISM: Artificial Sequence
<220> FEATURE:
<223> OTHER INFORMATION: Synthetic sequence

<400> SEQUENCE: 17

Phe Asp Thr Met Ser
1               5
```

```
<210> SEQ ID NO 18
<211> LENGTH: 17
<212> TYPE: PRT
<213> ORGANISM: Artificial Sequence
<220> FEATURE:
<223> OTHER INFORMATION: Synthetic sequence

<400> SEQUENCE: 18

Ser Ile Ser Pro Ser Gly Gly Ser Thr Tyr Tyr Asn Asp Asn Val Leu
1               5                   10                  15

Gly
```

```
<210> SEQ ID NO 19
<211> LENGTH: 7
<212> TYPE: PRT
<213> ORGANISM: Artificial Sequence
<220> FEATURE:
<223> OTHER INFORMATION: Synthetic sequence

<400> SEQUENCE: 19

Asp His Gly Tyr Phe Asp Met
1               5
```

```
<210> SEQ ID NO 20
<211> LENGTH: 11
<212> TYPE: PRT
<213> ORGANISM: Artificial Sequence
<220> FEATURE:
<223> OTHER INFORMATION: Synthetic sequence

<400> SEQUENCE: 20

Arg Ala Ser Gln Ser Ile Ser Ser Tyr Leu Ala
1               5                   10
```

```
<210> SEQ ID NO 21
<211> LENGTH: 7
```

```
<212> TYPE: PRT
<213> ORGANISM: Artificial Sequence
<220> FEATURE:
<223> OTHER INFORMATION: Synthetic sequence

<400> SEQUENCE: 21

Asp Ala Ser Trp Leu Glu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic sequence

<400> SEQUENCE: 22

Gln Gln Tyr Ser Ser Tyr Pro Tyr Thr
1               5

<210> SEQ ID NO 23
<211> LENGTH: 116
<212> TYPE: PRT
<213> ORGANISM: Artificial Sequence
<220> FEATURE:
<223> OTHER INFORMATION: Synthetic sequence

<400> SEQUENCE: 23

Thr Gln Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Phe Asp
            20                  25                  30

Thr Met Ser Trp Val Arg Gln Ala Pro Gly Lys Gly Leu Glu Trp Val
        35                  40                  45

Gly Ser Ile Ser Pro Ser Gly Gly Ser Thr Tyr Tyr Asn Asp Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Gly Tyr Phe Asp Met Trp Gly Gln Gly Thr Leu Val
            100                 105                 110

Thr Val Ser Ser
        115

<210> SEQ ID NO 24
<211> LENGTH: 107
<212> TYPE: PRT
<213> ORGANISM: Artificial Sequence
<220> FEATURE:
<223> OTHER INFORMATION: Synthetic sequence

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Trp Leu Glu Leu Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Tyr Pro Tyr
                 85                  90                  95

Thr Phe Gly Gln Gly Thr Lys Leu Glu Ile Lys
            100                 105

<210> SEQ ID NO 25
<211> LENGTH: 4
<212> TYPE: PRT
<213> ORGANISM: Artificial Sequence
<220> FEATURE:
<223> OTHER INFORMATION: Synthetic sequence

<400> SEQUENCE: 25

Lys Ala Met Ser
1

<210> SEQ ID NO 26
<211> LENGTH: 17
<212> TYPE: PRT
<213> ORGANISM: Artificial Sequence
<220> FEATURE:
<223> OTHER INFORMATION: Synthetic sequence

<400> SEQUENCE: 26

Ser Ile Ser Pro Ser Gly Gly Ser Thr Tyr Tyr Asn Asp Asn Val Leu
1               5                   10                  15

Gly

<210> SEQ ID NO 27
<211> LENGTH: 7
<212> TYPE: PRT
<213> ORGANISM: Artificial Sequence
<220> FEATURE:
<223> OTHER INFORMATION: Synthetic sequence

<400> SEQUENCE: 27

Asp Val Gly Phe Phe Asp Glu
1               5

<210> SEQ ID NO 28
<211> LENGTH: 11
<212> TYPE: PRT
<213> ORGANISM: Artificial Sequence
<220> FEATURE:
<223> OTHER INFORMATION: Synthetic sequence

<400> SEQUENCE: 28

Arg Ala Ser Gln Ser Ile Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic sequence

<400> SEQUENCE: 29

Asp Ala Ser Ile Arg Asp Ile
1               5

<210> SEQ ID NO 30
<211> LENGTH: 9
```

<212> TYPE: PRT
<213> ORGANISM: Artificial Sequence
<220> FEATURE:
<223> OTHER INFORMATION: Synthetic sequence

<400> SEQUENCE: 30

Gln Gln Tyr Ser Ser Tyr Pro Tyr Thr
1               5

<210> SEQ ID NO 31
<211> LENGTH: 114
<212> TYPE: PRT
<213> ORGANISM: Artificial Sequence
<220> FEATURE:
<223> OTHER INFORMATION: Synthetic sequence

<400> SEQUENCE: 31

Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
            20                  25                  30

Ser Trp Val Arg Gln Ala Pro Gly Lys Gly Leu Glu Trp Val Gly Ser
        35                  40                  45

Ile Ser Pro Ser Gly Gly Ser Thr Tyr Tyr Asn Asp Asn Val Leu Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Val Gly Phe Phe Asp Glu Trp Gly Gln Gly Thr Leu Val Thr Val
            100                 105                 110

Ser Ser

<210> SEQ ID NO 32
<211> LENGTH: 107
<212> TYPE: PRT
<213> ORGANISM: Artificial Sequence
<220> FEATURE:
<223> OTHER INFORMATION: Synthetic sequence

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ile Arg Asp Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 33
<211> LENGTH: 5
<212> TYPE: PRT
<213> ORGANISM: Artificial Sequence

```
<220> FEATURE:
<223> OTHER INFORMATION: Synthetic sequence

<400> SEQUENCE: 33

Ser Tyr Ala Met Ser
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic sequence

<400> SEQUENCE: 34

Ala Ile Ser Gly Ser Gly Gly Ser Thr Tyr Tyr Ala Asp Ser Val Lys
1               5                   10                  15

Gly

<210> SEQ ID NO 35
<211> LENGTH: 8
<212> TYPE: PRT
<213> ORGANISM: Artificial Sequence
<220> FEATURE:
<223> OTHER INFORMATION: Synthetic sequence

<400> SEQUENCE: 35

Ser Ser Tyr Glu Ala Tyr Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Synthetic sequence

<400> SEQUENCE: 36

Gln Gly Asp Ser Leu Arg Ser Tyr Tyr Ala Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic sequence

<400> SEQUENCE: 37

Gly Lys Asn Asn Arg Pro Ser
1               5

<210> SEQ ID NO 38
<211> LENGTH: 12
<212> TYPE: PRT
<213> ORGANISM: Artificial Sequence
<220> FEATURE:
<223> OTHER INFORMATION: Synthetic sequence

<400> SEQUENCE: 38

Asn Ser Arg Gln Ser Ser Tyr Tyr His His Ile Val
1               5                   10

<210> SEQ ID NO 39
<211> LENGTH: 117
<212> TYPE: PRT
```

```
<213> ORGANISM: Artificial Sequence
<220> FEATURE:
<223> OTHER INFORMATION: Synthetic sequence

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Glu Ala Tyr Asp Tyr Trp Gly Gln Gly Thr Leu
            100                 105                 110

Val Thr Val Ser Ser
            115

<210> SEQ ID NO 40
<211> LENGTH: 109
<212> TYPE: PRT
<213> ORGANISM: Artificial Sequence
<220> FEATURE:
<223> OTHER INFORMATION: Synthetic sequence

<400> SEQUENCE: 40

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Gln Ser Ser Tyr His
                85                  90                  95

His Ile Val Phe Gly Gly Gly Thr Lys Leu Thr Val Leu
            100                 105

<210> SEQ ID NO 41
<211> LENGTH: 5
<212> TYPE: PRT
<213> ORGANISM: Artificial Sequence
<220> FEATURE:
<223> OTHER INFORMATION: Synthetic sequence

<400> SEQUENCE: 41

Ser Tyr Ala Met Ser
1               5

<210> SEQ ID NO 42
<211> LENGTH: 17
<212> TYPE: PRT
<213> ORGANISM: Artificial Sequence
```

<220> FEATURE:
<223> OTHER INFORMATION: Synthetic sequence

<400> SEQUENCE: 42

Ala Ile Ser Gly Ser Gly Gly Ser Thr Tyr Tyr Ala Asp Ser Val Lys
1               5                   10                  15
Gly

<210> SEQ ID NO 43
<211> LENGTH: 8
<212> TYPE: PRT
<213> ORGANISM: Artificial Sequence
<220> FEATURE:
<223> OTHER INFORMATION: Synthetic sequence

<400> SEQUENCE: 43

Val Ser Tyr Glu Ser Phe Asp Tyr
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic sequence

<400> SEQUENCE: 44

Gln Gly Asp Ser Leu Arg Ser Tyr Tyr Ala Ser
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic sequence

<400> SEQUENCE: 45

Gly Lys Asn Asn Arg Pro Ser
1               5

<210> SEQ ID NO 46
<211> LENGTH: 12
<212> TYPE: PRT
<213> ORGANISM: Artificial Sequence
<220> FEATURE:
<223> OTHER INFORMATION: Synthetic sequence

<400> SEQUENCE: 46

Asn Ser Arg Met Ser Ser Arg Tyr His His Asp Val
1               5                   10

<210> SEQ ID NO 47
<211> LENGTH: 117
<212> TYPE: PRT
<213> ORGANISM: Artificial Sequence
<220> FEATURE:
<223> OTHER INFORMATION: Synthetic sequence

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Ser Tyr Glu Ser Phe Asp Tyr Trp Gly Gln Gly Thr Leu
                100                 105                 110

Val Thr Val Ser Ser
            115

<210> SEQ ID NO 48
<211> LENGTH: 109
<212> TYPE: PRT
<213> ORGANISM: Artificial Sequence
<220> FEATURE:
<223> OTHER INFORMATION: Synthetic sequence

<400> SEQUENCE: 48

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
                35                  40                  45

Gly Lys Asn Asn Arg Pro Ser Gly Ile Pro Asp Arg Phe Ser Gly Ser
        50                  55                  60

Ser Ser Ser Asn Thr Ala Ser Leu Thr Ile Thr Gly Ala Gln Ala Glu
 65                  70                  75                  80

Asp Glu Ala Asp Tyr Tyr Cys Asn Ser Arg Met Ser Ser Arg Tyr His
                85                  90                  95

His Asp Val Phe Gly Gly Gly Thr Lys Leu Thr Val Leu
                100                 105

<210> SEQ ID NO 49
<211> LENGTH: 116
<212> TYPE: PRT
<213> ORGANISM: Artificial Sequence
<220> FEATURE:
<223> OTHER INFORMATION: Synthetic sequence

<400> SEQUENCE: 49

Gln Val Gln Leu Gln Gln Ser Gly Gly Glu Val Met Lys Pro Gly Ala
 1               5                  10                  15

Ser Val Lys Leu Ser Cys Lys Ala Thr Gly Tyr Thr Phe Thr Gly Tyr
                20                  25                  30

Trp Ile Glu Trp Ile Lys Gln Arg Pro Gly His Gly Leu Glu Trp Ile
                35                  40                  45

Gly Glu Ile Leu Pro Gly Ser Gly Gly Thr Asn Tyr Asn Glu Lys Phe
        50                  55                  60

Lys Gly Lys Ala Thr Phe Thr Ala His Thr Ser Ser Asn Thr Ala Tyr
 65                  70                  75                  80

Met Gln Leu Ser Ser Leu Thr Thr Glu Asp Ser Ala Ile Tyr Tyr Cys
                85                  90                  95

Ala Arg Asp Ser Asn Ser Phe Thr Tyr Trp Gly Gln Gly Thr Leu Val
                100                 105                 110
```

Thr Val Ser Ser
        115

<210> SEQ ID NO 50
<211> LENGTH: 106
<212> TYPE: PRT
<213> ORGANISM: Artificial Sequence
<220> FEATURE:
<223> OTHER INFORMATION: Synthetic sequence

<400> SEQUENCE: 50

Gln Ile Val Leu Thr Gln Ser Pro Ala Ile Met Ser Ala Ser Pro Gly
1               5                   10                  15

Glu Lys Val Thr Ile Thr Cys Ser Val Ser Ser Ser Val Asp Tyr Ile
            20                  25                  30

His Trp Phe Gln Gln Lys Pro Gly Thr Ser Pro Lys Phe Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Ser Gly Thr Lys Leu Glu Ile Lys
            100                 105

<210> SEQ ID NO 51
<211> LENGTH: 5
<212> TYPE: PRT
<213> ORGANISM: Artificial Sequence
<220> FEATURE:
<223> OTHER INFORMATION: Synthetic sequence

<400> SEQUENCE: 51

Thr Tyr Ala Met Asn
1               5

<210> SEQ ID NO 52
<211> LENGTH: 19
<212> TYPE: PRT
<213> ORGANISM: Artificial Sequence
<220> FEATURE:
<223> OTHER INFORMATION: Synthetic sequence

<400> SEQUENCE: 52

Arg Ile Arg Ser Lys Tyr Asn Asn Tyr Ala Thr Tyr Tyr Ala Asp Ser
1               5                   10                  15

Val Lys Gly

<210> SEQ ID NO 53
<211> LENGTH: 14
<212> TYPE: PRT
<213> ORGANISM: Artificial Sequence
<220> FEATURE:
<223> OTHER INFORMATION: Synthetic sequence

<400> SEQUENCE: 53

His Gly Asn Phe Gly Asn Ser Tyr Val Ser Trp Phe Ala Tyr
1               5                   10

<210> SEQ ID NO 54
<211> LENGTH: 14
<212> TYPE: PRT

```
<213> ORGANISM: Artificial Sequence
<220> FEATURE:
<223> OTHER INFORMATION: Synthetic sequence

<400> SEQUENCE: 54

Gly Ser Ser Thr Gly Ala Val Thr Thr Ser Asn Tyr Ala Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic sequence

<400> SEQUENCE: 55

Gly Thr Asn Lys Arg Ala Pro
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic sequence

<400> SEQUENCE: 56

Ala Leu Trp Tyr Ser Asn Leu Trp Val
1               5

<210> SEQ ID NO 57
<211> LENGTH: 125
<212> TYPE: PRT
<213> ORGANISM: Artificial Sequence
<220> FEATURE:
<223> OTHER INFORMATION: Synthetic sequence

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 109
<212> TYPE: PRT
<213> ORGANISM: Artificial Sequence
<220> FEATURE:
<223> OTHER INFORMATION: Synthetic sequence

<400> SEQUENCE: 58
```

-continued

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 59
<211> LENGTH: 5
<212> TYPE: PRT
<213> ORGANISM: Artificial Sequence
<220> FEATURE:
<223> OTHER INFORMATION: Synthetic sequence

<400> SEQUENCE: 59

Gly Tyr Thr Met Asn
1               5

<210> SEQ ID NO 60
<211> LENGTH: 17
<212> TYPE: PRT
<213> ORGANISM: Artificial Sequence
<220> FEATURE:
<223> OTHER INFORMATION: Synthetic sequence

<400> SEQUENCE: 60

Leu Ile Asn Pro Tyr Lys Gly Val Ser Thr Tyr Asn Gln Lys Phe Lys
1               5                   10                  15

Asp

<210> SEQ ID NO 61
<211> LENGTH: 13
<212> TYPE: PRT
<213> ORGANISM: Artificial Sequence
<220> FEATURE:
<223> OTHER INFORMATION: Synthetic sequence

<400> SEQUENCE: 61

Ser Gly Tyr Tyr Gly Asp Ser Asp Trp Tyr Phe Asp Val
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic sequence

<400> SEQUENCE: 62

Arg Ala Ser Gln Asp Ile Arg Asn Tyr Leu Asn
1               5                   10

<210> SEQ ID NO 63
<211> LENGTH: 7
<212> TYPE: PRT

```
<213> ORGANISM: Artificial Sequence
<220> FEATURE:
<223> OTHER INFORMATION: Synthetic sequence

<400> SEQUENCE: 63

Tyr Thr Ser Arg Leu Glu Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic sequence

<400> SEQUENCE: 64

Gln Gln Gly Asn Thr Leu Pro Trp Thr
1               5

<210> SEQ ID NO 65
<211> LENGTH: 122
<212> TYPE: PRT
<213> ORGANISM: Artificial Sequence
<220> FEATURE:
<223> OTHER INFORMATION: Synthetic sequence

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 66
<211> LENGTH: 107
<212> TYPE: PRT
<213> ORGANISM: Artificial Sequence
<220> FEATURE:
<223> OTHER INFORMATION: Synthetic sequence

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
```

```
            65                  70                  75                  80
Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 67
<211> LENGTH: 667
<212> TYPE: PRT
<213> ORGANISM: Artificial Sequence
<220> FEATURE:
<223> OTHER INFORMATION: Synthetic sequence

<400> SEQUENCE: 67

Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
            20                  25                  30

Ser Trp Val Arg Gln Ala Pro Gly Lys Gly Leu Glu Trp Val Gly Ser
        35                  40                  45

Ile Ser Pro Ser Gly Gly Ser Thr Tyr Tyr Asn Asp Asn Val Leu Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Val Gly Phe Phe Asp Glu Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Gly Gly Gly Ser Gly
    210                 215                 220

Gly Gly Gly Ser Gln Ala Val Val Thr Gln Glu Pro Ser Leu Thr Val
225                 230                 235                 240

Ser Pro Gly Gly Thr Val Thr Leu Thr Cys Gly Ser Ser Thr Gly Ala
                245                 250                 255

Val Thr Thr Ser Asn Tyr Ala Asn Trp Val Gln Glu Lys Pro Gly Gln
            260                 265                 270

Ala Phe Arg Gly Leu Ile Gly Gly Thr Asn Lys Arg Ala Pro Gly Thr
        275                 280                 285

Pro Ala Arg Phe Ser Gly Ser Leu Leu Gly Gly Lys Ala Ala Leu Thr
    290                 295                 300

Leu Ser Gly Ala Gln Pro Glu Asp Glu Ala Glu Tyr Tyr Cys Ala Leu
305                 310                 315                 320

Trp Tyr Ser Asn Leu Trp Val Phe Gly Gly Gly Thr Lys Leu Thr Val
```

```
                    325                 330                 335
Leu Ser Ser Ala Ser Thr Lys Gly Pro Ser Val Phe Pro Leu Ala Pro
            340                 345                 350
Ser Ser Lys Ser Thr Ser Gly Gly Thr Ala Ala Leu Gly Cys Leu Val
        355                 360                 365
Lys Asp Tyr Phe Pro Glu Pro Val Thr Val Ser Trp Asn Ser Gly Ala
    370                 375                 380
Leu Thr Ser Gly Val His Thr Phe Pro Ala Val Leu Gln Ser Ser Gly
385                 390                 395                 400
Leu Tyr Ser Leu Ser Ser Val Val Thr Val Pro Ser Ser Ser Leu Gly
                405                 410                 415
Thr Gln Thr Tyr Ile Cys Asn Val Asn His Lys Pro Ser Asn Thr Lys
            420                 425                 430
Val Asp Lys Lys Val Glu Pro Lys Ser Cys Asp Lys Thr His Thr Cys
        435                 440                 445
Pro Pro Cys Pro Ala Pro Glu Ala Ala Gly Gly Pro Ser Val Phe Leu
    450                 455                 460
Phe Pro Pro Lys Pro Lys Asp Thr Leu Met Ile Ser Arg Thr Pro Glu
465                 470                 475                 480
Val Thr Cys Val Val Val Asp Val Ser His Glu Asp Pro Glu Val Lys
                485                 490                 495
Phe Asn Trp Tyr Val Asp Gly Val Glu Val His Asn Ala Lys Thr Lys
            500                 505                 510
Pro Arg Glu Glu Gln Tyr Asn Ser Thr Tyr Arg Val Val Ser Val Leu
        515                 520                 525
Thr Val Leu His Gln Asp Trp Leu Asn Gly Lys Glu Tyr Lys Cys Lys
    530                 535                 540
Val Ser Asn Lys Ala Leu Gly Ala Pro Ile Glu Lys Thr Ile Ser Lys
545                 550                 555                 560
Ala Lys Gly Gln Pro Arg Glu Pro Gln Val Tyr Thr Leu Pro Pro Cys
                565                 570                 575
Arg Asp Glu Leu Thr Lys Asn Gln Val Ser Leu Trp Cys Leu Val Lys
            580                 585                 590
Gly Phe Tyr Pro Ser Asp Ile Ala Val Glu Trp Glu Ser Asn Gly Gln
        595                 600                 605
Pro Glu Asn Asn Tyr Lys Thr Thr Pro Pro Val Leu Asp Ser Asp Gly
    610                 615                 620
Ser Phe Phe Leu Tyr Ser Lys Leu Thr Val Asp Lys Ser Arg Trp Gln
625                 630                 635                 640
Gln Gly Asn Val Phe Ser Cys Ser Val Met His Glu Ala Leu His Asn
                645                 650                 655
His Tyr Thr Gln Lys Ser Leu Ser Leu Ser Pro
            660                 665

<210> SEQ ID NO 68
<211> LENGTH: 665
<212> TYPE: PRT
<213> ORGANISM: Artificial Sequence
<220> FEATURE:
<223> OTHER INFORMATION: Synthetic sequence

<400> SEQUENCE: 68

Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
```

```
                20                  25                  30
Ser Trp Val Arg Gln Ala Pro Gly Lys Gly Leu Glu Trp Val Gly Ser
            35                  40                  45
Ile Ser Pro Ser Gly Gly Ser Thr Tyr Tyr Asn Asp Asn Val Leu Gly
        50                  55                  60
Arg Phe Thr Ile Ser Arg Asp Asn Ser Lys Asn Thr Leu Tyr Leu Gln
65                  70                  75                  80
Met Asn Ser Leu Arg Ala Glu Asp Thr Ala Val Tyr Tyr Cys Ala Lys
                85                  90                  95
Asp Val Gly Phe Phe Asp Glu Trp Gly Gln Gly Thr Leu Val Thr Val
            100                 105                 110
Ser Ser Ala Ser Thr Lys Gly Pro Ser Val Phe Pro Leu Ala Pro Ser
        115                 120                 125
Ser Lys Ser Thr Ser Gly Gly Thr Ala Ala Leu Gly Cys Leu Val Glu
        130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Glu Lys Val Glu Pro Lys Ser Cys Asp Gly Gly Gly Ser Gly
        210                 215                 220
Gly Gly Gly Ser Asp Ile Gln Met Thr Gln Ser Pro Ser Ser Leu Ser
225                 230                 235                 240
Ala Ser Val Gly Asp Arg Val Thr Ile Thr Cys Arg Ala Ser Gln Asp
                245                 250                 255
Ile Arg Asn Tyr Leu Asn Trp Tyr Gln Gln Lys Pro Gly Lys Ala Pro
            260                 265                 270
Lys Leu Leu Ile Tyr Tyr Thr Ser Arg Leu Glu Ser Gly Val Pro Ser
        275                 280                 285
Arg Phe Ser Gly Ser Gly Ser Gly Thr Asp Tyr Thr Leu Thr Ile Ser
        290                 295                 300
Ser Leu Gln Pro Glu Asp Phe Ala Thr Tyr Tyr Cys Gln Gln Gly Asn
305                 310                 315                 320
Thr Leu Pro Trp Thr Phe Gly Gln Gly Thr Lys Val Glu Ile Lys Ser
                325                 330                 335
Ser Ala Ser Thr Lys Gly Pro Ser Val Phe Pro Leu Ala Pro Ser Ser
            340                 345                 350
Lys Ser Thr Ser Gly Gly Thr Ala Ala Leu Gly Cys Leu Val Lys Asp
        355                 360                 365
Tyr Phe Pro Glu Pro Val Thr Val Ser Trp Asn Ser Gly Ala Leu Thr
        370                 375                 380
Ser Gly Val His Thr Phe Pro Ala Val Leu Gln Ser Ser Gly Leu Tyr
385                 390                 395                 400
Ser Leu Ser Ser Val Val Thr Val Pro Ser Ser Ser Leu Gly Thr Gln
                405                 410                 415
Thr Tyr Ile Cys Asn Val Asn His Lys Pro Ser Asn Thr Lys Val Asp
            420                 425                 430
Lys Lys Val Glu Pro Lys Ser Cys Asp Lys Thr His Thr Cys Pro Pro
        435                 440                 445
```

Cys Pro Ala Pro Glu Ala Ala Gly Gly Pro Ser Val Phe Leu Phe Pro
            450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
                500                 505                 510

Glu Glu Gln Tyr Asn Ser Thr Tyr Arg Val Val Ser Val Leu Thr Val
            515                 520                 525

Leu His Gln Asp Trp Leu Asn Gly Lys Glu Tyr Lys Cys Lys Val Ser
530                 535                 540

Asn Lys Ala Leu Gly Ala Pro Ile Glu Lys Thr Ile Ser Lys Ala Lys
545                 550                 555                 560

Gly Gln Pro Arg Glu Pro Gln Val Tyr Thr Leu Pro Pro Cys Arg Asp
                565                 570                 575

Glu Leu Thr Lys Asn Gln Val Ser Leu Trp Cys Leu Val Lys Gly Phe
            580                 585                 590

Tyr Pro Ser Asp Ile Ala Val Glu Trp Glu Ser Asn Gly Gln Pro Glu
            595                 600                 605

Asn Asn Tyr Lys Thr Thr Pro Pro Val Leu Asp Ser Asp Gly Ser Phe
610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro
            660                 665

<210> SEQ ID NO 69
<211> LENGTH: 442
<212> TYPE: PRT
<213> ORGANISM: Artificial Sequence
<220> FEATURE:
<223> OTHER INFORMATION: Synthetic sequence

<400> SEQUENCE: 69

Ala Gln Leu Val Glu Ser Gly Gly Gly Leu Val Gln Pro Gly Gly Ser
1               5                   10                  15

Leu Arg Leu Ser Cys Ala Ala Ser Ala Tyr Phe Ser Phe Lys Ala Met
            20                  25                  30

Ser Trp Val Arg Gln Ala Pro Gly Lys Gly Leu Glu Trp Val Gly Ser
        35                  40                  45

Ile Ser Pro Ser Gly Gly Ser Thr Tyr Tyr Asn Asp Asn Val Leu Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Val Gly Phe Phe Asp Glu Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

```
Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Cys Thr Leu Pro Pro Ser Arg
            340                 345                 350

Asp Glu Leu Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro
        435                 440

<210> SEQ ID NO 70
<211> LENGTH: 214
<212> TYPE: PRT
<213> ORGANISM: Artificial Sequence
<220> FEATURE:
<223> OTHER INFORMATION: Synthetic sequence

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Ile Arg Asp Ile Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Tyr Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 232
<212> TYPE: PRT
<213> ORGANISM: Artificial Sequence
<220> FEATURE:
<223> OTHER INFORMATION: Synthetic sequence

<400> SEQUENCE: 71

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Ala Met Asn Trp Val Arg Gln Ala Pro Gly Lys Gly Leu Glu Trp Val
         35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205
```

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 72
<211> LENGTH: 229
<212> TYPE: PRT
<213> ORGANISM: Artificial Sequence
<220> FEATURE:
<223> OTHER INFORMATION: Synthetic sequence

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 73
<211> LENGTH: 10
<212> TYPE: PRT
<213> ORGANISM: Homo sapiens

<400> SEQUENCE: 73

Gly Val Tyr Asp Gly Arg Glu His Thr Val
1               5                   10

<210> SEQ ID NO 74
<211> LENGTH: 317
<212> TYPE: PRT
<213> ORGANISM: Homo sapiens

<400> SEQUENCE: 74

```
Met Ser Ser Glu Gln Lys Ser Gln His Cys Lys Pro Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
                35                  40                  45

Gly Thr Leu Glu Glu Val Pro Ala Ala Glu Ser Ala Gly Pro Pro Gln
        50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
                100                 105                 110

Lys Val Asp Glu Leu Ala His Phe Leu Leu Arg Lys Tyr Arg Ala Lys
            115                 120                 125

Glu Leu Val Thr Lys Ala Glu Met Leu Glu Arg Val Ile Lys Asn Tyr
        130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
                180                 185                 190

Asn Asn Gln Ile Phe Pro Lys Thr Gly Leu Leu Ile Ile Val Leu Gly
            195                 200                 205

Thr Ile Ala Met Glu Gly Asp Ser Ala Ser Glu Glu Ile Trp Glu
        210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
                260                 265                 270

Leu Trp Gly Pro Arg Ala Leu Ala Glu Thr Ser Tyr Val Lys Val Leu
            275                 280                 285

Glu His Val Val Arg Val Asn Ala Arg Val Arg Ile Ala Tyr Pro Ser
        290                 295                 300

Leu Arg Glu Ala Ala Leu Leu Glu Glu Glu Gly Val
305                 310                 315
```

<210> SEQ ID NO 75
<211> LENGTH: 275
<212> TYPE: PRT
<213> ORGANISM: Homo sapiens

<400> SEQUENCE: 75

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45
```

```
Ala Pro Trp Ile Glu Gln Glu Gly Pro Glu Tyr Trp Asp Gly Glu Thr
 50                  55                  60

Arg Lys Val Lys Ala His Ser Gln Thr His Arg Val Asp Leu Gly Thr
 65                  70                  75                  80

Leu Arg Gly Tyr Tyr Asn Gln Ser Glu Ala Gly Ser His Thr Val Gln
                 85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 76
<211> LENGTH: 186
<212> TYPE: PRT
<213> ORGANISM: Homo sapiens

<400> SEQUENCE: 76

Gln Asp Gly Asn Glu Glu Met Gly Gly Ile Thr Gln Thr Pro Tyr Lys
 1                   5                  10                  15

Val Ser Ile Ser Gly Thr Thr Val Ile Leu Thr Cys Pro Gln Tyr Pro
                 20                  25                  30

Gly Ser Glu Ile Leu Trp Gln His Asn Asp Lys Asn Ile Gly Gly Asp
            35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125

Tyr Trp Ser Lys Asn Arg Lys Ala Lys Ala Lys Pro Val Thr Arg Gly
    130                 135                 140
```

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
            180                 185

<210> SEQ ID NO 77
<211> LENGTH: 177
<212> TYPE: PRT
<213> ORGANISM: Macaca fascicularis

<400> SEQUENCE: 77

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
                20                  25                  30

Gly Ser Glu Ala Gln Trp Gln His Asn Gly Lys Asn Lys Glu Asp Ser
            35                  40                  45

Gly Asp Arg Leu Phe Leu Pro Glu Phe Ser Glu Met Glu Gln Ser Gly
        50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

Val Met Ala Val Ala Thr Ile Val Ile Val Asp Ile Cys Ile Thr Leu
                100                 105                 110

Gly Leu Leu Leu Leu Val Tyr Tyr Trp Ser Lys Asn Arg Lys Ala Lys
            115                 120                 125

Ala Lys Pro Val Thr Arg Gly Ala Gly Ala Gly Gly Arg Gln Arg Gly
        130                 135                 140

Gln Asn Lys Glu Arg Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 78
<211> LENGTH: 225
<212> TYPE: PRT
<213> ORGANISM: Homo sapiens

<400> SEQUENCE: 78

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

-continued

```
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 79
<211> LENGTH: 107
<212> TYPE: PRT
<213> ORGANISM: Homo sapiens

<400> SEQUENCE: 79

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 80
<211> LENGTH: 105
<212> TYPE: PRT
<213> ORGANISM: Homo sapiens

<400> SEQUENCE: 80

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80
```

```
His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 81
<211> LENGTH: 328
<212> TYPE: PRT
<213> ORGANISM: Homo sapiens

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 82
```

```
<211> LENGTH: 10
<212> TYPE: PRT
<213> ORGANISM: Artificial Sequence
<220> FEATURE:
<223> OTHER INFORMATION: Synthetic sequence

<400> SEQUENCE: 82

Gly Gly Gly Gly Ser Gly Gly Gly Gly Ser
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic sequence

<400> SEQUENCE: 83

Asp Gly Gly Gly Gly Ser Gly Gly Gly Gly Ser
1               5                   10

<210> SEQ ID NO 84
<211> LENGTH: 9
<212> TYPE: PRT
<213> ORGANISM: Homo sapiens

<400> SEQUENCE: 84

Arg Met Phe Pro Asn Ala Pro Tyr Leu
1               5

<210> SEQ ID NO 85
<211> LENGTH: 9
<212> TYPE: PRT
<213> ORGANISM: Homo sapiens

<400> SEQUENCE: 85

Ser Leu Leu Met Trp Ile Thr Gln Cys
1               5

<210> SEQ ID NO 86
<211> LENGTH: 10
<212> TYPE: PRT
<213> ORGANISM: Homo sapiens

<400> SEQUENCE: 86

Gly Leu Tyr Glu Gly Arg Ile Lys Gln Leu
1               5                   10

<210> SEQ ID NO 87
<211> LENGTH: 10
<212> TYPE: PRT
<213> ORGANISM: Homo sapiens

<400> SEQUENCE: 87

Gly Met Ile Glu Ser Arg Asp Val Met Leu
1               5                   10

<210> SEQ ID NO 88
<211> LENGTH: 10
<212> TYPE: PRT
<213> ORGANISM: Homo sapiens

<400> SEQUENCE: 88

Gly Leu Tyr Asp Gly Pro Val His Glu Val
1               5                   10
```

```
<210> SEQ ID NO 89
<211> LENGTH: 10
<212> TYPE: PRT
<213> ORGANISM: Homo sapiens

<400> SEQUENCE: 89

Gly Met Tyr Asp Gly Pro Val Tyr Glu Val
1               5                   10

<210> SEQ ID NO 90
<211> LENGTH: 10
<212> TYPE: PRT
<213> ORGANISM: Homo sapiens

<400> SEQUENCE: 90

Gly Leu Tyr Asp Gly Pro Val Cys Glu Val
1               5                   10

<210> SEQ ID NO 91
<211> LENGTH: 10
<212> TYPE: PRT
<213> ORGANISM: Homo sapiens

<400> SEQUENCE: 91

Gly Leu Phe Asp Gly Pro Lys Pro Thr Val
1               5                   10

<210> SEQ ID NO 92
<211> LENGTH: 10
<212> TYPE: PRT
<213> ORGANISM: Homo sapiens

<400> SEQUENCE: 92

Gly Leu Val Asp Gly Arg Tyr Ser Pro Val
1               5                   10

<210> SEQ ID NO 93
<211> LENGTH: 10
<212> TYPE: PRT
<213> ORGANISM: Homo sapiens

<400> SEQUENCE: 93

Gly Leu Phe Asp Ala Arg Thr Ser Leu Val
1               5                   10

<210> SEQ ID NO 94
<211> LENGTH: 10
<212> TYPE: PRT
<213> ORGANISM: Homo sapiens

<400> SEQUENCE: 94

Gly Met Tyr Asp Gly Pro Val Phe Asp Leu
1               5                   10

<210> SEQ ID NO 95
<211> LENGTH: 10
<212> TYPE: PRT
<213> ORGANISM: Homo sapiens

<400> SEQUENCE: 95

Gly Met Val Asp Ala Arg Ser Ile Pro Val
1               5                   10

<210> SEQ ID NO 96
```

```
<211> LENGTH: 10
<212> TYPE: PRT
<213> ORGANISM: Homo sapiens

<400> SEQUENCE: 96

Gly Ile Ile Glu Ala Arg Phe Val Tyr Val
1               5                   10

<210> SEQ ID NO 97
<211> LENGTH: 10
<212> TYPE: PRT
<213> ORGANISM: Homo sapiens

<400> SEQUENCE: 97

Gly Leu Trp Asp Ser Arg Met Glu Gly Leu
1               5                   10

<210> SEQ ID NO 98
<211> LENGTH: 10
<212> TYPE: PRT
<213> ORGANISM: Homo sapiens

<400> SEQUENCE: 98

Gly Leu Ala Glu Gly Pro Trp Pro Ala Ala
1               5                   10

<210> SEQ ID NO 99
<211> LENGTH: 10
<212> TYPE: PRT
<213> ORGANISM: Homo sapiens

<400> SEQUENCE: 99

Gly Met Phe Glu Ser Arg Trp Leu Asn Ile
1               5                   10

<210> SEQ ID NO 100
<211> LENGTH: 10
<212> TYPE: PRT
<213> ORGANISM: Homo sapiens

<400> SEQUENCE: 100

Gly Thr Met Asp Gly Arg Ile Leu Gln Val
1               5                   10

<210> SEQ ID NO 101
<211> LENGTH: 10
<212> TYPE: PRT
<213> ORGANISM: Homo sapiens

<400> SEQUENCE: 101

Gly Val Tyr Gln Gly Arg Val Ser Ala Val
1               5                   10

<210> SEQ ID NO 102
<211> LENGTH: 10
<212> TYPE: PRT
<213> ORGANISM: Homo sapiens

<400> SEQUENCE: 102

Gly Val Tyr Ala Gly Arg Pro Leu Ser Val
1               5                   10

<210> SEQ ID NO 103
<211> LENGTH: 10
<212> TYPE: PRT
```

<213> ORGANISM: Homo sapiens

<400> SEQUENCE: 103

Gly Val Ile Asp Gly His Ile Tyr Ala Val
1               5                   10

<210> SEQ ID NO 104
<211> LENGTH: 10
<212> TYPE: PRT
<213> ORGANISM: Homo sapiens

<400> SEQUENCE: 104

Gly Leu Tyr Asp Gly Met Glu His Leu Ile
1               5                   10

<210> SEQ ID NO 105
<211> LENGTH: 10
<212> TYPE: PRT
<213> ORGANISM: Homo sapiens

<400> SEQUENCE: 105

Gly Val Tyr Asp Gly Glu Glu His Ser Val
1               5                   10

<210> SEQ ID NO 106
<211> LENGTH: 10
<212> TYPE: PRT
<213> ORGANISM: Homo sapiens

<400> SEQUENCE: 106

Gly Ile Tyr Asp Gly Ile Leu His Ser Ile
1               5                   10

<210> SEQ ID NO 107
<211> LENGTH: 10
<212> TYPE: PRT
<213> ORGANISM: Homo sapiens

<400> SEQUENCE: 107

Gly Val Tyr Asp Val Arg Gln Ala Tyr Val
1               5                   10

<210> SEQ ID NO 108
<211> LENGTH: 10
<212> TYPE: PRT
<213> ORGANISM: Homo sapiens

<400> SEQUENCE: 108

Gly Thr Ile Asp Gly Leu Glu Pro Gly Leu
1               5                   10

<210> SEQ ID NO 109
<211> LENGTH: 10
<212> TYPE: PRT
<213> ORGANISM: Homo sapiens

<400> SEQUENCE: 109

Gly Leu Phe Glu Gly Asp Glu Tyr Ala Thr
1               5                   10

<210> SEQ ID NO 110
<211> LENGTH: 10
<212> TYPE: PRT
<213> ORGANISM: Homo sapiens

```
<400> SEQUENCE: 110

Gly Leu Leu Glu Gly Arg Glu Gly Ala Leu
1               5                   10

<210> SEQ ID NO 111
<211> LENGTH: 10
<212> TYPE: PRT
<213> ORGANISM: Homo sapiens

<400> SEQUENCE: 111

Gly Leu Ala Asp Gly Val Glu Asp Leu Leu
1               5                   10

<210> SEQ ID NO 112
<211> LENGTH: 10
<212> TYPE: PRT
<213> ORGANISM: Homo sapiens

<400> SEQUENCE: 112

Gly Leu Phe Asp Gly Ala Glu Val Val Leu
1               5                   10

<210> SEQ ID NO 113
<211> LENGTH: 10
<212> TYPE: PRT
<213> ORGANISM: Homo sapiens

<400> SEQUENCE: 113

Gly Leu Tyr Glu Gly Leu Asp Trp Leu Ser
1               5                   10

<210> SEQ ID NO 114
<211> LENGTH: 10
<212> TYPE: PRT
<213> ORGANISM: Homo sapiens

<400> SEQUENCE: 114

Gly Leu Tyr Glu Gly Leu Asp Trp Leu Ala
1               5                   10

<210> SEQ ID NO 115
<211> LENGTH: 10
<212> TYPE: PRT
<213> ORGANISM: Homo sapiens

<400> SEQUENCE: 115

Gly Ile Val Glu Gly Leu Met Thr Thr Val
1               5                   10

<210> SEQ ID NO 116
<211> LENGTH: 10
<212> TYPE: PRT
<213> ORGANISM: Homo sapiens

<400> SEQUENCE: 116

Ala Leu Ala Glu Gly Leu Asp Ile Lys Leu
1               5                   10

<210> SEQ ID NO 117
<211> LENGTH: 10
<212> TYPE: PRT
<213> ORGANISM: Homo sapiens

<400> SEQUENCE: 117
```

```
Gly Met Phe Glu Val Leu Glu Pro Leu His
1               5                   10
```

<210> SEQ ID NO 118
<211> LENGTH: 10
<212> TYPE: PRT
<213> ORGANISM: Homo sapiens

<400> SEQUENCE: 118

```
Gly Leu Ile Asp Ser Leu Met Ala Tyr Val
1               5                   10
```

<210> SEQ ID NO 119
<211> LENGTH: 10
<212> TYPE: PRT
<213> ORGANISM: Homo sapiens

<400> SEQUENCE: 119

```
Gly Val Leu Ala Gly Thr Met Ala Thr Val
1               5                   10
```

<210> SEQ ID NO 120
<211> LENGTH: 10
<212> TYPE: PRT
<213> ORGANISM: Homo sapiens

<400> SEQUENCE: 120

```
Gly Leu Asn Asp Gly Gln Trp His Ser Val
1               5                   10
```

<210> SEQ ID NO 121
<211> LENGTH: 10
<212> TYPE: PRT
<213> ORGANISM: Homo sapiens

<400> SEQUENCE: 121

```
Gly Leu Asn Asp Gly Gln Trp His Glu Val
1               5                   10
```

<210> SEQ ID NO 122
<211> LENGTH: 10
<212> TYPE: PRT
<213> ORGANISM: Homo sapiens

<400> SEQUENCE: 122

```
Gly Val Thr Phe Gly Gly Ile Pro Thr Val
1               5                   10
```

<210> SEQ ID NO 123
<211> LENGTH: 10
<212> TYPE: PRT
<213> ORGANISM: Homo sapiens

<400> SEQUENCE: 123

```
Gly Val Tyr Ala Gly Thr Ala Ile Leu Val
1               5                   10
```

<210> SEQ ID NO 124
<211> LENGTH: 10
<212> TYPE: PRT
<213> ORGANISM: Homo sapiens

<400> SEQUENCE: 124

```
Gly Ser Tyr Asp Gly Ala Tyr Ala Pro Val
1               5                   10
```

<210> SEQ ID NO 125
<211> LENGTH: 10
<212> TYPE: PRT
<213> ORGANISM: Homo sapiens

<400> SEQUENCE: 125

Gly Val Tyr Asn Asn Met Ser Ile Thr Val
1               5                   10

<210> SEQ ID NO 126
<211> LENGTH: 10
<212> TYPE: PRT
<213> ORGANISM: Homo sapiens

<400> SEQUENCE: 126

Gly Val Leu Pro Gly Glu Asp Trp Thr Val
1               5                   10

<210> SEQ ID NO 127
<211> LENGTH: 10
<212> TYPE: PRT
<213> ORGANISM: Homo sapiens

<400> SEQUENCE: 127

Gly Leu Tyr Cys Gly Arg Ala Lys Pro Val
1               5                   10

<210> SEQ ID NO 128
<211> LENGTH: 10
<212> TYPE: PRT
<213> ORGANISM: Homo sapiens

<400> SEQUENCE: 128

Gly Met Tyr Tyr Gly Arg Asp Val Asn Val
1               5                   10

<210> SEQ ID NO 129
<211> LENGTH: 10
<212> TYPE: PRT
<213> ORGANISM: Homo sapiens

<400> SEQUENCE: 129

Gly Leu Tyr Arg Gly Tyr Lys Ser Thr Val
1               5                   10

<210> SEQ ID NO 130
<211> LENGTH: 10
<212> TYPE: PRT
<213> ORGANISM: Homo sapiens

<400> SEQUENCE: 130

Gly Leu Tyr Lys Gly Gly Glu Glu Pro Val
1               5                   10

<210> SEQ ID NO 131
<211> LENGTH: 10
<212> TYPE: PRT
<213> ORGANISM: Homo sapiens

<400> SEQUENCE: 131

Gly Leu Val Asp Gly Gln Glu Leu Ala Val
1               5                   10

<210> SEQ ID NO 132
<211> LENGTH: 10
<212> TYPE: PRT
<213> ORGANISM: Homo sapiens

<400> SEQUENCE: 132

Gly Val Tyr Ser His Leu Glu Ala Phe Val
1               5                   10

<210> SEQ ID NO 133
<211> LENGTH: 10
<212> TYPE: PRT
<213> ORGANISM: Homo sapiens

<400> SEQUENCE: 133

Leu Leu Cys Asp Gly Ser Glu Asn Thr Val
1               5                   10

<210> SEQ ID NO 134
<211> LENGTH: 10
<212> TYPE: PRT
<213> ORGANISM: Homo sapiens

<400> SEQUENCE: 134

Ser Leu Tyr His Gly Arg Glu Asp Gly Val
1               5                   10

<210> SEQ ID NO 135
<211> LENGTH: 10
<212> TYPE: PRT
<213> ORGANISM: Homo sapiens

<400> SEQUENCE: 135

Gly Met Val Phe Gly Lys Glu Tyr Thr Val
1               5                   10

<210> SEQ ID NO 136
<211> LENGTH: 10
<212> TYPE: PRT
<213> ORGANISM: Homo sapiens

<400> SEQUENCE: 136

Leu Leu Glu Asp Gly Cys Glu Val Thr Val
1               5                   10

<210> SEQ ID NO 137
<211> LENGTH: 10
<212> TYPE: PRT
<213> ORGANISM: Homo sapiens

<400> SEQUENCE: 137

Gly Leu Cys Asp Ile Ser Glu Gly Thr Val
1               5                   10

<210> SEQ ID NO 138
<211> LENGTH: 10
<212> TYPE: PRT
<213> ORGANISM: Homo sapiens

<400> SEQUENCE: 138

Gly Gln Tyr Thr Gly His Glu Tyr His Val
1               5                   10

<210> SEQ ID NO 139
<211> LENGTH: 10

<212> TYPE: PRT
<213> ORGANISM: Homo sapiens

<400> SEQUENCE: 139

Gly Val Tyr Leu Tyr Gly Glu Leu Met Val
1               5                   10

<210> SEQ ID NO 140
<211> LENGTH: 10
<212> TYPE: PRT
<213> ORGANISM: Homo sapiens

<400> SEQUENCE: 140

Gly Val Arg Glu Gly Ile Glu Trp Met Val
1               5                   10

<210> SEQ ID NO 141
<211> LENGTH: 10
<212> TYPE: PRT
<213> ORGANISM: Homo sapiens

<400> SEQUENCE: 141

Gly Thr Phe Asp Gly Glu Glu Asn Ala Val
1               5                   10

<210> SEQ ID NO 142
<211> LENGTH: 10
<212> TYPE: PRT
<213> ORGANISM: Homo sapiens

<400> SEQUENCE: 142

Gly Val Ala Asp Gly Val Ile Lys Ser Val
1               5                   10

<210> SEQ ID NO 143
<211> LENGTH: 10
<212> TYPE: PRT
<213> ORGANISM: Homo sapiens

<400> SEQUENCE: 143

Gly Val Tyr Thr Gly Pro Glu Phe Tyr Thr
1               5                   10

<210> SEQ ID NO 144
<211> LENGTH: 10
<212> TYPE: PRT
<213> ORGANISM: Homo sapiens

<400> SEQUENCE: 144

Gly Ala Tyr Asp Thr Thr Thr Ala Thr Val
1               5                   10

<210> SEQ ID NO 145
<211> LENGTH: 10
<212> TYPE: PRT
<213> ORGANISM: Homo sapiens

<400> SEQUENCE: 145

Gly Val Ile Asn Gly Arg Lys Phe Gly Val
1               5                   10

<210> SEQ ID NO 146
<211> LENGTH: 10
<212> TYPE: PRT
<213> ORGANISM: Homo sapiens

<400> SEQUENCE: 146

Gly Val Ala Asp Pro Arg Ile Phe Leu Val
1               5                   10

<210> SEQ ID NO 147
<211> LENGTH: 10
<212> TYPE: PRT
<213> ORGANISM: Homo sapiens

<400> SEQUENCE: 147

Gly Val Ile Ser Gly Tyr Asn Ala Thr Val
1               5                   10

<210> SEQ ID NO 148
<211> LENGTH: 10
<212> TYPE: PRT
<213> ORGANISM: Homo sapiens

<400> SEQUENCE: 148

Gly Val Phe Lys Gly Tyr Asn Ala Thr Val
1               5                   10

<210> SEQ ID NO 149
<211> LENGTH: 10
<212> TYPE: PRT
<213> ORGANISM: Homo sapiens

<400> SEQUENCE: 149

Gly Phe Ala Asp Gly Ala Pro His Tyr Val
1               5                   10

<210> SEQ ID NO 150
<211> LENGTH: 10
<212> TYPE: PRT
<213> ORGANISM: Homo sapiens

<400> SEQUENCE: 150

Gly Val Ser Leu Asn Arg Ile Phe Thr Val
1               5                   10

<210> SEQ ID NO 151
<211> LENGTH: 10
<212> TYPE: PRT
<213> ORGANISM: Homo sapiens

<400> SEQUENCE: 151

Gly Gly Ser Asp Leu Arg Leu Trp Thr Val
1               5                   10

<210> SEQ ID NO 152
<211> LENGTH: 10
<212> TYPE: PRT
<213> ORGANISM: Homo sapiens

<400> SEQUENCE: 152

Gly Val Val Asp Val Pro Glu Phe Leu Val
1               5                   10

<210> SEQ ID NO 153
<211> LENGTH: 10
<212> TYPE: PRT
<213> ORGANISM: Homo sapiens

<400> SEQUENCE: 153

```
Gly Val Tyr Asp Ser Ser Gly Ile Arg Val
1               5                   10
```

<210> SEQ ID NO 154
<211> LENGTH: 10
<212> TYPE: PRT
<213> ORGANISM: Homo sapiens

<400> SEQUENCE: 154

```
Gly Val Tyr Arg Ile Ile Leu His Arg Val
1               5                   10
```

<210> SEQ ID NO 155
<211> LENGTH: 10
<212> TYPE: PRT
<213> ORGANISM: Homo sapiens

<400> SEQUENCE: 155

```
Gly Val Tyr Phe Gly Pro Ala Ala Ala Val
1               5                   10
```

<210> SEQ ID NO 156
<211> LENGTH: 10
<212> TYPE: PRT
<213> ORGANISM: Homo sapiens

<400> SEQUENCE: 156

```
Gly Gly Tyr Cys Gly Tyr Leu Ala Thr Val
1               5                   10
```

<210> SEQ ID NO 157
<211> LENGTH: 10
<212> TYPE: PRT
<213> ORGANISM: Homo sapiens

<400> SEQUENCE: 157

```
Gly Val Tyr Pro Trp Leu Arg His Asn Val
1               5                   10
```

<210> SEQ ID NO 158
<211> LENGTH: 10
<212> TYPE: PRT
<213> ORGANISM: Homo sapiens

<400> SEQUENCE: 158

```
Gly Met Tyr Ala Leu Arg Glu Arg Arg Val
1               5                   10
```

<210> SEQ ID NO 159
<211> LENGTH: 10
<212> TYPE: PRT
<213> ORGANISM: Homo sapiens

<400> SEQUENCE: 159

```
Gly Val Gly Asp Met Val Met Ala Thr Val
1               5                   10
```

<210> SEQ ID NO 160
<211> LENGTH: 10
<212> TYPE: PRT
<213> ORGANISM: Homo sapiens

<400> SEQUENCE: 160

```
Gly Val Lys Asp Pro Asn Leu Trp Thr Val
```

```
1               5                   10
```

<210> SEQ ID NO 161
<211> LENGTH: 10
<212> TYPE: PRT
<213> ORGANISM: Homo sapiens

<400> SEQUENCE: 161

```
Gly Glu Tyr Asp Phe Arg Tyr Ile Phe Val
1               5                   10
```

<210> SEQ ID NO 162
<211> LENGTH: 10
<212> TYPE: PRT
<213> ORGANISM: Homo sapiens

<400> SEQUENCE: 162

```
Gly Val Tyr Trp Ala Thr Gly Cys Thr Val
1               5                   10
```

<210> SEQ ID NO 163
<211> LENGTH: 10
<212> TYPE: PRT
<213> ORGANISM: Homo sapiens

<400> SEQUENCE: 163

```
Gly Val Leu Gly Gly Arg Val Cys Pro Val
1               5                   10
```

<210> SEQ ID NO 164
<211> LENGTH: 10
<212> TYPE: PRT
<213> ORGANISM: Homo sapiens

<400> SEQUENCE: 164

```
Gly Thr Tyr Gln Gly Leu Thr Ala Thr Val
1               5                   10
```

<210> SEQ ID NO 165
<211> LENGTH: 10
<212> TYPE: PRT
<213> ORGANISM: Homo sapiens

<400> SEQUENCE: 165

```
Gly Leu Gly Leu Gly Arg Glu Val Gly Val
1               5                   10
```

<210> SEQ ID NO 166
<211> LENGTH: 10
<212> TYPE: PRT
<213> ORGANISM: Homo sapiens

<400> SEQUENCE: 166

```
Gly Val Tyr Ser Gly Pro Ser Leu Leu Val
1               5                   10
```

<210> SEQ ID NO 167
<211> LENGTH: 10
<212> TYPE: PRT
<213> ORGANISM: Homo sapiens

<400> SEQUENCE: 167

```
Arg Leu Lys Asp Gly Glu Glu Thr Thr Val
1               5                   10
```

<210> SEQ ID NO 168
<211> LENGTH: 10
<212> TYPE: PRT
<213> ORGANISM: Homo sapiens

<400> SEQUENCE: 168

Ser Ile Val Asp Gly Met Glu Pro Thr Val
1               5                   10

<210> SEQ ID NO 169
<211> LENGTH: 10
<212> TYPE: PRT
<213> ORGANISM: Homo sapiens

<400> SEQUENCE: 169

Arg Val Tyr Glu Val Arg Glu Thr Ala Val
1               5                   10

<210> SEQ ID NO 170
<211> LENGTH: 10
<212> TYPE: PRT
<213> ORGANISM: Homo sapiens

<400> SEQUENCE: 170

Ser Val Ile Asp Gly Asp Glu Ala Gln Val
1               5                   10

<210> SEQ ID NO 171
<211> LENGTH: 10
<212> TYPE: PRT
<213> ORGANISM: Homo sapiens

<400> SEQUENCE: 171

Gly Ala Tyr Tyr Glu Pro Glu Gln Thr Val
1               5                   10

<210> SEQ ID NO 172
<211> LENGTH: 10
<212> TYPE: PRT
<213> ORGANISM: Homo sapiens

<400> SEQUENCE: 172

His Phe Tyr Asp Gly Ser Glu Ile Val Val
1               5                   10

<210> SEQ ID NO 173
<211> LENGTH: 10
<212> TYPE: PRT
<213> ORGANISM: Homo sapiens

<400> SEQUENCE: 173

Tyr Asn Tyr Leu Gly Pro Glu Asp Thr Val
1               5                   10

<210> SEQ ID NO 174
<211> LENGTH: 10
<212> TYPE: PRT
<213> ORGANISM: Homo sapiens

<400> SEQUENCE: 174

Val Tyr Ile Asp Pro Arg Glu His Tyr Val
1               5                   10

<210> SEQ ID NO 175

```
<211> LENGTH: 10
<212> TYPE: PRT
<213> ORGANISM: Homo sapiens

<400> SEQUENCE: 175

Gly Leu Gln Asp Gly Phe Gln Ile Thr Val
1               5                   10

<210> SEQ ID NO 176
<211> LENGTH: 10
<212> TYPE: PRT
<213> ORGANISM: Homo sapiens

<400> SEQUENCE: 176

Gly Leu Gln Asp Gly Leu Gln Ile Thr Val
1               5                   10

<210> SEQ ID NO 177
<211> LENGTH: 10
<212> TYPE: PRT
<213> ORGANISM: Homo sapiens

<400> SEQUENCE: 177

Gly Leu Ile Asp Gly Ala Glu Ser Tyr Val
1               5                   10

<210> SEQ ID NO 178
<211> LENGTH: 10
<212> TYPE: PRT
<213> ORGANISM: Homo sapiens

<400> SEQUENCE: 178

Gly Leu Tyr Gln Gly Tyr Gly Ser Thr Val
1               5                   10

<210> SEQ ID NO 179
<211> LENGTH: 10
<212> TYPE: PRT
<213> ORGANISM: Homo sapiens

<400> SEQUENCE: 179

Phe Leu Cys Asp Pro Arg Glu His Leu Val
1               5                   10

<210> SEQ ID NO 180
<211> LENGTH: 10
<212> TYPE: PRT
<213> ORGANISM: Homo sapiens

<400> SEQUENCE: 180

Gly Met Glu Asp Ser Arg Phe Gln Asn Val
1               5                   10

<210> SEQ ID NO 181
<211> LENGTH: 10
<212> TYPE: PRT
<213> ORGANISM: Homo sapiens

<400> SEQUENCE: 181

Gly Gln Phe Glu Gly Arg Ala Val Ala Val
1               5                   10

<210> SEQ ID NO 182
<211> LENGTH: 10
<212> TYPE: PRT
```

<210> SEQ ID NO 182 (implied continuation)

<213> ORGANISM: Homo sapiens

<400> SEQUENCE: 182

Gly Phe Phe Asp Ala Arg Ala Leu Ala Val
1               5                   10

<210> SEQ ID NO 183
<211> LENGTH: 10
<212> TYPE: PRT
<213> ORGANISM: Homo sapiens

<400> SEQUENCE: 183

Gly Leu Val Asp Gly Arg Asp Leu Val Ile
1               5                   10

<210> SEQ ID NO 184
<211> LENGTH: 10
<212> TYPE: PRT
<213> ORGANISM: Homo sapiens

<400> SEQUENCE: 184

Gly Phe Tyr Glu Ser Arg Gly Phe Cys Val
1               5                   10

<210> SEQ ID NO 185
<211> LENGTH: 10
<212> TYPE: PRT
<213> ORGANISM: Homo sapiens

<400> SEQUENCE: 185

Gly Leu Thr Asp Ser Arg Ala Leu Pro Leu
1               5                   10

<210> SEQ ID NO 186
<211> LENGTH: 10
<212> TYPE: PRT
<213> ORGANISM: Homo sapiens

<400> SEQUENCE: 186

Gly Leu Ala Glu Gly Arg Phe Pro Pro Thr
1               5                   10

<210> SEQ ID NO 187
<211> LENGTH: 10
<212> TYPE: PRT
<213> ORGANISM: Homo sapiens

<400> SEQUENCE: 187

Gly Thr Val Asp Ala Pro Asn Phe Ile Val
1               5                   10

<210> SEQ ID NO 188
<211> LENGTH: 10
<212> TYPE: PRT
<213> ORGANISM: Homo sapiens

<400> SEQUENCE: 188

Gly Ala Phe Glu Gly Pro Arg Cys Glu Val
1               5                   10

<210> SEQ ID NO 189
<211> LENGTH: 10
<212> TYPE: PRT
<213> ORGANISM: Homo sapiens

<400> SEQUENCE: 189

Gly Val Ala Glu Ser Pro Leu Pro Ala Val
1               5                   10

<210> SEQ ID NO 190
<211> LENGTH: 10
<212> TYPE: PRT
<213> ORGANISM: Homo sapiens

<400> SEQUENCE: 190

Gly Ala Trp Glu Ala Pro Trp Cys Thr Val
1               5                   10

<210> SEQ ID NO 191
<211> LENGTH: 10
<212> TYPE: PRT
<213> ORGANISM: Homo sapiens

<400> SEQUENCE: 191

Gly Leu Ile Glu Ala Pro Glu His Ala Ala
1               5                   10

<210> SEQ ID NO 192
<211> LENGTH: 10
<212> TYPE: PRT
<213> ORGANISM: Homo sapiens

<400> SEQUENCE: 192

Gly Leu Thr Asp Gly Pro Ala Arg Leu Leu
1               5                   10

<210> SEQ ID NO 193
<211> LENGTH: 10
<212> TYPE: PRT
<213> ORGANISM: Homo sapiens

<400> SEQUENCE: 193

Gly Leu Ala Asp Ser Arg Asp Ile Ser Leu
1               5                   10

<210> SEQ ID NO 194
<211> LENGTH: 10
<212> TYPE: PRT
<213> ORGANISM: Homo sapiens

<400> SEQUENCE: 194

Gly Leu Ile Glu Gly Arg Ser Tyr Ile Phe
1               5                   10

<210> SEQ ID NO 195
<211> LENGTH: 10
<212> TYPE: PRT
<213> ORGANISM: Homo sapiens

<400> SEQUENCE: 195

Gly Leu Phe Glu Gly Arg Ser Tyr Ile Phe
1               5                   10

<210> SEQ ID NO 196
<211> LENGTH: 10
<212> TYPE: PRT
<213> ORGANISM: Homo sapiens

<400> SEQUENCE: 196

Gly Leu Ala Asp Gly Pro Pro Ser Ser Leu
1               5                   10

<210> SEQ ID NO 197
<211> LENGTH: 10
<212> TYPE: PRT
<213> ORGANISM: Homo sapiens

<400> SEQUENCE: 197

Gly Leu Val Asp Ser Arg Leu Ala Leu Thr
1               5                   10

<210> SEQ ID NO 198
<211> LENGTH: 10
<212> TYPE: PRT
<213> ORGANISM: Homo sapiens

<400> SEQUENCE: 198

Gly Met Glu Asp Ser Pro Asp Leu Leu Ala
1               5                   10

<210> SEQ ID NO 199
<211> LENGTH: 10
<212> TYPE: PRT
<213> ORGANISM: Homo sapiens

<400> SEQUENCE: 199

Gly Leu Trp Asp Ser Pro Arg Ser His Ala
1               5                   10

<210> SEQ ID NO 200
<211> LENGTH: 10
<212> TYPE: PRT
<213> ORGANISM: Homo sapiens

<400> SEQUENCE: 200

Gly Ile Ala Asp Ala Pro Leu Ser Pro Leu
1               5                   10

<210> SEQ ID NO 201
<211> LENGTH: 10
<212> TYPE: PRT
<213> ORGANISM: Homo sapiens

<400> SEQUENCE: 201

Gly Leu Val Glu Ser Arg Tyr Trp Ser Ala
1               5                   10

<210> SEQ ID NO 202
<211> LENGTH: 10
<212> TYPE: PRT
<213> ORGANISM: Homo sapiens

<400> SEQUENCE: 202

Gly Leu Glu Asp Ala Pro Pro Val Glu Leu
1               5                   10

<210> SEQ ID NO 203
<211> LENGTH: 10
<212> TYPE: PRT
<213> ORGANISM: Homo sapiens

<400> SEQUENCE: 203

Gly Leu Glu Glu Gly Pro Ala Pro Val Leu
1               5                   10

<210> SEQ ID NO 204
<211> LENGTH: 10
<212> TYPE: PRT
<213> ORGANISM: Homo sapiens

<400> SEQUENCE: 204

Gly Ser Tyr Glu Ala Pro Leu Pro Pro Gly
1               5                   10

<210> SEQ ID NO 205
<211> LENGTH: 10
<212> TYPE: PRT
<213> ORGANISM: Homo sapiens

<400> SEQUENCE: 205

Gly Leu Trp Glu Ala Arg Arg Glu Ala Leu
1               5                   10

<210> SEQ ID NO 206
<211> LENGTH: 10
<212> TYPE: PRT
<213> ORGANISM: Homo sapiens

<400> SEQUENCE: 206

Gly Leu Ala Glu Gly Pro Leu Cys Leu Asp
1               5                   10

<210> SEQ ID NO 207
<211> LENGTH: 10
<212> TYPE: PRT
<213> ORGANISM: Homo sapiens

<400> SEQUENCE: 207

Gly Thr Cys Glu Ala Pro Val Ala Val Val
1               5                   10

<210> SEQ ID NO 208
<211> LENGTH: 10
<212> TYPE: PRT
<213> ORGANISM: Homo sapiens

<400> SEQUENCE: 208

Gly Leu Glu Asp Ala Pro Gly Cys Phe Leu
1               5                   10

<210> SEQ ID NO 209
<211> LENGTH: 10
<212> TYPE: PRT
<213> ORGANISM: Homo sapiens

<400> SEQUENCE: 209

Gly Leu Trp Glu Ala Arg Pro Arg Val Leu
1               5                   10

<210> SEQ ID NO 210
<211> LENGTH: 10
<212> TYPE: PRT
<213> ORGANISM: Homo sapiens

<400> SEQUENCE: 210

Gly Leu Val Glu Ala Arg Asn Phe Pro Ala
1               5                   10

```
<210> SEQ ID NO 211
<211> LENGTH: 10
<212> TYPE: PRT
<213> ORGANISM: Homo sapiens

<400> SEQUENCE: 211

Gly Leu Glu Glu Ser Pro Pro Asn Glu Leu
1               5                   10

<210> SEQ ID NO 212
<211> LENGTH: 10
<212> TYPE: PRT
<213> ORGANISM: Homo sapiens

<400> SEQUENCE: 212

Gly Met Lys Glu Ser Pro Val Ile Pro Leu
1               5                   10

<210> SEQ ID NO 213
<211> LENGTH: 10
<212> TYPE: PRT
<213> ORGANISM: Homo sapiens

<400> SEQUENCE: 213

Gly Leu Trp Glu Ala Pro Arg Gln Gly Gly
1               5                   10

<210> SEQ ID NO 214
<211> LENGTH: 10
<212> TYPE: PRT
<213> ORGANISM: Homo sapiens

<400> SEQUENCE: 214

Gly Val Ser Asp Gly Arg Trp His Ser Val
1               5                   10

<210> SEQ ID NO 215
<211> LENGTH: 10
<212> TYPE: PRT
<213> ORGANISM: Homo sapiens

<400> SEQUENCE: 215

Arg Val Tyr Asp Gly Arg Glu Ile Leu Thr
1               5                   10

<210> SEQ ID NO 216
<211> LENGTH: 10
<212> TYPE: PRT
<213> ORGANISM: Homo sapiens

<400> SEQUENCE: 216

Gly Val Leu Asp Gly Arg Phe His Tyr Gly
1               5                   10

<210> SEQ ID NO 217
<211> LENGTH: 10
<212> TYPE: PRT
<213> ORGANISM: Homo sapiens

<400> SEQUENCE: 217

Ala Val Leu Asp Gly Arg Glu Leu Arg Val
1               5                   10

<210> SEQ ID NO 218
<211> LENGTH: 10
```

```
<212> TYPE: PRT
<213> ORGANISM: Homo sapiens

<400> SEQUENCE: 218

Gln Val Ile Asp Gly Arg Asn Val Thr Val
1               5                   10

<210> SEQ ID NO 219
<211> LENGTH: 10
<212> TYPE: PRT
<213> ORGANISM: Homo sapiens

<400> SEQUENCE: 219

Arg Ser Phe Asp Gly Arg Glu Leu Leu Val
1               5                   10

<210> SEQ ID NO 220
<211> LENGTH: 10
<212> TYPE: PRT
<213> ORGANISM: Homo sapiens

<400> SEQUENCE: 220

Ala Leu Leu Asp Gly Arg Asp Cys Thr Val
1               5                   10

<210> SEQ ID NO 221
<211> LENGTH: 10
<212> TYPE: PRT
<213> ORGANISM: Homo sapiens

<400> SEQUENCE: 221

Ala Val Ser Asp Gly Arg His Met Phe Val
1               5                   10

<210> SEQ ID NO 222
<211> LENGTH: 10
<212> TYPE: PRT
<213> ORGANISM: Homo sapiens

<400> SEQUENCE: 222

Pro Leu Arg Asp Gly Arg Val Phe Thr Val
1               5                   10

<210> SEQ ID NO 223
<211> LENGTH: 10
<212> TYPE: PRT
<213> ORGANISM: Homo sapiens

<400> SEQUENCE: 223

Arg Leu Asp Asp Gly Arg Trp His Gln Val
1               5                   10

<210> SEQ ID NO 224
<211> LENGTH: 10
<212> TYPE: PRT
<213> ORGANISM: Homo sapiens

<400> SEQUENCE: 224

Gly Val Met Leu Gly Ile Trp His Thr Val
1               5                   10

<210> SEQ ID NO 225
<211> LENGTH: 10
<212> TYPE: PRT
<213> ORGANISM: Homo sapiens
```

```
<400> SEQUENCE: 225

Gly Val Tyr Ser Phe Arg Phe His Val Val
1               5                   10

<210> SEQ ID NO 226
<211> LENGTH: 10
<212> TYPE: PRT
<213> ORGANISM: Homo sapiens

<400> SEQUENCE: 226

Gly Val Ser Asp Gly Gln Trp His Thr Val
1               5                   10

<210> SEQ ID NO 227
<211> LENGTH: 10
<212> TYPE: PRT
<213> ORGANISM: Homo sapiens

<400> SEQUENCE: 227

Gly Leu Ser Asp Gly Gln Trp His Thr Val
1               5                   10

<210> SEQ ID NO 228
<211> LENGTH: 10
<212> TYPE: PRT
<213> ORGANISM: Homo sapiens

<400> SEQUENCE: 228

Gly Val Tyr Gly Gly Ser Val His Glu Ala
1               5                   10

<210> SEQ ID NO 229
<211> LENGTH: 10
<212> TYPE: PRT
<213> ORGANISM: Homo sapiens

<400> SEQUENCE: 229

Gly Val Tyr Tyr Glu Pro Glu Gln Thr Val
1               5                   10

<210> SEQ ID NO 230
<211> LENGTH: 10
<212> TYPE: PRT
<213> ORGANISM: Homo sapiens

<400> SEQUENCE: 230

Gly Val Ala Ala Gly Arg Phe His Thr Val
1               5                   10

<210> SEQ ID NO 231
<211> LENGTH: 10
<212> TYPE: PRT
<213> ORGANISM: Homo sapiens

<400> SEQUENCE: 231

Gly Val Pro Asp Cys Arg Ile Phe Thr Val
1               5                   10

<210> SEQ ID NO 232
<211> LENGTH: 10
<212> TYPE: PRT
<213> ORGANISM: Homo sapiens

<400> SEQUENCE: 232
```

Gly Val Phe Asp Asn Cys Ser His Thr Val
1               5                   10

<210> SEQ ID NO 233
<211> LENGTH: 10
<212> TYPE: PRT
<213> ORGANISM: Homo sapiens

<400> SEQUENCE: 233

Gly Val Ser Asp Gly Gln Leu Lys Thr Val
1               5                   10

<210> SEQ ID NO 234
<211> LENGTH: 10
<212> TYPE: PRT
<213> ORGANISM: Homo sapiens

<400> SEQUENCE: 234

Thr Val Tyr Asp Leu Arg Glu Gln Ser Val
1               5                   10

<210> SEQ ID NO 235
<211> LENGTH: 10
<212> TYPE: PRT
<213> ORGANISM: Homo sapiens

<400> SEQUENCE: 235

Lys Val Cys Asp Gly Gln Glu His Val Val
1               5                   10

<210> SEQ ID NO 236
<211> LENGTH: 10
<212> TYPE: PRT
<213> ORGANISM: Homo sapiens

<400> SEQUENCE: 236

Ala Ser Tyr Asp Gly Thr Glu Val Thr Val
1               5                   10

<210> SEQ ID NO 237
<211> LENGTH: 10
<212> TYPE: PRT
<213> ORGANISM: Homo sapiens

<400> SEQUENCE: 237

Ile Val Val Glu Gly Arg Glu Phe Glu Val
1               5                   10

<210> SEQ ID NO 238
<211> LENGTH: 10
<212> TYPE: PRT
<213> ORGANISM: Homo sapiens

<400> SEQUENCE: 238

Val Ala Tyr Asp Gly Val Glu Ile Thr Val
1               5                   10

<210> SEQ ID NO 239
<211> LENGTH: 10
<212> TYPE: PRT
<213> ORGANISM: Homo sapiens

<400> SEQUENCE: 239

Ser Val Tyr Asp Ala Arg Glu Phe Ser Val

-continued

```
1               5                   10

<210> SEQ ID NO 240
<211> LENGTH: 10
<212> TYPE: PRT
<213> ORGANISM: Homo sapiens

<400> SEQUENCE: 240

Gly Met Ala Arg Gly Arg Glu Pro Gly Gly
1               5                   10

<210> SEQ ID NO 241
<211> LENGTH: 10
<212> TYPE: PRT
<213> ORGANISM: Homo sapiens

<400> SEQUENCE: 241

Gly Leu Tyr Asp Gly Leu Asp Trp Leu Ser
1               5                   10

<210> SEQ ID NO 242
<211> LENGTH: 10
<212> TYPE: PRT
<213> ORGANISM: Homo sapiens

<400> SEQUENCE: 242

Ala Leu Ala Glu Gly Arg Glu Trp Ser Leu
1               5                   10

<210> SEQ ID NO 243
<211> LENGTH: 10
<212> TYPE: PRT
<213> ORGANISM: Homo sapiens

<400> SEQUENCE: 243

Arg Ser Phe Glu Gly Arg Glu Leu Leu Val
1               5                   10

<210> SEQ ID NO 244
<211> LENGTH: 10
<212> TYPE: PRT
<213> ORGANISM: Homo sapiens

<400> SEQUENCE: 244

Gly Met Phe Asp Gly Gly Glu Ser Ser Pro
1               5                   10

<210> SEQ ID NO 245
<211> LENGTH: 10
<212> TYPE: PRT
<213> ORGANISM: Homo sapiens

<400> SEQUENCE: 245

Gly Leu Glu Pro Gly Arg Asp Tyr Glu Val
1               5                   10

<210> SEQ ID NO 246
<211> LENGTH: 10
<212> TYPE: PRT
<213> ORGANISM: Homo sapiens

<400> SEQUENCE: 246

Leu Leu Lys Asp Gly Pro Glu Ile Gly Leu
1               5                   10
```

<210> SEQ ID NO 247
<211> LENGTH: 10
<212> TYPE: PRT
<213> ORGANISM: Homo sapiens

<400> SEQUENCE: 247

Phe Met Phe Glu Gly Arg Glu Ile Lys Leu
1               5                   10

<210> SEQ ID NO 248
<211> LENGTH: 10
<212> TYPE: PRT
<213> ORGANISM: Homo sapiens

<400> SEQUENCE: 248

Gly Met Phe Asp Asn Arg Asp Val Ala Val
1               5                   10

<210> SEQ ID NO 249
<211> LENGTH: 10
<212> TYPE: PRT
<213> ORGANISM: Homo sapiens

<400> SEQUENCE: 249

Phe Ser Val Glu Gly Arg Glu Ile Pro Val
1               5                   10

<210> SEQ ID NO 250
<211> LENGTH: 10
<212> TYPE: PRT
<213> ORGANISM: Homo sapiens

<400> SEQUENCE: 250

Gly Thr Ile Asp Phe Arg Glu Phe Ile Ile
1               5                   10

<210> SEQ ID NO 251
<211> LENGTH: 10
<212> TYPE: PRT
<213> ORGANISM: Homo sapiens

<400> SEQUENCE: 251

Gly Leu Val Asp Phe Arg Asp Val Ala Leu
1               5                   10

<210> SEQ ID NO 252
<211> LENGTH: 10
<212> TYPE: PRT
<213> ORGANISM: Homo sapiens

<400> SEQUENCE: 252

Gly Leu Thr Glu Leu Arg Glu Leu Ser Leu
1               5                   10

<210> SEQ ID NO 253
<211> LENGTH: 10
<212> TYPE: PRT
<213> ORGANISM: Homo sapiens

<400> SEQUENCE: 253

Gly Leu Ser Glu Gly Pro Glu Pro Ser Ile
1               5                   10

<210> SEQ ID NO 254

```
<211> LENGTH: 10
<212> TYPE: PRT
<213> ORGANISM: Homo sapiens

<400> SEQUENCE: 254

Cys Leu Ala Asp Gly Arg Glu Pro Gly Gly
1               5                   10

<210> SEQ ID NO 255
<211> LENGTH: 10
<212> TYPE: PRT
<213> ORGANISM: Homo sapiens

<400> SEQUENCE: 255

Phe Ser Phe Asp Gly Pro Glu Ile Met Gly
1               5                   10

<210> SEQ ID NO 256
<211> LENGTH: 10
<212> TYPE: PRT
<213> ORGANISM: Homo sapiens

<400> SEQUENCE: 256

Arg Leu Ile Asp Gly Arg Glu Ala Val Thr
1               5                   10

<210> SEQ ID NO 257
<211> LENGTH: 10
<212> TYPE: PRT
<213> ORGANISM: Homo sapiens

<400> SEQUENCE: 257

Gly Ser Ile Asp Phe Arg Glu Tyr Val Ile
1               5                   10

<210> SEQ ID NO 258
<211> LENGTH: 10
<212> TYPE: PRT
<213> ORGANISM: Homo sapiens

<400> SEQUENCE: 258

Pro Met Ala Asp Gly Arg Glu Phe Asn Leu
1               5                   10

<210> SEQ ID NO 259
<211> LENGTH: 10
<212> TYPE: PRT
<213> ORGANISM: Homo sapiens

<400> SEQUENCE: 259

Ala Met Tyr Asp Ala Arg Glu Ala Ile Ile
1               5                   10

<210> SEQ ID NO 260
<211> LENGTH: 10
<212> TYPE: PRT
<213> ORGANISM: Homo sapiens

<400> SEQUENCE: 260

Ser Leu Ala Asp Gly Arg Asp Arg Pro Leu
1               5                   10

<210> SEQ ID NO 261
<211> LENGTH: 10
<212> TYPE: PRT
```

<213> ORGANISM: Homo sapiens

<400> SEQUENCE: 261

Gly Leu Val Glu Gly Leu Glu Tyr Ser Phe
1               5                   10

<210> SEQ ID NO 262
<211> LENGTH: 10
<212> TYPE: PRT
<213> ORGANISM: Homo sapiens

<400> SEQUENCE: 262

Gly Leu Thr Glu Gly Leu Glu Tyr Glu Phe
1               5                   10

<210> SEQ ID NO 263
<211> LENGTH: 10
<212> TYPE: PRT
<213> ORGANISM: Homo sapiens

<400> SEQUENCE: 263

Gly Ser Phe Glu Gly Leu Glu Ser Leu Val
1               5                   10

<210> SEQ ID NO 264
<211> LENGTH: 10
<212> TYPE: PRT
<213> ORGANISM: Homo sapiens

<400> SEQUENCE: 264

Gly Leu Ala Asp Gly Ala Asp Leu Leu Gly
1               5                   10

<210> SEQ ID NO 265
<211> LENGTH: 10
<212> TYPE: PRT
<213> ORGANISM: Homo sapiens

<400> SEQUENCE: 265

Ile Leu Val Glu Gly Arg Glu Phe Pro Thr
1               5                   10

<210> SEQ ID NO 266
<211> LENGTH: 10
<212> TYPE: PRT
<213> ORGANISM: Homo sapiens

<400> SEQUENCE: 266

Ile Met Phe Asp Gly Pro Glu Ala Trp Gly
1               5                   10

<210> SEQ ID NO 267
<211> LENGTH: 10
<212> TYPE: PRT
<213> ORGANISM: Homo sapiens

<400> SEQUENCE: 267

Gly Met Val Val Gly Arg Glu Leu Leu Ala
1               5                   10

<210> SEQ ID NO 268
<211> LENGTH: 10
<212> TYPE: PRT
<213> ORGANISM: Homo sapiens

```
<400> SEQUENCE: 268

Gly Ser Thr Asp Ile Pro Asp Trp Cys Val
1               5                   10

<210> SEQ ID NO 269
<211> LENGTH: 10
<212> TYPE: PRT
<213> ORGANISM: Homo sapiens

<400> SEQUENCE: 269

Ala Val Phe Asp Ser Leu Glu Gly Phe Val
1               5                   10

<210> SEQ ID NO 270
<211> LENGTH: 10
<212> TYPE: PRT
<213> ORGANISM: Homo sapiens

<400> SEQUENCE: 270

Ala Leu Ile Glu Val Pro Asp Gly Phe Thr
1               5                   10

<210> SEQ ID NO 271
<211> LENGTH: 10
<212> TYPE: PRT
<213> ORGANISM: Homo sapiens

<400> SEQUENCE: 271

Ala Leu Tyr Asp His Leu Met Asp Phe Leu
1               5                   10

<210> SEQ ID NO 272
<211> LENGTH: 10
<212> TYPE: PRT
<213> ORGANISM: Homo sapiens

<400> SEQUENCE: 272

Ala Met Val Asp Ala Leu Met Met Ala Tyr
1               5                   10

<210> SEQ ID NO 273
<211> LENGTH: 10
<212> TYPE: PRT
<213> ORGANISM: Homo sapiens

<400> SEQUENCE: 273

Ala Leu Val Glu Ser Pro Glu Ser Met Ile
1               5                   10

<210> SEQ ID NO 274
<211> LENGTH: 10
<212> TYPE: PRT
<213> ORGANISM: Homo sapiens

<400> SEQUENCE: 274

Ala Met Glu Asp Ala Leu Asp Glu Leu Ile
1               5                   10

<210> SEQ ID NO 275
<211> LENGTH: 10
<212> TYPE: PRT
<213> ORGANISM: Homo sapiens

<400> SEQUENCE: 275
```

Gly Leu Thr Asp Ser Leu Asp Tyr Pro Gly
1               5                   10

<210> SEQ ID NO 276
<211> LENGTH: 10
<212> TYPE: PRT
<213> ORGANISM: Homo sapiens

<400> SEQUENCE: 276

Ala Gln Ile Glu Gly Leu Met Asp Asp Val
1               5                   10

<210> SEQ ID NO 277
<211> LENGTH: 10
<212> TYPE: PRT
<213> ORGANISM: Homo sapiens

<400> SEQUENCE: 277

Gly Leu Phe Glu Val Leu Asp Leu Tyr Pro
1               5                   10

<210> SEQ ID NO 278
<211> LENGTH: 10
<212> TYPE: PRT
<213> ORGANISM: Homo sapiens

<400> SEQUENCE: 278

Ala Leu Val Asp Val Leu Glu Asp Lys Leu
1               5                   10

<210> SEQ ID NO 279
<211> LENGTH: 10
<212> TYPE: PRT
<213> ORGANISM: Homo sapiens

<400> SEQUENCE: 279

Gly Met Thr Asp Ile Pro Asp Phe Leu Trp
1               5                   10

<210> SEQ ID NO 280
<211> LENGTH: 10
<212> TYPE: PRT
<213> ORGANISM: Homo sapiens

<400> SEQUENCE: 280

Gly Leu Val Glu His Leu Glu Leu Leu Gln
1               5                   10

<210> SEQ ID NO 281
<211> LENGTH: 10
<212> TYPE: PRT
<213> ORGANISM: Homo sapiens

<400> SEQUENCE: 281

Ala Met Ala Asp Ile Leu Asp Ile Trp Ala
1               5                   10

<210> SEQ ID NO 282
<211> LENGTH: 10
<212> TYPE: PRT
<213> ORGANISM: Homo sapiens

<400> SEQUENCE: 282

Ala Leu Ala Glu Gly Leu Glu Pro Leu Ser
1               5                   10

<210> SEQ ID NO 283
<211> LENGTH: 10
<212> TYPE: PRT
<213> ORGANISM: Homo sapiens

<400> SEQUENCE: 283

Ala Ile Thr Asp Gly Leu Glu Ile Val Val
1               5                   10

<210> SEQ ID NO 284
<211> LENGTH: 10
<212> TYPE: PRT
<213> ORGANISM: Homo sapiens

<400> SEQUENCE: 284

Ala Gln Val Glu Ser Leu Glu Arg Glu Val
1               5                   10

<210> SEQ ID NO 285
<211> LENGTH: 10
<212> TYPE: PRT
<213> ORGANISM: Homo sapiens

<400> SEQUENCE: 285

Ala Val His Asp Val Leu Asp Leu Tyr Leu
1               5                   10

<210> SEQ ID NO 286
<211> LENGTH: 10
<212> TYPE: PRT
<213> ORGANISM: Homo sapiens

<400> SEQUENCE: 286

Ala Leu Val Glu Ile Leu Asp Val Ile Val
1               5                   10

<210> SEQ ID NO 287
<211> LENGTH: 10
<212> TYPE: PRT
<213> ORGANISM: Homo sapiens

<400> SEQUENCE: 287

Ala Ala Phe Glu Ala Leu Met Asn Gly Val
1               5                   10

<210> SEQ ID NO 288
<211> LENGTH: 10
<212> TYPE: PRT
<213> ORGANISM: Homo sapiens

<400> SEQUENCE: 288

Ala Ala Phe Glu Ala Leu Met Asp Gly Val
1               5                   10

<210> SEQ ID NO 289
<211> LENGTH: 10
<212> TYPE: PRT
<213> ORGANISM: Homo sapiens

<400> SEQUENCE: 289

Gly Leu Val Glu Gly Leu Asp Tyr Gln Phe
1               5                   10

```
<210> SEQ ID NO 290
<211> LENGTH: 10
<212> TYPE: PRT
<213> ORGANISM: Homo sapiens

<400> SEQUENCE: 290

Gly Leu Ala Asp Val Leu Glu Glu Pro Gly
1               5                   10

<210> SEQ ID NO 291
<211> LENGTH: 10
<212> TYPE: PRT
<213> ORGANISM: Homo sapiens

<400> SEQUENCE: 291

Gly Leu Tyr Asp Gly Arg Glu His Ser Val
1               5                   10

<210> SEQ ID NO 292
<211> LENGTH: 10
<212> TYPE: PRT
<213> ORGANISM: Homo sapiens

<400> SEQUENCE: 292

Gly Ile Thr Asp Ala Pro Ser Cys Ala Val
1               5                   10

<210> SEQ ID NO 293
<211> LENGTH: 10
<212> TYPE: PRT
<213> ORGANISM: Homo sapiens

<400> SEQUENCE: 293

Gly Leu His Glu Ala Arg Leu Trp Cys Glu
1               5                   10

<210> SEQ ID NO 294
<211> LENGTH: 10
<212> TYPE: PRT
<213> ORGANISM: Homo sapiens

<400> SEQUENCE: 294

Gly Val Ile Glu Ser Pro Leu Met Tyr Glu
1               5                   10

<210> SEQ ID NO 295
<211> LENGTH: 10
<212> TYPE: PRT
<213> ORGANISM: Homo sapiens

<400> SEQUENCE: 295

Gly Val Tyr Ala Gly Arg Glu His Phe Leu
1               5                   10

<210> SEQ ID NO 296
<211> LENGTH: 10
<212> TYPE: PRT
<213> ORGANISM: Homo sapiens

<400> SEQUENCE: 296

Gly Ala Tyr Asp Gly Glu Glu His Leu Ile
1               5                   10

<210> SEQ ID NO 297
<211> LENGTH: 10
```

```
<212> TYPE: PRT
<213> ORGANISM: Homo sapiens

<400> SEQUENCE: 297

Gly Leu Tyr Asp Gly Ile Glu His Phe Met
1               5                   10

<210> SEQ ID NO 298
<211> LENGTH: 10
<212> TYPE: PRT
<213> ORGANISM: Homo sapiens

<400> SEQUENCE: 298

Gly Val Tyr Ala Gly Arg Glu His Phe Val
1               5                   10

<210> SEQ ID NO 299
<211> LENGTH: 10
<212> TYPE: PRT
<213> ORGANISM: Homo sapiens

<400> SEQUENCE: 299

Gly Leu Val Cys Gly Pro Glu Pro Leu Val
1               5                   10

<210> SEQ ID NO 300
<211> LENGTH: 10
<212> TYPE: PRT
<213> ORGANISM: Homo sapiens

<400> SEQUENCE: 300

Ser Leu Lys Glu Gly Arg Glu Ile Gly Val
1               5                   10

<210> SEQ ID NO 301
<211> LENGTH: 10
<212> TYPE: PRT
<213> ORGANISM: Homo sapiens

<400> SEQUENCE: 301

Gly Leu Thr Asp Val Pro Glu Leu Gln Val
1               5                   10

<210> SEQ ID NO 302
<211> LENGTH: 10
<212> TYPE: PRT
<213> ORGANISM: Homo sapiens

<400> SEQUENCE: 302

Gly Leu Thr Asp Asp Pro Glu Leu Gln Ile
1               5                   10

<210> SEQ ID NO 303
<211> LENGTH: 10
<212> TYPE: PRT
<213> ORGANISM: Homo sapiens

<400> SEQUENCE: 303

Ala Leu Ala Asp Gly Leu Met Glu Leu Ser
1               5                   10

<210> SEQ ID NO 304
<211> LENGTH: 10
<212> TYPE: PRT
<213> ORGANISM: Homo sapiens
```

-continued

```
<400> SEQUENCE: 304

Ala Leu Glu Asp Val Leu Asp Gln Pro Leu
1               5                   10

<210> SEQ ID NO 305
<211> LENGTH: 10
<212> TYPE: PRT
<213> ORGANISM: Homo sapiens

<400> SEQUENCE: 305

Ala Leu Val Asp Val Leu Asp Gln Pro Leu
1               5                   10

<210> SEQ ID NO 306
<211> LENGTH: 10
<212> TYPE: PRT
<213> ORGANISM: Homo sapiens

<400> SEQUENCE: 306

Gly Ser Gly Asp Gly Arg Ile Val Ile Val
1               5                   10

<210> SEQ ID NO 307
<211> LENGTH: 10
<212> TYPE: PRT
<213> ORGANISM: Homo sapiens

<400> SEQUENCE: 307

Asp Val Ile Asp Gly Ser Asp His Gly Val
1               5                   10

<210> SEQ ID NO 308
<211> LENGTH: 10
<212> TYPE: PRT
<213> ORGANISM: Homo sapiens

<400> SEQUENCE: 308

Gly Leu Tyr Asp Gly Pro Arg Phe Glu Ser
1               5                   10

<210> SEQ ID NO 309
<211> LENGTH: 10
<212> TYPE: PRT
<213> ORGANISM: Homo sapiens

<400> SEQUENCE: 309

Gly Leu Trp Glu Ser Arg Pro His Thr Leu
1               5                   10

<210> SEQ ID NO 310
<211> LENGTH: 10
<212> TYPE: PRT
<213> ORGANISM: Homo sapiens

<400> SEQUENCE: 310

Gly Met Phe Glu Gly Arg Leu Phe Phe Ser
1               5                   10

<210> SEQ ID NO 311
<211> LENGTH: 10
<212> TYPE: PRT
<213> ORGANISM: Homo sapiens

<400> SEQUENCE: 311
```

Gly Met Phe Glu Gly Arg Phe Phe Ser
1               5                   10

<210> SEQ ID NO 312
<211> LENGTH: 10
<212> TYPE: PRT
<213> ORGANISM: Homo sapiens

<400> SEQUENCE: 312

Gly Glu Tyr Leu Gly Thr Glu His Pro Val
1               5                   10

<210> SEQ ID NO 313
<211> LENGTH: 10
<212> TYPE: PRT
<213> ORGANISM: Homo sapiens

<400> SEQUENCE: 313

Gly Thr Arg Asp Gly Ile Glu Phe Thr Val
1               5                   10

<210> SEQ ID NO 314
<211> LENGTH: 10
<212> TYPE: PRT
<213> ORGANISM: Homo sapiens

<400> SEQUENCE: 314

Ile Met Lys Asp Gly Arg Glu Ile Val Val
1               5                   10

<210> SEQ ID NO 315
<211> LENGTH: 10
<212> TYPE: PRT
<213> ORGANISM: Homo sapiens

<400> SEQUENCE: 315

Gly Val Tyr Leu Leu Arg Asp His Val Val
1               5                   10

<210> SEQ ID NO 316
<211> LENGTH: 10
<212> TYPE: PRT
<213> ORGANISM: Homo sapiens

<400> SEQUENCE: 316

Gly Val Met Val Gly Arg Glu His Glu Ile
1               5                   10

<210> SEQ ID NO 317
<211> LENGTH: 10
<212> TYPE: PRT
<213> ORGANISM: Homo sapiens

<400> SEQUENCE: 317

Ile Leu Phe Asp Gly Arg Asp Thr Gly Ala
1               5                   10

<210> SEQ ID NO 318
<211> LENGTH: 10
<212> TYPE: PRT
<213> ORGANISM: Homo sapiens

<400> SEQUENCE: 318

Val Leu Phe Asp Gly Arg Asp Asn Gly Ala

```
1               5                   10

<210> SEQ ID NO 319
<211> LENGTH: 10
<212> TYPE: PRT
<213> ORGANISM: Homo sapiens

<400> SEQUENCE: 319

Gly Ile Phe Asp Glu Arg Asp Tyr Gly Leu
1               5                   10

<210> SEQ ID NO 320
<211> LENGTH: 10
<212> TYPE: PRT
<213> ORGANISM: Homo sapiens

<400> SEQUENCE: 320

Gly Leu Thr Asp Gly Glu Asp Pro Glu Val
1               5                   10

<210> SEQ ID NO 321
<211> LENGTH: 10
<212> TYPE: PRT
<213> ORGANISM: Homo sapiens

<400> SEQUENCE: 321

Gly Ile Ala Asp Ile Arg Asp Lys Tyr Met
1               5                   10

<210> SEQ ID NO 322
<211> LENGTH: 10
<212> TYPE: PRT
<213> ORGANISM: Homo sapiens

<400> SEQUENCE: 322

Gly Leu Ala Glu Val Leu Glu Ile Leu Ala
1               5                   10

<210> SEQ ID NO 323
<211> LENGTH: 10
<212> TYPE: PRT
<213> ORGANISM: Homo sapiens

<400> SEQUENCE: 323

Ala Leu Val Glu Ser Leu Glu Leu Phe Ala
1               5                   10

<210> SEQ ID NO 324
<211> LENGTH: 10
<212> TYPE: PRT
<213> ORGANISM: Homo sapiens

<400> SEQUENCE: 324

Ala Ser Phe Glu Ile Arg Asp Gln Tyr Ile
1               5                   10

<210> SEQ ID NO 325
<211> LENGTH: 10
<212> TYPE: PRT
<213> ORGANISM: Homo sapiens

<400> SEQUENCE: 325

Ala Ile Ile Glu Ile Leu Met Ala Val Val
1               5                   10
```

<210> SEQ ID NO 326
<211> LENGTH: 10
<212> TYPE: PRT
<213> ORGANISM: Homo sapiens

<400> SEQUENCE: 326

Gly Val Trp Glu Ala Arg Gly Tyr Gly Leu
1               5                   10

<210> SEQ ID NO 327
<211> LENGTH: 10
<212> TYPE: PRT
<213> ORGANISM: Homo sapiens

<400> SEQUENCE: 327

Gly Met Ala Glu Ala Arg Val Leu Met Thr
1               5                   10

<210> SEQ ID NO 328
<211> LENGTH: 10
<212> TYPE: PRT
<213> ORGANISM: Homo sapiens

<400> SEQUENCE: 328

Asn Leu Thr Asp Gly Arg Trp His Arg Val
1               5                   10

<210> SEQ ID NO 329
<211> LENGTH: 10
<212> TYPE: PRT
<213> ORGANISM: Homo sapiens

<400> SEQUENCE: 329

Gly Met Tyr Lys Gly Arg Lys His Phe Ile
1               5                   10

<210> SEQ ID NO 330
<211> LENGTH: 10
<212> TYPE: PRT
<213> ORGANISM: Homo sapiens

<400> SEQUENCE: 330

Gly Leu Tyr Asp Leu Arg Ala Lys Thr Ile
1               5                   10

<210> SEQ ID NO 331
<211> LENGTH: 10
<212> TYPE: PRT
<213> ORGANISM: Homo sapiens

<400> SEQUENCE: 331

Gly Val Val Asp Gly Asn Val Ala Arg Val
1               5                   10

<210> SEQ ID NO 332
<211> LENGTH: 10
<212> TYPE: PRT
<213> ORGANISM: Homo sapiens

<400> SEQUENCE: 332

Gly Val Tyr Trp Gly Pro Gly His Pro Leu
1               5                   10

<210> SEQ ID NO 333

```
<211> LENGTH: 10
<212> TYPE: PRT
<213> ORGANISM: Homo sapiens

<400> SEQUENCE: 333

Gly Leu Tyr Glu Glu Arg Ala His Val Val
1               5                   10

<210> SEQ ID NO 334
<211> LENGTH: 10
<212> TYPE: PRT
<213> ORGANISM: Homo sapiens

<400> SEQUENCE: 334

Lys Ser Phe Asp Phe Arg Glu His Phe Val
1               5                   10

<210> SEQ ID NO 335
<211> LENGTH: 10
<212> TYPE: PRT
<213> ORGANISM: Homo sapiens

<400> SEQUENCE: 335

Ala Glu Tyr Asp Glu Arg Glu Ile Ser Val
1               5                   10

<210> SEQ ID NO 336
<211> LENGTH: 10
<212> TYPE: PRT
<213> ORGANISM: Homo sapiens

<400> SEQUENCE: 336

Ala Glu Tyr Asp Asp Arg Glu Ile Ser Val
1               5                   10

<210> SEQ ID NO 337
<211> LENGTH: 10
<212> TYPE: PRT
<213> ORGANISM: Homo sapiens

<400> SEQUENCE: 337

Ser Leu Ala Asp Gly Arg Ile Val Thr Val
1               5                   10

<210> SEQ ID NO 338
<211> LENGTH: 10
<212> TYPE: PRT
<213> ORGANISM: Homo sapiens

<400> SEQUENCE: 338

Gly Thr Tyr Glu Cys Arg Leu His Leu Val
1               5                   10

<210> SEQ ID NO 339
<211> LENGTH: 10
<212> TYPE: PRT
<213> ORGANISM: Homo sapiens

<400> SEQUENCE: 339

Ile Val Ile Asp Gly Lys Glu Ile Glu Val
1               5                   10

<210> SEQ ID NO 340
<211> LENGTH: 10
<212> TYPE: PRT
```

<213> ORGANISM: Homo sapiens

<400> SEQUENCE: 340

Glu Leu Tyr Ala Gly Arg Glu Tyr Thr Leu
1               5                   10

<210> SEQ ID NO 341
<211> LENGTH: 10
<212> TYPE: PRT
<213> ORGANISM: Homo sapiens

<400> SEQUENCE: 341

Val Met Ala Glu Gly Arg Glu Leu Ile Leu
1               5                   10

<210> SEQ ID NO 342
<211> LENGTH: 10
<212> TYPE: PRT
<213> ORGANISM: Homo sapiens

<400> SEQUENCE: 342

Gly Leu Ala Glu Leu Arg Glu Leu Asp Leu
1               5                   10

<210> SEQ ID NO 343
<211> LENGTH: 10
<212> TYPE: PRT
<213> ORGANISM: Homo sapiens

<400> SEQUENCE: 343

Gly Gln Tyr Glu Gly His Glu Ala Glu Leu
1               5                   10

<210> SEQ ID NO 344
<211> LENGTH: 10
<212> TYPE: PRT
<213> ORGANISM: Homo sapiens

<400> SEQUENCE: 344

Gly Ile Val Asp Ala Ser Glu Val Ala Val
1               5                   10

<210> SEQ ID NO 345
<211> LENGTH: 10
<212> TYPE: PRT
<213> ORGANISM: Homo sapiens

<400> SEQUENCE: 345

Gly Leu Val Asp Gly His Asp Val Val Ile
1               5                   10

<210> SEQ ID NO 346
<211> LENGTH: 10
<212> TYPE: PRT
<213> ORGANISM: Homo sapiens

<400> SEQUENCE: 346

Gly Leu Ser Glu Ala Arg Glu Lys Ala Val
1               5                   10

<210> SEQ ID NO 347
<211> LENGTH: 10
<212> TYPE: PRT
<213> ORGANISM: Homo sapiens

```
<400> SEQUENCE: 347

Val Leu Ala Glu Gly Arg Glu Arg Lys Val
1               5                   10

<210> SEQ ID NO 348
<211> LENGTH: 10
<212> TYPE: PRT
<213> ORGANISM: Homo sapiens

<400> SEQUENCE: 348

Gly Ile Val Glu Gly Leu Glu Ser Pro Leu
1               5                   10

<210> SEQ ID NO 349
<211> LENGTH: 10
<212> TYPE: PRT
<213> ORGANISM: Homo sapiens

<400> SEQUENCE: 349

Ala Val Phe Asp Ala Leu Glu Ser Glu Ala
1               5                   10

<210> SEQ ID NO 350
<211> LENGTH: 10
<212> TYPE: PRT
<213> ORGANISM: Homo sapiens

<400> SEQUENCE: 350

Ala Gln Trp Asp Ala Pro Glu Glu Ala Leu
1               5                   10

<210> SEQ ID NO 351
<211> LENGTH: 10
<212> TYPE: PRT
<213> ORGANISM: Homo sapiens

<400> SEQUENCE: 351

Gly Leu His Glu Ala Leu Glu Lys Gln Leu
1               5                   10

<210> SEQ ID NO 352
<211> LENGTH: 10
<212> TYPE: PRT
<213> ORGANISM: Homo sapiens

<400> SEQUENCE: 352

Gly Val Tyr Thr Gly Gln Met Ser Asn Val
1               5                   10

<210> SEQ ID NO 353
<211> LENGTH: 10
<212> TYPE: PRT
<213> ORGANISM: Homo sapiens

<400> SEQUENCE: 353

Gly Val Thr Asp Leu Gln Val Leu Thr Val
1               5                   10

<210> SEQ ID NO 354
<211> LENGTH: 10
<212> TYPE: PRT
<213> ORGANISM: Homo sapiens

<400> SEQUENCE: 354
```

```
Gly Val Val Leu Gly Leu Met Glu Thr Val
1               5                   10

<210> SEQ ID NO 355
<211> LENGTH: 10
<212> TYPE: PRT
<213> ORGANISM: Homo sapiens

<400> SEQUENCE: 355

Gly Val Pro Ser Gly Leu Glu Phe Leu Val
1               5                   10

<210> SEQ ID NO 356
<211> LENGTH: 10
<212> TYPE: PRT
<213> ORGANISM: Homo sapiens

<400> SEQUENCE: 356

Gly Val Gly Ala Gly Leu Ala Ala Thr Val
1               5                   10

<210> SEQ ID NO 357
<211> LENGTH: 10
<212> TYPE: PRT
<213> ORGANISM: Homo sapiens

<400> SEQUENCE: 357

Phe Asn Leu Asp Gly Met Glu His His Val
1               5                   10

<210> SEQ ID NO 358
<211> LENGTH: 10
<212> TYPE: PRT
<213> ORGANISM: Homo sapiens

<400> SEQUENCE: 358

Thr Val Tyr Arg Gly Leu Glu Gly Phe Val
1               5                   10

<210> SEQ ID NO 359
<211> LENGTH: 10
<212> TYPE: PRT
<213> ORGANISM: Homo sapiens

<400> SEQUENCE: 359

Ser Val Tyr Asp Leu Arg Gln Gln Ser Val
1               5                   10

<210> SEQ ID NO 360
<211> LENGTH: 10
<212> TYPE: PRT
<213> ORGANISM: Homo sapiens

<400> SEQUENCE: 360

Glu Leu Tyr Asp Leu Arg Gln His Phe Val
1               5                   10

<210> SEQ ID NO 361
<211> LENGTH: 10
<212> TYPE: PRT
<213> ORGANISM: Homo sapiens

<400> SEQUENCE: 361

Trp Val Tyr Asp Val Gly Glu Leu Ala Val
1               5                   10
```

<210> SEQ ID NO 362
<211> LENGTH: 10
<212> TYPE: PRT
<213> ORGANISM: Homo sapiens

<400> SEQUENCE: 362

Gly Leu Arg Pro Gly Ser Glu Tyr Thr Val
1               5                   10

<210> SEQ ID NO 363
<211> LENGTH: 10
<212> TYPE: PRT
<213> ORGANISM: Homo sapiens

<400> SEQUENCE: 363

Leu Val Leu Asp Gly Glu Glu Ile Pro Val
1               5                   10

<210> SEQ ID NO 364
<211> LENGTH: 10
<212> TYPE: PRT
<213> ORGANISM: Homo sapiens

<400> SEQUENCE: 364

Arg Val Tyr Cys Gly His Glu Tyr Thr Ile
1               5                   10

<210> SEQ ID NO 365
<211> LENGTH: 10
<212> TYPE: PRT
<213> ORGANISM: Homo sapiens

<400> SEQUENCE: 365

Gln Leu Ser Asp Gly Gly Glu Tyr Thr Val
1               5                   10

<210> SEQ ID NO 366
<211> LENGTH: 10
<212> TYPE: PRT
<213> ORGANISM: Homo sapiens

<400> SEQUENCE: 366

Leu Val Tyr Asp Gly Lys Ile Tyr Thr Leu
1               5                   10

<210> SEQ ID NO 367
<211> LENGTH: 10
<212> TYPE: PRT
<213> ORGANISM: Homo sapiens

<400> SEQUENCE: 367

Gly Leu Arg Ala Trp Arg Glu His Gly Val
1               5                   10

<210> SEQ ID NO 368
<211> LENGTH: 10
<212> TYPE: PRT
<213> ORGANISM: Homo sapiens

<400> SEQUENCE: 368

Gly Lys Leu Asp Phe Gly Glu Thr Thr Val
1               5                   10

```
<210> SEQ ID NO 369
<211> LENGTH: 10
<212> TYPE: PRT
<213> ORGANISM: Homo sapiens

<400> SEQUENCE: 369

Tyr Gln Tyr Ser Gly Leu Glu Asp Thr Val
1               5                   10

<210> SEQ ID NO 370
<211> LENGTH: 10
<212> TYPE: PRT
<213> ORGANISM: Homo sapiens

<400> SEQUENCE: 370

Glu Leu Tyr Asp Gly Leu Lys His Lys Val
1               5                   10

<210> SEQ ID NO 371
<211> LENGTH: 10
<212> TYPE: PRT
<213> ORGANISM: Homo sapiens

<400> SEQUENCE: 371

Lys Phe Tyr Asp Gly Val Val Gln Thr Val
1               5                   10

<210> SEQ ID NO 372
<211> LENGTH: 10
<212> TYPE: PRT
<213> ORGANISM: Homo sapiens

<400> SEQUENCE: 372

Tyr Val Tyr Asn Gly Lys Glu Thr Thr Leu
1               5                   10

<210> SEQ ID NO 373
<211> LENGTH: 10
<212> TYPE: PRT
<213> ORGANISM: Homo sapiens

<400> SEQUENCE: 373

Leu Val Tyr Asp Gly Asp Thr Val Ser Val
1               5                   10

<210> SEQ ID NO 374
<211> LENGTH: 10
<212> TYPE: PRT
<213> ORGANISM: Homo sapiens

<400> SEQUENCE: 374

Met Ile Tyr Val Gly Arg Arg Ala Thr Val
1               5                   10

<210> SEQ ID NO 375
<211> LENGTH: 10
<212> TYPE: PRT
<213> ORGANISM: Homo sapiens

<400> SEQUENCE: 375

His Val Tyr Asp Leu Phe Glu Lys Ala Val
1               5                   10

<210> SEQ ID NO 376
<211> LENGTH: 10
```

```
<212> TYPE: PRT
<213> ORGANISM: Homo sapiens

<400> SEQUENCE: 376

Thr Val Leu Asp Gly Leu Glu Phe Lys Val
1               5                   10

<210> SEQ ID NO 377
<211> LENGTH: 10
<212> TYPE: PRT
<213> ORGANISM: Homo sapiens

<400> SEQUENCE: 377

Gly Leu Gln Asp Gln Gln Glu His Val Val
1               5                   10

<210> SEQ ID NO 378
<211> LENGTH: 10
<212> TYPE: PRT
<213> ORGANISM: Homo sapiens

<400> SEQUENCE: 378

Gly Leu Arg Pro Gly Val Glu Tyr Thr Val
1               5                   10

<210> SEQ ID NO 379
<211> LENGTH: 10
<212> TYPE: PRT
<213> ORGANISM: Homo sapiens

<400> SEQUENCE: 379

Gly Leu Arg Pro Gly Met Glu Tyr Thr Val
1               5                   10

<210> SEQ ID NO 380
<211> LENGTH: 10
<212> TYPE: PRT
<213> ORGANISM: Homo sapiens

<400> SEQUENCE: 380

Leu Met Met Asp Gly His Glu Val Thr Val
1               5                   10

<210> SEQ ID NO 381
<211> LENGTH: 10
<212> TYPE: PRT
<213> ORGANISM: Homo sapiens

<400> SEQUENCE: 381

Gly Gln Tyr Gly Cys Gly Glu Met Thr Val
1               5                   10

<210> SEQ ID NO 382
<211> LENGTH: 10
<212> TYPE: PRT
<213> ORGANISM: Homo sapiens

<400> SEQUENCE: 382

Tyr Met Tyr Asp Ser Leu Glu His Thr Gly
1               5                   10

<210> SEQ ID NO 383
<211> LENGTH: 10
<212> TYPE: PRT
<213> ORGANISM: Homo sapiens
```

<400> SEQUENCE: 383

Val Val Asp Asp Leu Arg Leu Cys Thr Val
1               5                   10

<210> SEQ ID NO 384
<211> LENGTH: 10
<212> TYPE: PRT
<213> ORGANISM: Homo sapiens

<400> SEQUENCE: 384

Leu Val Trp Asp Thr Pro Tyr His Thr Val
1               5                   10

<210> SEQ ID NO 385
<211> LENGTH: 10
<212> TYPE: PRT
<213> ORGANISM: Homo sapiens

<400> SEQUENCE: 385

Leu Val Ser Asp Leu Arg Asn His Pro Val
1               5                   10

<210> SEQ ID NO 386
<211> LENGTH: 10
<212> TYPE: PRT
<213> ORGANISM: Homo sapiens

<400> SEQUENCE: 386

Leu Val Gln Asp Thr Arg Ile His Leu Val
1               5                   10

<210> SEQ ID NO 387
<211> LENGTH: 10
<212> TYPE: PRT
<213> ORGANISM: Homo sapiens

<400> SEQUENCE: 387

Ile Val Tyr Leu Gly Asp Tyr Leu Thr Val
1               5                   10

<210> SEQ ID NO 388
<211> LENGTH: 10
<212> TYPE: PRT
<213> ORGANISM: Homo sapiens

<400> SEQUENCE: 388

Ala Val Ala Ala Gly Asp Val His Thr Val
1               5                   10

<210> SEQ ID NO 389
<211> LENGTH: 10
<212> TYPE: PRT
<213> ORGANISM: Homo sapiens

<400> SEQUENCE: 389

Leu Val Asp Asp Ser Phe Leu His Thr Val
1               5                   10

<210> SEQ ID NO 390
<211> LENGTH: 10
<212> TYPE: PRT
<213> ORGANISM: Homo sapiens

<400> SEQUENCE: 390

Cys Val Ser Asp Pro Phe Glu Leu Thr Val
1               5                   10

<210> SEQ ID NO 391
<211> LENGTH: 10
<212> TYPE: PRT
<213> ORGANISM: Homo sapiens

<400> SEQUENCE: 391

Ser Val Tyr Ser Gly Cys Leu His Leu Val
1               5                   10

<210> SEQ ID NO 392
<211> LENGTH: 10
<212> TYPE: PRT
<213> ORGANISM: Homo sapiens

<400> SEQUENCE: 392

Val Val Ile Asp Asp Arg Leu Pro Thr Val
1               5                   10

<210> SEQ ID NO 393
<211> LENGTH: 10
<212> TYPE: PRT
<213> ORGANISM: Homo sapiens

<400> SEQUENCE: 393

Arg Val Tyr Ser Ile Tyr Val His Thr Val
1               5                   10

<210> SEQ ID NO 394
<211> LENGTH: 10
<212> TYPE: PRT
<213> ORGANISM: Homo sapiens

<400> SEQUENCE: 394

Tyr Val Phe Arg Gly Val Glu His Ala Val
1               5                   10

<210> SEQ ID NO 395
<211> LENGTH: 10
<212> TYPE: PRT
<213> ORGANISM: Homo sapiens

<400> SEQUENCE: 395

Ile Val Ile Thr Gly Phe Glu Val Thr Val
1               5                   10

<210> SEQ ID NO 396
<211> LENGTH: 10
<212> TYPE: PRT
<213> ORGANISM: Homo sapiens

<400> SEQUENCE: 396

Cys Val Ala Asp Pro Phe Glu Val Thr Val
1               5                   10

<210> SEQ ID NO 397
<211> LENGTH: 10
<212> TYPE: PRT
<213> ORGANISM: Homo sapiens

<400> SEQUENCE: 397

Ser Val Asn Asp Gly Thr Trp His Glu Val

```
1               5                   10
```

\<210\> SEQ ID NO 398
\<211\> LENGTH: 10
\<212\> TYPE: PRT
\<213\> ORGANISM: Homo sapiens

\<400\> SEQUENCE: 398

```
Arg Val Ala Asp Gly Ala Trp His Arg Val
1               5                   10
```

\<210\> SEQ ID NO 399
\<211\> LENGTH: 10
\<212\> TYPE: PRT
\<213\> ORGANISM: Homo sapiens

\<400\> SEQUENCE: 399

```
Lys Val Leu Arg Gly Val Glu Val Thr Val
1               5                   10
```

\<210\> SEQ ID NO 400
\<211\> LENGTH: 10
\<212\> TYPE: PRT
\<213\> ORGANISM: Homo sapiens

\<400\> SEQUENCE: 400

```
Tyr Leu Ala Trp Ile Arg Glu His Thr Val
1               5                   10
```

\<210\> SEQ ID NO 401
\<211\> LENGTH: 10
\<212\> TYPE: PRT
\<213\> ORGANISM: Homo sapiens

\<400\> SEQUENCE: 401

```
Ala Val Asn Asp Gly Ser Trp His Ser Val
1               5                   10
```

\<210\> SEQ ID NO 402
\<211\> LENGTH: 10
\<212\> TYPE: PRT
\<213\> ORGANISM: Homo sapiens

\<400\> SEQUENCE: 402

```
Lys Val Ser Asp Gly His Phe His Thr Val
1               5                   10
```

\<210\> SEQ ID NO 403
\<211\> LENGTH: 10
\<212\> TYPE: PRT
\<213\> ORGANISM: Homo sapiens

\<400\> SEQUENCE: 403

```
Ser Val Tyr Gly Glu Arg Arg Val Thr Val
1               5                   10
```

\<210\> SEQ ID NO 404
\<211\> LENGTH: 10
\<212\> TYPE: PRT
\<213\> ORGANISM: Homo sapiens

\<400\> SEQUENCE: 404

```
Ile Val Asp Pro Gly Asp Glu Pro Thr Val
1               5                   10
```

<210> SEQ ID NO 405
<211> LENGTH: 10
<212> TYPE: PRT
<213> ORGANISM: Homo sapiens

<400> SEQUENCE: 405

Gly Val Phe Gly Phe Glu Glu Lys Thr Val
1               5                   10

<210> SEQ ID NO 406
<211> LENGTH: 10
<212> TYPE: PRT
<213> ORGANISM: Homo sapiens

<400> SEQUENCE: 406

Lys Val Phe Cys Gly His Glu His Thr Leu
1               5                   10

<210> SEQ ID NO 407
<211> LENGTH: 10
<212> TYPE: PRT
<213> ORGANISM: Homo sapiens

<400> SEQUENCE: 407

Leu Val Asp Asp Gly Gly Trp Asn Thr Val
1               5                   10

<210> SEQ ID NO 408
<211> LENGTH: 10
<212> TYPE: PRT
<213> ORGANISM: Homo sapiens

<400> SEQUENCE: 408

Ser Val Met Lys Tyr Asp Glu His Thr Val
1               5                   10

<210> SEQ ID NO 409
<211> LENGTH: 10
<212> TYPE: PRT
<213> ORGANISM: Homo sapiens

<400> SEQUENCE: 409

Lys Val Leu Ser Ser Arg Val His Thr Val
1               5                   10

<210> SEQ ID NO 410
<211> LENGTH: 10
<212> TYPE: PRT
<213> ORGANISM: Homo sapiens

<400> SEQUENCE: 410

Leu Leu Ser Asp Gly Lys Trp His Thr Val
1               5                   10

<210> SEQ ID NO 411
<211> LENGTH: 10
<212> TYPE: PRT
<213> ORGANISM: Homo sapiens

<400> SEQUENCE: 411

Phe Val Tyr Asp Glu Pro Gly His Ala Val
1               5                   10

<210> SEQ ID NO 412

```
<211> LENGTH: 10
<212> TYPE: PRT
<213> ORGANISM: Homo sapiens

<400> SEQUENCE: 412

Val Gln Tyr Asp His Pro Asn His Thr Val
1               5                   10

<210> SEQ ID NO 413
<211> LENGTH: 10
<212> TYPE: PRT
<213> ORGANISM: Homo sapiens

<400> SEQUENCE: 413

Ser Val Leu Asp Gly Thr Leu Leu Thr Val
1               5                   10

<210> SEQ ID NO 414
<211> LENGTH: 10
<212> TYPE: PRT
<213> ORGANISM: Homo sapiens

<400> SEQUENCE: 414

Ser Val Met Lys Gly Arg Val Ala Thr Val
1               5                   10

<210> SEQ ID NO 415
<211> LENGTH: 10
<212> TYPE: PRT
<213> ORGANISM: Homo sapiens

<400> SEQUENCE: 415

Thr Val Leu Ser Gly Pro Glu Ala Thr Val
1               5                   10

<210> SEQ ID NO 416
<211> LENGTH: 10
<212> TYPE: PRT
<213> ORGANISM: Homo sapiens

<400> SEQUENCE: 416

Ser Val Gly Ile Gly Val Glu Phe Thr Val
1               5                   10

<210> SEQ ID NO 417
<211> LENGTH: 10
<212> TYPE: PRT
<213> ORGANISM: Homo sapiens

<400> SEQUENCE: 417

Met Ile Glu Asp Gly Lys Ile His Thr Val
1               5                   10

<210> SEQ ID NO 418
<211> LENGTH: 10
<212> TYPE: PRT
<213> ORGANISM: Homo sapiens

<400> SEQUENCE: 418

Met Thr Ala Asp Gly Ile Leu His Thr Val
1               5                   10

<210> SEQ ID NO 419
<211> LENGTH: 10
<212> TYPE: PRT
```

<213> ORGANISM: Homo sapiens

<400> SEQUENCE: 419

Phe Val Phe Asp Pro Arg Gln His Pro Val
1               5                   10

<210> SEQ ID NO 420
<211> LENGTH: 10
<212> TYPE: PRT
<213> ORGANISM: Homo sapiens

<400> SEQUENCE: 420

Tyr Val Leu Asp Gly Met Val Asp Thr Val
1               5                   10

<210> SEQ ID NO 421
<211> LENGTH: 10
<212> TYPE: PRT
<213> ORGANISM: Homo sapiens

<400> SEQUENCE: 421

Thr Ile Asn Asp Gly Gln Phe His Thr Val
1               5                   10

<210> SEQ ID NO 422
<211> LENGTH: 10
<212> TYPE: PRT
<213> ORGANISM: Homo sapiens

<400> SEQUENCE: 422

Thr Val Asn Asp Gly Gln Phe His Ser Val
1               5                   10

<210> SEQ ID NO 423
<211> LENGTH: 10
<212> TYPE: PRT
<213> ORGANISM: Homo sapiens

<400> SEQUENCE: 423

Val Leu Cys Ser Gly Arg Arg His Thr Val
1               5                   10

<210> SEQ ID NO 424
<211> LENGTH: 10
<212> TYPE: PRT
<213> ORGANISM: Homo sapiens

<400> SEQUENCE: 424

His Val Pro Glu Gly Arg Ile Tyr Thr Val
1               5                   10

<210> SEQ ID NO 425
<211> LENGTH: 10
<212> TYPE: PRT
<213> ORGANISM: Homo sapiens

<400> SEQUENCE: 425

Val Val Tyr Gly Ile Gly Glu Ser Thr Val
1               5                   10

<210> SEQ ID NO 426
<211> LENGTH: 10
<212> TYPE: PRT
<213> ORGANISM: Homo sapiens

```
<400> SEQUENCE: 426

Ser Val Leu Ala Gly His Ser His Thr Val
1               5                   10

<210> SEQ ID NO 427
<211> LENGTH: 10
<212> TYPE: PRT
<213> ORGANISM: Homo sapiens

<400> SEQUENCE: 427

Ile Val Tyr Leu Gln Lys Glu His Pro Val
1               5                   10

<210> SEQ ID NO 428
<211> LENGTH: 10
<212> TYPE: PRT
<213> ORGANISM: Homo sapiens

<400> SEQUENCE: 428

Tyr Gln Tyr Tyr Gly Phe Ser His Thr Val
1               5                   10

<210> SEQ ID NO 429
<211> LENGTH: 10
<212> TYPE: PRT
<213> ORGANISM: Homo sapiens

<400> SEQUENCE: 429

Val Val Pro Asp Gly Glu Thr His Leu Val
1               5                   10

<210> SEQ ID NO 430
<211> LENGTH: 10
<212> TYPE: PRT
<213> ORGANISM: Homo sapiens

<400> SEQUENCE: 430

Gly Val Met Cys Val Ile Glu Lys Thr Val
1               5                   10

<210> SEQ ID NO 431
<211> LENGTH: 10
<212> TYPE: PRT
<213> ORGANISM: Homo sapiens

<400> SEQUENCE: 431

Ser Val Val Asp Tyr Val Glu Val Thr Val
1               5                   10

<210> SEQ ID NO 432
<211> LENGTH: 10
<212> TYPE: PRT
<213> ORGANISM: Homo sapiens

<400> SEQUENCE: 432

Ala Val Tyr Asp Thr Leu Leu Asn Thr Val
1               5                   10

<210> SEQ ID NO 433
<211> LENGTH: 10
<212> TYPE: PRT
<213> ORGANISM: Homo sapiens

<400> SEQUENCE: 433
```

```
Ser Val Ser Asp Asp Thr Glu His Leu Val
1               5                   10

<210> SEQ ID NO 434
<211> LENGTH: 10
<212> TYPE: PRT
<213> ORGANISM: Homo sapiens

<400> SEQUENCE: 434

Cys Val His Ser Gly His Phe His Thr Val
1               5                   10

<210> SEQ ID NO 435
<211> LENGTH: 10
<212> TYPE: PRT
<213> ORGANISM: Homo sapiens

<400> SEQUENCE: 435

Gly Leu Gly Gly Ala Arg Leu His Thr Val
1               5                   10

<210> SEQ ID NO 436
<211> LENGTH: 10
<212> TYPE: PRT
<213> ORGANISM: Homo sapiens

<400> SEQUENCE: 436

Thr Val Tyr Gln Gly Ile Lys His Ala Val
1               5                   10

<210> SEQ ID NO 437
<211> LENGTH: 10
<212> TYPE: PRT
<213> ORGANISM: Homo sapiens

<400> SEQUENCE: 437

Gly Leu Val Asp Ala Pro Glu Ala Ala Val
1               5                   10

<210> SEQ ID NO 438
<211> LENGTH: 10
<212> TYPE: PRT
<213> ORGANISM: Homo sapiens

<400> SEQUENCE: 438

Gly Ile Tyr Asp Gly Glu Thr Leu Thr Val
1               5                   10

<210> SEQ ID NO 439
<211> LENGTH: 10
<212> TYPE: PRT
<213> ORGANISM: Homo sapiens

<400> SEQUENCE: 439

Gly Leu Ala Met Gly Arg Met His Pro Val
1               5                   10

<210> SEQ ID NO 440
<211> LENGTH: 10
<212> TYPE: PRT
<213> ORGANISM: Homo sapiens

<400> SEQUENCE: 440

Gly Tyr Met Asp Gly Arg Ala Leu Thr Val
1               5                   10
```

<210> SEQ ID NO 441
<211> LENGTH: 10
<212> TYPE: PRT
<213> ORGANISM: Homo sapiens

<400> SEQUENCE: 441

Leu Leu Val Asp Gly Arg Thr Val Thr Val
1               5                   10

<210> SEQ ID NO 442
<211> LENGTH: 10
<212> TYPE: PRT
<213> ORGANISM: Homo sapiens

<400> SEQUENCE: 442

Ala Leu Ala Glu Gly Arg Glu Met Ser Leu
1               5                   10

<210> SEQ ID NO 443
<211> LENGTH: 10
<212> TYPE: PRT
<213> ORGANISM: Homo sapiens

<400> SEQUENCE: 443

Gly Leu Lys Asp Gly Phe Asp Trp Leu Leu
1               5                   10

<210> SEQ ID NO 444
<211> LENGTH: 10
<212> TYPE: PRT
<213> ORGANISM: Homo sapiens

<400> SEQUENCE: 444

Gly Leu Ala Glu Gly Val Glu Val Gln Val
1               5                   10

<210> SEQ ID NO 445
<211> LENGTH: 10
<212> TYPE: PRT
<213> ORGANISM: Homo sapiens

<400> SEQUENCE: 445

Gly Met His Asp Gly Leu Met Tyr Tyr Thr
1               5                   10

<210> SEQ ID NO 446
<211> LENGTH: 10
<212> TYPE: PRT
<213> ORGANISM: Homo sapiens

<400> SEQUENCE: 446

Ala Met Ala Asp Ser Leu Glu Ala Ala Ala
1               5                   10

<210> SEQ ID NO 447
<211> LENGTH: 10
<212> TYPE: PRT
<213> ORGANISM: Homo sapiens

<400> SEQUENCE: 447

Ala Met Ile Glu Ala Arg Met His Glu Ile
1               5                   10

```
<210> SEQ ID NO 448
<211> LENGTH: 10
<212> TYPE: PRT
<213> ORGANISM: Homo sapiens

<400> SEQUENCE: 448

Ala Leu Ala Glu His Leu Glu Ile Lys Val
1               5                   10

<210> SEQ ID NO 449
<211> LENGTH: 10
<212> TYPE: PRT
<213> ORGANISM: Homo sapiens

<400> SEQUENCE: 449

Ala Leu Trp Asp Ala Leu Asp Cys Arg Val
1               5                   10

<210> SEQ ID NO 450
<211> LENGTH: 10
<212> TYPE: PRT
<213> ORGANISM: Homo sapiens

<400> SEQUENCE: 450

Phe Val Tyr Val Gly Ala Glu Val Ser Val
1               5                   10

<210> SEQ ID NO 451
<211> LENGTH: 10
<212> TYPE: PRT
<213> ORGANISM: Homo sapiens

<400> SEQUENCE: 451

Ser Val Tyr Asp Gly Ile Pro His Leu Leu
1               5                   10

<210> SEQ ID NO 452
<211> LENGTH: 10
<212> TYPE: PRT
<213> ORGANISM: Homo sapiens

<400> SEQUENCE: 452

Gly Val Tyr Trp Gly Tyr Ile Thr Met Val
1               5                   10

<210> SEQ ID NO 453
<211> LENGTH: 10
<212> TYPE: PRT
<213> ORGANISM: Homo sapiens

<400> SEQUENCE: 453

Gly Val Tyr Trp Gly Tyr Ile Ala Met Val
1               5                   10

<210> SEQ ID NO 454
<211> LENGTH: 10
<212> TYPE: PRT
<213> ORGANISM: Homo sapiens

<400> SEQUENCE: 454

Glu Val Leu Asp Glu His Phe His Thr Val
1               5                   10

<210> SEQ ID NO 455
<211> LENGTH: 10
```

```
<212> TYPE: PRT
<213> ORGANISM: Homo sapiens

<400> SEQUENCE: 455

Thr Leu Tyr Asp Gly Ser Tyr His Asp Val
1               5                   10

<210> SEQ ID NO 456
<211> LENGTH: 10
<212> TYPE: PRT
<213> ORGANISM: Homo sapiens

<400> SEQUENCE: 456

Lys Leu Tyr Asp Gly Ser Tyr His Asp Val
1               5                   10

<210> SEQ ID NO 457
<211> LENGTH: 10
<212> TYPE: PRT
<213> ORGANISM: Homo sapiens

<400> SEQUENCE: 457

Gly Val Tyr Ser His Tyr Ile Pro Thr Val
1               5                   10

<210> SEQ ID NO 458
<211> LENGTH: 10
<212> TYPE: PRT
<213> ORGANISM: Homo sapiens

<400> SEQUENCE: 458

Leu Val Tyr Asp Gly Ala Ala Leu Ala Val
1               5                   10

<210> SEQ ID NO 459
<211> LENGTH: 10
<212> TYPE: PRT
<213> ORGANISM: Homo sapiens

<400> SEQUENCE: 459

Gly Thr Tyr Ala Gly Leu Ala His Pro Val
1               5                   10

<210> SEQ ID NO 460
<211> LENGTH: 10
<212> TYPE: PRT
<213> ORGANISM: Homo sapiens

<400> SEQUENCE: 460

Gly Val Leu Gly Gly Leu Ala Ala Thr Val
1               5                   10

<210> SEQ ID NO 461
<211> LENGTH: 10
<212> TYPE: PRT
<213> ORGANISM: Homo sapiens

<400> SEQUENCE: 461

Gly Tyr Met Asp Gly His Pro Leu Thr Val
1               5                   10

<210> SEQ ID NO 462
<211> LENGTH: 10
<212> TYPE: PRT
<213> ORGANISM: Homo sapiens
```

<400> SEQUENCE: 462

Gly Tyr Met Asp Gly His Pro Met Thr Val
1               5                   10

<210> SEQ ID NO 463
<211> LENGTH: 10
<212> TYPE: PRT
<213> ORGANISM: Homo sapiens

<400> SEQUENCE: 463

Lys Leu Ser Asp Gly Thr Glu His Glu Val
1               5                   10

<210> SEQ ID NO 464
<211> LENGTH: 10
<212> TYPE: PRT
<213> ORGANISM: Homo sapiens

<400> SEQUENCE: 464

Gly Val Leu Asp Glu Ala Leu Thr Thr Val
1               5                   10

<210> SEQ ID NO 465
<211> LENGTH: 10
<212> TYPE: PRT
<213> ORGANISM: Homo sapiens

<400> SEQUENCE: 465

Lys Val Tyr Pro Gly Leu Tyr His Glu Val
1               5                   10

<210> SEQ ID NO 466
<211> LENGTH: 10
<212> TYPE: PRT
<213> ORGANISM: Homo sapiens

<400> SEQUENCE: 466

Gly Val Tyr Ala His Gly Phe Leu Thr Val
1               5                   10

<210> SEQ ID NO 467
<211> LENGTH: 10
<212> TYPE: PRT
<213> ORGANISM: Homo sapiens

<400> SEQUENCE: 467

Phe Val Tyr Asp Val Ala Glu Ser Ala Val
1               5                   10

<210> SEQ ID NO 468
<211> LENGTH: 10
<212> TYPE: PRT
<213> ORGANISM: Homo sapiens

<400> SEQUENCE: 468

Gly Val Tyr Asp Met Val Leu His Gln Val
1               5                   10

<210> SEQ ID NO 469
<211> LENGTH: 10
<212> TYPE: PRT
<213> ORGANISM: Homo sapiens

<400> SEQUENCE: 469

Phe Val Leu Asp Gly Tyr Pro Arg Thr Val
1               5                   10

<210> SEQ ID NO 470
<211> LENGTH: 10
<212> TYPE: PRT
<213> ORGANISM: Homo sapiens

<400> SEQUENCE: 470

Phe Val Ala Asp Gly Ala Tyr His Asn Val
1               5                   10

<210> SEQ ID NO 471
<211> LENGTH: 10
<212> TYPE: PRT
<213> ORGANISM: Homo sapiens

<400> SEQUENCE: 471

Gly Leu Tyr Asp Leu Ile Gly His Asp Val
1               5                   10

<210> SEQ ID NO 472
<211> LENGTH: 10
<212> TYPE: PRT
<213> ORGANISM: Homo sapiens

<400> SEQUENCE: 472

Ala Val Tyr Asp Gly Asn Leu Asp Leu Val
1               5                   10

<210> SEQ ID NO 473
<211> LENGTH: 10
<212> TYPE: PRT
<213> ORGANISM: Homo sapiens

<400> SEQUENCE: 473

Gly Val Ala Asp Lys Tyr Trp Pro Thr Val
1               5                   10

<210> SEQ ID NO 474
<211> LENGTH: 10
<212> TYPE: PRT
<213> ORGANISM: Homo sapiens

<400> SEQUENCE: 474

Gly Glu Leu Asp Gly Val Val Ile Thr Val
1               5                   10

<210> SEQ ID NO 475
<211> LENGTH: 10
<212> TYPE: PRT
<213> ORGANISM: Homo sapiens

<400> SEQUENCE: 475

Gly Val Tyr Asp Ile His Ser Pro Asn Val
1               5                   10

<210> SEQ ID NO 476
<211> LENGTH: 10
<212> TYPE: PRT
<213> ORGANISM: Homo sapiens

<400> SEQUENCE: 476

Ile Val Leu Leu Gly Ala Glu Ile Thr Val

```
1               5                   10

<210> SEQ ID NO 477
<211> LENGTH: 10
<212> TYPE: PRT
<213> ORGANISM: Homo sapiens

<400> SEQUENCE: 477

Phe Val Tyr Asp Glu Leu Glu Arg Leu Val
1               5                   10

<210> SEQ ID NO 478
<211> LENGTH: 10
<212> TYPE: PRT
<213> ORGANISM: Homo sapiens

<400> SEQUENCE: 478

Gly Val Leu Asp Lys Val Ala Pro Thr Val
1               5                   10

<210> SEQ ID NO 479
<211> LENGTH: 10
<212> TYPE: PRT
<213> ORGANISM: Homo sapiens

<400> SEQUENCE: 479

Gly Met Ala Glu Ala Arg Ala Glu Glu Leu
1               5                   10

<210> SEQ ID NO 480
<211> LENGTH: 10
<212> TYPE: PRT
<213> ORGANISM: Homo sapiens

<400> SEQUENCE: 480

Gly Leu Tyr Asp Ser Arg Glu Glu Lys Leu
1               5                   10

<210> SEQ ID NO 481
<211> LENGTH: 10
<212> TYPE: PRT
<213> ORGANISM: Homo sapiens

<400> SEQUENCE: 481

Gly Thr Ile Glu Ala Arg Phe Tyr Pro Ile
1               5                   10

<210> SEQ ID NO 482
<211> LENGTH: 10
<212> TYPE: PRT
<213> ORGANISM: Homo sapiens

<400> SEQUENCE: 482

Gly Leu Leu Asp Gly Arg Pro Lys Thr Leu
1               5                   10

<210> SEQ ID NO 483
<211> LENGTH: 10
<212> TYPE: PRT
<213> ORGANISM: Homo sapiens

<400> SEQUENCE: 483

Ser Val Phe Asp Gly Arg Arg Thr Tyr Val
1               5                   10
```

<210> SEQ ID NO 484
<211> LENGTH: 10
<212> TYPE: PRT
<213> ORGANISM: Homo sapiens

<400> SEQUENCE: 484

Gly Val Ala Asp Thr Ala Asp Trp Thr Val
1               5                   10

<210> SEQ ID NO 485
<211> LENGTH: 10
<212> TYPE: PRT
<213> ORGANISM: Homo sapiens

<400> SEQUENCE: 485

Phe Val Ile Asp Gly Asn Glu Val Asp Val
1               5                   10

<210> SEQ ID NO 486
<211> LENGTH: 10
<212> TYPE: PRT
<213> ORGANISM: Homo sapiens

<400> SEQUENCE: 486

Gly Leu Ala Asp Ala Ile Glu Ala Arg Met
1               5                   10

<210> SEQ ID NO 487
<211> LENGTH: 10
<212> TYPE: PRT
<213> ORGANISM: Homo sapiens

<400> SEQUENCE: 487

Ala Leu Tyr Glu Gly Arg Asp Ile Gly Ala
1               5                   10

<210> SEQ ID NO 488
<211> LENGTH: 10
<212> TYPE: PRT
<213> ORGANISM: Homo sapiens

<400> SEQUENCE: 488

Gly Ile Thr Glu Gly Leu Met Thr Thr Val
1               5                   10

<210> SEQ ID NO 489
<211> LENGTH: 10
<212> TYPE: PRT
<213> ORGANISM: Homo sapiens

<400> SEQUENCE: 489

Ala Leu Ile Glu Ser Leu Glu Gln Val Phe
1               5                   10

<210> SEQ ID NO 490
<211> LENGTH: 10
<212> TYPE: PRT
<213> ORGANISM: Homo sapiens

<400> SEQUENCE: 490

Ala Ile Ala Glu Ala Leu Met Gln Arg Leu
1               5                   10

<210> SEQ ID NO 491

```
<211> LENGTH: 10
<212> TYPE: PRT
<213> ORGANISM: Homo sapiens

<400> SEQUENCE: 491

Ala Leu Thr Asp Val Pro Asp Gly Trp Val
1               5                   10

<210> SEQ ID NO 492
<211> LENGTH: 10
<212> TYPE: PRT
<213> ORGANISM: Homo sapiens

<400> SEQUENCE: 492

Ala Val Val Glu Val Leu Glu Ala Lys Val
1               5                   10

<210> SEQ ID NO 493
<211> LENGTH: 10
<212> TYPE: PRT
<213> ORGANISM: Homo sapiens

<400> SEQUENCE: 493

Ala Met Ala Asp Ser Leu Glu Ala Ala Thr
1               5                   10

<210> SEQ ID NO 494
<211> LENGTH: 10
<212> TYPE: PRT
<213> ORGANISM: Homo sapiens

<400> SEQUENCE: 494

Ala Leu Ala Glu His Leu Asp Gly Glu Ile
1               5                   10

<210> SEQ ID NO 495
<211> LENGTH: 10
<212> TYPE: PRT
<213> ORGANISM: Homo sapiens

<400> SEQUENCE: 495

Ala Leu Thr Asp His Leu Asp Thr Phe Ala
1               5                   10

<210> SEQ ID NO 496
<211> LENGTH: 10
<212> TYPE: PRT
<213> ORGANISM: Homo sapiens

<400> SEQUENCE: 496

Val Val Ser Asp Gly Asp Ala Tyr Thr Val
1               5                   10

<210> SEQ ID NO 497
<211> LENGTH: 10
<212> TYPE: PRT
<213> ORGANISM: Homo sapiens

<400> SEQUENCE: 497

Arg Leu Thr Asp Gly Gln Gly His Thr Val
1               5                   10

<210> SEQ ID NO 498
<211> LENGTH: 10
<212> TYPE: PRT
```

-continued

```
<213> ORGANISM: Homo sapiens

<400> SEQUENCE: 498

Gly Val Tyr Asp Leu Tyr Asn Asp Glu Val
1               5                   10

<210> SEQ ID NO 499
<211> LENGTH: 10
<212> TYPE: PRT
<213> ORGANISM: Homo sapiens

<400> SEQUENCE: 499

Gly Val Met Asp Met Phe Pro His Thr Ala
1               5                   10

<210> SEQ ID NO 500
<211> LENGTH: 10
<212> TYPE: PRT
<213> ORGANISM: Homo sapiens

<400> SEQUENCE: 500

Gly Val Tyr Asp Ile His Ser Pro Arg Val
1               5                   10

<210> SEQ ID NO 501
<211> LENGTH: 10
<212> TYPE: PRT
<213> ORGANISM: Homo sapiens

<400> SEQUENCE: 501

Ser Val Tyr Asp Val Arg Val Leu Asn Val
1               5                   10

<210> SEQ ID NO 502
<211> LENGTH: 10
<212> TYPE: PRT
<213> ORGANISM: Homo sapiens

<400> SEQUENCE: 502

Gly Val Ser Asp Ala Leu Ala His Ala Val
1               5                   10

<210> SEQ ID NO 503
<211> LENGTH: 10
<212> TYPE: PRT
<213> ORGANISM: Homo sapiens

<400> SEQUENCE: 503

Arg Val Ala Asp Ile Val Glu His Gln Val
1               5                   10

<210> SEQ ID NO 504
<211> LENGTH: 10
<212> TYPE: PRT
<213> ORGANISM: Homo sapiens

<400> SEQUENCE: 504

Val Val Thr Asp Gly Val Ala His Pro Val
1               5                   10

<210> SEQ ID NO 505
<211> LENGTH: 10
<212> TYPE: PRT
<213> ORGANISM: Homo sapiens
```

<400> SEQUENCE: 505

Gly Val Asp Asp Val Ile Thr Thr Val
1               5                   10

<210> SEQ ID NO 506
<211> LENGTH: 10
<212> TYPE: PRT
<213> ORGANISM: Homo sapiens

<400> SEQUENCE: 506

Leu Thr Phe Asp Gly Thr Gln His Thr Val
1               5                   10

<210> SEQ ID NO 507
<211> LENGTH: 10
<212> TYPE: PRT
<213> ORGANISM: Homo sapiens

<400> SEQUENCE: 507

Ile Val Ile Asp Gln Arg Ala His Pro Val
1               5                   10

<210> SEQ ID NO 508
<211> LENGTH: 10
<212> TYPE: PRT
<213> ORGANISM: Homo sapiens

<400> SEQUENCE: 508

Ser Val Phe His Phe Arg Glu Leu Thr Val
1               5                   10

<210> SEQ ID NO 509
<211> LENGTH: 10
<212> TYPE: PRT
<213> ORGANISM: Homo sapiens

<400> SEQUENCE: 509

Phe Val Asp Asp Arg Gly Gly His Thr Val
1               5                   10

<210> SEQ ID NO 510
<211> LENGTH: 10
<212> TYPE: PRT
<213> ORGANISM: Homo sapiens

<400> SEQUENCE: 510

Ala Val Leu Arg Gly Arg Leu His Pro Val
1               5                   10

<210> SEQ ID NO 511
<211> LENGTH: 10
<212> TYPE: PRT
<213> ORGANISM: Homo sapiens

<400> SEQUENCE: 511

Val Leu Leu Asp Gly Arg Arg Ala Thr Val
1               5                   10

<210> SEQ ID NO 512
<211> LENGTH: 10
<212> TYPE: PRT
<213> ORGANISM: Homo sapiens

<400> SEQUENCE: 512

```
Gly Leu Tyr Arg Gly Ala Gly Ala Thr Val
1               5                   10

<210> SEQ ID NO 513
<211> LENGTH: 10
<212> TYPE: PRT
<213> ORGANISM: Homo sapiens

<400> SEQUENCE: 513

Gly Val Leu Asp Leu His Pro Ser Thr Val
1               5                   10

<210> SEQ ID NO 514
<211> LENGTH: 10
<212> TYPE: PRT
<213> ORGANISM: Homo sapiens

<400> SEQUENCE: 514

Gly Ile Tyr Arg Thr Ala Leu His Thr Val
1               5                   10

<210> SEQ ID NO 515
<211> LENGTH: 10
<212> TYPE: PRT
<213> ORGANISM: Homo sapiens

<400> SEQUENCE: 515

Gly Glu Leu Tyr Gly Cys Glu His Ser Val
1               5                   10

<210> SEQ ID NO 516
<211> LENGTH: 10
<212> TYPE: PRT
<213> ORGANISM: Homo sapiens

<400> SEQUENCE: 516

Phe Gly Leu Asp Gly Lys Glu His Ala Val
1               5                   10

<210> SEQ ID NO 517
<211> LENGTH: 10
<212> TYPE: PRT
<213> ORGANISM: Homo sapiens

<400> SEQUENCE: 517

Phe Val Pro Asp Gly Asn Tyr Lys Thr Val
1               5                   10

<210> SEQ ID NO 518
<211> LENGTH: 10
<212> TYPE: PRT
<213> ORGANISM: Homo sapiens

<400> SEQUENCE: 518

Leu Val Tyr Asn Gly Ile Ser His Val Val
1               5                   10

<210> SEQ ID NO 519
<211> LENGTH: 10
<212> TYPE: PRT
<213> ORGANISM: Homo sapiens

<400> SEQUENCE: 519

Gly Val Ile Lys Gly Ser Trp Leu Thr Val
1               5                   10
```

<210> SEQ ID NO 520
<211> LENGTH: 10
<212> TYPE: PRT
<213> ORGANISM: Homo sapiens

<400> SEQUENCE: 520

Lys Val Leu Asp Asp Ala Glu Thr Thr Val
1               5                   10

<210> SEQ ID NO 521
<211> LENGTH: 10
<212> TYPE: PRT
<213> ORGANISM: Homo sapiens

<400> SEQUENCE: 521

Thr Val Trp Asn Gly Ser Ala His Thr Val
1               5                   10

<210> SEQ ID NO 522
<211> LENGTH: 10
<212> TYPE: PRT
<213> ORGANISM: Homo sapiens

<400> SEQUENCE: 522

Gly Leu Val Asp Ser Pro Asn His Leu Ala
1               5                   10

<210> SEQ ID NO 523
<211> LENGTH: 10
<212> TYPE: PRT
<213> ORGANISM: Homo sapiens

<400> SEQUENCE: 523

Gly Ile Ala Asp Gly Arg Leu Gln Ala Val
1               5                   10

<210> SEQ ID NO 524
<211> LENGTH: 10
<212> TYPE: PRT
<213> ORGANISM: Homo sapiens

<400> SEQUENCE: 524

Gly Ile Thr Glu Ala Pro Leu Ala Val Val
1               5                   10

<210> SEQ ID NO 525
<211> LENGTH: 10
<212> TYPE: PRT
<213> ORGANISM: Homo sapiens

<400> SEQUENCE: 525

Glu Val Tyr Glu Gly Gln Glu Tyr Pro Val
1               5                   10

<210> SEQ ID NO 526
<211> LENGTH: 10
<212> TYPE: PRT
<213> ORGANISM: Homo sapiens

<400> SEQUENCE: 526

Gly Ile Tyr Asp Gly Thr Thr Leu Thr Ala
1               5                   10

```
<210> SEQ ID NO 527
<211> LENGTH: 10
<212> TYPE: PRT
<213> ORGANISM: Homo sapiens

<400> SEQUENCE: 527

Thr Ile Ala Glu Ile Arg Glu His Thr Val
1               5                   10

<210> SEQ ID NO 528
<211> LENGTH: 10
<212> TYPE: PRT
<213> ORGANISM: Homo sapiens

<400> SEQUENCE: 528

Val Val Val Asp Ala Val Glu His Val Val
1               5                   10

<210> SEQ ID NO 529
<211> LENGTH: 10
<212> TYPE: PRT
<213> ORGANISM: Homo sapiens

<400> SEQUENCE: 529

Ala Leu Ala Asp Gly Arg Glu Leu Thr Ala
1               5                   10

<210> SEQ ID NO 530
<211> LENGTH: 10
<212> TYPE: PRT
<213> ORGANISM: Homo sapiens

<400> SEQUENCE: 530

Gly Ala Ala Asp Gly Phe Thr Val Thr Val
1               5                   10

<210> SEQ ID NO 531
<211> LENGTH: 10
<212> TYPE: PRT
<213> ORGANISM: Homo sapiens

<400> SEQUENCE: 531

Gly Val Ala Asp Gly Thr Val Gly Val Val
1               5                   10

<210> SEQ ID NO 532
<211> LENGTH: 10
<212> TYPE: PRT
<213> ORGANISM: Homo sapiens

<400> SEQUENCE: 532

Gly Leu Gln Lys Gly Arg Glu Tyr Val Val
1               5                   10

<210> SEQ ID NO 533
<211> LENGTH: 10
<212> TYPE: PRT
<213> ORGANISM: Homo sapiens

<400> SEQUENCE: 533

Gly Val Tyr Asp Phe Ala Asp Asn Gln Val
1               5                   10

<210> SEQ ID NO 534
<211> LENGTH: 10
```

```
<212> TYPE: PRT
<213> ORGANISM: Homo sapiens

<400> SEQUENCE: 534

Glu Met Tyr Glu Phe Arg Asp His Thr Val
1               5                   10

<210> SEQ ID NO 535
<211> LENGTH: 10
<212> TYPE: PRT
<213> ORGANISM: Homo sapiens

<400> SEQUENCE: 535

Gly Val Tyr Ile Gly Pro Phe Cys Ile Val
1               5                   10

<210> SEQ ID NO 536
<211> LENGTH: 10
<212> TYPE: PRT
<213> ORGANISM: Homo sapiens

<400> SEQUENCE: 536

Phe Val Ala Asp Gly Arg Leu Lys Thr Ile
1               5                   10

<210> SEQ ID NO 537
<211> LENGTH: 10
<212> TYPE: PRT
<213> ORGANISM: Homo sapiens

<400> SEQUENCE: 537

Arg Leu Val Asp Gly Arg Asp Trp Ala Thr
1               5                   10

<210> SEQ ID NO 538
<211> LENGTH: 10
<212> TYPE: PRT
<213> ORGANISM: Homo sapiens

<400> SEQUENCE: 538

Ser Leu Val Asp Gly Arg Asp Trp Ser Thr
1               5                   10

<210> SEQ ID NO 539
<211> LENGTH: 10
<212> TYPE: PRT
<213> ORGANISM: Homo sapiens

<400> SEQUENCE: 539

Gly Leu Lys Glu Gly Ile Glu Thr Leu Leu
1               5                   10

<210> SEQ ID NO 540
<211> LENGTH: 10
<212> TYPE: PRT
<213> ORGANISM: Homo sapiens

<400> SEQUENCE: 540

Ala Leu Ala Asp Gly Arg Asp Leu Ser Ala
1               5                   10

<210> SEQ ID NO 541
<211> LENGTH: 10
<212> TYPE: PRT
<213> ORGANISM: Homo sapiens
```

```
<400> SEQUENCE: 541

Gly Gln Ala Glu Gly Glu Ile Phe Ile
1               5                   10

<210> SEQ ID NO 542
<211> LENGTH: 10
<212> TYPE: PRT
<213> ORGANISM: Homo sapiens

<400> SEQUENCE: 542

Gly Leu Ile Gly Gly Arg Asp Asp Tyr Leu
1               5                   10

<210> SEQ ID NO 543
<211> LENGTH: 10
<212> TYPE: PRT
<213> ORGANISM: Homo sapiens

<400> SEQUENCE: 543

Gly Leu Ile Asp Ala Ser Glu Gln Asn Ala
1               5                   10

<210> SEQ ID NO 544
<211> LENGTH: 10
<212> TYPE: PRT
<213> ORGANISM: Homo sapiens

<400> SEQUENCE: 544

Ala Thr Val Glu His Leu Met Ala Ala Leu
1               5                   10

<210> SEQ ID NO 545
<211> LENGTH: 10
<212> TYPE: PRT
<213> ORGANISM: Homo sapiens

<400> SEQUENCE: 545

Gly Ile Glu Glu Gly Leu Met Thr Thr Val
1               5                   10

<210> SEQ ID NO 546
<211> LENGTH: 10
<212> TYPE: PRT
<213> ORGANISM: Homo sapiens

<400> SEQUENCE: 546

Ala Ile Cys Asp Ala Leu Asp Val Pro Leu
1               5                   10

<210> SEQ ID NO 547
<211> LENGTH: 10
<212> TYPE: PRT
<213> ORGANISM: Homo sapiens

<400> SEQUENCE: 547

Ala Val Val Asp Gly Leu Asp Ala Ala Ile
1               5                   10

<210> SEQ ID NO 548
<211> LENGTH: 10
<212> TYPE: PRT
<213> ORGANISM: Homo sapiens

<400> SEQUENCE: 548
```

Ala Thr Ala Asp Ala Pro Glu Phe Gly Val
1               5                   10

<210> SEQ ID NO 549
<211> LENGTH: 10
<212> TYPE: PRT
<213> ORGANISM: Homo sapiens

<400> SEQUENCE: 549

Ala Leu Ile Asp Ala Leu Glu Ser Leu Pro
1               5                   10

<210> SEQ ID NO 550
<211> LENGTH: 10
<212> TYPE: PRT
<213> ORGANISM: Homo sapiens

<400> SEQUENCE: 550

Arg Val Tyr Gly Gly Gly Ala Asn Thr Val
1               5                   10

<210> SEQ ID NO 551
<211> LENGTH: 10
<212> TYPE: PRT
<213> ORGANISM: Homo sapiens

<400> SEQUENCE: 551

Gly Val Tyr Leu Gly Ser Thr Val Gln Val
1               5                   10

<210> SEQ ID NO 552
<211> LENGTH: 10
<212> TYPE: PRT
<213> ORGANISM: Homo sapiens

<400> SEQUENCE: 552

Thr Val Phe Gln Gly Arg Ser Pro Thr Val
1               5                   10

<210> SEQ ID NO 553
<211> LENGTH: 10
<212> TYPE: PRT
<213> ORGANISM: Homo sapiens

<400> SEQUENCE: 553

Ala Val Tyr Asp Thr Arg Ala Ser Gly Val
1               5                   10

<210> SEQ ID NO 554
<211> LENGTH: 10
<212> TYPE: PRT
<213> ORGANISM: Homo sapiens

<400> SEQUENCE: 554

Asn Val Tyr Asp Ile Leu Glu Val Asp Val
1               5                   10

<210> SEQ ID NO 555
<211> LENGTH: 10
<212> TYPE: PRT
<213> ORGANISM: Homo sapiens

<400> SEQUENCE: 555

Ala Val Ala Asp Tyr Arg Gly Leu Thr Val

```
1               5                   10
```

<210> SEQ ID NO 556
<211> LENGTH: 10
<212> TYPE: PRT
<213> ORGANISM: Homo sapiens

<400> SEQUENCE: 556

```
Gly Val Met Asp Met Phe Pro His Thr Met
1               5                   10
```

<210> SEQ ID NO 557
<211> LENGTH: 10
<212> TYPE: PRT
<213> ORGANISM: Homo sapiens

<400> SEQUENCE: 557

```
Gly Val Asn Asp Val Leu Glu Ala Leu Val
1               5                   10
```

<210> SEQ ID NO 558
<211> LENGTH: 10
<212> TYPE: PRT
<213> ORGANISM: Homo sapiens

<400> SEQUENCE: 558

```
Val Val Ala Asp Tyr Arg Gly Leu Thr Val
1               5                   10
```

<210> SEQ ID NO 559
<211> LENGTH: 10
<212> TYPE: PRT
<213> ORGANISM: Homo sapiens

<400> SEQUENCE: 559

```
Gly Val Phe Ser Thr Val Glu Gln Thr Val
1               5                   10
```

<210> SEQ ID NO 560
<211> LENGTH: 10
<212> TYPE: PRT
<213> ORGANISM: Homo sapiens

<400> SEQUENCE: 560

```
Arg Val Leu Asp Gly Arg Val Ala Val Val
1               5                   10
```

<210> SEQ ID NO 561
<211> LENGTH: 10
<212> TYPE: PRT
<213> ORGANISM: Homo sapiens

<400> SEQUENCE: 561

```
Lys Val Tyr Pro Met Arg Ser His Thr Val
1               5                   10
```

<210> SEQ ID NO 562
<211> LENGTH: 10
<212> TYPE: PRT
<213> ORGANISM: Homo sapiens

<400> SEQUENCE: 562

```
Gly Val Leu Asp Val Gly Ser Asn Thr Val
1               5                   10
```

```
<210> SEQ ID NO 563
<211> LENGTH: 10
<212> TYPE: PRT
<213> ORGANISM: Homo sapiens

<400> SEQUENCE: 563

Gly Val Tyr Gln Ser Leu His Thr Thr Val
1               5                   10

<210> SEQ ID NO 564
<211> LENGTH: 10
<212> TYPE: PRT
<213> ORGANISM: Homo sapiens

<400> SEQUENCE: 564

Gly Ile Arg Asp Gly Val Val Ala Thr Val
1               5                   10

<210> SEQ ID NO 565
<211> LENGTH: 10
<212> TYPE: PRT
<213> ORGANISM: Homo sapiens

<400> SEQUENCE: 565

Arg Thr Ser Asp Gly Val Glu His Pro Val
1               5                   10

<210> SEQ ID NO 566
<211> LENGTH: 10
<212> TYPE: PRT
<213> ORGANISM: Homo sapiens

<400> SEQUENCE: 566

Met Val Ser Arg Gly Arg Val His Ala Val
1               5                   10

<210> SEQ ID NO 567
<211> LENGTH: 10
<212> TYPE: PRT
<213> ORGANISM: Homo sapiens

<400> SEQUENCE: 567

Leu Val Ala Lys Gly Ile Glu Ala Thr Val
1               5                   10

<210> SEQ ID NO 568
<211> LENGTH: 10
<212> TYPE: PRT
<213> ORGANISM: Homo sapiens

<400> SEQUENCE: 568

Lys Val Leu Asp Tyr Lys Glu His Thr Leu
1               5                   10

<210> SEQ ID NO 569
<211> LENGTH: 10
<212> TYPE: PRT
<213> ORGANISM: Homo sapiens

<400> SEQUENCE: 569

Thr Val Leu Asp Gly Arg Gly Ala Pro Val
1               5                   10

<210> SEQ ID NO 570
```

```
<211> LENGTH: 10
<212> TYPE: PRT
<213> ORGANISM: Homo sapiens

<400> SEQUENCE: 570

Thr Val Ile Asp Arg Arg Leu His Leu Val
1               5                   10

<210> SEQ ID NO 571
<211> LENGTH: 10
<212> TYPE: PRT
<213> ORGANISM: Homo sapiens

<400> SEQUENCE: 571

Leu Val Leu Asp Gly Thr Glu Glu Ile Val
1               5                   10

<210> SEQ ID NO 572
<211> LENGTH: 10
<212> TYPE: PRT
<213> ORGANISM: Homo sapiens

<400> SEQUENCE: 572

Ala Val Tyr Asn Gly Arg Gly Leu Pro Val
1               5                   10

<210> SEQ ID NO 573
<211> LENGTH: 10
<212> TYPE: PRT
<213> ORGANISM: Homo sapiens

<400> SEQUENCE: 573

Thr Val Leu Asp Arg Arg Leu His Leu Val
1               5                   10

<210> SEQ ID NO 574
<211> LENGTH: 10
<212> TYPE: PRT
<213> ORGANISM: Homo sapiens

<400> SEQUENCE: 574

Val Glu Leu Asp Gly Gln Thr His Thr Val
1               5                   10

<210> SEQ ID NO 575
<211> LENGTH: 10
<212> TYPE: PRT
<213> ORGANISM: Homo sapiens

<400> SEQUENCE: 575

Phe Val Tyr His Val Gln Glu Arg Thr Val
1               5                   10

<210> SEQ ID NO 576
<211> LENGTH: 10
<212> TYPE: PRT
<213> ORGANISM: Homo sapiens

<400> SEQUENCE: 576

Arg Arg Leu Asp Gly Arg Ala Ile Thr Val
1               5                   10

<210> SEQ ID NO 577
<211> LENGTH: 10
<212> TYPE: PRT
```

```
<213> ORGANISM: Homo sapiens

<400> SEQUENCE: 577

Gly Leu Arg Leu Gly Arg Leu Lys Thr Val
1               5                   10

<210> SEQ ID NO 578
<211> LENGTH: 10
<212> TYPE: PRT
<213> ORGANISM: Homo sapiens

<400> SEQUENCE: 578

Gly Glu Leu His Gly Cys Glu His Ser Val
1               5                   10

<210> SEQ ID NO 579
<211> LENGTH: 10
<212> TYPE: PRT
<213> ORGANISM: Homo sapiens

<400> SEQUENCE: 579

Gly Val Tyr Asp Asp Gln Thr Val Asp Val
1               5                   10

<210> SEQ ID NO 580
<211> LENGTH: 10
<212> TYPE: PRT
<213> ORGANISM: Homo sapiens

<400> SEQUENCE: 580

Gly Val Met Gly Gly Arg Asn Ser Glu Val
1               5                   10

<210> SEQ ID NO 581
<211> LENGTH: 10
<212> TYPE: PRT
<213> ORGANISM: Homo sapiens

<400> SEQUENCE: 581

Leu Val Asp Asp Leu Ile Glu Lys Thr Val
1               5                   10

<210> SEQ ID NO 582
<211> LENGTH: 10
<212> TYPE: PRT
<213> ORGANISM: Homo sapiens

<400> SEQUENCE: 582

Gly Glu Ile Asp Glu Asn Leu His Thr Val
1               5                   10

<210> SEQ ID NO 583
<211> LENGTH: 10
<212> TYPE: PRT
<213> ORGANISM: Homo sapiens

<400> SEQUENCE: 583

Gly Val Trp Pro Arg Ala Glu Leu Thr Val
1               5                   10

<210> SEQ ID NO 584
<211> LENGTH: 10
<212> TYPE: PRT
<213> ORGANISM: Homo sapiens
```

```
<400> SEQUENCE: 584

Arg Val Val Asp Gly Val Arg Leu Thr Val
1               5                   10

<210> SEQ ID NO 585
<211> LENGTH: 10
<212> TYPE: PRT
<213> ORGANISM: Homo sapiens

<400> SEQUENCE: 585

Lys Leu Ser Asp Gly Arg Arg His Asp Val
1               5                   10

<210> SEQ ID NO 586
<211> LENGTH: 10
<212> TYPE: PRT
<213> ORGANISM: Homo sapiens

<400> SEQUENCE: 586

Lys Val Phe Pro Thr Arg Ser His Thr Val
1               5                   10

<210> SEQ ID NO 587
<211> LENGTH: 10
<212> TYPE: PRT
<213> ORGANISM: Homo sapiens

<400> SEQUENCE: 587

Phe Val Ala Gln Cys Arg Glu His Gly Val
1               5                   10

<210> SEQ ID NO 588
<211> LENGTH: 10
<212> TYPE: PRT
<213> ORGANISM: Homo sapiens

<400> SEQUENCE: 588

Ser Ile Tyr Thr Pro Thr Glu His Thr Val
1               5                   10

<210> SEQ ID NO 589
<211> LENGTH: 10
<212> TYPE: PRT
<213> ORGANISM: Homo sapiens

<400> SEQUENCE: 589

Gly Leu Tyr Asp Gly Arg Glu His Ser Val
1               5                   10
```

ANTIBODIES BINDING TO HLA-A2/MAGE-A4

CROSS REFERENCE TO RELATED APPLICATIONS

This application is a Continuation of European Application No. 19217463.9, filed Dec. 18, 2019, which is incorporated herein by reference in its entirety.

SEQUENCE LISTING

This application contains a Sequence Listing which has been submitted electronically in ASCII format and is hereby incorporated by reference in its entirety. Said ASCII copy, created on Dec. 4, 2020, is named P35782-US_Sequence_listing_ST25.txt and is 147,396 bytes in size.

FIELD OF THE INVENTION

The present invention generally relates to antibodies that bind to HLA-A2/MAGE-A4, including multispecific antibodies e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

MAGE-A4 (Melanoma-associated antigen 4) is a member of the MAGE family of Cancer Testis Antigens (CTAs). The MAGE-A family of proteins encompasses 12 highly homologous genes clustered at Xq26-28 and characterized by the presence of a conserved domain (MAGE Homology Domain, MHD). Despite having been discovered more than 20 years ago, biological functions of MAGE proteins still remain poorly understood. Based on their expression pattern, the MAGE family can be divided into two subfamilies, type-I and type-II, with the MAGE-A group belonging to the type-I subfamily whose expression is restricted to germ line and cancer cells. A correlation between overexpression of type-I MAGEs and cancer malignance, tumor growth and poor patient prognosis has been suggested by many reports. Intracellular proteins such as MAGE-A4 can be degraded in the proteasome, processed and presented on the cell surface by major histocompatibility complex (MHC) I as T cell epitopes. As such, MAGE-A4-derived peptides such as MAGE-A4$_{p230-239}$ (GVYDGREHTV) are presented in the context of HLA-A2 on the cell surface and can trigger T cell recognition.

Given its expression pattern, MAGE-A4 may be a promising target for cancer therapy. Approaches taken to date to exploit MAGE-A4 as target for cancer (immuno) therapy mostly focus on the development of T cell receptors (TCRs) targeting HLA-A2/MAGE-A4 and use thereof in genetically engineered T cells (WO 2017/174824) or fusion molecules (WO 2017/175006). A TCR-like antibody against the HLA-A2/MAGE-A4 complex, including a bispecific derivative thereof (additionally targeting CD3), has also been generated (WO 2016/199141).

Bispecific antibodies that bind to a surface antigen on target cells and an activating T cell antigen such as CD3 on T-cells (also called herein T cell bispecific antibodies or "TCBs") hold great promise for the treatment of various cancers. The simultaneous binding of such an antibody to both of its targets will force a temporary interaction between target cell and T cell, causing crosslinking of the T cell receptor and subsequent activation of any cytotoxic T cell and subsequent lysis of the target cell. Given their potency in target cell killing, the choice of target and the specificity of the targeting antibody is of utmost importance for T cell bispecific antibodies to avoid on- and off-target toxicities. Intracellular proteins such as MAGE-A4 represent attractive targets, but are only accessible to T cell receptor (TCR)-like antibodies that bind major histocompatibility complex (MHC) presenting peptide antigens derived from the intracellular protein on the cell surface. An inherent issue of TCR-like antibodies is potential cross-reactivity with MHC molecules per se, or MHC molecules presenting peptides other than the desired one, which could compromise organ or tissue selectivity.

SUMMARY OF THE INVENTION

The present invention provides novel antibodies, including multispecific (e.g. bispecific) antibodies, that bind HLA-A2/MAGE-A4 and have particularly favorable properties for therapeutic purposes. In particular, the (multispecific) antibodies bind HLA-A2/MAGE-A4 with good affinity and remarkable specificity, and combine good efficacy and produceability with low toxicity and favorable pharmacokinetic properties.

In one aspect, the invention provides an antibody that binds to HLA-A2/MAGE-A4, wherein the antibody comprises a first antigen binding domain, comprising
  (i) a heavy chain variable region (VH) comprising a heavy chain complementary determining region (HCDR) 1 of SEQ ID NO: 25, a HCDR 2 of SEQ ID NO: 26, and a HCDR 3 of SEQ ID NO: 27, and a light chain variable region (VL) comprising a light chain complementarity determining region (LCDR) 1 of SEQ ID NO: 28, a LCDR 2 of SEQ ID NO: 29 and a LCDR 3 of SEQ ID NO: 30;
  (ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
  (iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
  (iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
  (v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
  (vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38.

In one aspect, the first antigen binding domain comprises
  (i) a VH comprising an amino acid sequence that is at least about 95%, 96%, 97%, 98%, 99% or 100% identical to the amino acid sequence of SEQ ID NO: 31, and/or a VL comprising an amino acid sequence that is at least about 95%, 96%, 97%, 98%, 99% or 100% identical to the amino acid sequence of SEQ ID NO: 32;
(ii) a VH comprising an amino acid sequence that is at least about 95%, 96%, 97%, 98%, 99% or 100% identical to the amino acid sequence of SEQ ID NO: 7, and/or a VL comprising an amino acid sequence that is at least about 95%, 96%, 97%, 98%, 99% or 100% identical to the amino acid sequence of SEQ ID NO: 8;
(iii) a VH comprising an amino acid sequence that is at least about 95%, 96%, 97%, 98%, 99% or 100% identical to the amino acid sequence of SEQ ID NO: 47, and/or a VL comprising an amino acid sequence that is at least about 95%, 96%, 97%, 98%, 99% or 100% identical to the amino acid sequence of SEQ ID NO: 48;
(iv) a VH comprising an amino acid sequence that is at least about 95%, 96%, 97%, 98%, 99% or 100% identical to the amino acid sequence of SEQ ID NO: 15, and/or a VL comprising an amino acid sequence that is at least about 95%, 96%, 97%, 98%, 99% or 100% identical to the amino acid sequence of SEQ ID NO: 16;
(v) a VH comprising an amino acid sequence that is at least about 95%, 96%, 97%, 98%, 99% or 100% identical to the amino acid sequence of SEQ ID NO: 23, and/or a VL comprising an amino acid sequence that is at least about 95%, 96%, 97%, 98%, 99% or 100% identical to the amino acid sequence of SEQ ID NO: 24; or
(vi) a VH comprising an amino acid sequence that is at least about 95%, 96%, 97%, 98%, 99% or 100% identical to the amino acid sequence of SEQ ID NO: 39, and/or a VL comprising an amino acid sequence that is at least about 95%, 96%, 97%, 98%, 99% or 100% identical to the amino acid sequence of SEQ ID NO: 40.

In a further aspect, the invention provides an antibody that binds to HLA-A2/MAGE-A4, wherein the antibody comprises a first antigen binding domain comprising
(i) a VH comprising the amino acid sequence of SEQ ID NO: 31, and/or a VL comprising the amino acid sequence of SEQ ID NO: 32;
(ii) a VH comprising the amino acid sequence of SEQ ID NO: 7, and/or a VL comprising the amino acid sequence of SEQ ID NO: 8;
(iii) a VH comprising the amino acid sequence of SEQ ID NO: 47, and/or a VL comprising the amino acid sequence of SEQ ID NO: 48;
(iv) a VH comprising the amino acid sequence of SEQ ID NO: 15, and/or a VL comprising the amino acid sequence of SEQ ID NO: 16;
(v) a VH comprising the amino acid sequence of SEQ ID NO: 23, and/or a VL comprising the amino acid sequence of SEQ ID NO: 24; or
(vi) a VH comprising the amino acid sequence of SEQ ID NO: 39, and/or a VL comprising the amino acid sequence of SEQ ID NO: 40.

In one aspect, the antibody is a multispecific, particularly a bispecific, antibody.

In one aspect, the antibody comprises a second antigen binding domain which binds to a second antigen.

In one aspect, the second antigen is an activating T cell antigen, particularly CD3, most particularly CD3ε.

In one aspect, the second antigen binding domain comprises
(i) a VH comprising a HCDR 1 of SEQ ID NO: 59, a HCDR 2 of SEQ ID NO: 60, and a HCDR 3 of SEQ ID NO: 61, and a VL comprising a LCDR 1 of SEQ ID NO: 62, a LCDR 2 of SEQ ID NO: 63 and a LCDR 3 of SEQ ID NO: 64; or
(ii) a VH comprising a HCDR 1 of SEQ ID NO: 51, a HCDR 2 of SEQ ID NO: 52, and a HCDR 3 of SEQ ID NO: 53, and a VL comprising a LCDR 1 of SEQ ID NO: 54, a LCDR 2 of SEQ ID NO: 55 and a LCDR 3 of SEQ ID NO: 56.

In one aspect, the second antigen binding domain comprises
(i) a VH comprising an amino acid sequence that is at least about 95%, 96%, 97%, 98%, 99% or 100% identical to the amino acid sequence of SEQ ID NO: 65, and/or a VL comprising an amino acid sequence that is at least about 95%, 96%, 97%, 98%, 99% or 100% identical to the amino acid sequence of SEQ ID NO: 66; or
(ii) a VH comprising an amino acid sequence that is at least about 95%, 96%, 97%, 98%, 99% or 100% identical to the amino acid sequence of SEQ ID NO: 57, and/or a VL comprising an amino acid sequence that is at least about 95%, 96%, 97%, 98%, 99% or 100% identical to the amino acid sequence of SEQ ID NO: 58.

In one aspect, the second antigen binding domain comprises
(i) a VH comprising the amino acid sequence of SEQ ID NO: 65, and/or a VL comprising the amino acid sequence of SEQ ID NO: 66;
(ii) a VH comprising the amino acid sequence of SEQ ID NO: 57, and/or a VL comprising the amino acid sequence of SEQ ID NO: 58.

In one aspect, the antibody comprises a third antigen binding domain. In one aspect, the third antigen domain binds to HLA-A2/MAGE-A4. The third antigen binding domain may incorporate, singly or in combination, any of the features described herein in relation to the first antigen binding domain. In one aspect, the third antigen domain is identical to the first antigen binding domain.

In one aspect, the first antigen binding domain, the second antigen binding domain (where present) and/or the third antigen binding domain (where present) is a Fab molecule.

In one aspect, the second antigen binding domain is a Fab molecule wherein the variable domains VL and VH or the constant domains CL and CH1, particularly the variable domains VL and VH, of the Fab light chain and the Fab heavy chain are replaced by each other.

In one aspect the first and, where present, the third antigen binding domain is a conventional Fab molecule.

In one aspect, the first and, where present, the third antigen binding domain is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, the first and the second antigen binding domain are fused to each other, optionally via a peptide linker.

In one aspect, the first and the second antigen binding domain are each a Fab molecule and either (i) the first antigen binding domain is fused at the C-terminus of the Fab heavy chain to the N-terminus of the Fab heavy chain of the second antigen binding domain, or (ii) the second antigen binding domain is fused at the C-terminus of the Fab heavy chain to the N-terminus of the Fab heavy chain of the first antigen binding domain.

In one aspect, the antibody comprises an Fc domain composed of a first and a second subunit.

In one aspect, the first, the second and, where present, the third antigen binding domain are each a Fab molecule and the antibody comprises an Fc domain composed of a first and a second subunit; and either (i) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain, or (ii) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain; and the third antigen binding domain, where present, is fused at the C-terminus of the Fab heavy chain to the N-terminus of the second subunit of the Fc domain.

In one aspect, the Fc domain is an IgG, particularly an IgG$_1$, Fc domain. In one aspect the Fc domain is a human Fc domain. In one aspect, the Fc comprises a modification promoting the association of the first and the second subunit of the Fc domain. In one aspect, the Fc domain comprises one or more amino acid substitution that reduces binding to an Fc receptor and/or effector function.

According to a further aspect of the invention there is provided an isolated polynucleotide encoding an antibody of the invention, and a host cell comprising the isolated polynucleotide of the invention.

In another aspect is provided a method of producing an antibody that binds to HLA-A2/MAGE-A4, comprising the steps of (a) culturing the host cell of the invention under conditions suitable for the expression of the antibody and optionally (b) recovering the antibody. The invention also encompasses an antibody that binds to HLA-A2/MAGE-A4 produced by the method of the invention.

The invention further provides a pharmaceutical composition comprising the antibody of the invention and a pharmaceutically acceptable carrier.

Also encompassed by the invention are methods of using the antibody and pharmaceutical composition of the invention. In one aspect, the invention provides an antibody or pharmaceutical composition according to the invention for use as a medicament. In one aspect is provided an antibody or pharmaceutical composition according to the invention for use in the treatment of a disease. In a specific aspect, the disease is cancer.

Also provided is the use of an antibody or pharmaceutical composition according to the invention in the manufacture of a medicament, the use of an antibody or pharmaceutical composition according to the invention in the manufacture of a medicament for the treatment of a disease, particularly cancer. The invention also provides a method of treating a disease in an individual, comprising administering to said individual an effective amount of the antibody or pharmaceutical composition according to the invention. In a specific aspect, the disease is cancer.

BRIEF DESCRIPTION OF THE DRAWINGS

FIG. 7. Identification of binding residues of the MAGE-A4 peptide for MAGE-A4 CD3 TCBs by alanine scan. (A) EC50 values as determined by Jurkat activation, upon simultaneous binding of different MAGE-A4 CD3 TCB molecules to human CD3 on Jurkat-NFAT reporter cells and T2 cells pulsed with different ALA-scan peptides. Panel (B)

depicts the x-fold change in EC50 for the different mutated ALA-scan peptides. Critical contact residues are marked in bold.

FIG. 8. Jurkat activation, as determined by luminescence, upon simultaneous binding of different MAGE-A4 CD3 TCB molecules to human CD3 on Jurkat-NFAT reporter cells and T2 cells pulsed with either the MAGE-A4$_{p230-239}$ peptide (GVYDGREHTV) or one of the indicated 33 predicted off target peptides. Plotted is the ratio of MAGE-A4-induced signal vs. POTP-induced signal in percent ((CPS[POTP]–CPS[unpulsed cells])/(CPS[MAGE-A4]–CPS[unpulsed cells])*100). Off-target peptides with a ratio >2% were considered as relevant and are highlighted in grey.

FIG. 9. Summary of identified off-target peptide for Molecule D assessed by a Jurkat activation assay on 509 predicted off-target peptides. Depicted is the ratio of MAGE-A4-induced signal vs. POTP-induced signal in percent ((CPS[POTP]–CPS[unpulsed cells])/(CPS[MAGE-A4]–CPS[unpulsed cells])*100). Depicted are all off-target peptides that showed a signal >2% in one of the 2 assays performed.

Figure 10:
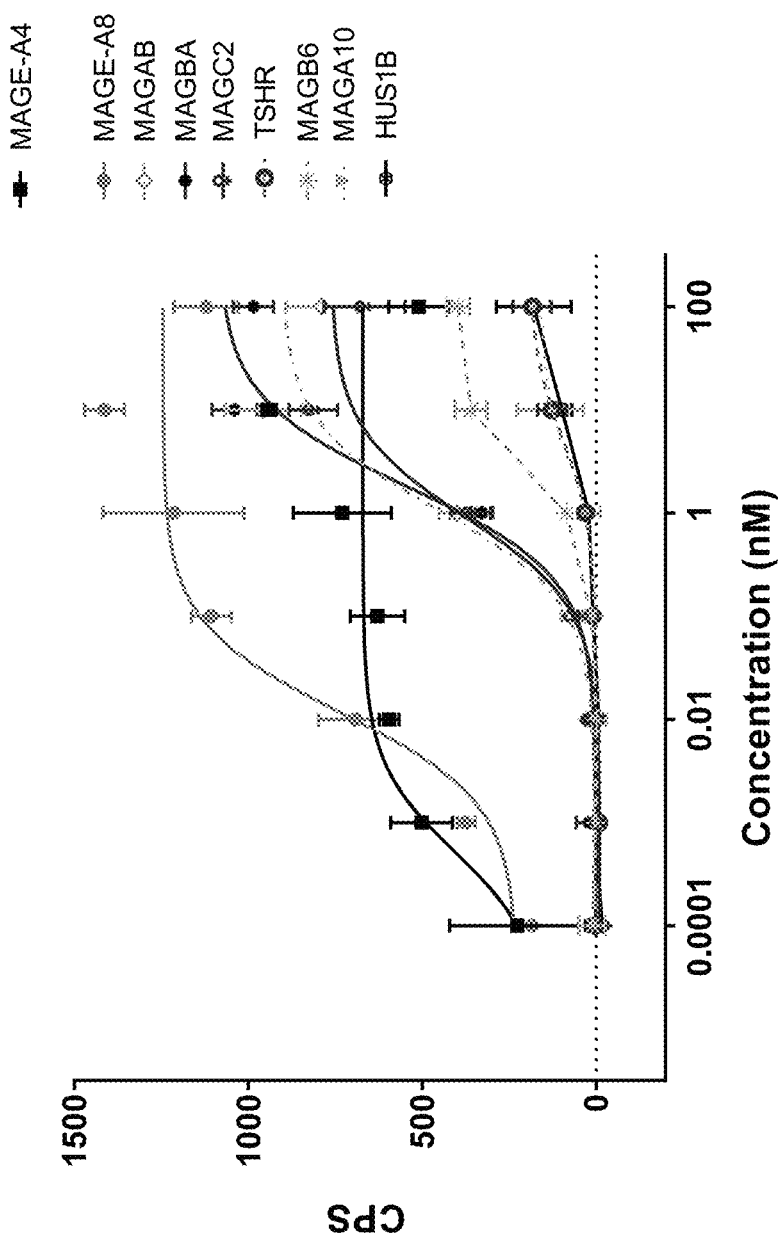

FIG. 10. Verification of identified off-target peptides of Molecule D in a Jurkat activation assay. Depicted is the measured luminescence upon simultaneous binding of Molecule D to human CD3 on Jurkat-NFAT reporter cells and T2 cells pulsed with the off-target peptides of interest.

FIG. 11. Summary of identified off-target peptides for Molecule G assessed by a Jurkat activation assay on 509 predicted off-target peptides. Depicted is the ratio of MAGE-A4-induced signal vs. POTP-induced signal in percent ((CPS[POTP]–CPS[unpulsed cells])/(CPS[MAGE-A4]–CPS[unpulsed cells])*100). Depicted are all off-target peptides that showed a signal >2%.

Figure 12:
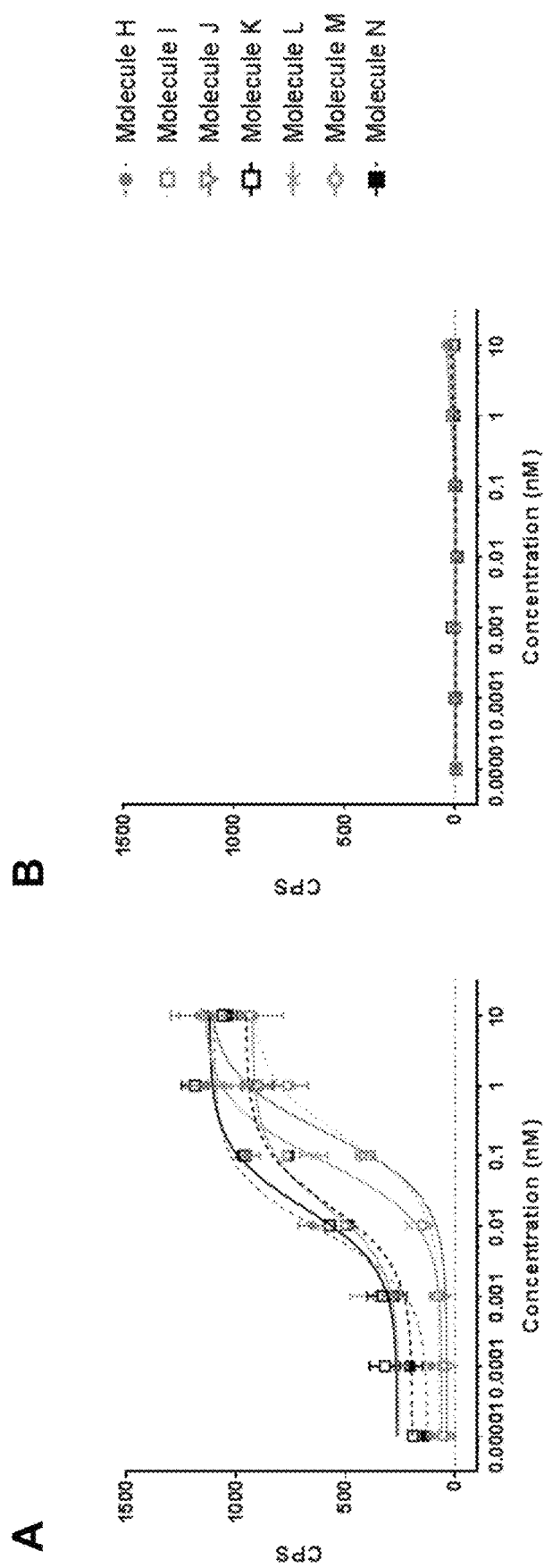

FIG. 12. PGLALA-CAR-J activation, upon simultaneous binding of the PGLALA-modified Fc domain of different MAGE-A4 IgG molecules to Jurkat-NFAT reporter cells, which were genetically engineered to express a TCR-directed against the PGLALA mutation in the Fc part of IgG molecules and T2 cells pulsed with the MAGE-A4$_{p230-239}$ peptide (GVYDGREHTV) (A) or to MAGE-A4-/HLA-A2+ MDA-MB231 cells (B). Depicted are triplicates with SD.

Figure 13:
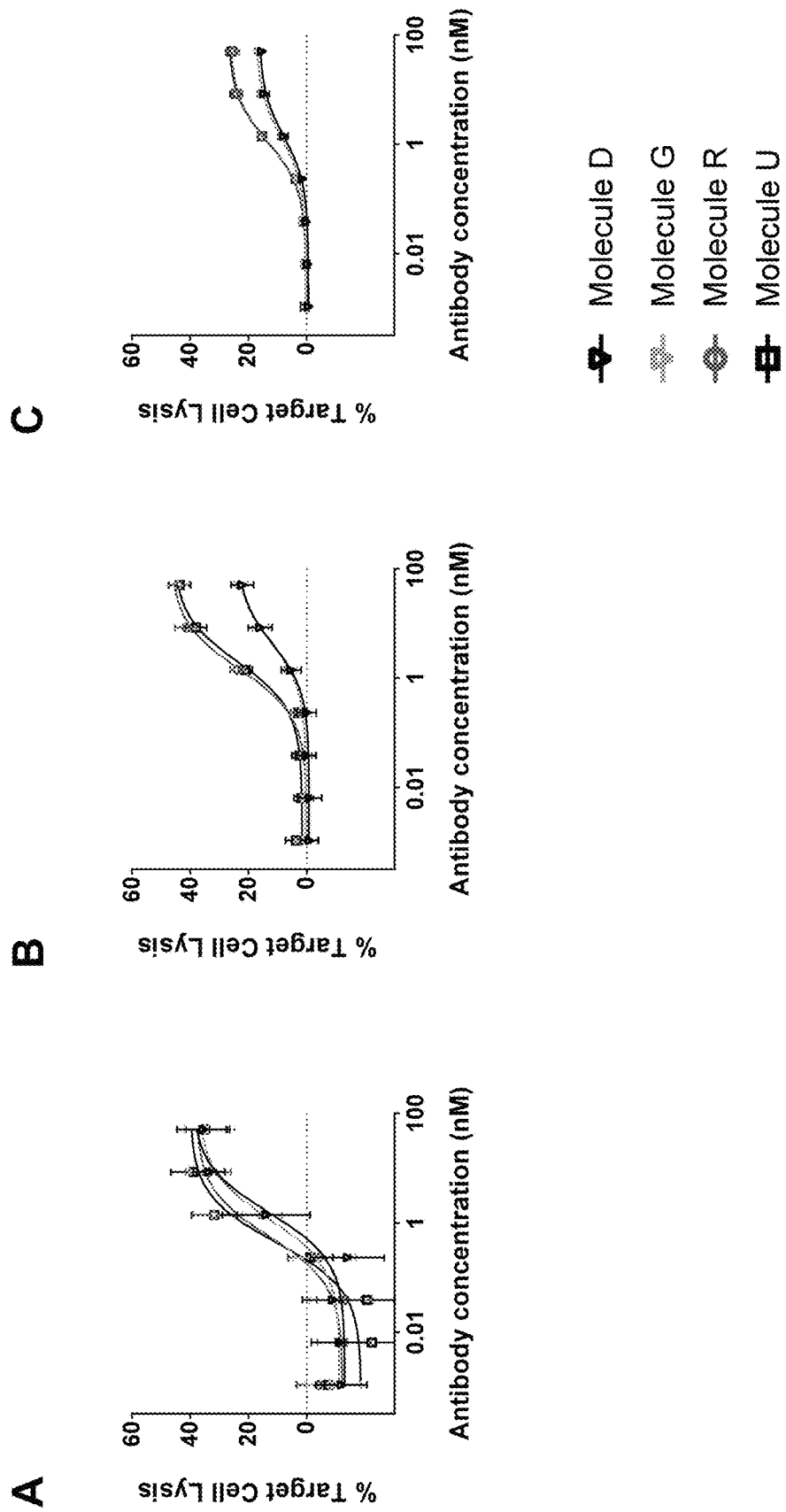

FIG. 13. T-cell mediated lysis of various HLA-A2+/MAGE-A4+ tumor cell lines of different indications induced by different MAGE-A4 CD3 TCB molecules containing a combination of different MAGE-A4 and CD3 binders (E:T=10:1, human PBMC effector cells). Depicted are triplicates with SD. (A) UMUC-3 cells, (B) A375 cells, (C) NCI-H2023.

Figure 14:
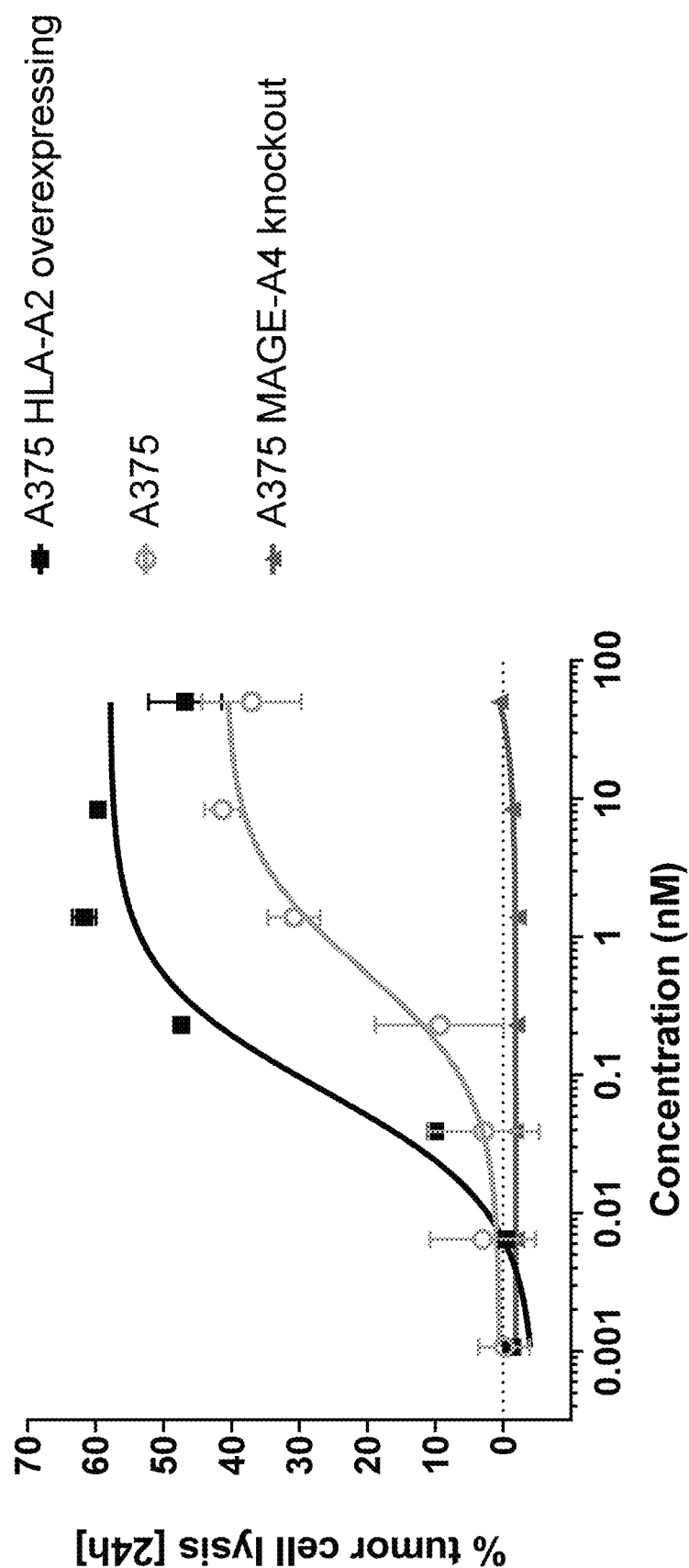

FIG. 14. T-cell mediated lysis of A375 cells, A375 cells engineered to overexpress HLA-A2 and A375 cells with MAGE-A4 knockout, induced by MAGE-A4 CD3 TCB Molecule R (E:T=10:1, human PBMC effector cells).

Figure 15:
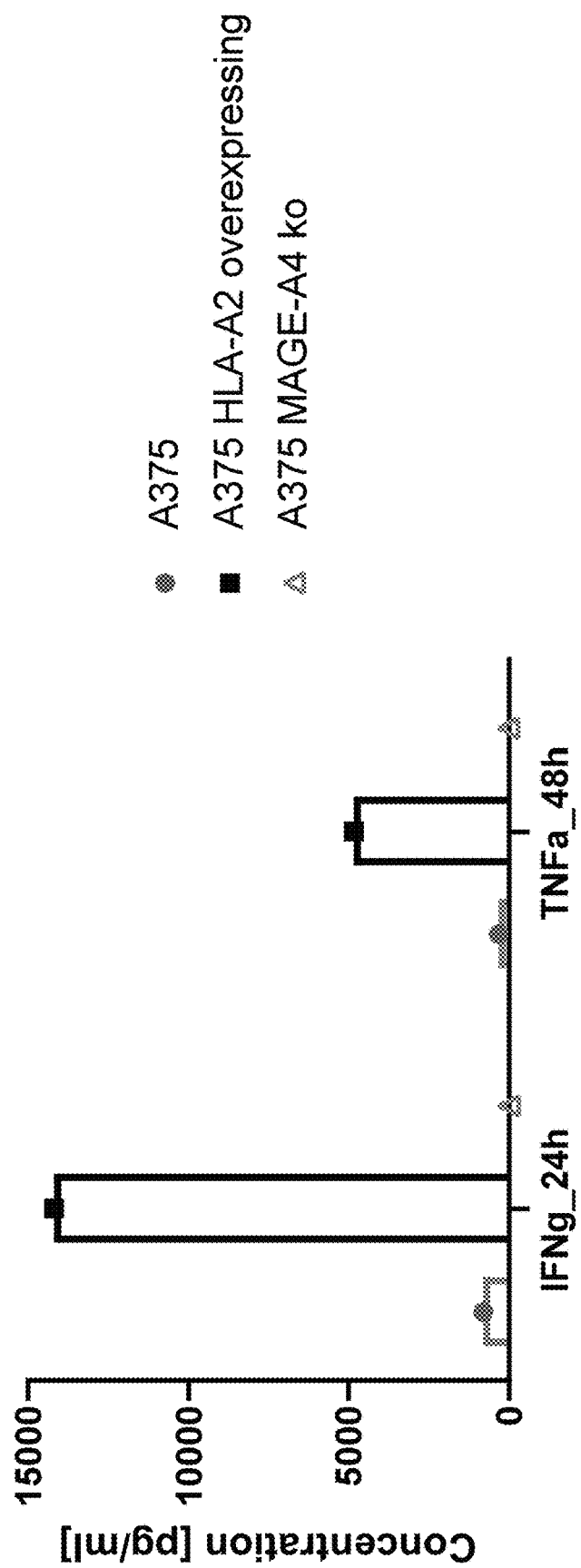

FIG. 15. Cytokine release upon T-cell mediated lysis of A375 cells, A375 cells engineered to overexpress HLA-A2 and A375 cells with MAGE-A4 knockout (ko), induced by MAGE-A4 CD3 TCB Molecule R (E:T=10:1, human PBMC effector cells).

Figure 16:
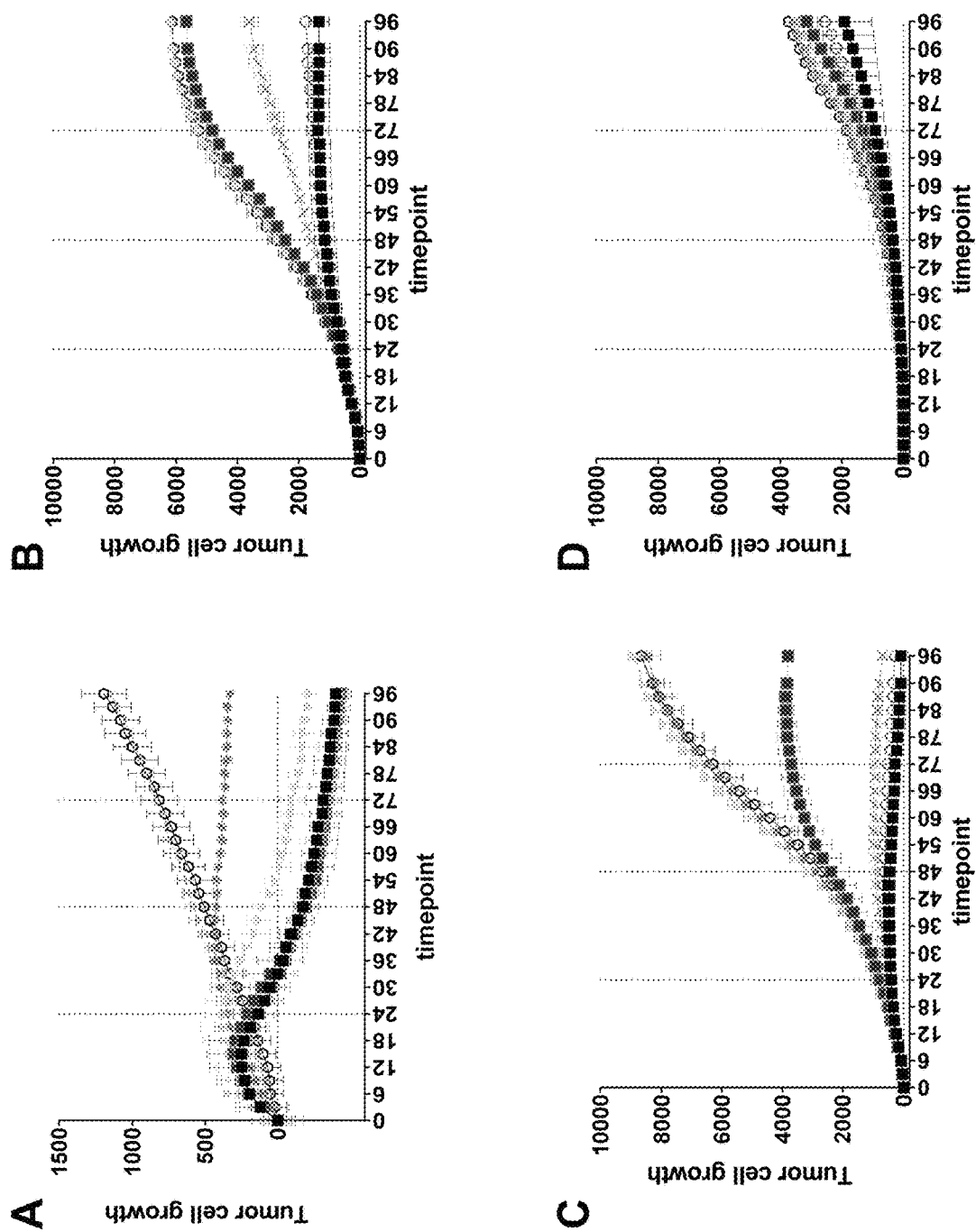
Figure 16:
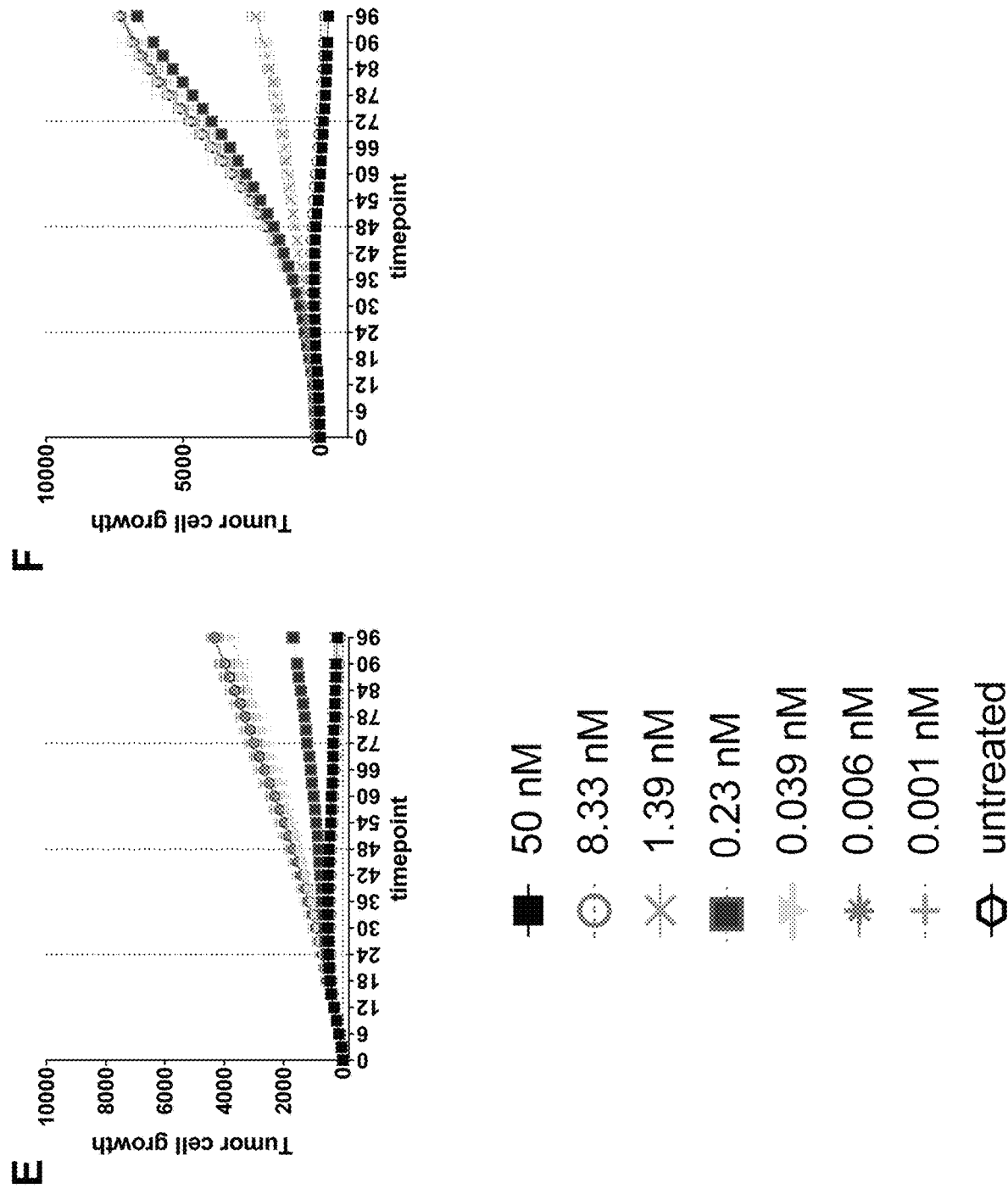

FIG. 16. Real-time assessment of growth of different HLA-A2+/MAGE-A4+ tumor cells lines upon treatment with MAGE-A4 CD3 TCB Molecule R (E:T=5:1, human PBMC effector cells). (A) NCI-H1755; (B) UMUC-3; (C) A375; (D) ScaBer; (E) NCI-H1703; (F) NCI-H2023.

Figure 17:
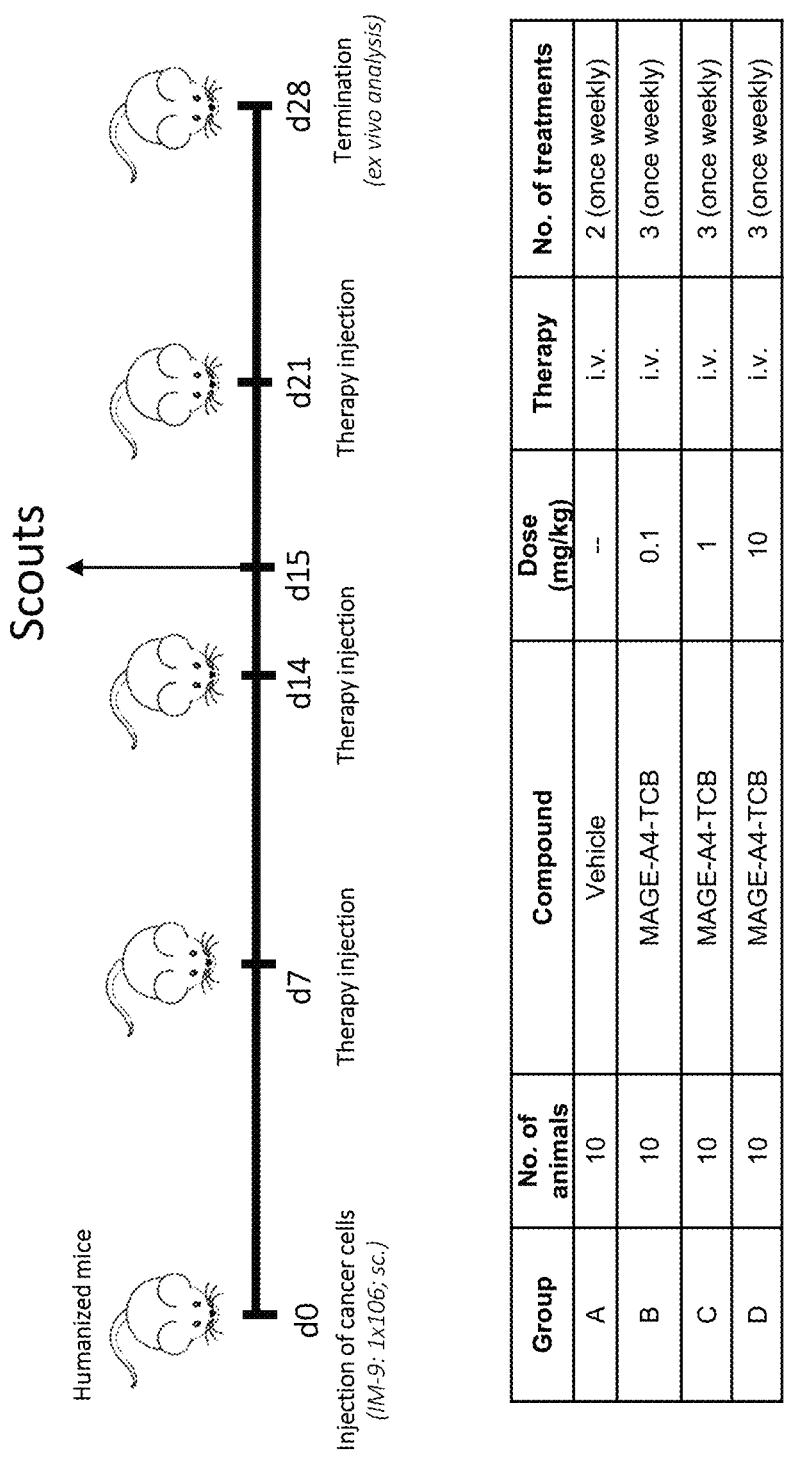

FIG. 17. Study design and groups of dose finding efficacy study with MAGE-A4 CD3 TCB Molecule R in IM-9 xenograft in humanized mice as described in Example 13.

Figure 18:
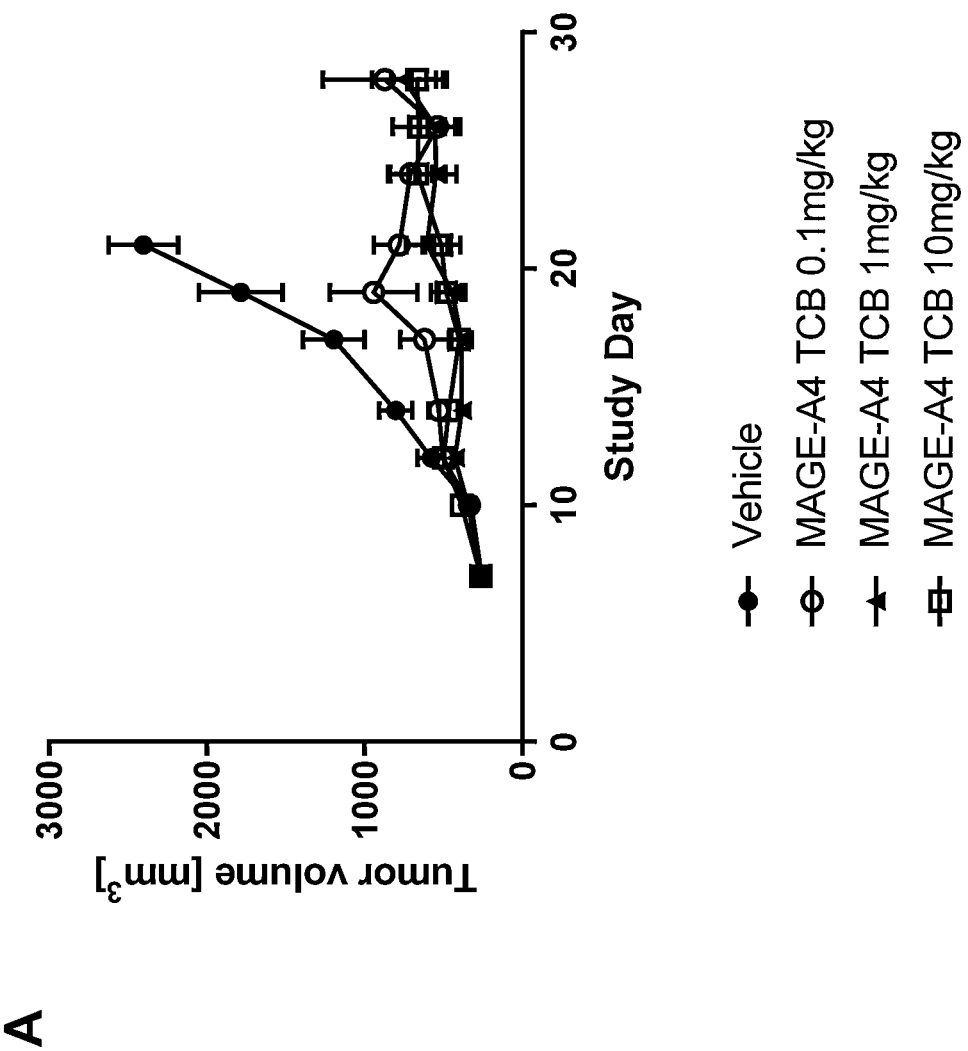
Figure 18:
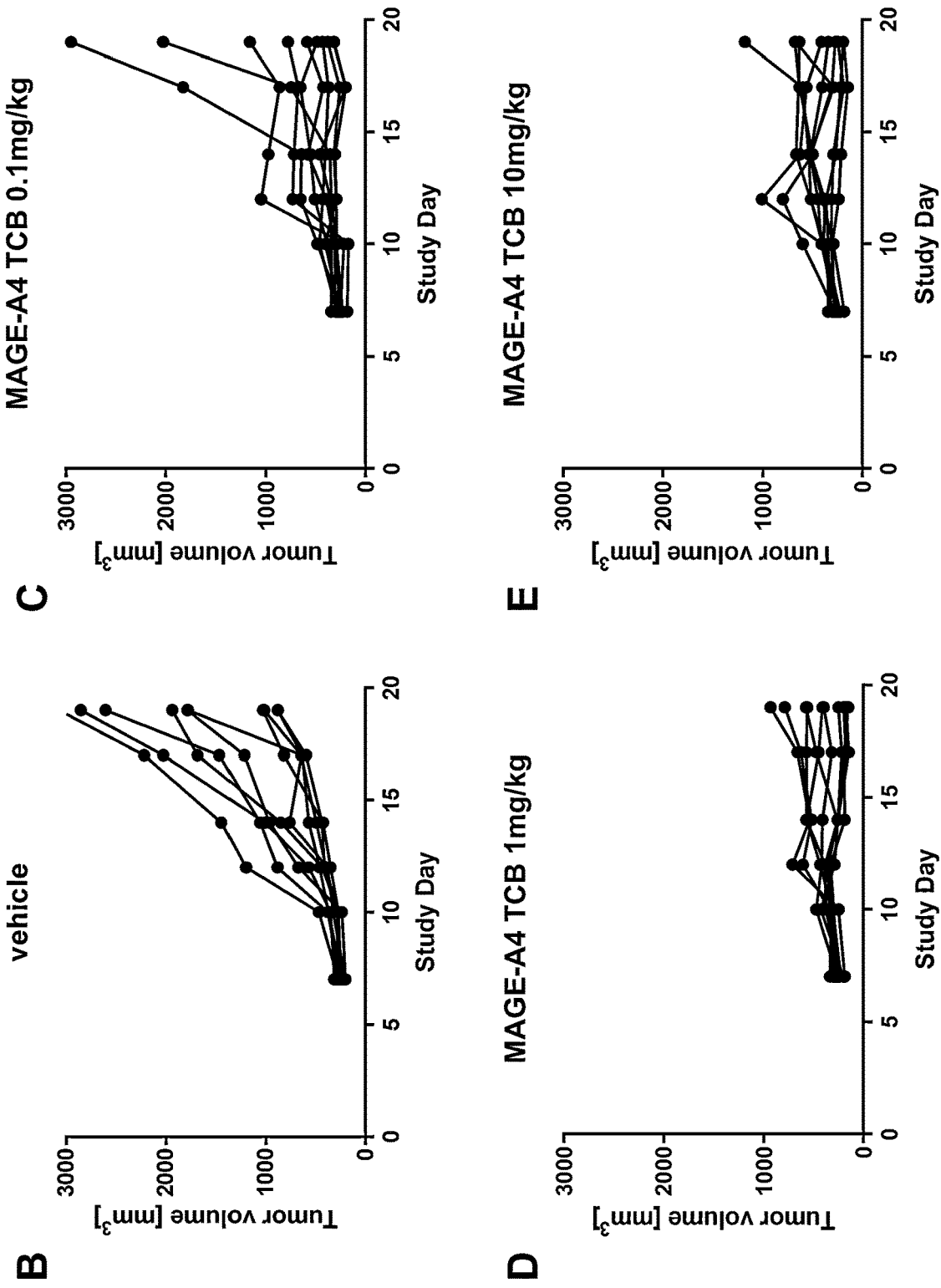

FIG. 18. Tumor growth kinetics in all groups in the dose finding efficacy study with MAGE-A4 CD3 TCB Molecule R in IM-9 xenograft in humanized mice as described in Example 13. (A) mean+/–SEM; (B-E) individual tumor growth per mouse.

Figure 19:
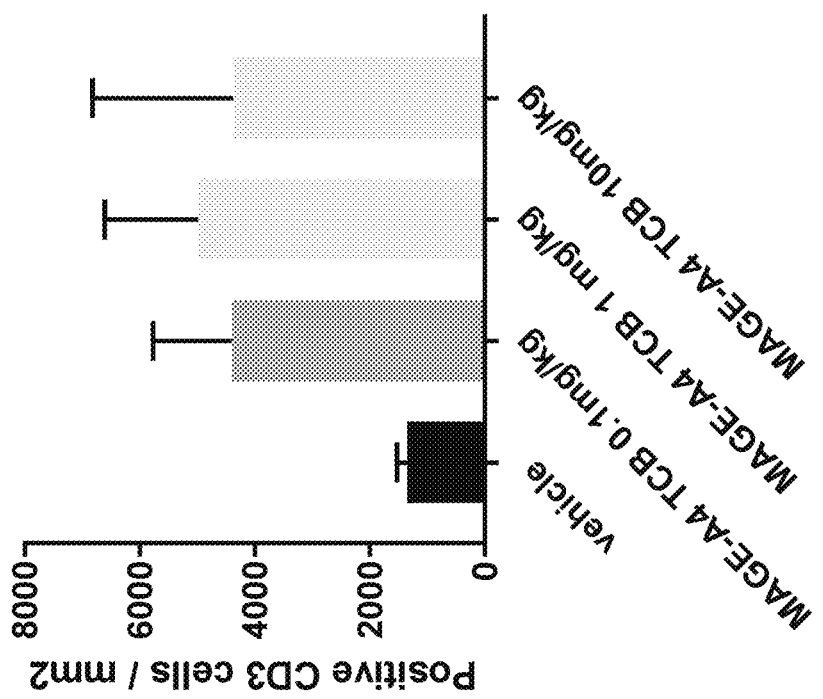

FIG. 19. T cell infiltration in the tumor (B) in the dose finding efficacy study with MAGE-A4 CD3 TCB Molecule R in IM-9 xenograft in humanized mice as described in Example 13.

DETAILED DESCRIPTION OF THE INVENTION

I. Definitions

Terms are used herein as generally used in the art, unless otherwise defined in the following.

As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated. Generally, however, the antigen binding domain that binds to HLA-A2/MAGE-A4 is referred to herein as "first antigen binding domain" (and in case of a further antigen binding domain being present that binds to HLA-A2/MAGE-A4, as "third antigen binding domain"), and the antigen binding domain that binds to the second antigen is referred to herein as "second antigen binding domain".

The terms "anti-HLA-A2/MAGE-A4 antibody" and "an antibody that binds to HLA-A2/MAGE-A4" refer to an antibody that is capable of binding HLA-A2/MAGE-A4 with sufficient affinity such that the antibody is useful as a diagnostic and/or therapeutic agent in targeting HLA-A2/MAGE-A4. In one aspect, the extent of binding of an anti-HLA-A2/MAGE-A4 antibody to an unrelated, non-HLA-A2/MAGE-A4 protein is less than about 10% of the binding of the antibody to HLA-A2/MAGE-A4 as measured, e.g., by surface plasmon resonance (SPR). In certain aspects, an antibody that binds to HLA-A2/MAGE-A4 has a dissociation constant ($K_D$) of ≤1 µM, ≤500 nM, ≤200 nM, ≤100 nM, ≤10 nM, ≤1 nM, or ≤0.1 nM.

By "specific binding" is meant that the binding is selective for the antigen and can be discriminated from unwanted or non-specific interactions. Suitable assays for determining the specificity of the antibody of the present invention are described herein, e.g. in Example 9 hereinbelow. In one aspect, the extent of binding of an antibody to an unrelated protein is less than about 10% of the binding of the antibody to the antigen as measured, e.g., by SPR.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv and scFab), single-domain antibodies, and multispecific antibodies formed from antibody fragments. For a review of certain antibody fragments, see Hollinger and Hudson, Nature Biotechnology 23:1126-1136 (2005).

The terms "full-length antibody," "intact antibody," and "whole antibody" are used herein interchangeably to refer to an antibody having a structure substantially similar to a native antibody structure.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC, affinity chromatography, size exclusion chromatography) methods. For review of methods for assessment of antibody purity, see, e.g., Flatman et al., *J. Chromatogr. B* 848:79-87 (2007). In some aspects, the antibodies provided by the present invention are isolated antibodies.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some aspects, some FR residues in a humanized antibody are substituted with corresponding residues from a non-human antibody (e.g., the antibody from which the CDR residues are derived), e.g., to restore or improve antibody specificity or affinity. A "humanized form" of an antibody, e.g. of a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain aspects, a human antibody is derived from a non-human transgenic mammal, for example a mouse, a rat, or a rabbit. In certain aspects, a human antibody is derived from a hybridoma cell line. Antibodies or antibody fragments isolated from human antibody libraries are also considered human antibodies or human antibody fragments herein.

The term "antigen binding domain" refers to the part of an antibody that comprises the area which binds to and is complementary to part or all of an antigen. An antigen binding domain may be provided by, for example, one or more antibody variable domains (also called antibody variable regions). In preferred aspects, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and complementarity determining regions (CDRs). See, e.g., Kindt et al., *Kuby Immunology*, $6^{th}$ ed., W.H. Freeman & Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, hinge, CH2 and CH3), which is herein further clarified by referring to "numbering according to Kabat EU index" or "Kabat EU index numbering" in this case.

The term "hypervariable region" or "HVR", as used herein, refers to each of the regions of an antibody variable domain which are hypervariable in sequence and which determine antigen binding specificity, for example "complementarity determining regions" ("CDRs"). Generally, antibodies comprise six CDRs; three in the VH (HCDR1, HCDR2, HCDR3), and three in the VL (LCDR1, LCDR2, LCDR3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementarity determining regions (CDRs). The FR of a variable domain generally consists of four FR domains: FR1, FR2, FR3, and FR4. Accordingly, the HVR and FR sequences generally appear in the following order in VH (or VL): FR1-HCDR1(LCDR1)-FR2-HCDR2(LCDR2)-FR3-HCDR3(LCDR3)-FR4.

Unless otherwise indicated, CDR residues and other residues in the variable domain (e.g., FR residues) are numbered herein according to Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes is 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3.

The term "immunoglobulin molecule" herein refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "Fc domain" or "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present. Amino acid sequences of heavy chains including an Fc region (or a subunit of an Fc domain as defined herein) are denoted herein without C-terminal glycine-lysine dipeptide if not indicated otherwise. In one aspect, a heavy chain including an Fc region (subunit) as specified herein, comprised in an antibody according to the invention, comprises an additional C-terminal glycine-lysine dipeptide (G446 and K447, numbering according to Kabat EU index). In one aspect, a heavy chain including an Fc region (subunit) as specified herein, comprised in an antibody according to the invention, comprises an additional C-terminal glycine residue (G446, numbering according to Kabat EU index). Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain. By "fused" is meant that the components (e.g. a Fab molecule and an Fc domain subunit) are linked by peptide bonds, either directly or via one or more peptide linkers.

The term "multispecific" means that the antibody is able to specifically bind to at least two distinct antigenic determinants. A multispecific antibody can be, for example, a bispecific antibody. Typically, a bispecific antibody comprises two antigen binding sites, each of which is specific for a different antigenic determinant. In certain aspects the multispecific (e.g. bispecific) antibody is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigenic determinant" or "antigen" refers to a site (e.g. a contiguous stretch of amino acids or a conformational configuration made up of different regions of non-contiguous amino acids) on a polypeptide macromolecule to which an antigen binding domain binds, forming an antigen binding domain-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). In a preferred aspect, the antigen is a human protein.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular aspect, the activating T cell antigen is CD3, particularly the epsilon subunit of CD3.

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one aspect, CD3 is human CD3, particularly the epsilon subunit of human CD3 (CD3ε). The amino acid sequence of human CD3ε is shown in SEQ ID NO: 76 (without signal peptide). See also UniProt (www.uniprot.org) accession no. P07766 (version 189), or NCBI (www.ncbi.nlm.nih.gov/) RefSeq NP_000724.1. In another aspect, CD3 is cynomolgus (*Macaca fascicularis*) CD3, particularly cynomolgus CD3ε. The amino acid sequence of cynomolgus CD3ε is shown in SEQ ID NO: 77 (without signal peptide). See also NCBI GenBank no. BAB71849.1. In certain aspects the antibody of the invention binds to an epitope of CD3 that is conserved among the CD3 antigens from different species, particularly human and cynomolgus CD3. In preferred aspects, the antibody binds to human CD3.

A "target cell antigen" as used herein refers to an antigenic determinant presented on the surface of a target cell, for example a cell in a tumor such as a cancer cell or a cell of the tumor stroma (in that case a "tumor cell antigen"). According to the present invention, the target cell antigen is HLA-A2/MAGE-A4, particularly HLA-A2/MAGE-A4$_{p230-239}$.

"MAGE-A4" stands for "Melanoma-associated antigen 4", which is a member of the MAGE family of Cancer Testis Antigens (CTAs). The MAGE-A family of proteins encompasses 12 highly homologous genes clustered at Xq26-28 and characterized by the presence of a conserved domain (MAGE Homology Domain, MHD). Human MAGE-A4 is described in UniProt (www.uniprot.org) accession no. P43358 (entry version 163), and an amino acid sequence of human MAGE-A4 is also shown in SEQ ID NO: 74 herein. "MAGE-A4" as used herein, refers to any native MAGE-A4 from any vertebrate source, including mammals such as primates (e.g. humans), non-human primates (e.g. cynomolgus monkeys) and rodents (e.g. mice and rats), unless otherwise indicated. The term encompasses "full-length," unprocessed MAGE-A4 as well as any form of MAGE-A4 that results from processing in the cell. The term also encompasses naturally occurring variants of MAGE-A4, e.g., splice variants or allelic variants. In one aspect, MAGE-A4 is human MAGE-A4, particularly the protein of SEQ ID NO: 74.

By "MAGE-A4$_{p230-239}$" or "p230-239 peptide" is meant the MAGE-A4 derived peptide having the amino acid sequence GVYDGREHTV (SEQ ID NO: 73; position 230-239 of the MAGE-A4 protein of SEQ ID NO: 74).

"HLA-A2", "HLA-A*02", "HLA-A02", or "HLA-A*2" (used interchangeably) refers to a human leukocyte antigen serotype in the HLA-A serotype group. The HLA-A2 protein (encoded by the respective HLA gene) constitutes the a chain of the respective class I MHC (major histocompatibility complex) protein, which further comprises a β2 microglobulin subunit. A specific HLA-A2 protein is HLA-A201 (also referred to as HLA-A0201, HLA-A02.01, or HLA-A*02:01). In specific aspects, the HLA-A2 protein described herein is HLA-A201.

"HLA-A2/MAGE-A4" refers to a complex of a HLA-A2 molecule and a MAGE-A4 derived peptide (also referred to herein as a "MAGE-A4 peptide"), specifically the p230-239 peptide ("HLA-A2/MAGE-A4$_{p230-239}$").

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., an antibody and an antigen). The affinity of a molecule X for its partner Y can generally be represented by the dissociation constant ($K_D$). Affinity can be measured by well-established methods known in the art, including those described herein. A preferred method for measuring affinity is Surface Plasmon Resonance (SPR).

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein preferably includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which may be non-identical in the sense that further components fused to each of the subunits (e.g. antigen binding domains) are not the same. In some aspects, the modification promoting the association of the first and the second subunit of the Fc domain comprises an amino acid mutation in the Fc domain, specifically an amino acid substitution. In a preferred aspect, the modification promoting the association of the first and the second subunit of the Fc domain comprises a separate amino acid mutation, specifically an amino acid substitution, in each of the two subunits of the Fc domain. The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Preferred amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, % amino acid sequence identity values are generated using the ggsearch program of the FASTA package version 36.3.8c or later with a BLOSUM50 comparison matrix. The FASTA program package was authored by W. R. Pearson and D. J. Lipman ("Improved Tools for Biological Sequence Analysis", PNAS 85 (1988) 2444-2448), W. R. Pearson ("Effective protein sequence comparison" Meth. Enzymol. 266 (1996) 227-258), and Pearson et. al. (Genomics 46 (1997) 24-36) and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" or "nucleic acid molecule" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

An "isolated" nucleic acid molecule refers to a nucleic acid molecule that has been separated from a component of its natural environment. An isolated nucleic acid molecule includes a nucleic acid molecule contained in cells that ordinarily contain the nucleic acid molecule, but the nucleic acid molecule is present extrachromosomally or at a chromosomal location that is different from its natural chromosomal location.

"Isolated polynucleotide (or nucleic acid) encoding an antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies of the present invention. Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. In one aspect, the host cell of the invention is a eukaryotic cell, particularly a mammalian cell. In one aspect, the host cell is not a cell within a human body.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain aspects, the individual or subject is a human.

An "effective amount" of an agent, e.g., a pharmaceutical composition, refers to an amount effective, at dosages and for periods of time necessary, to achieve the desired therapeutic or prophylactic result.

The term "package insert" is used to refer to instructions customarily included in commercial packages of therapeutic products, that contain information about the indications, usage, dosage, administration, combination therapy, contraindications and/or warnings concerning the use of such therapeutic products.

II. Compositions and Methods

The invention provides antibodies that bind HLA-A2/MAGE-A4, including multispecific antibodies that bind HLA-A2/MAGE-A4 and a second antigen. The (multispecific) antibodies show good affinity and remarkable specificity, combined with other favorable properties for therapeutic application, e.g. with respect to efficacy and safety, pharmacokinetics, as well as produceability. Antibodies of the invention as useful, e.g., for the treatment of diseases such as cancer.

A. Anti-HLA-A2/MAGE-A4 Antibodies

In one aspect, the invention provides antibodies that bind to HLA-A2/MAGE-A4. In one aspect, provided are isolated antibodies that bind to HLA-A2/MAGE-A4. In one aspect, the invention provides antibodies that specifically bind to HLA-A2/MAGE-A4.

In one aspect, the invention provides an antibody that binds to HLA-A2/MAGE-A4, wherein the antibody comprises a first antigen binding domain, comprising (i) a heavy chain variable region (VH) comprising a heavy chain complementary determining region (HCDR) 1 of SEQ ID NO: 25, a HCDR 2 of SEQ ID NO: 26, and a HCDR 3 of SEQ ID NO: 27, and a light chain variable region (VL) comprising a light chain complementarity determining region (LCDR) 1 of SEQ ID NO: 28, a LCDR 2 of SEQ ID NO: 29 and a LCDR 3 of SEQ ID NO: 30;
(ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
(iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
(iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
(v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
(vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38.

In one aspect, the invention provides an antibody that binds to HLA-A2/MAGE-A4, wherein the antibody comprises a first antigen binding domain, comprising a heavy chain variable region (VH) comprising a heavy chain complementary determining region (HCDR) 1 of SEQ ID NO: 25, a HCDR 2 of SEQ ID NO: 26, and a HCDR 3 of SEQ ID NO: 27, and a light chain variable region (VL) comprising a light chain complementarity determining region (LCDR) 1 of SEQ ID NO: 28, a LCDR 2 of SEQ ID NO: 29 and a LCDR 3 of SEQ ID NO: 30.

In one aspect, the antibody is a humanized antibody. In one aspect, the antigen binding domain is a humanized antigen binding domain (i.e. an antigen binding domain of a humanized antibody). In one aspect, the VH and/or the VL is a humanized variable region.

In one aspect, the VH and/or the VL comprises an acceptor human framework, e.g. a human immunoglobulin framework or a human consensus framework.

In one aspect, the antibody is a human antibody. In one aspect, the antigen binding domain is a human antigen binding domain (i.e. an antigen binding domain of a human antibody). In one aspect, the VH and/or the VL is a human variable region.

In one aspect, the VH comprises one or more heavy chain framework sequence (i.e. the FR1, FR2, FR3 and/or FR4 sequence) of a heavy chain variable region sequence selected from the group consisting of SEQ ID NO: 7, SEQ ID NO: 15, SEQ ID NO: 23, SEQ ID NO: 31, SEQ ID NO: 39 and SEQ ID NO: 47, particularly of the heavy chain variable region sequence of SEQ ID NO: 31. In one aspect, the VH comprises an amino acid sequence that is at least about 95%, 96%, 97%, 98%, or 99% identical to an amino acid sequence selected from the group consisting of SEQ ID NO: 7, SEQ ID NO: 15, SEQ ID NO: 23, SEQ ID NO: 31, SEQ ID NO: 39 and SEQ ID NO: 47, particularly the amino acid sequence of SEQ ID NO: 31. In one aspect, the VH comprises an amino acid sequence that is at least about 95% identical to an amino acid sequence selected from the group consisting of SEQ ID NO: 7, SEQ ID NO: 15, SEQ ID NO: 23, SEQ ID NO: 31, SEQ ID NO: 39 and SEQ ID NO: 47, particularly the amino acid sequence of SEQ ID NO: 31. In one aspect, the VH comprises an amino acid sequence that is at least about 98% identical to an amino acid sequence selected from the group consisting of SEQ ID NO: 7, SEQ ID NO: 15, SEQ ID NO: 23, SEQ ID NO: 31, SEQ ID NO: 39 and SEQ ID NO: 47, particularly the amino acid sequence of SEQ ID NO: 31. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to HLA-A2/MAGE-A4. In certain aspects, a total of 1 to 10 amino acids have been substituted, inserted and/or deleted in the amino acid sequence of SEQ ID NO: 7, SEQ ID NO: 15, SEQ ID NO: 23, SEQ ID NO: 31, SEQ ID NO: 39 or SEQ ID NO: 47. In certain aspects, substitutions, insertions, or deletions occur in regions outside the CDRs (i.e., in the FRs). In one aspect, the VH comprises an amino acid sequence selected from the group consisting of SEQ ID NO: 7, SEQ ID NO: 15, SEQ ID NO: 23, SEQ ID NO: 31, SEQ ID NO: 39 and SEQ ID NO: 47, particularly the amino acid sequence of SEQ ID NO: 31. Optionally, the VH comprises an amino acid sequence selected from the group consisting of SEQ ID NO: 7, SEQ ID NO: 15, SEQ ID NO: 23, SEQ ID NO: 31, SEQ ID NO: 39 and SEQ ID NO: 47, particularly the amino acid sequence of SEQ ID NO: 31, including post-translational modifications of that sequence.

In one aspect, the VL comprises one or more light chain framework sequence (i.e. the FR1, FR2, FR3 and/or FR4 sequence) of a light chain variable region sequence selected from the group consisting of SEQ ID NO: 8, SEQ ID NO: 16, SEQ ID NO: 24, SEQ ID NO: 32, SEQ ID NO: 40 and SEQ ID NO: 48, particularly of the light chain variable region sequence of SEQ ID NO: 32. In one aspect, the VL comprises an amino acid sequence that is at least about 95%, 96%, 97%, 98%, or 99% identical to an amino acid sequence selected from the group consisting of SEQ ID NO: 8, SEQ ID NO: 16, SEQ ID NO: 24, SEQ ID NO: 32, SEQ ID NO: 40 and SEQ ID NO: 48, particularly the amino acid sequence of SEQ ID NO: 32. In one aspect, the VL comprises an amino acid sequence that is at least about 95% identical to an amino acid sequence selected from the group consisting of SEQ ID NO: 8, SEQ ID NO: 16, SEQ ID NO: 24, SEQ ID NO: 32, SEQ ID NO: 40 and SEQ ID NO: 48, particularly the amino acid sequence of SEQ ID NO: 32. In one aspect, the VL comprises an amino acid sequence that is at least about 98% identical to an amino acid sequence selected from the group consisting of SEQ ID NO: 8, SEQ ID NO: 16, SEQ ID NO: 24, SEQ ID NO: 32, SEQ ID NO: 40 and SEQ ID NO: 48, particularly the amino acid sequence of SEQ ID NO: 32. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to HLA-A2/MAGE-A4. In certain aspects, a total of 1 to 10 amino acids have been substituted, inserted and/or deleted in the amino acid sequence of SEQ ID NO: 8, SEQ ID NO: 16, SEQ ID NO: 24, SEQ ID NO: 32, SEQ ID NO: 40 or SEQ ID NO: 48. In certain aspects, substitutions, insertions, or deletions occur in regions outside the CDRs (i.e., in the FRs). In one aspect, the VL comprises an amino acid sequence selected from the group consisting of SEQ ID NO: 8, SEQ ID NO: 16, SEQ ID NO: 24, SEQ ID NO: 32, SEQ ID NO: 40 and SEQ ID NO: 48, particularly the amino acid sequence of SEQ ID NO: 32. Optionally, the VL comprises an amino acid sequence selected from the group consisting of SEQ ID NO: 8, SEQ ID NO: 16, SEQ ID NO: 24, SEQ ID NO: 32, SEQ ID NO: 40 and SEQ ID NO: 48, particularly the amino acid sequence of SEQ ID NO: 32, including post-translational modifications of that sequence.

In one aspect, the first antigen binding domain comprises
(i) a VH comprising an amino acid sequence that is at least about 95%, 96%, 97%, 98%, or 99% identical to the amino acid sequence of SEQ ID NO: 31, and/or a VL comprising an amino acid sequence that is at least about 95%, 96%, 97%, 98%, or 99% identical to the amino acid sequence of SEQ ID NO: 32;
(ii) a VH comprising an amino acid sequence that is at least about 95%, 96%, 97%, 98%, or 99% identical to the amino acid sequence of SEQ ID NO: 7, and/or a VL comprising an amino acid sequence that is at least about 95%, 96%, 97%, 98%, or 99% identical to the amino acid sequence of SEQ ID NO: 8;
(iii) a VH comprising an amino acid sequence that is at least about 95%, 96%, 97%, 98%, or 99% identical to the amino acid sequence of SEQ ID NO: 47, and/or a VL comprising an amino acid sequence that is at least about 95%, 96%, 97%, 98%, or 99% identical to the amino acid sequence of SEQ ID NO: 48;
(iv) a VH comprising an amino acid sequence that is at least about 95%, 96%, 97%, 98%, or 99% identical to the amino acid sequence of SEQ ID NO: 15, and/or a VL comprising an amino acid sequence that is at least about 95%, 96%, 97%, 98%, or 99% identical to the amino acid sequence of SEQ ID NO: 16;
(v) a VH comprising an amino acid sequence that is at least about 95%, 96%, 97%, 98%, or 99% identical to the amino acid sequence of SEQ ID NO: 23, and/or a VL comprising an amino acid sequence that is at least about 95%, 96%, 97%, 98%, or 99% identical to the amino acid sequence of SEQ ID NO: 24; or
(vi) a VH comprising an amino acid sequence that is at least about 95%, 96%, 97%, 98%, or 99% identical to the amino acid sequence of SEQ ID NO: 39, and/or a VL comprising an amino acid sequence that is at least about 95%, 96%, 97%, 98%, or 99% identical to the amino acid sequence of SEQ ID NO: 40.

In one aspect, the first antigen binding domain comprises
(i) a VH comprising the amino acid sequence of SEQ ID NO: 31, and/or a VL comprising the amino acid sequence of SEQ ID NO: 32;
(ii) a VH comprising the amino acid sequence of SEQ ID NO: 7, and/or a VL comprising the amino acid sequence of SEQ ID NO: 8;
(iii) a VH comprising the amino acid sequence of SEQ ID NO: 47, and/or a VL comprising the amino acid sequence of SEQ ID NO: 48;
(iv) a VH comprising the amino acid sequence of SEQ ID NO: 15, and/or a VL comprising the amino acid sequence of SEQ ID NO: 16;
(v) a VH comprising the amino acid sequence of SEQ ID NO: 23, and/or a VL comprising the amino acid sequence of SEQ ID NO: 24; or
(vi) a VH comprising the amino acid sequence of SEQ ID NO: 39, and/or a VL comprising the amino acid sequence of SEQ ID NO: 40.

In one aspect, the first antigen binding domain comprises a VH comprising an amino acid sequence that is at least about 95%, 96%, 97%, 98%, or 99% identical to the amino acid sequence of SEQ ID NO: 31, and a VL comprising an amino acid sequence that is at least about 95%, 96%, 97%, 98%, or 99% identical to the amino acid sequence of SEQ ID NO: 32. In one aspect, the first antigen binding domain comprises a VH comprising the amino acid sequence of SEQ ID NO: 31, and the VL comprises the amino acid sequence of SEQ ID NO: 32.

In a further aspect, the invention provides an antibody that binds to HLA-A2/MAGE-A4, wherein the antibody comprises a first antigen binding domain comprising
  (i) a VH comprising the amino acid sequence of SEQ ID NO: 31, and/or a VL comprising the amino acid sequence of SEQ ID NO: 32;
  (ii) a VH comprising the amino acid sequence of SEQ ID NO: 7, and/or a VL comprising the amino acid sequence of SEQ ID NO: 8;
  (iii) a VH comprising the amino acid sequence of SEQ ID NO: 47, and/or a VL comprising the amino acid sequence of SEQ ID NO: 48;
  (iv) a VH comprising the amino acid sequence of SEQ ID NO: 15, and/or a VL comprising the amino acid sequence of SEQ ID NO: 16;
  (v) a VH comprising the amino acid sequence of SEQ ID NO: 23, and/or a VL comprising the amino acid sequence of SEQ ID NO: 24; or
  (vi) a VH comprising the amino acid sequence of SEQ ID NO: 39, and/or a VL comprising the amino acid sequence of SEQ ID NO: 40.

In one aspect, the invention provides an antibody that binds to HLA-A2/MAGE-A4, wherein the antibody comprises a first antigen binding domain comprising a VH comprising the amino acid sequence of SEQ ID NO: 31, and a VL comprising the amino acid sequence of SEQ ID NO: 32.

In another aspect, the invention provides an antibody that binds to HLA-A2/MAGE-A4, wherein the antibody comprises a first antigen binding domain comprising
  (i) a VH comprising the heavy chain CDR sequences of the VH of SEQ ID NO: 31, and a VL comprising the light chain CDR sequences of the VL of SEQ ID NO: 32;
  (ii) a VH comprising the heavy chain CDR sequences of the VH of SEQ ID NO: 7, and a VL comprising the light chain CDR sequences of the VL of SEQ ID NO: 8;
  (iii) a VH comprising the heavy chain CDR sequences of the VH of SEQ ID NO: 47, and a VL comprising the light chain CDR sequences of the VL of SEQ ID NO: 48;
  (iv) a VH comprising the heavy chain CDR sequences of the VH of SEQ ID NO: 15, and a VL comprising the light chain CDR sequences of the VL of SEQ ID NO: 16;
  (v) a VH comprising the heavy chain CDR sequences of the VH of SEQ ID NO: 23, and a VL comprising the light chain CDR sequences of the VL of SEQ ID NO: 24; or
  (vi) a VH comprising the heavy chain CDR sequences of the VH of SEQ ID NO: 39, and a VL comprising the light chain CDR sequences of the VL of SEQ ID NO: 40.

In one aspect, the invention provides an antibody that binds to HLA-A2/MAGE-A4, wherein the antibody comprises a first antigen binding domain comprising a VH comprising the heavy chain CDR sequences of the VH of SEQ ID NO: 31, and a VL comprising the light chain CDR sequences of the VL of SEQ ID NO: 32.

In a further aspect, the first antigen binding domain comprises
  (i) the HCDR1, HCDR2 and HCDR3 amino acid sequences of the VH of SEQ ID NO: 31, and the LCDR1, LCDR2 and LCDR3 amino acid sequences of the VL of SEQ ID NO: 32;
  (ii) the HCDR1, HCDR2 and HCDR3 amino acid sequences of the VH of SEQ ID NO: 7, and the LCDR1, LCDR2 and LCDR3 amino acid sequences of the VL of SEQ ID NO: 8;
  (iii) the HCDR1, HCDR2 and HCDR3 amino acid sequences of the VH of SEQ ID NO: 47, and the LCDR1, LCDR2 and LCDR3 amino acid sequences of the VL of SEQ ID NO: 48;
  (iv) the HCDR1, HCDR2 and HCDR3 amino acid sequences of the VH of SEQ ID NO: 15, and the LCDR1, LCDR2 and LCDR3 amino acid sequences of the VL of SEQ ID NO: 16;
  (v) the HCDR1, HCDR2 and HCDR3 amino acid sequences of the VH of SEQ ID NO: 23, and the LCDR1, LCDR2 and LCDR3 amino acid sequences of the VL of SEQ ID NO: 24; or
  (vi) the HCDR1, HCDR2 and HCDR3 amino acid sequences of the VH of SEQ ID NO: 39, and the LCDR1, LCDR2 and LCDR3 amino acid sequences of the VL of SEQ ID NO: 40.

In one aspect, the first antigen binding domain comprises the HCDR1, HCDR2 and HCDR3 amino acid sequences of the VH of SEQ ID NO: 31, and the LCDR1, LCDR2 and LCDR3 amino acid sequences of the VL of SEQ ID NO: 32.

In one aspect, the first antigen binding domain comprises
  (i) a VH comprising the heavy chain CDR sequences of the VH of SEQ ID NO: 31, and a framework of at least 95%, 96%, 97%, 98% or 99%, particularly at least 95% or at least 98%, sequence identity to the framework sequence of the VH of SEQ ID NO: 31, and/or a VL comprising the light chain CDR sequences of the VL of SEQ ID NO: 32, and a framework of at least 95%, 96%, 97%, 98% or 99%, particularly at least 95% or at least 98%, sequence identity to the framework sequence of the VL of SEQ ID NO: 32;
  (i) a VH comprising the heavy chain CDR sequences of the VH of SEQ ID NO: 7, and a framework of at least 95%, 96%, 97%, 98% or 99%, particularly at least 95% or at least 98%, sequence identity to the framework sequence of the VH of SEQ ID NO: 7, and/or a VL comprising the light chain CDR sequences of the VL of SEQ ID NO: 8, and a framework of at least 95%, 96%, 97%, 98% or 99%, particularly at least 95% or at least 98%, sequence identity to the framework sequence of the VL of SEQ ID NO: 8;
  (i) a VH comprising the heavy chain CDR sequences of the VH of SEQ ID NO: 47, and a framework of at least 95%, 96%, 97%, 98% or 99%, particularly at least 95% or at least 98%, sequence identity to the framework sequence of the VH of SEQ ID NO: 47, and/or a VL comprising the light chain CDR sequences of the VL of SEQ ID NO: 48, and a framework of at least 95%, 96%, 97%, 98% or 99%, particularly at least 95% or at least 98%, sequence identity to the framework sequence of the VL of SEQ ID NO: 48;
  (i) a VH comprising the heavy chain CDR sequences of the VH of SEQ ID NO: 15, and a framework of at least 95%, 96%, 97%, 98% or 99%, particularly at least 95% or at least 98%, sequence identity to the framework sequence of the VH of SEQ ID NO: 15, and/or a VL comprising the light chain CDR sequences of the VL of SEQ ID NO: 16, and a framework of at least 95%, 96%, 97%, 98% or 99%, particularly at least 95% or at least 98%, sequence identity to the framework sequence of the VL of SEQ ID NO: 16;

(i) a VH comprising the heavy chain CDR sequences of the VH of SEQ ID NO: 23, and a framework of at least 95%, 96%, 97%, 98% or 99%, particularly at least 95% or at least 98%, sequence identity to the framework sequence of the VH of SEQ ID NO: 23, and/or a VL comprising the light chain CDR sequences of the VL of SEQ ID NO: 24, and a framework of at least 95%, 96%, 97%, 98% or 99%, particularly at least 95% or at least 98%, sequence identity to the framework sequence of the VL of SEQ ID NO: 24; or (i) a VH comprising the heavy chain CDR sequences of the VH of SEQ ID NO: 39, and a framework of at least 95%, 96%, 97%, 98% or 99%, particularly at least 95% or at least 98%, sequence identity to the framework sequence of the VH of SEQ ID NO: 39, and/or a VL comprising the light chain CDR sequences of the VL of SEQ ID NO: 40, and a framework of at least 95%, 96%, 97%, 98% or 99%, particularly at least 95% or at least 98%, sequence identity to the framework sequence of the VL of SEQ ID NO: 40.

In one aspect, the VH comprises the heavy chain CDR sequences of the VH of SEQ ID NO: 31, and a framework of at least 95%, 96%, 97%, 98% or 99% sequence identity to the framework sequence of the VH of SEQ ID NO: 31. In one aspect, the VH comprises the heavy chain CDR sequences of the VH of SEQ ID NO: 31, and a framework of at least 95% sequence identity to the framework sequence of the VH of SEQ ID NO: 31. In another aspect, the VH comprises the heavy chain CDR sequences of the VH of SEQ ID NO: 31, and a framework of at least 98% sequence identity to the framework sequence of the VH of SEQ ID NO: 31.

In one aspect, the VL comprises the light chain CDR sequences of the VL of SEQ ID NO: 32 and a framework of at least 95%, 96%, 97%, 98% or 99% sequence identity to the framework sequence of the VL of SEQ ID NO: 32. In one aspect, the VL comprises the light chain CDR sequences of the VL of SEQ ID NO: 32 and a framework of at least 95% sequence identity to the framework sequence of the VL of SEQ ID NO: 32. In another aspect, the VL comprises the light chain CDR sequences of the VL of SEQ ID NO: 32 and a framework of at least 98% sequence identity to the framework sequence of the VL of SEQ ID NO: 32.

In one aspect, the invention provides an antibody that binds to HLA-A2/MAGE-A4, wherein the antibody comprises a first antigen binding domain comprising a VH sequence as in any of the aspects provided above, and a VL sequence as in any of the aspects provided above.

In one aspect, the antibody comprises a human constant region. In one aspect, the antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 79 and 80 (human kappa and lambda CL domains, respectively) and SEQ ID NO: 81 (human IgG$_1$ heavy chain constant domains CH1-CH2-CH3). In one aspect, the antibody comprises a light chain constant region comprising an amino acid sequence that is at least about 95%, 96%, 97%, 98%, 99% or 100% identical to the amino acid sequence of SEQ ID NO: 79 or SEQ ID NO: 80, particularly the amino acid sequence of SEQ ID NO: 79. In one aspect, the antibody comprises a heavy chain constant region comprising an amino acid sequence that is at least about 95%, 96%, 97%, 98%, 99% or 100% identical to the amino acid sequence of SEQ ID NO: 81. Particularly, the heavy chain constant region may comprise amino acid mutations in the Fc domain as described herein.

In one aspect, the first antigen binding domain comprises a human constant region. In one aspect, the first antigen binding moiety is a Fab molecule comprising a human constant region, particularly a human CH1 and/or CL domain. In one aspect, the first antigen binding domain comprises a light chain constant region comprising an amino acid sequence that is at least about 95%, 96%, 97%, 98%, 99% or 100% identical to the amino acid sequence of SEQ ID NO: 79 or SEQ ID NO: 80, particularly the amino acid sequence of SEQ ID NO: 79. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the first antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 81. Particularly, the heavy chain constant region (specifically CH1 domain) may comprise amino acid mutations as described herein under "charge modifications".

In one aspect, the antibody is a monoclonal antibody.

In one aspect, the antibody is an IgG, particularly an IgG$_1$, antibody. In one aspect, the antibody is a full-length antibody.

In another aspect, the antibody is an antibody fragment selected from the group of an Fv molecule, a scFv molecule, a Fab molecule, and a F(ab')2 molecule; particularly a Fab molecule. In another aspect, the antibody fragment is a diabody, a triabody or a tetrabody.

In one aspect, the first antigen binding domain is a Fab molecule. In a preferred aspect the first antigen binding domain is a conventional Fab molecule. In an alternative aspect, the first antigen binding domain is a Fab molecule wherein the variable domains VL and VH or the constant domains CL and CH1, particularly the variable domains VL and VH, of the Fab light chain and the Fab heavy chain are replaced by each other (i.e. the first antigen binding domain is a crossover Fab molecule).

In a further aspect, the antibody according to any of the above aspects may incorporate any of the features, singly or in combination, as described in sections II. A. 1.-10. below.

In a preferred aspect, the antibody comprises an Fc domain, particularly an IgG Fc domain, more particularly an IgG$_1$ Fc domain. In one aspect the Fc domain is a human Fc domain. In one aspect, the Fc domain is a human IgG$_1$ Fc domain. The Fc domain is composed of a first and a second subunit and may incorporate any of the features, singly or in combination, described hereinbelow in relation to Fc domain variants (section II. A. 10.).

In another preferred aspect, the antibody comprises a second antigen binding domain which binds to a second antigen (i.e. the antibody is a multispecific antibody, as further described hereinbelow (section II. A. 9.).

1. Antibody Fragments

In certain aspects, an antibody provided herein is an antibody fragment.

In one aspect, the antibody fragment is a Fab, Fab', Fab'-SH, or F(ab')$_2$ molecule, in particular a Fab molecule as described herein. "Fab' molecule" differ from Fab molecules by the addition of residues at the carboxy terminus of the CH1 domain including one or more cysteines from the antibody hinge region. Fab'-SH are Fab' molecules in which the cysteine residue(s) of the constant domains bear a free thiol group. Pepsin treatment yields an F(ab')$_2$ molecule that has two antigen-binding sites (two Fab molecules) and a part of the Fc region.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab molecule. A "single chain Fab molecule" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab molecules are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as recombinant production by recombinant host cells (e.g., E. coli), as described herein.

2. Humanized Antibodies

In certain aspects, an antibody provided herein is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

3. Human Antibodies

In certain aspects, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boemer et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating variable domain sequences selected from human-derived phage display libraries. Such variable domain sequences may then be combined with a desired human constant domain. Techniques for selecting human antibodies from antibody libraries are described below.

4. Library-Derived Antibodies

In certain aspects, an antibody provided herein is derived from a library. Antibodies of the invention may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antibodies possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178: 1-37 (O'Brien et al., ed., Human Press, Totowa, N.J., 2001) and in Marks and Bradbury in Methods in Molecular Biology 248:161-175 (Lo, ed., Human Press, Totowa, N.J., 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in EMBO Journal 12: 725-734 (1993). Furthermore, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936.

Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319: 155-175 (2015) as well as in Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997).

Antibodies or antibody fragments isolated from human antibody libraries are considered human antibodies or human antibody fragments herein.

5. Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

6. Cysteine Engineered Antibody Variants

In certain aspects, it may be desirable to create cysteine engineered antibodies, e.g., THIOMAB™ antibodies, in which one or more residues of an antibody are substituted with cysteine residues. In preferred aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

7. Antibody Derivatives

In certain aspects, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

8. Immunoconjugates

The invention also provides immunoconjugates comprising an anti-HLA-A2/MAGE-A4 antibody herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another aspect, an immunoconjugate comprises an antibody of the invention conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody of the invention conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$ or a spin label for nuclear magnetic resonance (NMR) imaging (also known as magnetic resonance imaging, MRI), such as $I^{123}$, $I^{131}$, $In^{111}$, $F^{19}$, $C^{13}$, $N^{15}$, $O^{17}$, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

9. Multispecific Antibodies

In certain aspects, an antibody provided herein is a multispecific antibody, particularly a bispecific antibody. Multispecific antibodies are monoclonal antibodies that have binding specificities for at least two different antigenic determinants (e.g., two different proteins, or two different epitopes on the same protein). In certain aspects, the multispecific antibody has three or more binding specificities. In certain aspects, one of the binding specificities is for HLA-A2/MAGE-A4 and the other specificity is for any other antigen. In certain aspects, multispecific antibodies may bind to two (or more) different epitopes of HLA-A2/MAGE-A4. Multispecific (e.g., bispecific) antibodies may also be used to localize cytotoxic agents or cells to cells which express HLA-A2/MAGE-A4. Multispecific antibodies may be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more antigen binding sites, including for example, "Octopus antibodies", or DVD-Ig are also included herein (see, e.g., WO 2001/77342 and WO 2008/024715).

Other examples of multispecific antibodies with three or more antigen binding sites can be found in WO 2010/115589, WO 2010/112193, WO 2010/136172, WO 2010/145792, and WO 2013/026831. The multispecific antibody or antigen binding fragment thereof also includes a "Dual Acting FAb" or "DAF" comprising an antigen binding site that binds to CD3 as well as another different antigen, or two different epitopes of CD3 (see, e.g., US 2008/0069820 and WO 2015/095539).

Multi-specific antibodies may also be provided in an asymmetric form with a domain crossover in one or more binding arms of the same antigen specificity (so-called "CrossMab" technology), i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

A particular type of multispecific antibodies, also included herein, are bispecific antibodies designed to simultaneously bind to a surface antigen on a target cell, e.g., a tumor cell, and to an activating, invariant component of the T cell receptor (TCR) complex, such as CD3, for retargeting of T cells to kill target cells. Hence, in preferred aspects, an antibody provided herein is a multispecific antibody, particularly a bispecific antibody, wherein one of the binding specificities is for HLA-A2/MAGE-A4 and the other is for an activating T cell antigen, particularly CD3. Examples of bispecific antibody formats that may be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Büerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

Preferred aspects of the multispecific antibodies of the present invention are described in the following.

In one aspect, the invention provides an antibody that binds to HLA-A2/MAGE-A4, comprising a first antigen binding domain that binds to HLA-A2/MAGE-A4, as described herein, and comprising a second antigen binding domain which binds to a second antigen (and optionally a third antigen binding domain which binds to HLA-A2/MAGE-A4).

According to preferred aspects of the invention, the antigen binding domains comprised in the antibody are Fab molecules (i.e. antigen binding domains composed of a heavy and a light chain, each comprising a variable and a constant domain). In one aspect, the first, the second and/or, where present, the third antigen binding domain is a Fab molecule. In one aspect, said Fab molecule is human. In another aspect, said Fab molecule is humanized. In yet another aspect, said Fab molecule comprises human heavy and light chain constant domains.

Preferably, at least one of the antigen binding domains is a crossover Fab molecule. Such modification reduces mispairing of heavy and light chains from different Fab molecules, thereby improving the yield and purity of the (multispecific) antibody of the invention in recombinant production. In a preferred crossover Fab molecule useful for the (multispecific) antibody of the invention, the variable domains of the Fab light chain and the Fab heavy chain (VL and VH, respectively) are exchanged. Even with this domain exchange, however, the preparation of the (multispecific) antibody may comprise certain side products due to a so-called Bence Jones-type interaction between mispaired heavy and light chains (see Schaefer et al, PNAS, 108 (2011)

11187-11191). To further reduce mispairing of heavy and light chains from different Fab molecules and thus increase the purity and yield of the desired (multispecific) antibody, charged amino acids with opposite charges may be introduced at specific amino acid positions in the CH1 and CL domains of either the Fab molecule binding to the first antigen (HLA-A2/MAGE-A4), or the Fab molecule(s) binding to the second antigen (e.g. CD3), as further described herein. Charge modifications are made either in the conventional Fab molecule(s) comprised in the (multispecific) antibody (such as shown e.g. in FIGS. 1 A-C, G-J), or in the VH/VL crossover Fab molecule(s) comprised in the (multispecific) antibody (such as shown e.g. in FIG. 1 D-F, K-N) (but not in both). In preferred aspects, the charge modifications are made in the conventional Fab molecule(s) comprised in the (multispecific) antibody (which in preferred aspects bind(s) to the first antigen, i.e. HLA-A2/MAGE-A4).

In a preferred aspect according to the invention, the (multispecific) antibody is capable of simultaneous binding to the first antigen (i.e. HLA-A2/MAGE-A4), and the second antigen (e.g. an activating T cell antigen, such as CD3). In one aspect, the (multispecific) antibody is capable of crosslinking a T cell and a target cell by simultaneous binding to the second antigen (e.g. an activating T cell antigen, such as CD3) and HLA-A2/MAGE-A4. In an even more preferred aspect, such simultaneous binding results in lysis of the target cell, particularly a target cell antigen (i.e. HLA-A2/MAGE-A4)-expressing tumor cell. In one aspect, such simultaneous binding results in activation of the T cell. In other aspects, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one aspect, binding of the (multispecific) antibody to the second antigen (e.g. an activating T cell antigen, such as CD3) without simultaneous binding to the target cell antigen (i.e. HLA-A2/MAGE-A4) does not result in T cell activation.

In one aspect, the (multispecific) antibody is capable of re-directing cytotoxic activity of a T cell to a target cell. In a preferred aspect, said re-direction is independent of MHC-mediated peptide antigen presentation by the target cell and/or specificity of the T cell.

Preferably, a T cell according to any of the aspects of the invention is a cytotoxic T cell. In some aspects the T cell is a $CD4^+$ or a $CD8^+$ T cell, particularly a $CD8^+$ T cell.

a) First (and Third) Antigen Binding Domain

The (multispecific) antibody of the invention comprises at least one antigen binding domain (the first antigen binding domain) that binds to HLA-A2/MAGE-A4. In preferred aspects, HLA-A2/MAGE-A4 is human HLA-A2/MAGE-A4. In a particular aspect, HLA-A2/MAGE-A4 is HLA-A2/MAGE-A4$_{p230-239}$.

The first antigen binding domain is able to direct the (multispecific) antibody to a target site, for example to a specific type of tumor cell that expresses HLA-A2/MAGE-A4.

In a preferred aspect, the (multispecific) antibody comprises two antigen binding domains that bind to HLA-A2/MAGE-A4. In one aspect the (multispecific) antibody provides bivalent binding to HLA-A2/MAGE-A4.

In one aspect, the antigen binding domain that binds to HLA-A2/MAGE-A4 is an antibody fragment selected from the group of an Fv molecule, a scFv molecule, a Fab molecule, and a F(ab')2 molecule. In a preferred aspect, the antigen binding domain that binds to HLA-A2/MAGE-A4 is a Fab molecule.

In certain aspects, the (multispecific) antibody comprises two antigen binding domains, particularly Fab molecules, that bind to HLA-A2/MAGE-A4. In a particular aspect, all of these antigen binding domains are identical, i.e. they have the same molecular format (e.g. conventional or crossover Fab molecule) and comprise the same amino acid sequences including the same amino acid substitutions in the CH1 and CL domain as described herein (if any). In one aspect, the (multispecific) antibody comprises not more than two antigen binding domains, particularly Fab molecules, that bind to HLA-A2/MAGE-A4.

In preferred aspects, the antigen binding domain(s) that bind to HLA-A2/MAGE-A4 is/are a conventional Fab molecule. In such aspects, the antigen binding domain(s) that binds to the second antigen is a crossover Fab molecule as described herein, i.e. a Fab molecule wherein the variable domains VH and VL or the constant domains CH1 and CL of the Fab heavy and light chains are exchanged/replaced by each other.

In alternative aspects, the antigen binding domain(s) that bind to HLA-A2/MAGE-A4 is/are a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to the second antigen is a conventional Fab molecule.

In one aspect, the first (and, where present, third) antigen binding domain comprises a human constant region. In one aspect, the first (and, where present, third) antigen binding domain is a Fab molecule comprising a human constant region, particularly a human CH1 and/or CL domain.

Exemplary sequences of human constant domains are given in SEQ ID NOs 79 and 80 (human kappa and lambda CL domains, respectively) and SEQ ID NO: 81 (human IgG$_1$ heavy chain constant domains CH1-CH2-CH3). In one aspect, the first (and, where present, third) antigen binding domain comprises a light chain constant region comprising an amino acid sequence that is at least about 95%, 96%, 97%, 98%, 99% or 100% identical to the amino acid sequence of SEQ ID NO: 79 or SEQ ID NO: 80, particularly the amino acid sequence of SEQ ID NO: 79. Particularly, the light chain constant region may comprise amino acid mutations as described herein under "charge modifications" and/or may comprise deletion or substitutions of one or more (particularly two) N-terminal amino acids if in a crossover Fab molecule. In some aspects, the first (and, where present, third) antigen binding domain comprises a heavy chain constant region comprising an amino acid sequence that is at least about 95%, 96%, 97%, 98%, 99% or 100% identical to the CH1 domain sequence comprised in the amino acid sequence of SEQ ID NO: 81. Particularly, the heavy chain constant region (specifically CH1 domain) may comprise amino acid mutations as described herein under "charge modifications".

b) Second Antigen Binding Domain

In certain aspects, the (multispecific) antibody of the invention comprises at least one antigen binding domain, particularly a Fab molecule, that binds to a second antigen. The second antigen preferably is not HLA-A2/MAGE-A4, i.e. different from HLA-A2/MAGE-A4. In one aspect, the second antigen is an antigen expressed on a different cell than HLA-A2/MAGE-A4 (e.g. expressed on a cell other than a target cell such as a tumor cell). In one aspect, the second antigen is a T cell antigen, particularly an activating T cell antigen. In a specific aspect, the second antigen is CD3. In preferred aspects, CD3 is human CD3 (SEQ ID NO: 76) or cynomolgus CD3 (SEQ ID NO: 77), most particularly human CD3. In one aspect the second antigen binding domain is cross-reactive for (i.e. specifically binds to) human and cynomolgus CD3. In some aspects, CD3 is the epsilon subunit of CD3 (CD3 epsilon).

In a preferred aspect, the (multispecific) antibody comprises not more than one antigen binding domain that binds to the second antigen (e.g. an activating T cell antigen, such as CD3). In one aspect, the (multispecific) antibody provides monovalent binding to the second antigen (e.g. an activating T cell antigen, such as CD3).

In one aspect, the antigen binding domain that binds to the second antigen is an antibody fragment selected from the group of an Fv molecule, a scFv molecule, a Fab molecule, and a F(ab')2 molecule. In a preferred aspect, the antigen binding domain that binds to the second antigen is a Fab molecule.

In preferred aspects, the antigen binding domain that binds to the second antigen (e.g. an activating T cell antigen, such as CD3) is a crossover Fab molecule as described herein, i.e. a Fab molecule wherein the variable domains VH and VL or the constant domains CH1 and CL of the Fab heavy and light chains are exchanged/replaced by each other. In such aspects, the antigen binding domain(s) that binds to HLA-A2/MAGE-A4 is preferably a conventional Fab molecule. In aspects where there is more than one antigen binding domain, particularly Fab molecule, that binds to HLA-A2/MAGE-A4 comprised in the (multispecific) antibody, the antigen binding domain that binds to the second antigen preferably is a crossover Fab molecule and the antigen binding domain that bind to HLA-A2/MAGE-A4 are conventional Fab molecules.

In alternative aspects, the antigen binding domain that binds to the second antigen (e.g. an activating T cell antigen, such as CD3) is a conventional Fab molecule. In such aspects, the antigen binding domain(s) that binds to HLA-A2/MAGE-A4 is a crossover Fab molecule as described herein, i.e. a Fab molecule wherein the variable domains VH and VL or the constant domains CH1 and CL of the Fab heavy and light chains are exchanged/replaced by each other. In aspects where there is more than one antigen binding domain, particularly Fab molecule, that binds to the second antigen comprised in the (multispecific) antibody, the antigen binding domain that binds to HLA-A2/MAGE-A4 preferably is a crossover Fab molecule and the antigen binding domains that bind to the second antigen are conventional Fab molecules.

In preferred aspects, the second antigen binding domain is a Fab molecule wherein the variable domains VL and VH or the constant domains CL and CH1, particularly the variable domains VL and VH, of the Fab light chain and the Fab heavy chain are replaced by each other (i.e. according to such aspect, the second antigen binding domain is a crossover Fab molecule wherein the variable or constant domains of the Fab light chain and the Fab heavy chain are exchanged). In one such aspect, the first (and the third, if any) antigen binding domain is a conventional Fab molecule.

In preferred aspects, the second antigen is CD3, as described hereinabove.

In one aspect, the second antigen binding domain comprises
(i) a heavy chain variable region (VH) comprising a heavy chain complementary determining region (HCDR) 1 of SEQ ID NO: 59, a HCDR 2 of SEQ ID NO: 60, and a HCDR 3 of SEQ ID NO: 61, and a light chain variable region (VL) comprising a light chain complementarity determining region (LCDR) 1 of SEQ ID NO: 62, a LCDR 2 of SEQ ID NO: 63 and a LCDR 3 of SEQ ID NO: 64; or
(ii) a VH comprising a HCDR 1 of SEQ ID NO: 51, a HCDR 2 of SEQ ID NO: 52, and a HCDR 3 of SEQ ID NO: 53, and a light chain variable region (VL) comprising a light chain complementarity determining region (LCDR) 1 of SEQ ID NO: 54, a LCDR 2 of SEQ ID NO: 55 and a LCDR 3 of SEQ ID NO: 56.

In one aspect, the second antigen binding domain is (derived from) a humanized antibody. In one aspect, the second antigen binding domain is a humanized antigen binding domain (i.e. an antigen binding domain of a humanized antibody). In one aspect, the VH and/or the VL of the second antigen binding domain is a humanized variable region.

In one aspect, the VH and/or the VL of the second antigen binding domain comprises an acceptor human framework, e.g. a human immunoglobulin framework or a human consensus framework.

In some aspects, the second antigen binding domain comprises
(i) a heavy chain variable region (VH) comprising a heavy chain complementary determining region (HCDR) 1 of SEQ ID NO: 59, a HCDR 2 of SEQ ID NO: 60, and a HCDR 3 of SEQ ID NO: 61, and a light chain variable region (VL) comprising a light chain complementarity determining region (LCDR) 1 of SEQ ID NO: 62, a LCDR 2 of SEQ ID NO: 63 and a LCDR 3 of SEQ ID NO: 64.

In one aspect, the VH of the second antigen binding domain comprises one or more heavy chain framework sequence (i.e. the FR1, FR2, FR3 and/or FR4 sequence) of SEQ ID NO: 65. In one aspect, the VH comprises an amino acid sequence that is at least about 95%, 96%, 97%, 98%, or 99% identical to the amino acid sequence of SEQ ID NO: 65. In one aspect, the VH comprises an amino acid sequence that is at least about 95% identical to the amino acid sequence of SEQ ID NO: 65. In one aspect, the VH comprises an amino acid sequence that is at least about 98% identical to the amino acid sequence of SEQ ID NO: 65. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen (e.g. an activating T cell antigen, such as CD3). In certain aspects, a total of 1 to 10 amino acids have been substituted, inserted and/or deleted in the amino acid sequence of SEQ ID NO: 65. In certain aspects, substitutions, insertions, or deletions occur in regions outside the CDRs (i.e., in the FRs). In one aspect, the VH comprises the amino acid sequence of SEQ ID NO: 65. Optionally, the VH comprises the amino acid sequence of SEQ ID NO: 65, including post-translational modifications of that sequence.

In one aspect, the VL of the second antigen binding domain comprises one or more light chain framework sequence (i.e. the FR1, FR2, FR3 and/or FR4 sequence) of SEQ ID NO: 66. In one aspect, the VL comprises an amino acid sequence that is at least about 95%, 96%, 97%, 98%, or 99% identical to the amino acid sequence of SEQ ID NO: 66. In one aspect, the VL comprises an amino acid sequence that is at least about 95% identical to the amino acid sequence of SEQ ID NO: 66. In one aspect, the VL comprises an amino acid sequence that is at least about 98% identical to the amino acid sequence of SEQ ID NO: 66. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen (e.g. an activating T cell antigen, such as CD3). In certain aspects, a total of 1 to 10 amino acids have been substituted, inserted and/or deleted in the amino acid sequence of SEQ ID NO: 66. In certain aspects, substitutions, insertions, or deletions occur in regions outside the CDRs (i.e., in the FRs). In one aspect, the VL comprises the amino acid sequence of SEQ ID NO: 66. Optionally, the VL comprises the amino acid sequence of SEQ ID NO: 66, including post-translational modifications of that sequence.

In one aspect, the VH of the second antigen binding domain comprises an amino acid sequence that is at least about 95%, 96%, 97%, 98%, or 99% identical to the amino acid sequence of SEQ ID NO: 65, and the VL of the second antigen binding domain comprises an amino acid sequence that is at least about 95%, 96%, 97%, 98%, or 99% identical to the amino acid sequence of SEQ ID NO: 66. In one aspect, the VH comprises the amino acid sequence of SEQ ID NO: 65 and the VL comprises the amino acid sequence of SEQ ID NO: 66.

In a further aspect, the second antigen binding domain comprises a VH comprising the sequence of SEQ ID NO: 65 and a VL comprising the sequence of SEQ ID NO: 66.

In a further aspect, the second antigen binding domain comprises a VH sequence of SEQ ID NO: 65 and a VL sequence of SEQ ID NO: 66.

In another aspect, the second antigen binding domain comprises a VH comprising the heavy chain CDR sequences of the VH of SEQ ID NO: 65, and a VL comprising the light chain CDR sequences of the VL of SEQ ID NO: 66.

In a further aspect, the second antigen binding domain comprises the HCDR1, HCDR2 and HCDR3 amino acid sequences of the VH of SEQ ID NO: 65 and the LCDR1, LCDR2 and LCDR3 amino acid sequences of the VL of SEQ ID NO: 66.

In one aspect, the VH of the second antigen binding domain comprises the heavy chain CDR sequences of the VH of SEQ ID NO: 65 and a framework of at least 95%, 96%, 97%, 98% or 99% sequence identity to the framework sequence of the VH of SEQ ID NO: 65. In one aspect, the VH comprises the heavy chain CDR sequences of the VH of SEQ ID NO: 65 and a framework of at least 95% sequence identity to the framework sequence of the VH of SEQ ID NO: 65. In another aspect, the VH comprises the heavy chain CDR sequences of the VH of SEQ ID NO: 65 and a framework of at least 98% sequence identity to the framework sequence of the VH of SEQ ID NO: 65.

In one aspect, the VL of the second antigen binding domain comprises the light chain CDR sequences of the VL of SEQ ID NO: 66 and a framework of at least 95%, 96%, 97%, 98% or 99% sequence identity to the framework sequence of the VL of SEQ ID NO: 66. In one aspect, the VL comprises the light chain CDR sequences of the VL of SEQ ID NO: 66 and a framework of at least 95% sequence identity to the framework sequence of the VL of SEQ ID NO: 66. In another aspect, the VL comprises the light chain CDR sequences of the VL of SEQ ID NO: 66 and a framework of at least 98% sequence identity to the framework sequence of the VL of SEQ ID NO: 66.

In some aspects, the second antigen binding domain comprises
(i) a heavy chain variable region (VH) comprising a heavy chain complementary determining region (HCDR) 1 of SEQ ID NO: 51, a HCDR 2 of SEQ ID NO: 52, and a HCDR 3 of SEQ ID NO: 53, and a light chain variable region (VL) comprising a light chain complementarity determining region (LCDR) 1 of SEQ ID NO: 54, a LCDR 2 of SEQ ID NO: 55 and a LCDR 3 of SEQ ID NO: 56.

In one aspect, the VH of the second antigen binding domain comprises one or more heavy chain framework sequence (i.e. the FR1, FR2, FR3 and/or FR4 sequence) of SEQ ID NO: 57. In one aspect, the VH comprises an amino acid sequence that is at least about 95%, 96%, 97%, 98%, or 99% identical to the amino acid sequence of SEQ ID NO: 57. In one aspect, the VH comprises an amino acid sequence that is at least about 95% identical to the amino acid sequence of SEQ ID NO: 57. In one aspect, the VH comprises an amino acid sequence that is at least about 98% identical to the amino acid sequence of SEQ ID NO: 57. In certain aspects, a VH sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen (e.g. an activating T cell antigen, such as CD3). In certain aspects, a total of 1 to 10 amino acids have been substituted, inserted and/or deleted in the amino acid sequence of SEQ ID NO: 57. In certain aspects, substitutions, insertions, or deletions occur in regions outside the CDRs (i.e., in the FRs). In one aspect, the VH comprises the amino acid sequence of SEQ ID NO: 57. Optionally, the VH comprises the amino acid sequence of SEQ ID NO: 57, including post-translational modifications of that sequence.

In one aspect, the VL of the second antigen binding domain comprises one or more light chain framework sequence (i.e. the FR1, FR2, FR3 and/or FR4 sequence) of SEQ ID NO: 58. In one aspect, the VL comprises an amino acid sequence that is at least about 95%, 96%, 97%, 98%, or 99% identical to the amino acid sequence of SEQ ID NO: 58. In one aspect, the VL comprises an amino acid sequence that is at least about 95% identical to the amino acid sequence of SEQ ID NO: 58. In one aspect, the VL comprises an amino acid sequence that is at least about 98% identical to the amino acid sequence of SEQ ID NO: 58. In certain aspects, a VL sequence having at least 95%, 96%, 97%, 98%, or 99% identity contains substitutions (e.g., conservative substitutions), insertions, or deletions relative to the reference sequence, but an antibody comprising that sequence retains the ability to bind to the second antigen (e.g. an activating T cell antigen, such as CD3). In certain aspects, a total of 1 to 10 amino acids have been substituted, inserted and/or deleted in the amino acid sequence of SEQ ID NO: 58. In certain aspects, substitutions, insertions, or deletions occur in regions outside the CDRs (i.e., in the FRs). In one aspect, the VL comprises the amino acid sequence of SEQ ID NO: 58. Optionally, the VL comprises the amino acid sequence of SEQ ID NO: 58, including post-translational modifications of that sequence.

In one aspect, the VH of the second antigen binding domain comprises an amino acid sequence that is at least about 95%, 96%, 97%, 98%, or 99% identical to the amino acid sequence of SEQ ID NO: 57, and the VL of the second antigen binding domain comprises an amino acid sequence that is at least about 95%, 96%, 97%, 98%, or 99% identical to the amino acid sequence of SEQ ID NO: 58. In one aspect, the VH comprises the amino acid sequence of SEQ ID NO: 57 and the VL comprises the amino acid sequence of SEQ ID NO: 58.

In a further aspect, the second antigen binding domain comprises a VH comprising the sequence of SEQ ID NO: 57 and a VL comprising the sequence of SEQ ID NO: 58.

In a further aspect, the second antigen binding domain comprises a VH sequence of SEQ ID NO: 57 and a VL sequence of SEQ ID NO: 58.

In another aspect, the second antigen binding domain comprises a VH comprising the heavy chain CDR sequences of the VH of SEQ ID NO: 57, and a VL comprising the light chain CDR sequences of the VL of SEQ ID NO: 58.

In a further aspect, the second antigen binding domain comprises the HCDR1, HCDR2 and HCDR3 amino acid sequences of the VH of SEQ ID NO: 57 and the LCDR1, LCDR2 and LCDR3 amino acid sequences of the VL of SEQ ID NO: 58.

In one aspect, the VH of the second antigen binding domain comprises the heavy chain CDR sequences of the VH of SEQ ID NO: 57 and a framework of at least 95%, 96%, 97%, 98% or 99% sequence identity to the framework sequence of the VH of SEQ ID NO: 57. In one aspect, the VH comprises the heavy chain CDR sequences of the VH of SEQ ID NO: 57 and a framework of at least 95% sequence identity to the framework sequence of the VH of SEQ ID NO: 57. In another aspect, the VH comprises the heavy chain CDR sequences of the VH of SEQ ID NO: 57 and a framework of at least 98% sequence identity to the framework sequence of the VH of SEQ ID NO: 57.

In one aspect, the VL of the second antigen binding domain comprises the light chain CDR sequences of the VL of SEQ ID NO: 58 and a framework of at least 95%, 96%, 97%, 98% or 99% sequence identity to the framework sequence of the VL of SEQ ID NO: 58. In one aspect, the VL comprises the light chain CDR sequences of the VL of SEQ ID NO: 58 and a framework of at least 95% sequence identity to the framework sequence of the VL of SEQ ID NO: 58. In another aspect, the VL comprises the light chain CDR sequences of the VL of SEQ ID NO: 58 and a framework of at least 98% sequence identity to the framework sequence of the VL of SEQ ID NO: 58.

c) Charge Modifications

The (multispecific) antibody of the invention may comprise amino acid substitutions in Fab molecules comprised therein which are particularly efficient in reducing mispairing of light chains with non-matching heavy chains (Bence-Jones-type side products), which can occur in the production of Fab-based multispecific antibodies with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired (multispecific) antibody compared to undesired side products, in particular Bence Jones-type side products occurring in multispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some aspects wherein the first and the second (and, where present, third) antigen binding domain of the (multispecific) antibody are both Fab molecules, and in one of the antigen binding domains (particularly the second antigen binding domain) the variable domains VL and VH of the Fab light chain and the Fab heavy chain are replaced by each other, i) in the constant domain CL of the first (and, where present, third) antigen binding domain the amino acid at position 124 is substituted by a positively charged amino acid (numbering according to Kabat), and wherein in the constant domain CH1 of the first (and, where present, third) antigen binding domain the amino acid at position 147 or the amino acid at position 213 is substituted by a negatively charged amino acid (numbering according to Kabat EU index); or ii) in the constant domain CL of the second antigen binding domain the amino acid at position 124 is substituted by a positively charged amino acid (numbering according to Kabat), and wherein in the constant domain CH1 of the second antigen binding domain the amino acid at position 147 or the amino acid at position 213 is substituted by a negatively charged amino acid (numbering according to Kabat EU index).

The (multispecific) antibody does not comprise both modifications mentioned under i) and ii). The constant domains CL and CH1 of the antigen binding domain having the VH/VL exchange are not replaced by each other (i.e. remain unexchanged).

In a more specific aspect, i) in the constant domain CL of the first (and, where present, third) antigen binding domain the amino acid at position 124 is substituted independently by lysine (K), arginine (R) or histidine (H) (numbering according to Kabat), and in the constant domain CH1 of the first (and, where present, third) antigen binding domain the amino acid at position 147 or the amino acid at position 213 is substituted independently by glutamic acid (E), or aspartic acid (D) (numbering according to Kabat EU index); or ii) in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index).

In one such aspect, in the constant domain CL of the first (and, where present, third) antigen binding domain the amino acid at position 124 is substituted independently by lysine (K), arginine (R) or histidine (H) (numbering according to Kabat), and in the constant domain CH1 of the first (and, where present, third) antigen binding domain the amino acid at position 147 or the amino acid at position 213 is substituted independently by glutamic acid (E), or aspartic acid (D) (numbering according to Kabat EU index).

In a further aspect, in the constant domain CL of the first (and, where present, third) antigen binding domain the amino acid at position 124 is substituted independently by lysine (K), arginine (R) or histidine (H) (numbering according to Kabat), and in the constant domain CH1 of the first (and, where present, third) antigen binding domain the amino acid at position 147 is substituted independently by glutamic acid (E), or aspartic acid (D) (numbering according to Kabat EU index). In a preferred aspect, in the constant domain CL of the first (and, where present, third) antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more preferred aspect, in the constant domain CL of the first (and, where present, third) antigen binding domain the amino acid at position 124 is substituted by lysine (K) (numbering according to Kabat) and the amino acid at position 123 is substituted by lysine (K) (numbering according to Kabat), and in the constant domain CH1 of the first (and, where present, third) antigen binding domain the amino acid at position 147 is substituted by glutamic acid (E) (numbering according to Kabat EU index) and the amino acid at position 213 is substituted by glutamic acid (E) (numbering according to Kabat EU index).

In an even more preferred aspect, in the constant domain CL of the first (and, where present, third) antigen binding domain the amino acid at position 124 is substituted by lysine (K) (numbering according to Kabat) and the amino acid at position 123 is substituted by arginine (R) (numbering according to Kabat), and in the constant domain CH1 of the first (and, where present, third) antigen binding domain the amino acid at position 147 is substituted by glutamic acid (E) (numbering according to Kabat EU index) and the amino acid at position 213 is substituted by glutamic acid (E) (numbering according to Kabat EU index).

In preferred aspects, if amino acid substitutions according to the above aspects are made in the constant domain CL and the constant domain CH1 of the first (and, where present, third) antigen binding domain, the constant domain CL of the first (and, where present, third) antigen binding domain is of kappa isotype.

Alternatively, the amino acid substitutions according to the above aspects may be made in the constant domain CL and the constant domain CH1 of the second antigen binding domain instead of in the constant domain CL and the constant domain CH1 of the first (and, where present, third) antigen binding domain. In preferred such aspects, the constant domain CL of the second antigen binding domain is of kappa isotype.

Accordingly, in one aspect, in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index). In a further aspect, in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index).

In still another aspect, in the constant domain CL of the second antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one aspect, in the constant domain CL of the second antigen binding domain the amino acid at position 124 is substituted by lysine (K) (numbering according to Kabat) and the amino acid at position 123 is substituted by lysine (K) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).

In another aspect, in the constant domain CL of the second antigen binding domain the amino acid at position 124 is substituted by lysine (K) (numbering according to Kabat) and the amino acid at position 123 is substituted by arginine (R) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).

In a preferred aspect, the (multispecific) antibody of the invention comprises (A) a first and optionally a third antigen binding domain that binds to HLA-A2/MAGE-A4;
wherein the first (and, where present, third) antigen binding domain is a conventional Fab molecule and comprises
(i) a VH comprising a HCDR 1 of SEQ ID NO: 25, a HCDR 2 of SEQ ID NO: 26 and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(ii) a VH comprising a HCDR 1 of SEQ ID NO: 25, a HCDR 2 of SEQ ID NO: 26 and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(iii) a VH comprising a HCDR 1 of SEQ ID NO: 25, a HCDR 2 of SEQ ID NO: 26 and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(iv) a VH comprising a HCDR 1 of SEQ ID NO: 25, a HCDR 2 of SEQ ID NO: 26 and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(v) a VH comprising a HCDR 1 of SEQ ID NO: 25, a HCDR 2 of SEQ ID NO: 26 and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(vi) a VH comprising a HCDR 1 of SEQ ID NO: 25, a HCDR 2 of SEQ ID NO: 26 and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30; and
wherein in the constant domain CL of the first (and, where present, third) antigen binding domain the amino acid at position 124 is substituted independently by lysine (K), arginine (R) or histidine (H) (numbering according to Kabat) (in a preferred aspect independently by lysine (K) or arginine (R)) and the amino acid at position 123 is substituted independently by lysine (K), arginine (R) or histidine (H) (numbering according to Kabat) (in a preferred aspect independently by lysine (K) or arginine (R)), and in the constant domain CH1 of the second (and, where present, third) antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index);
and
(B) a second antigen binding domain that binds to a second antigen, preferably CD3, wherein the second antigen binding domain is a Fab molecule wherein the variable domains VL and VH of the Fab light chain and the Fab heavy chain are replaced by each other.

d) Multispecific Antibody Formats

Figure 1:
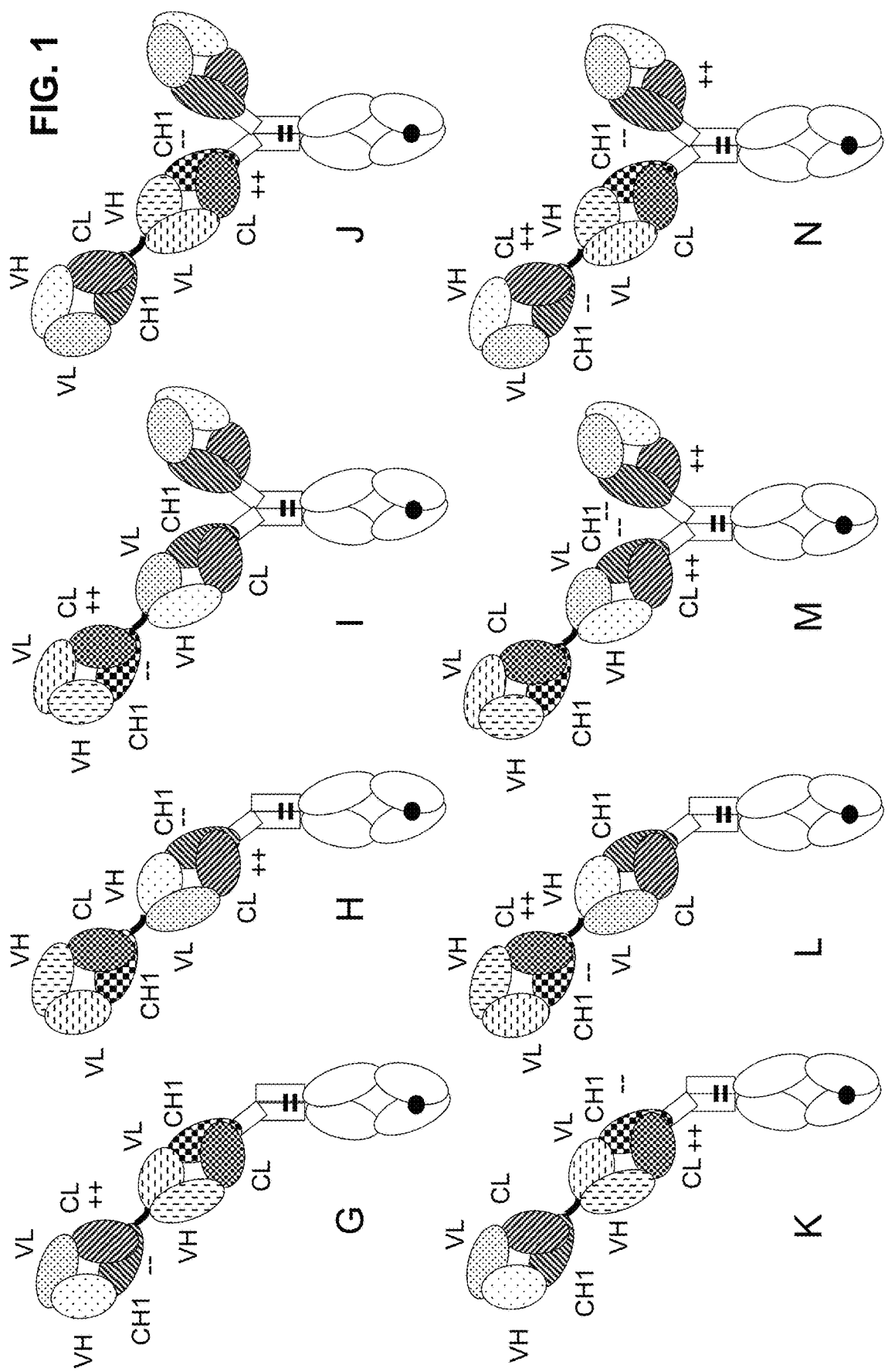
FIG. 1. Exemplary configurations of the bispecific antigen binding molecules of the invention. (A, D) Illustration of the "1+1 CrossMab" molecule. (B, E) Illustration of the "2+1 IgG Crossfab" molecule with alternative order of Crossfab and Fab components ("inverted"). (C, F) Illustration of the "2+1 IgG Crossfab" molecule. (G, K) Illustration of the "1+1 IgG Crossfab" molecule with alternative order of Crossfab and Fab components ("inverted"). (H, L) Illustration of the "1+1 IgG Crossfab" molecule. (I, M) Illustration of the "2+1 IgG Crossfab" molecule with two CrossFabs. (J, N) Illustration of the "2+1 IgG Crossfab" molecule with two CrossFabs and alternative order of Crossfab and Fab components ("inverted"). (O, S) Illustration of the "Fab-Crossfab" molecule. (P, T) Illustration of the "Crossfab-Fab" molecule. (Q, U) Illustration of the "(Fab)$_2$-Crossfab" molecule. (R, V) Illustration of the "Crossfab-(Fab)$_2$" molecule. (W, Y) Illustration of the "Fab-(Crossfab)$_2$" molecule. (X, Z) Illustration of the "(Crossfab)$_2$-Fab" molecule. Black dot: optional modification in the Fc domain promoting heterodimerization. ++, --: amino acids of opposite charges optionally introduced in the CH1 and CL domains. Crossfab molecules are depicted as comprising an exchange of VH and VL regions, but may—in aspects wherein no charge modifications are introduced in CH1 and CL domains—alternatively comprise an exchange of the CH1 and CL domains.
Figure 1:
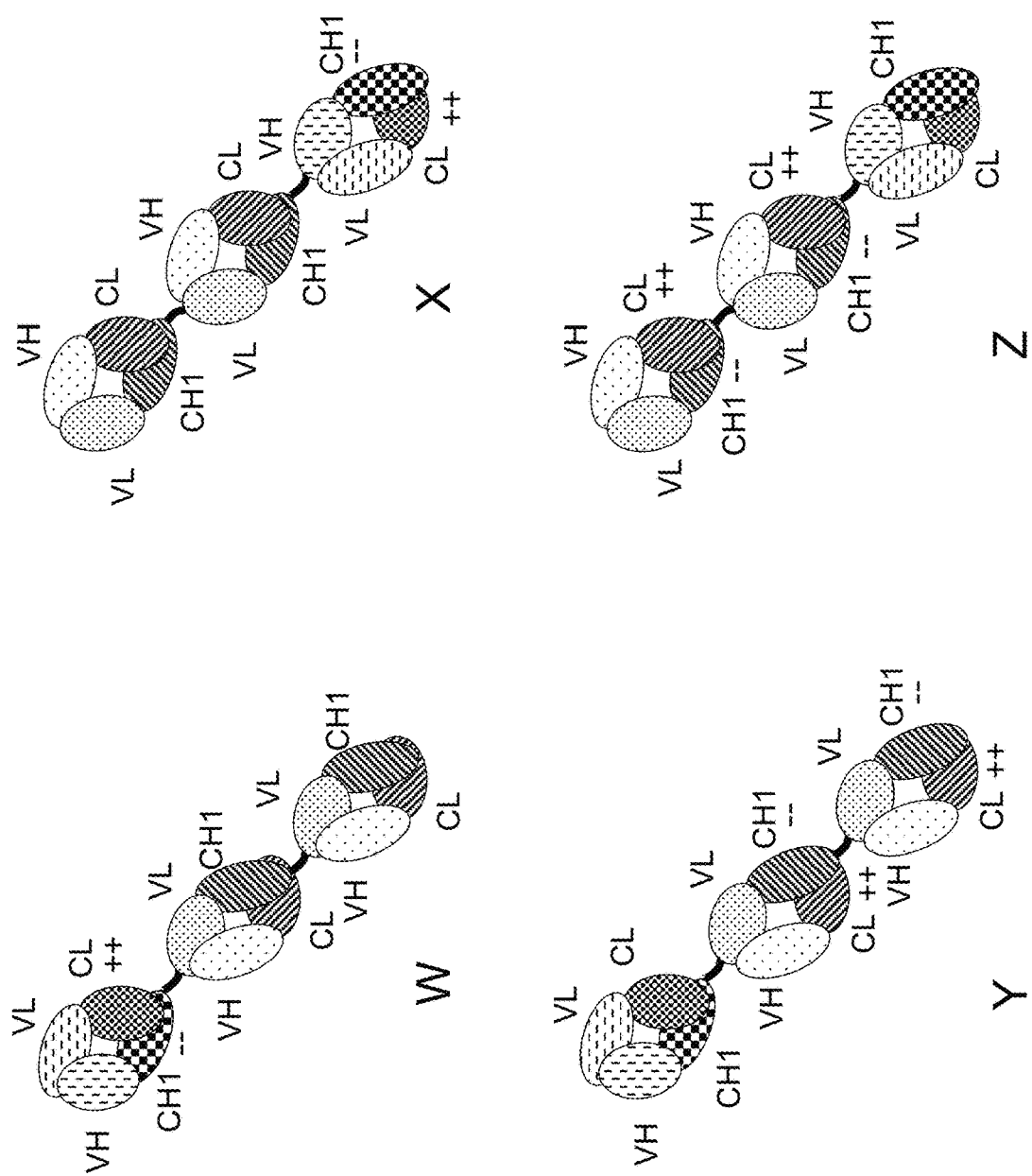

The (multispecific) antibody according to the present invention can have a variety of configurations. Exemplary configurations are depicted in FIG. 1.

In preferred aspects, the antigen binding domains comprised in the (multispecific) antibody are Fab molecules. In such aspects, the first, second, third etc. antigen binding domain may be referred to herein as first, second, third etc. Fab molecule, respectively.

In one aspect, the first and the second antigen binding domain of the (multispecific) antibody are fused to each other, optionally via a peptide linker. In preferred aspects, the first and the second antigen binding domain are each a Fab molecule. In one such aspect, the first antigen binding domain is fused at the C-terminus of the Fab heavy chain to the N-terminus of the Fab heavy chain of the second antigen binding domain. In another such aspect, the second antigen binding domain is fused at the C-terminus of the Fab heavy chain to the N-terminus of the Fab heavy chain of the first antigen binding domain. In aspects wherein either (i) the first antigen binding domain is fused at the C-terminus of the Fab heavy chain to the N-terminus of the Fab heavy chain of the second antigen binding domain or (ii) the second antigen binding domain is fused at the C-terminus of the Fab heavy chain to the N-terminus of the Fab heavy chain of the first antigen binding domain, additionally the Fab light chain of the first antigen binding domain and the Fab light chain of the second antigen binding domain may be fused to each other, optionally via a peptide linker.

A (multispecific) antibody with a single antigen binding domain (such as a Fab molecule) capable of specific binding to HLA-A2/MAGE-A4, (for example as shown in FIG. 1A, D, G, H, K, L) is useful, particularly in cases where internalization of the antigen is to be expected following binding of a high affinity antigen binding domain. In such cases, the presence of more than one antigen binding domain specific for HLA-A2/MAGE-A4 may enhance internalization of the antigen, thereby reducing its availability.

In other cases, however, it will be advantageous to have a (multispecific) antibody comprising two or more antigen binding domains (such as Fab molecules) specific for HLA-A2/MAGE-A4 (see examples shown in FIG. 1B, 1C, 1E, 1F, 1I, 1J, 1M or 1N), for example to optimize targeting to the target site or to allow crosslinking of target cell antigens.

Accordingly, in preferred aspects, the (multispecific) antibody according to the present invention comprises a third antigen binding domain.

In one aspect, the third antigen binding domain binds to HLA-A2/MAGE-A4. In one aspect, the third antigen binding domain is a Fab molecule.

In one aspect, the third antigen domain is identical to the first antigen binding domain.

In some aspects, the third and the first antigen binding domain are each a Fab molecule and the third antigen binding domain is identical to the first antigen binding domain. Thus, in these aspects, the first and the third antigen binding domain comprise the same heavy and light chain amino acid sequences and have the same arrangement of domains (i.e. conventional or crossover). Furthermore, in these aspects, the third antigen binding domain comprises the same amino acid substitutions, if any, as the first antigen binding domain. For example, the amino acid substitutions described herein as "charge modifications" will be made in the constant domain CL and the constant domain CH1 of each of the first antigen binding domain and the third antigen binding domain. Alternatively, said amino acid substitutions may be made in the constant domain CL and the constant domain CH1 of the second antigen binding domain (which in preferred aspects is also a Fab molecule), but not in the constant domain CL and the constant domain CH1 of the first antigen binding domain and the third antigen binding domain.

Like the first antigen binding domain, the third antigen binding domain preferably is a conventional Fab molecule. Aspects wherein the first and the third antigen binding domains are crossover Fab molecules (and the second antigen binding domain is a conventional Fab molecule) are, however, also contemplated. Thus, in preferred aspects, the first and the third antigen binding domains are each a conventional Fab molecule, and the second antigen binding domain is a crossover Fab molecule as described herein, i.e. a Fab molecule wherein the variable domains VH and VL or the constant domains CL and CH1 of the Fab heavy and light chains are exchanged/replaced by each other. In other aspects, the first and the third antigen binding domains are each a crossover Fab molecule and the second antigen binding domain is a conventional Fab molecule.

If a third antigen binding domain is present, in a preferred aspect the first and third antigen binding domain bind to HLA-A2/MAGE-A4, and the second antigen domain binds to a second antigen (e.g. an activating T cell antigen, such as CD3).

In preferred aspects, the (multispecific) antibody of the invention comprises an Fc domain composed of a first and a second subunit. The first and the second subunit of the Fc domain are capable of stable association.

The (multispecific) antibody according to the invention can have different configurations, i.e. the first, second (and optionally third) antigen binding domain may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some aspects, the first and the second antigen binding domain are each a Fab molecule and the second antigen binding domain is fused at the C-terminus of the Fab heavy chain to the N-terminus of the first or the second subunit of the Fc domain. In such aspects, the first antigen binding domain may be fused at the C-terminus of the Fab heavy chain to the N-terminus of the Fab heavy chain of the second antigen binding domain or to the N-terminus of the other one of the subunits of the Fc domain. In preferred such aspects, the first antigen binding domain is a conventional Fab molecule, and the second antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, the first antigen binding domain is a crossover Fab molecule and the second antigen binding domain is a conventional Fab molecule.

In one aspect, the first and the second antigen binding domain are each a Fab molecule, the second antigen binding domain is fused at the C-terminus of the Fab heavy chain to the N-terminus of the first or the second subunit of the Fc domain, and the first antigen binding domain is fused at the C-terminus of the Fab heavy chain to the N-terminus of the Fab heavy chain of the second antigen binding domain. In a specific aspect, the (multispecific) antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIGS. 1G and 1K (with the second antigen binding domain in these examples being a VH/VL crossover Fab molecule). Optionally, the Fab light chain of the first Fab molecule and the Fab light chain of the second Fab molecule may additionally be fused to each other.

In another aspect, the first and the second antigen binding domain are each a Fab molecule and the first and the second antigen binding domain are each fused at the C-terminus of the Fab heavy chain to the N-terminus of one of the subunits of the Fc domain. In a specific aspect, the (multispecific) antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIGS. 1A and 1D (in these examples with the second antigen binding domain being a VH/VL crossover Fab molecule and the first antigen binding domain being a conventional Fab molecule). The first and the second Fab molecule may be fused to the Fc domain directly or through a peptide linker. In a preferred aspect the first and the second Fab molecule are each fused to the Fc domain through an immunoglobulin hinge region. In a specific aspect, the immunoglobulin hinge region is a human $IgG_1$ hinge region, particularly where the Fc domain is an $IgG_1$ Fc domain.

In some aspects, the first and the second antigen binding domain are each a Fab molecule and the first antigen binding domain is fused at the C-terminus of the Fab heavy chain to the N-terminus of the first or the second subunit of the Fc domain. In such aspects, the second antigen binding domain may be fused at the C-terminus of the Fab heavy chain to the N-terminus of the Fab heavy chain of the second antigen binding domain or (as described above) to the N-terminus of the other one of the subunits of the Fc domain. In preferred such aspects, said first antigen binding domain is a conventional Fab molecule, and the second antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said first antigen binding domain is a crossover Fab molecule and the second antigen binding domain is a conventional Fab molecule.

In one aspect, the first and the second antigen binding domain are each a Fab molecule, the first antigen binding domain is fused at the C-terminus of the Fab heavy chain to the N-terminus of the first or the second subunit of the Fc domain, and the second antigen binding domain is fused at the C-terminus of the Fab heavy chain to the N-terminus of the Fab heavy chain of the first antigen binding domain. In a specific aspect, the (multispecific) antibody essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIGS. 1H and 1L (in these examples with the second antigen binding domain being a VH/VL crossover Fab molecule and the first antigen binding domain being a conventional Fab molecule). Optionally, the Fab light chain of the first Fab molecule and the Fab light chain of the second Fab molecule may additionally be fused to each other.

In some aspects, a third antigen binding domain, particularly a third Fab molecule, is fused at the C-terminus of the Fab heavy chain to the N-terminus of the first or second subunit of the Fc domain. In preferred such aspects, said first and third antigen binding domains are each a conventional Fab molecule, and the second antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said first and third antigen binding domains are each a crossover Fab molecule and the second antigen binding domain is a conventional Fab molecule.

In a preferred such aspect, the second and the third antigen binding domain are each fused at the C-terminus of the Fab heavy chain to the N-terminus of one of the subunits of the Fc domain, and the first antigen binding domain is fused at the C-terminus of the Fab heavy chain to the N-terminus of the Fab heavy chain of the second antigen binding domain. In a specific aspect, the (multispecific) antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1B and 1E (in these examples with the second antigen binding domain being a VH/VL crossover Fab molecule, and the first and the third antigen binding domain being a conventional Fab molecule), and FIGS. 1J and 1N (in these examples with the second antigen binding domain being a conventional Fab molecule, and the first and the third antigen binding domain being a VH/VL crossover Fab molecule). The second and the third Fab molecule may be fused to the Fc domain directly or through a peptide linker. In a preferred aspect, the second and the third Fab molecule are each fused to the Fc domain through an immunoglobulin hinge region. In a specific aspect, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In another such aspect, the first and the third antigen binding domain are each fused at the C-terminus of the Fab heavy chain to the N-terminus of one of the subunits of the Fc domain, and the second antigen binding domain is fused at the C-terminus of the Fab heavy chain to the N-terminus of the Fab heavy chain of the first antigen binding domain. In a specific aspect, the (multispecific) antibody essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1C and 1F (in these examples with the second antigen binding domain being a VH/VL crossover Fab molecule, and the first and the third antigen binding domain being a conventional Fab molecule) and in FIGS. 1I and 1M (in these examples with the second antigen binding domain being a conventional Fab molecule, and the first and the third antigen binding domain being a VH/VL crossover Fab molecule). The first and the third Fab molecule may be fused to the Fc domain directly or through a peptide linker. In a preferred aspect, the first and the third Fab molecule are each fused to the Fc domain through an immunoglobulin hinge region. In a specific aspect, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In configurations of the (multispecific) antibody wherein a Fab molecule is fused at the C-terminus of the Fab heavy chain to the N-terminus of each of the subunits of the Fc domain through an immunoglobulin hinge region, the two Fab molecules, the hinge regions and the Fc domain essentially form an immunoglobulin molecule. In a preferred aspect, the immunoglobulin molecule is an IgG class immunoglobulin. In an even more preferred aspect, the immunoglobulin is an IgG$_1$ subclass immunoglobulin. In another aspect, the immunoglobulin is an IgG$_4$ subclass immunoglobulin. In a further preferred aspect, the immunoglobulin is a human immunoglobulin. In other aspects, the immunoglobulin is a chimeric immunoglobulin or a humanized immunoglobulin. In one aspect, the immunoglobulin comprises a human constant region, particularly a human Fc region.

In some of the (multispecific) antibodies of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the (multispecific) antibody of the invention.

The antigen binding domains may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one aspect, said peptide linker has a length of at least 5 amino acids, in one aspect a length of 5 to 100, in a further aspect of 10 to 50 amino acids. In one aspect, said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one aspect x=4 and n=2 or 3, in a further aspect x=4 and n=2. In one aspect, said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 82 and 83). Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In certain aspects the (multispecific) antibody according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VL_{(2)}$-$CL_{(2)}$-CH2-CH3(-CH4)), and a polypeptide wherein the Fab heavy chain of the first Fab molecule shares a carboxy-terminal peptide bond with an Fc domain subunit ($VH_{(1)}$-$CH1_{(1)}$-CH2-CH3(-CH4)). In some aspects the (multispecific) antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In certain aspects the polypeptides are covalently linked, e.g., by a disulfide bond.

In certain aspects the (multispecific) antibody according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit ($VH_{(2)}$-$CL_{(2)}$-CH2-CH3(-CH4)), and a polypeptide wherein the Fab heavy chain of the first Fab molecule shares a carboxy-terminal peptide bond with an Fc domain subunit ($VH_{(1)}$-$CH1_{(1)}$-CH2-CH3(-CH4)). In some aspects the (multispecific) antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In certain aspects the polypeptides are covalently linked, e.g., by a disulfide bond.

In some aspects, the (multispecific) antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit ($VL_{(2)}$-$CH1_{(2)}$-$VH_{(1)}$-$CH1_{(1)}$-CH2-CH3(-CH4)). In other aspects, the (multispecific) antibody comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VH_{(1)}$-$CH1_{(1)}$-$VL_{(2)}$-$CH1_{(2)}$-CH2-CH3(-CH4)). In some of these aspects the (multispecific) antibody further comprises a crossover Fab light chain polypeptide of the second Fab molecule, wherein the Fab heavy chain variable region of the second Fab molecule shares a carboxy-terminal peptide bond with the Fab light chain constant region of the second Fab molecule ($VH_{(2)}$-$CL_{(2)}$), and the Fab light chain polypeptide of the first Fab molecule ($VL_{(1)}$-$CL_{(1)}$). In others of these aspects the (multispecific) antibody further comprises a polypeptide wherein the Fab heavy chain variable region of the second Fab molecule shares a carboxy-terminal peptide bond with the Fab light chain constant region of the second Fab molecule which in turn shares a carboxy-terminal peptide bond with the Fab light chain polypeptide of the first Fab molecule ($VH_{(2)}$-$CL_{(2)}$-$VL_{(1)}$-$CL_{(1)}$, or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule ($VL_{(1)}$-$CL_{(1)}$-$VH_{(2)}$-$CL_{(2)}$), as appropriate. The (multispecific) antibody according to these aspects may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain aspects the polypeptides are covalently linked, e.g., by a disulfide bond.

In some aspects, the (multispecific) antibody comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with an Fc domain subunit ($VH_{(2)}$-$CL_{(2)}$-$VH_{(1)}$-$CH1_{(1)}$-CH2-CH3(-CH4)). In other aspects, the (multispecific) antibody comprises a polypeptide wherein the Fab heavy chain of the first Fab molecule shares a carboxy-terminal peptide bond with the Fab heavy chain variable region of the second Fab molecule which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit ($VH_{(1)}$-$CH1_{(1)}$-$VH_{(2)}$-$CL_{(2)}$-CH2-CH3(-CH4)). In some of these aspects the (multispecific) antibody further comprises a crossover Fab light chain polypeptide of the second Fab molecule, wherein the Fab light chain variable region of the second Fab molecule shares a carboxy-terminal peptide bond with the Fab heavy chain constant region of the second Fab molecule ($VL_{(2)}$-$CH1_{(2)}$), and the Fab light chain polypeptide of the first Fab molecule ($VL_{(1)}$-$CL_{(1)}$). In others of these aspects the (multispecific) antibody further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule ($VL_{(2)}$-$CH1_{(2)}$-$VL_{(1)}$-$CL_{(1)}$, or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule ($VL_{(1)}$-$CL_{(1)}$-$VH_{(2)}$-$CL_{(2)}$), as appropriate. The (multispecific) antibody according to these aspects may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain aspects the polypeptides are covalently linked, e.g., by a disulfide bond.

In certain aspects, the (multispecific) antibody does not comprise an Fc domain. In preferred such aspects, said first and, if present, third antigen binding domains are each a conventional Fab molecule, and the second antigen binding domain is a crossover Fab molecule as described herein, i.e. a Fab molecule wherein the variable domains VH and VL or the constant domains CL and CH1 of the Fab heavy and light chains are exchanged/replaced by each other. In other such aspects, said first and, if present, third antigen binding domains are each a crossover Fab molecule and the second antigen binding domain is a conventional Fab molecule.

In one such aspect, the (multispecific) antibody essentially consists of the first and the second antigen binding domain, and optionally one or more peptide linkers, wherein the first and the second antigen binding domain are both Fab molecules and the first antigen binding domain is fused at the C-terminus of the Fab heavy chain to the N-terminus of the Fab heavy chain of the second antigen binding domain. Such a configuration is schematically depicted in FIGS. 1O and 1S (in these examples with the second antigen binding domain being a VH/VL crossover Fab molecule and the first antigen binding domain being a conventional Fab molecule).

In another such aspect, the (multispecific) antibody essentially consists of the first and the second antigen binding domain, and optionally one or more peptide linkers, wherein the first and the second antigen binding domain are both Fab molecules and the second antigen binding domain is fused at the C-terminus of the Fab heavy chain to the N-terminus of the Fab heavy chain of the first antigen binding domain. Such a configuration is schematically depicted in FIGS. 1P and 1T (in these examples with the second antigen binding domain being a VH/VL crossover Fab molecule and the first antigen binding domain being a conventional Fab molecule).

In some aspects, the first Fab molecule is fused at the C-terminus of the Fab heavy chain to the N-terminus of the Fab heavy chain of the second Fab molecule, and the (multispecific) antibody further comprises a third antigen binding domain, particularly a third Fab molecule, wherein said third Fab molecule is fused at the C-terminus of the Fab heavy chain to the N-terminus of the Fab heavy chain of the first Fab molecule. In certain such aspects, the (multispecific) antibody essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the C-terminus of the Fab heavy chain to the N-terminus of the Fab heavy chain of the first Fab molecule. Such a configuration is schematically depicted in FIGS. 1Q and 1U (in these examples with the second antigen binding domain being a VH/VL crossover Fab molecule and the first and the third antigen binding domain each being a conventional Fab molecule), or FIGS. 1X and 1Z (in these examples with the second antigen binding domain being a conventional Fab molecule and the first and the third antigen binding domain each being a VH/VL crossover Fab molecule).

In some aspects, the second Fab molecule is fused at the C-terminus of the Fab heavy chain to the N-terminus of the Fab heavy chain of the first Fab molecule, and the (multispecific) antibody further comprises a third antigen binding domain, particularly a third Fab molecule, wherein said third Fab molecule is fused at the N-terminus of the Fab heavy chain to the C-terminus of the Fab heavy chain of the first Fab molecule. In certain such aspects, the (multispecific) antibody essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIGS. 1R and 1V (in these examples with the second antigen binding domain being a VH/VL crossover Fab molecule and the first and the third antigen binding domain each being a conventional Fab molecule), or FIGS. 1W and 1Y (in these examples with the second antigen binding domain being a conventional Fab molecule and the first and the third antigen binding domain each being a VH/VL crossover Fab molecule).

In certain aspects the (multispecific) antibody according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$). In some aspects the (multispecific) antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain aspects the (multispecific) antibody according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some aspects the (multispecific) antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain aspects the (multispecific) antibody according to the invention comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) ($VH_{(1)}$-$CH1_{(1)}$-$VH_{(2)}$-$CL_{(2)}$). In some aspects the (multispecific) antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$).

In certain aspects the (multispecific) antibody according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(2)}$-$CL_{(2)}$-$VH_{(1)}$-$CH1_{(1)}$). In some aspects the (multispecific) antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$).

In certain aspects the (multispecific) antibody according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-$CH1_{(3)}$-$VH_{(1)}$-$CH1_{(1)}$-$VL_{(2)}$-$CH1_{(2)}$). In some aspects the (multispecific) antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some aspects the (multispecific) antibody further comprises the Fab light chain polypeptide of a third Fab molecule (VL$_{(3)}$-CL$_{(3)}$).

In certain aspects the (multispecific) antibody according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) (VH$_{(3)}$-CH1$_{(3)}$-VH$_{(1)}$-CH1$_{(1)}$-VH$_{(2)}$-CL$_{(2)}$). In some aspects the (multispecific) antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In some aspects the (multispecific) antibody further comprises the Fab light chain polypeptide of a third Fab molecule (VL$_{(3)}$-CL$_{(3)}$). In certain aspects the (multispecific) antibody according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule (VL$_{(2)}$-CH1$_{(2)}$-VH$_{(1)}$-CH1$_{(1)}$-VH$_{(3)}$-CH1$_{(3)}$). In some aspects the (multispecific) antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some aspects the (multispecific) antibody further comprises the Fab light chain polypeptide of a third Fab molecule (VL$_{(3)}$-CL$_{(3)}$). In certain aspects the (multispecific) antibody according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule (VH$_{(2)}$-CL$_{(2)}$-VH$_{(1)}$-CH1$_{(1)}$-VH$_{(3)}$-CH1$_{(3)}$). In some aspects the (multispecific) antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In some aspects the (multispecific) antibody further comprises the Fab light chain polypeptide of a third Fab molecule (VL$_{(3)}$-CL$_{(3)}$).

In certain aspects the (multispecific) antibody according to the invention comprises a polypeptide wherein the Fab heavy chain of the second Fab molecule shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) (VH$_{(2)}$-CH1$_{(2)}$-VL$_{(1)}$-CH1$_{(1)}$-VL$_{(3)}$-CH1$_{(3)}$). In some aspects the (multispecific) antibody further comprises a polypeptide wherein the Fab heavy chain variable region of the first Fab molecule shares a carboxy-terminal peptide bond with the Fab light chain constant region of the first Fab molecule (VH$_{(1)}$-CL$_{(1)}$) and the Fab light chain polypeptide of the second Fab molecule (VL$_{(2)}$-CL$_{(2)}$). In some aspects the (multispecific) antibody further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain aspects the (multispecific) antibody according to the invention comprises a polypeptide wherein the Fab heavy chain of the second Fab molecule shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) (VH$_{(2)}$-CH1$_{(2)}$-VH$_{(1)}$-CL$_{(1)}$-VH$_{(3)}$-CL$_{(3)}$). In some aspects the (multispecific) antibody further comprises a polypeptide wherein the Fab light chain variable region of the first Fab molecule shares a carboxy-terminal peptide bond with the Fab heavy chain constant region of the first Fab molecule (VL$_{(1)}$-CH1$_{(1)}$) and the Fab light chain polypeptide of the second Fab molecule (VL$_{(2)}$-CL$_{(2)}$). In some aspects the (multispecific) antibody further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In certain aspects the (multispecific) antibody according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule (VL$_{(3)}$-CH1$_{(3)}$-VL$_{(1)}$-CH1$_{(1)}$-VH$_{(2)}$-CH1$_{(2)}$). In some aspects the (multispecific) antibody further comprises a polypeptide wherein the Fab heavy chain variable region of the first Fab molecule shares a carboxy-terminal peptide bond with the Fab light chain constant region of the first Fab molecule (VH$_{(1)}$-CL$_{(1)}$) and the Fab light chain polypeptide of the second Fab molecule (VL$_{(2)}$-CL$_{(2)}$). In some aspects the (multispecific) antibody further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain aspects the (multispecific) antibody according to the invention comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule (VH$_{(3)}$-CL$_{(3)}$-VH$_{(1)}$-CL$_{(1)}$-VH$_{(2)}$-CH1$_{(2)}$). In some aspects the (multispecific) antibody further comprises a polypeptide wherein the Fab light chain variable region of the first Fab molecule shares a carboxy-terminal peptide bond with the Fab heavy chain constant region of the first Fab molecule (VL$_{(1)}$-CH1$_{(1)}$) and the Fab light chain polypeptide of the second Fab molecule (VL$_{(2)}$-CL$_{(2)}$). In some aspects the (multispecific) antibody further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In one aspect, the invention provides a (multispecific) antibody comprising
(A) a first antigen binding domain that binds to HLA-A2/MAGE-A4, wherein the first antigen binding domain is a (conventional) Fab molecule and comprises
(i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
(iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
(iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
(v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
(vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
(particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);
(B) a second antigen binding domain that binds to a second antigen, particularly an activating T cell antigen, more particularly CD3, wherein the second antigen binding domain is a Fab molecule wherein the variable domains VL and VH or the constant domains CL and CH1 of the Fab light chain and the Fab heavy chain are replaced by each other;
(C) an Fc domain composed of a first and a second subunit;
wherein
(i) the first antigen binding domain under (A) is fused at the C-terminus of the Fab heavy chain to the N-terminus of the Fab heavy chain of the second antigen binding domain under (B), and the second antigen binding domain under (B) is fused at the C-terminus of the Fab heavy chain to the N-terminus of one of the subunits of the Fc domain under (C), or
(ii) the second antigen binding domain under (B) is fused at the C-terminus of the Fab heavy chain to the N-terminus of the Fab heavy chain of the first antigen binding domain under (A), and the first antigen binding domain under (A) is fused at the C-terminus of the Fab heavy chain to the N-terminus of one of the subunits of the Fc domain under (C).

In a preferred aspect, the invention provides a (multispecific) antibody comprising
(A) a first and a third antigen binding domain that binds to HLA-A2/MAGE-A4, wherein each of the first and the third antigen binding domain is a (conventional) Fab molecule and comprises
(i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
(iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
(iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
(v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
(vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
(particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);
(B) a second antigen binding domain that binds to a second antigen, particularly an activating T cell antigen, more particularly CD3, wherein the second antigen binding domain is a Fab molecule wherein the variable domains VL and VH or the constant domains CL and CH1 of the Fab light chain and the Fab heavy chain are replaced by each other; and
(C) an Fc domain composed of a first and a second subunit;
wherein
(i) the first antigen binding domain under (A) is fused at the C-terminus of the Fab heavy chain to the N-terminus of the Fab heavy chain of the second antigen binding domain under (B), and the second antigen binding domain under (B) and the third antigen binding domain under (A) are each fused at the C-terminus of the Fab heavy chain to the N-terminus of one of the subunits of the Fc domain under (C), or
(ii) the second antigen binding domain under (B) is fused at the C-terminus of the Fab heavy chain to the N-terminus of the Fab heavy chain of the first antigen binding domain under (A), and the first antigen binding domain under (A) and the third antigen binding domain under (A) are each fused at the C-terminus of the Fab heavy chain to the N-terminus of one of the subunits of the Fc domain under (C).

In another aspect, the invention provides a (multispecific) antibody comprising
(A) a first antigen binding domain that binds to HLA-A2/MAGE-A4, wherein the first antigen binding domain is a (conventional) Fab molecule and comprises
(i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
(ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
(iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
(iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
(v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
(vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
(particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);
(B) a second antigen binding domain that binds to a second antigen, particularly an activating T cell antigen, more particularly CD3, wherein the second antigen binding domain is a Fab molecule wherein the variable domains VL and VH or the constant domains CL and CH1 of the Fab light chain and the Fab heavy chain are replaced by each other; and
(C) an Fc domain composed of a first and a second subunit;
wherein
(i) the first antigen binding domain under (A) and the second antigen binding domain under (B) are each fused at the C-terminus of the Fab heavy chain to the N-terminus of one of the subunits of the Fc domain under (C).

In all of the different configurations of the (multispecific) antibody according to the invention, the amino acid substitutions ("charge modifications") described herein, if present, may either be in the CH1 and CL domains of the first and (if present) the third antigen binding domain/Fab molecule, or in the CH1 and CL domains of the second antigen binding domain/Fab molecule. Preferably, they are in the CH1 and CL domains of the first and (if present) the third antigen binding domain/Fab molecule. In accordance with the concept of the invention, if amino acid substitutions as described herein are made in the first (and, if present, the third) antigen binding domain/Fab molecule, no such amino acid substitutions are made in the second antigen binding domain/Fab molecule. Conversely, if amino acid substitutions as described herein are made in the second antigen binding domain/Fab molecule, no such amino acid substitutions are made in the first (and, if present, the third) antigen binding domain/Fab molecule. Amino acid substitutions are preferably made in (multispecific) antibodies comprising a Fab molecule wherein the variable domains VL and VH1 of the Fab light chain and the Fab heavy chain are replaced by each other.

In preferred aspects of the (multispecific) antibody according to the invention, particularly wherein amino acid substitutions as described herein are made in the first (and, if present, the third) antigen binding domain/Fab molecule, the constant domain CL of the first (and, if present, the third) Fab molecule is of kappa isotype. In other aspects of the (multispecific) antibody according to the invention, particularly wherein amino acid substitutions as described herein are made in the second antigen binding domain/Fab molecule, the constant domain CL of the second antigen binding domain/Fab molecule is of kappa isotype. In some aspects, the constant domain CL of the first (and, if present, the third)

antigen binding domain/Fab molecule and the constant domain CL of the second antigen binding domain/Fab molecule are of kappa isotype.

In one aspect, the invention provides a (multispecific) antibody comprising
- (A) a first antigen binding domain that binds to HLA-A2/MAGE-A4, wherein the first antigen binding domain is a (conventional) Fab molecule and comprises
  - (i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
  - (ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
  - (iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
  - (iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
  - (v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
  - (vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
  - (particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);
- (B) a second antigen binding domain that binds to a second antigen, particularly an activating T cell antigen, more particularly CD3, wherein the second antigen binding domain is a Fab molecule wherein the variable domains VL and VH of the Fab light chain and the Fab heavy chain are replaced by each other; and
- (C) an Fc domain composed of a first and a second subunit;
  wherein in the constant domain CL of the first antigen binding domain under (A) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the second antigen binding domain under (A) the amino acid at position 147 is substituted by glutamic acid (E) (numbering according to Kabat EU index) and the amino acid at position 213 is substituted by glutamic acid (E) (numbering according to Kabat EU index); and wherein
  - (i) the first antigen binding domain under (A) is fused at the C-terminus of the Fab heavy chain to the N-terminus of the Fab heavy chain of the second antigen binding domain under (B), and the second antigen binding domain under (B) is fused at the C-terminus of the Fab heavy chain to the N-terminus of one of the subunits of the Fc domain under (C), or
  - (ii) the second antigen binding domain under (B) is fused at the C-terminus of the Fab heavy chain to the N-terminus of the Fab heavy chain of the first antigen binding domain under (A), and the first antigen binding domain under (A) is fused at the C-terminus of the Fab heavy chain to the N-terminus of one of the subunits of the Fc domain under (C).

In a preferred aspect, the invention provides a (multispecific) antibody comprising
- (A) a first and a third antigen binding domain that binds to HLA-A2/MAGE-A4, wherein each of the first and the third antigen binding domain is a (conventional) Fab molecule and comprises
  - (i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
  - (ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
  - (iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
  - (iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
  - (v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
  - (vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
  - (particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);
- (B) a second antigen binding domain that binds to a second antigen, particularly an activating T cell antigen, more particularly CD3, wherein the second antigen binding domain is a Fab molecule wherein the variable domains VL and VH of the Fab light chain and the Fab heavy chain are replaced by each other; and
- (C) an Fc domain composed of a first and a second subunit;
  wherein in the constant domain CL of the first antigen binding domain under (A) and the third antigen binding domain under (A) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the first antigen binding domain under (A) and the third antigen binding domain under (A) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding domain under (A) is fused at the C-terminus of the Fab heavy chain to the N-terminus of the Fab heavy chain of the second antigen binding domain under (B), and the second antigen binding domain under (B) and the third antigen binding domain under (A) are each fused at the C-terminus of the Fab heavy chain to the N-terminus of one of the subunits of the Fc domain under (C), or (ii) the second antigen binding domain under (B) is fused at the C-terminus of the Fab heavy chain to the N-terminus of the Fab heavy chain of the first antigen binding domain under (A), and the first antigen binding domain under (A) and the third antigen binding domain under (A) are each fused at the C-terminus of the Fab heavy chain to the N-terminus of one of the subunits of the Fc domain under (C).

In another aspect, the invention provides a (multispecific) antibody comprising (A) a first antigen binding domain that binds to HLA-A2/MAGE-A4, wherein the first antigen binding domain is a (conventional) Fab molecule and comprises (i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;

(iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;

(iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or (vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;

(particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);

(B) a second antigen binding domain that binds to a second antigen, particularly an activating T cell antigen, more particularly CD3, wherein the second antigen binding domain is a Fab molecule wherein the variable domains VL and VH of the Fab light chain and the Fab heavy chain are replaced by each other; and (C) an Fc domain composed of a first and a second subunit;

wherein in the constant domain CL of the first antigen binding domain under (A) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the first antigen binding domain under (A) the amino acid at position 147 is substituted by glutamic acid (E) (numbering according to Kabat EU index) and the amino acid at position 213 is substituted by glutamic acid (E) (numbering according to Kabat EU index); and wherein the first antigen binding domain under (A) and the second antigen binding domain under (B) are each fused at the C-terminus of the Fab heavy chain to the N-terminus of one of the subunits of the Fc domain under (C).

According to any of the above aspects, components of the (multispecific) antibody (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally an integer from 1 to 10, typically from 2 to 4.

Further, according to any of the above aspects, the second antigen binding domain may comprise (i) a VH comprising a HCDR 1 of SEQ ID NO: 59, a HCDR 2 of SEQ ID NO: 60, and a HCDR 3 of SEQ ID NO: 61, and a VL comprising a LCDR 1 of SEQ ID NO: 62, a LCDR 2 of SEQ ID NO: 63 and a LCDR 3 of SEQ ID NO: 64, or (ii) a VH comprising a HCDR 1 of SEQ ID NO: 51, a HCDR 2 of SEQ ID NO: 52, and a HCDR 3 of SEQ ID NO: 53, and a VL comprising a LCDR 1 of SEQ ID NO: 54, a LCDR 2 of SEQ ID NO: 55 and a LCDR 3 of SEQ ID NO: 56 (particularly a VH comprising a HCDR 1 of SEQ ID NO: 59, a HCDR 2 of SEQ ID NO: 60, and a HCDR 3 of SEQ ID NO: 61, and a VL comprising a LCDR 1 of SEQ ID NO: 62, a LCDR 2 of SEQ ID NO: 63 and a LCDR 3 of SEQ ID NO: 64); and/or (i) a VH comprising the amino acid sequence of SEQ ID NO: 65, and a VL comprising the amino acid sequence of SEQ ID NO: 66, or (ii) a VH comprising the amino acid sequence of SEQ ID NO: 57, and a VL comprising the amino acid sequence of SEQ ID NO: 58 (particularly a VH comprising the amino acid sequence of SEQ ID NO: 65, and a VL comprising the amino acid sequence of SEQ ID NO: 66).

In a preferred aspect, the invention provides a (multispecific) antibody comprising (A) a first and a third antigen binding domain that binds to HLA-A2/MAGE-A4, wherein each of the first and the third antigen binding domain is a (conventional) Fab molecule and comprises (i) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(ii) a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6;
(iii) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
(iv) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
(v) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22; or
(vi) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
(particularly a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30);
(B) a second antigen binding domain that binds to a second antigen, particularly an activating T cell antigen, more particularly CD3, wherein the second antigen binding domain is a Fab molecule wherein the variable domains VL and VH of the Fab light chain and the Fab heavy chain are replaced by each other and comprises
(i) a VH comprising a HCDR 1 of SEQ ID NO: 59, a HCDR 2 of SEQ ID NO: 60, and a HCDR 3 of SEQ ID NO: 61, and a VL comprising a LCDR 1 of SEQ ID NO: 62, a LCDR 2 of SEQ ID NO: 63 and a LCDR 3 of SEQ ID NO: 64; or
(ii) a VH comprising a HCDR 1 of SEQ ID NO: 51, a HCDR 2 of SEQ ID NO: 52, and a HCDR 3 of SEQ ID NO: 53, and a VL comprising a LCDR 1 of SEQ ID NO: 54, a LCDR 2 of SEQ ID NO: 55 and a LCDR 3 of SEQ ID NO: 56;
(particularly a VH comprising a HCDR 1 of SEQ ID NO: 59, a HCDR 2 of SEQ ID NO: 60, and a HCDR 3 of SEQ ID NO: 61, and a VL comprising a LCDR 1 of SEQ ID NO: 62, a LCDR 2 of SEQ ID NO: 63 and a LCDR 3 of SEQ ID NO: 64); and
(C) an Fc domain composed of a first and a second subunit;
wherein
in the constant domain CL of the first and the third antigen binding domain under (A) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the first and the third antigen binding domain under (A) the amino acid at position 147 is substituted by glutamic acid (E) (numbering according to Kabat EU index) and the amino acid at position 213 is substituted by glutamic acid (E) (numbering according to Kabat EU index);
and wherein further
the first antigen binding domain under (A) is fused at the C-terminus of the Fab heavy chain to the N-terminus of the Fab heavy chain of the second antigen binding domain under (B), and the second antigen binding domain under (B) and the third antigen binding domain under (A) are each fused at the C-terminus of the Fab heavy chain to the N-terminus of one of the subunits of the Fc domain under (C).

In a further preferred aspect, the invention provides a (multispecific) antibody comprising
(A) a first and a third antigen binding domain that binds to HLA-A2/MAGE-A4, wherein each of the first and the third antigen binding domain is a (conventional) Fab molecule and comprises
(i) a VH comprising the amino acid sequence of SEQ ID NO: 31, and a VL comprising the amino acid sequence of SEQ ID NO: 32;
(i) a VH comprising the amino acid sequence of SEQ ID NO: 7, and a VL comprising the amino acid sequence of SEQ ID NO: 8;
(i) a VH comprising the amino acid sequence of SEQ ID NO: 47, and a VL comprising the amino acid sequence of SEQ ID NO: 48;
(i) a VH comprising the amino acid sequence of SEQ ID NO: 15, and a VL comprising the amino acid sequence of SEQ ID NO: 16;
(i) a VH comprising the amino acid sequence of SEQ ID NO: 23, and a VL comprising the amino acid sequence of SEQ ID NO: 24;
(i) a VH comprising the amino acid sequence of SEQ ID NO: 39, and a VL comprising the amino acid sequence of SEQ ID NO: 40;
(particularly a VH comprising the amino acid sequence of SEQ ID NO: 31, and a VL comprising the amino acid sequence of SEQ ID NO: 32);
(B) a second antigen binding domain that binds to a second antigen, particularly an activating T cell antigen, more particularly CD3, wherein the second antigen binding domain is a Fab molecule wherein the variable domains VL and VH of the Fab light chain and the Fab heavy chain are replaced by each other and comprises
(i) a VH comprising the amino acid sequence of SEQ ID NO: 65, and a VL comprising the amino acid sequence of SEQ ID NO: 66; or
(ii) a VH comprising the amino acid sequence of SEQ ID NO: 57, and a VL comprising the amino acid sequence of SEQ ID NO: 58;
(particularly a VH comprising the amino acid sequence of SEQ ID NO: 65, and a VL comprising the amino acid sequence of SEQ ID NO: 66); and
(C) an Fc domain composed of a first and a second subunit;
wherein
in the constant domain CL of the first and the third antigen binding domain under (A) the amino acid at position 124 is substituted by lysine (K) (numbering according to Kabat) and the amino acid at position 123 is substituted by lysine (K) or arginine (R) (numbering according to Kabat) (most preferably by arginine (R)), and wherein in the constant domain CH1 of the first and the third antigen binding domain under (A) the amino acid at position 147 is substituted by glutamic acid (E) (numbering according to Kabat EU index) and the amino acid at position 213 is substituted by glutamic acid (E) (numbering according to Kabat EU index);

and wherein further
the first antigen binding domain under (A) is fused at the C-terminus of the Fab heavy chain to the N-terminus of the Fab heavy chain of the second antigen binding domain under (B), and the second antigen binding domain under (B) and the third antigen binding domain under (A) are each fused at the C-terminus of the Fab heavy chain to the N-terminus of one of the subunits of the Fc domain under (C).

In one aspect according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further aspect according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further aspect according to these aspects of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further aspect according to these aspects of the invention, the Fc domain is a human $IgG_1$ Fc domain.

In a specific aspect, the (multispecific) antibody comprises a polypeptide comprising an amino acid sequence that is at least 95%, 96%, 97%, 98%, or 99% identical to the sequence of SEQ ID NO: 68, a polypeptide comprising an amino acid sequence that is at least 95%, 96%, 97%, 98%, or 99% identical to the sequence of SEQ ID NO: 69, a polypeptide (particularly two polypeptides) comprising an amino acid sequence that is at least 95%, 96%, 97%, 98%, or 99% identical to the sequence of SEQ ID NO: 70, and a polypeptide comprising an amino acid sequence that is at least 95%, 96%, 97%, 98%, or 99% identical to the sequence of SEQ ID NO: 72. In a further specific aspect, the (multispecific) antibody comprises a polypeptide comprising the amino acid sequence of SEQ ID NO: 68, a polypeptide comprising the amino acid sequence of SEQ ID NO: 69, a polypeptide (particularly two polypeptides) comprising the amino acid sequence of SEQ ID NO: 70 and a polypeptide comprising the amino acid sequence of SEQ ID NO: 72.

In one aspect, the invention provides a (multispecific) antibody that binds to HLA-A2/MAGE-A4 and CD3, comprising a polypeptide comprising an amino acid sequence that is at least 95%, 96%, 97%, 98%, or 99% identical to the sequence of SEQ ID NO: 68, a polypeptide comprising an amino acid sequence that is at least 95%, 96%, 97%, 98%, or 99% identical to the sequence of SEQ ID NO: 69, a polypeptide (particularly two polypeptides) comprising an amino acid sequence that is at least 95%, 96%, 97%, 98%, or 99% identical to the sequence of SEQ ID NO: 70, and a polypeptide comprising an amino acid sequence that is at least 95%, 96%, 97%, 98%, or 99% identical to the sequence of SEQ ID NO: 72. In one aspect the invention provides a (multispecific) antibody that binds to HLA-A2/MAGE-A4 and CD3, comprising a polypeptide comprising the amino acid sequence of SEQ ID NO: 68, a polypeptide comprising the amino acid sequence of SEQ ID NO: 69, a polypeptide (particularly two polypeptides) comprising the amino acid sequence of SEQ ID NO: 70 and a polypeptide comprising the amino acid sequence of SEQ ID NO: 72.

In a further specific aspect, the (multispecific) antibody comprises a polypeptide comprising an amino acid sequence that is at least 95%, 96%, 97%, 98%, or 99% identical to the sequence of SEQ ID NO: 67, a polypeptide comprising an amino acid sequence that is at least 95%, 96%, 97%, 98%, or 99% identical to the sequence of SEQ ID NO: 69, a polypeptide (particularly two polypeptides) comprising an amino acid sequence that is at least 95%, 96%, 97%, 98%, or 99% identical to the sequence of SEQ ID NO: 70, and a polypeptide comprising an amino acid sequence that is at least 95%, 96%, 97%, 98%, or 99% identical to the sequence of SEQ ID NO: 71. In a further specific aspect, the (multispecific) antibody comprises a polypeptide comprising the amino acid sequence of SEQ ID NO: 67, a polypeptide comprising the amino acid sequence of SEQ ID NO: 69, a polypeptide (particularly two polypeptides) comprising the amino acid sequence of SEQ ID NO: 70 and a polypeptide comprising the amino acid sequence of SEQ ID NO: 71.

In one aspect, the invention provides a (multispecific) antibody that binds to HLA-A2/MAGE-A4 and CD3, comprising a polypeptide comprising an amino acid sequence that is at least 95%, 96%, 97%, 98%, or 99% identical to the sequence of SEQ ID NO: 67, a polypeptide comprising an amino acid sequence that is at least 95%, 96%, 97%, 98%, or 99% identical to the sequence of SEQ ID NO: 69, a polypeptide (particularly two polypeptides) comprising an amino acid sequence that is at least 95%, 96%, 97%, 98%, or 99% identical to the sequence of SEQ ID NO: 70, and a polypeptide comprising an amino acid sequence that is at least 95%, 96%, 97%, 98%, or 99% identical to the sequence of SEQ ID NO: 71. In one aspect the invention provides a (multispecific) antibody that binds to HLA-A2/MAGE-A4 and CD3, comprising a polypeptide comprising the amino acid sequence of SEQ ID NO: 67, a polypeptide comprising the amino acid sequence of SEQ ID NO: 69, a polypeptide (particularly two polypeptides) comprising the amino acid sequence of SEQ ID NO: 70 and a polypeptide comprising the amino acid sequence of SEQ ID NO: 71.

10. Fc Domain Variants

In preferred aspects, the (multispecific) antibody of the invention comprises an Fc domain composed of a first and a second subunit.

The Fc domain of the (multispecific) antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one aspect, the (multispecific) antibody of the invention comprises not more than one Fc domain.

In one aspect, the Fc domain of the (multispecific) antibody is an IgG Fc domain. In a preferred aspect, the Fc domain is an $IgG_1$ Fc domain. In another aspect the Fc domain is an $IgG_4$ Fc domain. In a more specific aspect, the Fc domain is an $IgG_4$ Fc domain comprising an amino acid substitution at position S228 (Kabat EU index numbering), particularly the amino acid substitution S228P. This amino acid substitution reduces in vivo Fab arm exchange of IgG$_4$ antibodies (see Stubenrauch et al., Drug Metabolism and Disposition 38, 84-91 (2010)). In a further preferred aspect, the Fc domain is a human Fc domain. In an even more preferred aspect, the Fc domain is a human IgG$_1$ Fc domain. An exemplary sequence of a human IgG$_1$ Fc region is given in SEQ ID NO: 78.

a) Fc Domain Modifications Promoting Heterodimerization (Multispecific) antibodies according to the invention comprise different antigen binding domains, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of (multispecific) antibodies in recombinant production, it will thus be advantageous to introduce in the Fc domain of the (multispecific) antibody a modification promoting the association of the desired polypeptides.

Accordingly, in preferred aspects, the Fc domain of the (multispecific) antibody according to the invention comprises a modification promoting the association of the first and the second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291.

Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the (multispecific) antibody which reduce heavy/light chain mispairing and Bence Jones-type side products.

In a specific aspect said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a preferred aspect, in the CH3 domain of the first subunit of the Fc domain of the (multispecific) antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific aspect, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further aspect, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a preferred aspect, the first subunit of the Fc domain comprises the amino acid substitutions S354C and T366W, and the second subunit of the Fc domain comprises the amino acid substitutions Y349C, T366S, L368A and Y407V (numbering according to Kabat EU index). In a preferred aspect the second antigen binding domain, which preferably binds to an activating T cell antigen such as CD3, is fused (optionally via the first antigen binding domain, which binds to HLA-A2/MAGE-A4, and/or a peptide linker) to the first subunit of the Fc domain (comprising the "knob" modification). Without wishing to be bound by theory, fusion of the antigen binding domain that binds to the second antigen (e.g. CD3) to the knob-containing subunit of the Fc domain will (further) minimize the generation of antibodies comprising two antigen binding domains that bind to the second antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one aspect, the heterodimerization approach described in EP 1870459, is used alternatively. This approach is based on the introduction of charged amino acids with opposite charges at specific amino acid positions in the CH3/CH3 domain interface between the two subunits of the Fc domain. A particular aspect for the (multispecific) antibody of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another aspect, the (multispecific) antibody of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another aspect, the (multispecific) antibody of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said (multispecific) antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one aspect, the heterodimerization approach described in WO 2013/157953 is used alternatively. In one aspect, a first CH3 domain comprises amino acid mutation T366K and a second CH3 domain comprises amino acid mutation L351D (numberings according to Kabat EU index). In a further aspect, the first CH3 domain comprises further amino acid mutation L351K.

In a further aspect, the second CH3 domain comprises further an amino acid mutation selected from Y349E, Y349D and L368E (particularly L368E) (numberings according to Kabat EU index). In one aspect, the heterodimerization approach described in WO 2012/058768 is used alternatively. In one aspect a first CH3 domain comprises amino acid mutations L351Y, Y407A and a second CH3 domain comprises amino acid mutations T366A, K409F. In a further aspect the second CH3 domain comprises a further amino acid mutation at position T411, D399, 5400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F4051, F405M, F405T, F405S, F405V or F405W, e) N390R, N390K or N390D, f) K392V, K392M, K392R, K392L, K392F or K392E (numberings according to Kabat EU index). In a further aspect a first CH3 domain comprises amino acid mutations L351Y, Y407A and a second CH3 domain comprises amino acid mutations T366V, K409F. In a further aspect, a first CH3 domain comprises amino acid mutation Y407A and a second CH3 domain comprises amino acid mutations T366A, K409F. In a further aspect, the second CH3 domain further comprises amino acid mutations K392E, T411E, D399R and S400R (numberings according to Kabat EU index).

In one aspect, the heterodimerization approach described in WO 2011/143545 is used alternatively, e.g. with the amino acid modification at a position selected from the group consisting of 368 and 409 (numbering according to Kabat EU index).

In one aspect, the heterodimerization approach described in WO 2011/090762, which also uses the knobs-into-holes technology described above, is used alternatively. In one aspect a first CH3 domain comprises amino acid mutation T366W and a second CH3 domain comprises amino acid mutation Y407A. In one aspect, a first CH3 domain comprises amino acid mutation T366Y and a second CH3 domain comprises amino acid mutation Y407T (numberings according to Kabat EU index).

In one aspect, the (multispecific) antibody or its Fc domain is of $IgG_2$ subclass and the heterodimerization approach described in WO 2010/129304 is used alternatively.

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such aspect, a first CH3 domain comprises amino acid substitution of K392 or N392 with a negatively charged amino acid (e.g. glutamic acid (E), or aspartic acid (D), particularly K392D or N392D) and a second CH3 domain comprises amino acid substitution of D399, E356, D356, or E357 with a positively charged amino acid (e.g. lysine (K) or arginine (R), particularly D399K, E356K, D356K, or E357K, and more particularly D399K and E356K). In a further aspect, the first CH3 domain further comprises amino acid substitution of K409 or R409 with a negatively charged amino acid (e.g. glutamic acid (E), or aspartic acid (D), particularly K409D or R409D). In a further aspect first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further aspect, the heterodimerization approach described in WO 2007/147901 is used alternatively. In one aspect, a first CH3 domain comprises amino acid mutations K253E, D282K, and K322D and a second CH3 domain comprises amino acid mutations D239K, E240K, and K292D (numberings according to Kabat EU index).

In still another aspect, the heterodimerization approach described in WO 2007/110205 can be used alternatively.

In one aspect, the first subunit of the Fc domain comprises amino acid substitutions K392D and K409D, and the second subunit of the Fc domain comprises amino acid substitutions D356K and D399K (numbering according to Kabat EU index).

b) Fc Domain Modifications Reducing Fc Receptor Binding and/or Effector Function The Fc domain confers to the (multispecific) antibody favorable pharmacokinetic properties, including a long serum half-life which contributes to good accumulation in the target tissue and a favorable tissue-blood distribution ratio. At the same time it may, however, lead to undesirable targeting of the (multispecific) antibody to cells expressing Fc receptors rather than to the preferred antigen-bearing cells. Moreover, the co-activation of Fc receptor signaling pathways may lead to cytokine release which, in combination with the T cell activating properties and the long half-life of the (multispecific) antibody, results in excessive activation of cytokine receptors and severe side effects upon systemic administration. Activation of (Fc receptor-bearing) immune cells other than T cells may even reduce efficacy of the (multispecific) antibody due to the potential destruction of T cells e.g. by NK cells.

Accordingly, in preferred aspects, the Fc domain of the (multispecific) antibody according to the invention exhibits reduced binding affinity to an Fc receptor and/or reduced effector function, as compared to a native IgG$_1$ Fc domain. In one such aspect the Fc domain (or the (multispecific) antibody comprising said Fc domain) exhibits less than 50%, particularly less than 20%, more particularly less than 10% and most particularly less than 5% of the binding affinity to an Fc receptor, as compared to a native IgG$_1$ Fc domain (or a (multispecific) antibody comprising a native IgG$_1$ Fc domain), and/or less than 50%, particularly less than 20%, more particularly less than 10% and most particularly less than 5% of the effector function, as compared to a native IgG$_1$ Fc domain domain (or a (multispecific) antibody comprising a native IgG$_1$ Fc domain). In one aspect, the Fc domain domain (or the (multispecific) antibody comprising said Fc domain) does not substantially bind to an Fc receptor and/or induce effector function. In a preferred aspect the Fc receptor is an Fcγ receptor. In one aspect the Fc receptor is a human Fc receptor. In one aspect the Fc receptor is an activating Fc receptor. In a specific aspect the Fc receptor is an activating human Fcγ receptor, more specifically human FcγRIIIa, FcγRI or FcγRIIa, most specifically human FcγRIIIa. In one aspect the effector function is one or more selected from the group of CDC, ADCC, ADCP, and cytokine secretion. In a preferred aspect, the effector function is ADCC. In one aspect, the Fc domain domain exhibits substantially similar binding affinity to neonatal Fc receptor (FcRn), as compared to a native IgG$_1$ Fc domain domain. Substantially similar binding to FcRn is achieved when the Fc domain (or the (multispecific) antibody comprising said Fc domain) exhibits greater than about 70%, particularly greater than about 80%, more particularly greater than about 90% of the binding affinity of a native IgG$_1$ Fc domain (or the (multispecific) antibody comprising a native IgG$_1$ Fc domain) to FcRn.

In certain aspects the Fc domain is engineered to have reduced binding affinity to an Fc receptor and/or reduced effector function, as compared to a non-engineered Fc domain. In preferred aspects, the Fc domain of the (multispecific) antibody comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In one aspect, the amino acid mutation reduces the binding affinity of the Fc domain to an Fc receptor by at least 2-fold, at least 5-fold, or at least 10-fold. In aspects where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one aspect the (multispecific) antibody comprising an engineered Fc domain exhibits less than 20%, particularly less than 10%, more particularly less than 5% of the binding affinity to an Fc receptor as compared to a (multispecific) antibody comprising a non-engineered Fc domain. In a preferred aspect, the Fc receptor is an Fcγ receptor. In some aspects, the Fc receptor is a human Fc receptor. In some aspects, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the (multispecific) antibody comprising said Fc domain) exhibits greater than about 70% of the binding affinity of a non-engineered form of the Fc domain (or the (multispecific) antibody comprising said non-engineered form of the Fc domain) to FcRn. The Fc domain, or (multispecific) antibodies of the invention comprising said Fc domain, may exhibit greater than about 80% and even greater than about 90% of such affinity. In certain aspects, the Fc domain of the (multispecific) antibody is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced cross-linking of target-bound antibodies, reduced dendritic cell maturation, or reduced T cell priming. In one aspect, the reduced effector function is one or more selected from the group of reduced CDC, reduced ADCC, reduced ADCP, and reduced cytokine secretion. In a preferred aspect, the reduced effector function is reduced ADCC. In one aspect the reduced ADCC is less than 20% of the ADCC induced by a non-engineered Fc domain (or a (multispecific) antibody comprising a non-engineered Fc domain).

In one aspect, the amino acid mutation that reduces the binding affinity of the Fc domain to an Fc receptor and/or effector function is an amino acid substitution. In one aspect, the Fc domain comprises an amino acid substitution at a position selected from the group of E233, L234, L235, N297, P331 and P329 (numberings according to Kabat EU index). In a more specific aspect, the Fc domain comprises an amino acid substitution at a position selected from the group of L234, L235 and P329 (numberings according to Kabat EU index). In some aspects, the Fc domain comprises the amino acid substitutions L234A and L235A (numberings according to Kabat EU index). In one such aspect, the Fc domain is an IgG$_1$ Fc domain, particularly a human IgG$_1$ Fc domain. In one aspect, the Fc domain comprises an amino acid substitution at position P329. In a more specific aspect, the amino acid substitution is P329A or P329G, particularly P329G (numberings according to Kabat EU index). In one aspect, the Fc domain comprises an amino acid substitution at position P329 and a further amino acid substitution at a position selected from E233, L234, L235, N297 and P331 (numberings according to Kabat EU index). In a more specific aspect, the further amino acid substitution is E233P, L234A, L235A, L235E, N297A, N297D or P331S. In preferred aspects, the Fc domain comprises amino acid substitutions at positions P329, L234 and L235 (numberings according to Kabat EU index). In more preferred aspects, the Fc domain comprises the amino acid mutations L234A, L235A and P329G ("P329G LALA", "PGLALA" or "LALAPG"). Specifically, in preferred aspects, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such aspect, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some aspects, the Fc domain of the (multispecific) antibodies of the invention is an $IgG_4$ Fc domain, particularly a human $IgG_4$ Fc domain. In one aspect, the $IgG_4$ Fc domain comprises an amino acid substitution at position S228, specifically the amino acid substitution S228P (numberings according to Kabat EU index). To further reduce its binding affinity to an Fc receptor and/or its effector function, in one aspect, the $IgG_4$ Fc domain comprises an amino acid substitution at position L235, specifically the amino acid substitution L235E (numberings according to Kabat EU index). In another aspect, the $IgG_4$ Fc domain comprises an amino acid substitution at position P329, specifically the amino acid substitution P329G (numberings according to Kabat EU index). In a preferred aspect, the $IgG_4$ Fc domain comprises amino acid substitutions at positions S228, L235 and P329, specifically amino acid substitutions S228P, L235E and P329G (numberings according to Kabat EU index). Such $IgG_4$ Fc domain mutants and their Fcγ receptor binding properties are described in PCT publication no. WO 2012/130831, incorporated herein by reference in its entirety.

In a preferred aspect, the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A and optionally P329G, or a human $IgG_4$ Fc domain comprising the amino acid substitutions S228P, L235E and optionally P329G (numberings according to Kabat EU index).

In certain aspects, N-glycosylation of the Fc domain has been eliminated. In one such aspect, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or (multispecific) antibodies comprising an Fc domain for Fc receptors may be evaluated using cell lines known to express particular Fc receptors, such as human NK cells expressing FcγIIIa receptor.

Effector function of an Fc domain, or a (multispecific) antibody comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. C1q binding assays may be carried out to determine whether the Fc domain, or the (multispecific) antibody comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)). FcRn binding and in vivo clearance/half life determinations can also be performed using methods known in the art (see, e.g., Petkova, S. B. et al., Int'l. Immunol. 18(12):1759-1769 (2006); WO 2013/120929).

B. Polynucleotides

The invention further provides an isolated polynucleotide encoding an antibody of the invention. Said isolated polynucleotide may be a single polynucleotide or a plurality of polynucleotides.

The polynucleotides encoding (multispecific) antibodies of the invention may be expressed as a single polynucleotide that encodes the entire antibody or as multiple (e.g., two or more) polynucleotides that are co-expressed. Polypeptides encoded by polynucleotides that are co-expressed may associate through, e.g., disulfide bonds or other means to form a functional antibody. For example, the light chain portion of an antibody may be encoded by a separate polynucleotide from the portion of the antibody comprising the heavy chain of the antibody. When co-expressed, the heavy chain polypeptides will associate with the light chain polypeptides to form the antibody. In another example, the portion of the antibody comprising one of the two Fc domain subunits and optionally (part of) one or more Fab molecules could be encoded by a separate polynucleotide from the portion of the antibody comprising the other of the two Fc domain subunits and optionally (part of) a Fab molecule. When co-expressed, the Fc domain subunits will associate to form the Fc domain.

In some aspects, the isolated polynucleotide encodes the entire antibody molecule according to the invention as described herein. In other aspects, the isolated polynucleotide encodes a polypeptide comprised in the antibody according to the invention as described herein.

In certain aspects, the polynucleotide or nucleic acid is DNA. In other aspects, a polynucleotide of the present invention is RNA, for example, in the form of messenger RNA (mRNA). RNA of the present invention may be single stranded or double stranded.

C. Recombinant Methods

Antibodies of the invention may be obtained, for example, by solid-state peptide synthesis (e.g. Merrifield solid phase synthesis) or recombinant production. For recombinant production one or more polynucleotide encoding the antibody, e.g., as described above, is isolated and inserted into one or more vectors for further cloning and/or expression in a host cell. Such polynucleotide may be readily isolated and sequenced using conventional procedures. In one aspect a vector, particularly an expression vector, comprising the polynucleotide (i.a. a single polynucleotide or a plurality of polynucleotides) of the invention is provided. Methods which are well known to those skilled in the art can be used to construct expression vectors containing the coding sequence of an antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible by tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain aspects, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody may be included within or at the ends of the antibody (fragment) encoding polynucleotide.

In a further aspect, a host cell comprising a polynucleotide (i.e. a single polynucleotide or a plurality of polynucleotides) of the invention is provided. In certain aspects a host cell comprising a vector of the invention is provided. The polynucleotides and vectors may incorporate any of the features, singly or in combination, described herein in relation to polynucleotides and vectors, respectively. In one such aspect a host cell comprises (e.g. has been transformed or transfected with) one or more vector comprising one or more polynucleotide that encodes (part of) an antibody of the invention. As used herein, the term "host cell" refers to any kind of cellular system which can be engineered to generate the antibody of the invention or fragments thereof. Host cells suitable for replicating and for supporting expression of antibodies are well known in the art. Such cells may be transfected or transduced as appropriate with the particular expression vector and large quantities of vector containing cells can be grown for seeding large scale fermenters to obtain sufficient quantities of the antibody for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gemgross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr$^-$ CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one aspect, the host cell is a eukaryotic cell, particularly a mammalian cell, such as a Chinese Hamster Ovary (CHO) cell, a human embryonic kidney (HEK) cell or a lymphoid cell (e.g., Y0, NS0, Sp20 cell). In one aspect, the host cell is not a cell within a human body.

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one aspect, a method of producing an antibody according to the invention is provided, wherein the method comprises culturing a host cell comprising a polynucleotide encoding the antibody, as provided herein, under conditions suitable for expression of the antibody, and optionally recovering the antibody from the host cell (or host cell culture medium).

The components of the (multispecific) antibody of the invention may be genetically fused to each other. The (multispecific) antibody can be designed such that its components are fused directly to each other or indirectly through a linker sequence. The composition and length of the linker may be determined in accordance with methods well known in the art and may be tested for efficacy. Examples of linker sequences between different components of (multispecific) antibodies are provided herein. Additional sequences may also be included to incorporate a cleavage site to separate the individual components of the fusion if desired, for example an endopeptidase recognition sequence.

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody binds. For example, for affinity chromatography purification of antibodies of the invention, a matrix with protein A or protein G may be used. Sequential Protein A or G affinity chromatography and size exclusion chromatography can be used to isolate an antibody essentially as described in the Examples. The purity of the antibody can be determined by any of a variety of well-known analytical methods including gel electrophoresis, high pressure liquid chromatography, and the like.

D. Assays

Antibodies provided herein may be identified, screened for, or characterized for their physical/chemical properties and/or biological activities by various assays known in the art.

1. Binding Assays

The binding (affinity) of the antibody to a target antigen or an Fc receptor can be determined for example by surface plasmon resonance (SPR), using standard instrumentation such as a BIAcore instrument (GE Healthcare), and receptors or target antigens such as may be obtained by recombinant expression. Alternatively, binding of antibodies to different receptors or target antigens may be evaluated using cell lines expressing the particular receptor or target antigen, for example by flow cytometry (FACS). A specific illustrative and exemplary aspect for measuring binding activity to HLA-A2/MAGE-A4 is described in the following.

In one aspect, the binding affinity of a (multispecific) antibody of the invention to HLA-A2/MAGE-A4 is determined by SPR as follows:

SPR is performed on a Biacore T200 instrument (GE Healthcare) at 25° C. with HBS-EP+ (10 mM HEPES, 150 mM NaCl pH 7.4, 0.005% Surfactant P20 (GE Healthcare, #BR-1006-69)) as running buffer. Anti-human Fc specific antibody (GE Healthcare, #BR-1008-39) is directly immobilized by amine coupling on a CM5 chip (GE Healthcare). The HLA-A2/MAGE-A4 antibody is captured for 60 s at 2.5 nM. A three-fold dilution series of the HLA-A2/MAGE-A4$_{p230-239}$ complex in HBS-EP (6.17 to 1500 nM) is passed over the ligand at 30 µl/min for 240 sec to record the association phase. The dissociation phase is monitored for 240 s and triggered by switching from the sample solution to HBS-EP+. The chip surface is regenerated after every cycle using an injection of 3 M MgCl$_2$ at 10 µl/min for 30 sec. Bulk refractive index differences are corrected for by subtracting the response obtained on a reference flow cell which contains the anti-human Fc antibody, but no HLA-A2/MAGE-A4 antibody captured on it. The affinity constants are derived from the kinetic rate constants by fitting to a 1:1 Langmuir binding using the BIAeval software (GE Healthcare).

2. Activity Assays

Biological activity of the (multispecific) antibodies of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

E. Compositions, Formulations, and Routes of Administration

In a further aspect, the invention provides pharmaceutical compositions comprising any of the antibodies provided herein, e.g., for use in any of the below therapeutic methods. In one aspect, a pharmaceutical composition comprises an antibody according to the invention and a pharmaceutically acceptable carrier. In another aspect, a pharmaceutical composition comprises an antibody according to the invention and at least one additional therapeutic agent, e.g., as described below.

Further provided is a method of producing an antibody of the invention in a form suitable for administration in vivo, the method comprising (a) obtaining an antibody according to the invention, and (b) formulating the antibody with at least one pharmaceutically acceptable carrier, whereby a preparation of antibody is formulated for administration in vivo.

Pharmaceutical compositions of the present invention comprise an effective amount of antibody dissolved or dispersed in a pharmaceutically acceptable carrier. The phrase "pharmaceutically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies of the invention may be formulated in aqueous solutions, particularly in physiologically compatible buffers such as Hanks' solution, Ringer's solution, or physiological saline buffer. The solution may contain formulatory agents such as suspending, stabilizing and/or dispersing agents. Alternatively, the antibodies may be in powder form for constitution with a suitable vehicle, e.g., sterile pyrogen-free water, before use. Sterile injectable solutions are prepared by incorporating the antibodies of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular aspects, prolonged absorption of an injectable composition can be brought about by the use in the compositions of agents delaying absorption, such as, for example, aluminum monostearate, gelatin or combinations thereof.

In addition to the compositions described previously, the antibodies may also be formulated as a depot preparation. Such long acting formulations may be administered by implantation (for example subcutaneously or intramuscularly) or by intramuscular injection. Thus, for example, the antibodies may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

F. Therapeutic Methods and Compositions

Any of the antibodies provided herein may be used in therapeutic methods. Antibodies of the invention may be used as immunotherapeutic agents, for example in the treatment of cancers.

For use in therapeutic methods, antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies of the invention for use as a medicament are provided. In further aspects, antibodies of the invention for use in treating a disease are provided. In certain aspects, antibodies of the invention for use in a method of treatment are provided. In one aspect, the invention provides an antibody of the invention for use in the treatment of a disease in an individual in need thereof. In certain aspects, the invention provides an antibody for use in a method of treating an individual having a disease comprising administering to the individual an effective amount of the antibody. In certain aspects, the disease to be treated is a proliferative disorder. In a preferred aspect, the disease is cancer. In certain aspects, the method further comprises administering to the individual an effective amount of at least one additional therapeutic agent, e.g., an anti-cancer agent if the disease to be treated is cancer. In further aspects, the invention provides an antibody of the invention for use in inducing lysis of a target cell, particularly a tumor cell. In certain aspects, the invention provides an antibody of the invention for use in a method of inducing lysis of a target cell, particularly a tumor cell, in an individual comprising administering to the individual an effective amount of the antibody to induce lysis of a target cell. An "individual" according to any of the above aspects may be a mammal, preferably a human.

In a further aspect, the invention provides for the use of an antibody of the invention in the manufacture or preparation of a medicament. In one aspect, the medicament is for the treatment of a disease in an individual in need thereof. In a further aspect, the medicament is for use in a method of treating a disease comprising administering to an individual having the disease an effective amount of the medicament. In certain aspects, the disease to be treated is a proliferative disorder. In a preferred aspect, the disease is cancer. In one aspect, the method further comprises administering to the individual an effective amount of at least one additional therapeutic agent, e.g., an anti-cancer agent if the disease to be treated is cancer. In a further aspect, the medicament is for inducing lysis of a target cell, particularly a tumor cell. In still a further aspect, the medicament is for use in a method of inducing lysis of a target cell, particularly a tumor cell, in an individual comprising administering to the individual an effective amount of the medicament to induce lysis of a target cell. An "individual" according to any of the above aspects may be a mammal, preferably a human.

In a further aspect, the invention provides a method for treating a disease. In one aspect, the method comprises administering to an individual having such disease an effective amount of an antibody of the invention. In one aspect, a composition is administered to said individual, comprising the antibody of the invention in a pharmaceutically acceptable form. In certain aspects, the disease to be treated is a proliferative disorder. In a preferred aspect, the disease is cancer. In certain aspects, the method further comprises administering to the individual an effective amount of at least one additional therapeutic agent, e.g., an anti-cancer agent if the disease to be treated is cancer. An "individual" according to any of the above aspects may be a mammal, preferably a human.

In a further aspect, the invention provides a method for inducing lysis of a target cell, particularly a tumor cell. In one aspect the method comprises contacting a target cell with an antibody of the invention in the presence of a T cell, particularly a cytotoxic T cell. In a further aspect, a method for inducing lysis of a target cell, particularly a tumor cell, in an individual is provided. In one such aspect, the method comprises administering to the individual an effective amount of an antibody of the invention to induce lysis of a target cell. In one aspect, an "individual" is a human. In certain aspects, the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an antibody of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain aspects, the cancer is a cancer expressing HLA-A2/MAGE-A4. In certain aspects, the cancer is a cancer selected from the group consisting of lung cancer, head and neck cancer, bladder cancer, esophageal cancer, skin cancer, gastric cancer and ovarian cancer. A skilled artisan readily recognizes that in many cases the antibody may not provide a cure but may only provide partial benefit. In some aspects, a physiological change having some benefit is also considered therapeutically beneficial. Thus, in some aspects, an amount of antibody that provides a physiological change is considered an "effective amount". The subject, patient, or individual in need of treatment is typically a mammal, more specifically a human.

In some aspects, an effective amount of an antibody of the invention is administered to an individual for the treatment of disease.

For the prevention or treatment of disease, the appropriate dosage of an antibody of the invention (when used alone or in combination with one or more other additional therapeutic agents) will depend on the type of disease to be treated, the route of administration, the body weight of the patient, the type of antibody, the severity and course of the disease, whether the antibody is administered for preventive or therapeutic purposes, previous or concurrent therapeutic interventions, the patient's clinical history and response to the antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various timepoints, bolus administration, and pulse infusion are contemplated herein.

The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The antibodies of the invention will generally be used in an amount effective to achieve the intended purpose. For use to treat or prevent a disease condition, the antibodies of the invention, or pharmaceutical compositions thereof, are administered or applied in an effective amount.

For systemic administration, an effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art.

Dosage amount and interval may be adjusted individually to provide plasma levels of the antibodies which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

An effective dose of the antibodies of the invention will generally provide therapeutic benefit without causing substantial toxicity. Toxicity and therapeutic efficacy of an antibody can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies that exhibit large therapeutic indices are preferred. In one aspect, the antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The antibodies of the invention may be administered in combination with one or more other agents in therapy. For instance, an antibody of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular disease being treated, preferably those with complementary activities that do not adversely affect each other. In certain aspects, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a preferred aspect, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of antibody used, the type of disorder or treatment, and other factors discussed above. The antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody of the invention can occur prior to, simultaneously, and/or following, administration of the additional therapeutic agent and/or adjuvant. Antibodies of the invention may also be used in combination with radiation therapy.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

H. Methods and Compositions for Diagnostics and Detection

In certain aspects, any of the antibodies provided herein is useful for detecting the presence of its target (e.g. HLA-A2/MAGE-A4) in a biological sample. The term "detecting" as used herein encompasses quantitative or qualitative detection. In certain aspects, a biological sample comprises a cell or tissue, such as prostate tissue.

In one aspect, an antibody according to the invention for use in a method of diagnosis or detection is provided. In a further aspect, a method of detecting the presence of HLA-A2/MAGE-A4 in a biological sample is provided. In certain aspects, the method comprises contacting the biological sample with an antibody of the present invention under conditions permissive for binding of the antibody to HLA-A2/MAGE-A4, and detecting whether a complex is formed between the antibody and HLA-A2/MAGE-A4. Such method may be an in vitro or in vivo method. In one aspect, an antibody of the invention is used to select subjects eligible for therapy with an antibody that binds HLA-A2/MAGE-A4, e.g. where HLA-A2/MAGE-A4 is a biomarker for selection of patients.

Exemplary disorders that may be diagnosed using an antibody of the invention include cancer, particularly skin cancer or brain cancer.

In certain aspects, an antibody according to the present invention is provided, wherein the antibody is labelled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

| III. SEQUENCES | | |
|---|---|---|
| | Amino Acid Sequence | SEQ ID NO |
| 007A09 HCDR1 | LDMS | 1 |
| 007A09 HCDR2 | SISPKGGSTYYNDNVLG | 2 |
| 007A09 HCDR3 | DWGFFDL | 3 |
| 007A09 LCDR1 | RASQSISNYLA | 4 |
| 007A09 LCDR2 | DANAHEN | 5 |
| 007A09 LCDR3 | QQYSSHPYT | 6 |
| 007A09 VH | YVQLVESGGGLVKPGGSLRLSCAAPLPFTGLDMSWVRQAPGKGLEWVGSISPKGGSTYYNDNVLGRFTISRDNSKNTLYLQMNSLRAEDTAVYYCARDWGFFDLWGQGTLVTVSS | 7 |
| 007A09 VL | AIQMTQSPSSLSASVGDRVTITCRASQSISNYLAWYQQKPGKAPKLLIYDANAHENDVPSRFSGSGSGTDFTLTISSLQPEDFATYYCQQYSSHPYTFGQGTKLEIK | 8 |
| 007D10 HCDR1 | LDMS | 9 |
| 007D10 HCDR2 | SISPKGGSTYYNDNVLG | 10 |

III. SEQUENCES

| | Amino Acid Sequence | SEQ ID NO |
|---|---|---|
| 007D10 HCDR3 | DWGFFDN | 11 |
| 007D10 LCDR1 | RASQSISNYLA | 12 |
| 007D10 LCDR2 | NASHPEY | 13 |
| 007D10 LCDR3 | QQYSSHPYT | 14 |
| 007D10 VH | YPQLVESGGGLVKPGGSLRLSCAARYPFTRLDMSWVRQAPGKGLEWVGSISPKGGSTYYNDNVLGRFTISRDNSKNTLYLQMNSLRAEDTAVYYCARDWGFFDNWGQGTLVTVSS | 15 |
| 007D10 VL | AIQMTQSPSSLSASVGDRVTITCRASQSISNYLAWYQQKPGKAPKLLIYNASHPEYDVPSRFSGSGSGTDFTLTISSLQPEDFATYYCQQYSSHPYTFGQGTKLEIK | 16 |
| 057B04 HCDR1 | FDTMS | 17 |
| 057B04 HCDR2 | SISPSGGSTYYNDNVLG | 18 |
| 057B04 HCDR3 | DHGYFDM | 19 |
| 057B04 LCDR1 | RASQSISSYLA | 20 |
| 057B04 LCDR2 | DASWLEL | 21 |
| 057B04 LCDR3 | QQYSSYPYT | 22 |
| 057B04 VH | TQQLVESGGGLVQPGGSLRLSCAASGFSFSFDTMSWVRQAPGKGLEWVGSISPSGGSTYYNDNVLGRFTISRDNSKNTLYLQMNSLRAEDTAVYYCARDHGYFDMWGQGTLVTVSS | 23 |
| 057B04 VL | DIQMTQSPSSLSASVGDRVTITCRASQSISSYLAWYQQKPGKAPKLLIYDASWLELGVPSRFSGSGSGTDFTLTISSLQPEDFATYYCQQYSSYPYTFGQGTKLEIK | 24 |
| 057D03 HCDR1 | KAMS | 25 |
| 057D03 HCDR2 | SISPSGGSTYYNDNVLG | 26 |
| 057D03 HCDR3 | DVGFFDE | 27 |
| 057D03 LCDR1 | RASQSISSYLA | 28 |
| 057D03 LCDR2 | DASIRDI | 29 |
| 057D03 LCDR3 | QQYSSYPYT | 30 |
| 057D03 VH | AQLVESGGGLVQPGGSLRLSCAASAYFSFKAMSWVRQAPGKGLEWVGSISPSGGSTYYNDNVLGRFTISRDNSKNTLYLQMNSLRAEDTAVYYCAKDVGFFDEWGQGTLVTVSS | 31 |
| 057D03 VL | DIQMTQSPSSLSASVGDRVTITCRASQSISSYLAWYQQKPGKAPKLLIYDASIRDIGVPSRFSGSGSGTDFTLTISSLQPEDFATYYCQQYSSYPYTFGQGTKLEIK | 32 |

III. SEQUENCES

| | Amino Acid Sequence | SEQ ID NO |
|---|---|---|
| 032G09 HCDR1 | SYAMS | 33 |
| 032G09 HCDR2 | AISGSGGSTYYADSVKG | 34 |
| 032G09 HCDR3 | SSYEAYDY | 35 |
| 032G09 LCDR1 | QGDSLRSYYAS | 36 |
| 032G09 LCDR2 | GKNNRPS | 37 |
| 032G09 LCDR3 | NSRQSSYYHHIV | 38 |
| 032G09 VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARSSYEAYDYWGQGTLVTVSS | 39 |
| 032G09 VL | SSELTQDPAVSVALGQTVRITCQGDSLRSYYASWYQQKPGQAPVLVIYGKNNRPSGIPDRFSGSSSGNTASLTITGAQAEDEADYYCNSRQSSYYHHIVFGGGTKLTVL | 40 |
| 034F05 HCDR1 | SYAMS | 41 |
| 034F05 HCDR2 | AISGSGGSTYYADSVKG | 42 |
| 034F05 HCDR3 | VSYESFDY | 43 |
| 034F05 LCDR1 | QGDSLRSYYAS | 44 |
| 034F05 LCDR2 | GKNNRPS | 45 |
| 034F05 LCDR3 | NSRMSSRYHHDV | 46 |
| 034F05 VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKVSYESFDYWGQGTLVTVSS | 47 |
| 034F05 VL | SSELTQDPAVSVALGQTVRITCQGDSLRSYYASWYQQKPGQAPVLVIYGKNNRPSGIPDRFSGSSSSNTASLTITGAQAEDEADYYCNSRMSSRYHHDVFGGGTKLTVL | 48 |
| C106B9 VH | QVQLQQSGGEVMKPGASVKLSCKATGYTFTGYWIEWIKQRPGHGLEWIGEILPGSGGTNYNEKFKGKATFTAHTSSNTAYMQLSSLTTEDSAIYYCARDSNSFTYWGQGTLVTVSS | 49 |
| C106B9 VL | QIVLTQSPAIMSASPGEKVTITCSVSSSVDYIHWFQQKPGTSPKFWIYSTSILASGVPARFSGSGSGTSYSLTISRMEAEDAATYYCQQRSSYPPTFGSGTKLEIK | 50 |
| CH2527 HCDR1 | TYAMN | 51 |
| CH2527 HCDR2 | RIRSKYNNYATYYADSVKG | 52 |
| CH2527 HCDR3 | HGNFGNSYVSWFAY | 53 |
| CH2527 LCDR1 | GSSTGAVTTSNYAN | 54 |

III. SEQUENCES

| | Amino Acid Sequence | SEQ ID NO |
|---|---|---|
| CH2527 LCDR2 | GTNKRAP | 55 |
| CH2527 LCDR3 | ALWYSNLWV | 56 |
| CH2527 VH | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSS | 57 |
| CH2527 VL | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVL | 58 |
| V9 HCDR1 | GYTMN | 59 |
| V9 HCDR2 | LINPYKGVSTYNQKFKD | 60 |
| V9 HCDR3 | SGYYGDSDWYFDV | 61 |
| V9 LCDR1 | RASQDIRNYLN | 62 |
| V9 LCDR2 | YTSRLES | 63 |
| V9 LCDR3 | QQGNTLPWT | 64 |
| V9 VH | EVQLVESGGGLVQPGGSLRLSCAASGYSFTGYTMNWVRQ APGKGLEWVALINPYKGVSTYNQKFKDRFTISVDKSKNTA YLQMNSLRAEDTAVYYCARSGYYGDSDWYFDVWGQGTL VTVSS | 65 |
| V9 VL | DIQMTQSPSSLSASVGDRVTITCRASQDIRNYLNWYQQKPG KAPKLLIYYTSRLESGVPSRFSGSGSGTDYTLTISSLQPEDFA TYYCQQGNTLPWTFGQGTKVEIK | 66 |
| MAGEA4 VH-CH1-CD3 (CH2527) VL-CH1-Fc | AQLVESGGGLVQPGGSLRLSCAASAYFSFKAMSWVRQAP GKGLEWVGSISPSGGSTYYNDNVLGRFTISRDNSKNTLYLQ MNSLRAEDTAVYYCAKDVGFFDEWGQGTLVTVSSASTKG PSVFPLAPSSKSTSGGTAALGCLVEDYFPEPVTVSWNSGAL TSGVHTFPAVLQSSGLYSLSSVVTVPSSSLGTQTYICNVNH KPSNTKVDEKVEPKSCDGGGGSGGGGSQAVVTQEPSLTVS PGGTVTLTCGSSTGAVTTSNYANWVQEKPGQAFRGLIGGT NKRAPGTPARFSGSLLGGKAALTLSGAQPEDEAEYYCALW YSNLWVFGGGTKLTVLSSASTKGPSVFPLAPSSKSTSGGTA ALGCLVKDYFPEPVTVSWNSGALTSGVHTFPAVLQSSGLY SLSSVVTVPSSSLGTQTYICNVNHKPSNTKVDKKVEPKSCD KTHTCPPCPAPEAAGGPSVFLFPPKPKDTLMISRTPEVTCVV VDVSHEDPEVKFNWYVDGVEVHNAKTKPREEQYNSTYRV VSVLTVLHQDWLNGKEYKCKVSNKALGAPIEKTISKAKGQ PREPQVYTLPPCRDELTKNQVSLWCLVKGFYPSDIAVEWES NGQPENNYKTTPPVLDSDGSFFLYSKLTVDKSRWQQGNVF SCSVMHEALHNHYTQKSLSLSP | 67 |
| MAGEA4 VH-CH1-CD3 (V9) VL-CH1-Fc | AQLVESGGGLVQPGGSLRLSCAASAYFSFKAMSWVRQAP GKGLEWVGSISPSGGSTYYNDNVLGRFTISRDNSKNTLYLQ MNSLRAEDTAVYYCAKDVGFFDEWGQGTLVTVSSASTKG PSVFPLAPSSKSTSGGTAALGCLVEDYFPEPVTVSWNSGAL TSGVHTFPAVLQSSGLYSLSSVVTVPSSSLGTQTYICNVNH KPSNTKVDEKVEPKSCDGGGGSGGGGSDIQMTQSPSSLSAS VGDRVTITCRASQDIRNYLNWYQQKPGKAPKLLIYYTSRLE SGVPSRFSGSGSGTDYTLTISSLQPEDFATYYCQQGNTLPW TFGQGTKVEIKSSASTKGPSVFPLAPSSKSTSGGTAALGCLV KDYFPEPVTVSWNSGALTSGVHTFPAVLQSSGLYSLSSVVT VPSSSLGTQTYICNVNHKPSNTKVDKKVEPKSCDKTHTCPP CPAPEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALGAPIEKTISKAKGQPREPQV YTLPPCRDELTKNQVSLWCLVKGFYPSDIAVEWESNGQPE NNYKTTPPVLDSDGSFFLYSKLTVDKSRWQQGNVFSCSVM HEALHNHYTQKSLSLSP | 68 |

III. SEQUENCES

| | Amino Acid Sequence | SEQ ID NO |
|---|---|---|
| MAGEA4 VH-CH1-Fc | AQLVESGGGLVQPGGSLRLSCAASAYFSFKAMSWVRQAP GKGLEWVGSISPSGGSTYYNDNVLGRFTISRDNSKNTLYLQ MNSLRAEDTAVYYCAKDVGFFDEWGQGTLVTVSSASTKG PSVFPLAPSSKSTSGGTAALGCLVEDYFPEPVTVSWNSGAL TSGVHTFPAVLQSSGLYSLSSVVTVPSSSLGTQTYICNVNH KPSNTKVDEKVEPKSCDKTHTCPPCPAPEAAGGPSVFLFPP KPKDTLMISRTPEVTCVVVDVSHEDPEVKFNWYVDGVEV HNAKTKPREEQYNSTYRVVSVLTVLHQDWLNGKEYKCKV SNKALGAPIEKTISKAKGQPREPQVCTLPPSRDELTKNQVSL SCAVKGFYPSDIAVEWESNGQPENNYKTTPPVLDSDGSFFL VSKLTVDKSRWQQGNVFSCSVMHEALHNHYTQKSLSLSP | 69 |
| MAGEA4 VL-CL | DIQMTQSPSSLSASVGDRVTITCRASQSISSYLAWYQQKPG KAPKLLIYDASIRDIGVPSRFSGSGSGTDFTLTISSLQPEDFA TYYCQQYSSYPYTFGQGTKLEIKRTVAAPSVFIFPPSDRKLK SGTASVVCLLNNFYPREAKVQWKVDNALQSGNSQESVTE QDSKDSTYSLSSTLTLSKADYEKHKVYACEVTHQGLSSPVT KSFNRGEC | 70 |
| CD3 (CH2527) VH-CL | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 71 |
| CD3 (V9) VH-CL | EVQLVESGGGLVQPGGSLRLSCAASGYSFTGYTMNWVRQ APGKGLEWVALINPYKGVSTYNQKFKDRFTISVDKSKNTA YLQMNSLRAEDTAVYYCARSGYYGDSDWYFDVWGQGTL VTVSSASVAAPSVFIFPPSDEQLKSGTASVVCLLNNFYPREA KVQWKVDNALQSGNSQESVTEQDSKDSTYSLSSTLTLSKA DYEKHKVYACEVTHQGLSSPVTKSFNRGEC | 72 |
| MAGE-A4 p230-239 | GVYDGREHTV | 73 |
| Human MAGE-A4 | MSSEQKSQHCKPEEGVEAQEEALGLVGAQAPTTEEQEAAV SSSSPLVPGTLEEVPAAESAGPPQSPQGASALPTTISFTCWR QPNEGSSSQEEEGPSTSPDAESLFREALSNKVDELAHFLLRK YRAKELVTKAEMLERVIKNYKRCFPVIFGKASESLKMIFGI DVKEVDPASNTYTLVTCLGLSYDGLLGNNQIFPKTGLLIIVL GTIAMEGDSASEEEIWEELGVMGVYDGREHTVYGEPRKLL TQDWVQENYLEYRQVPGSNPARYEFLWGPRALAETSYVK VLEHVVRVNARVRIAYPSLREAALLEEEEGV | 74 |
| HLA-A2 | GSHSMRYFFTSVSRPGRGEPRFIAVGYVDDTQFVRFDSDAA SQRMEPRAPWIEQEGPEYWDGETRKVKAHSQTHRVDLGT LRGYYNQSEAGSHTVQRMYGCDVGSDWRFLRGYHQYAY DGKDYIALKEDLRSWTAADMAAQTTKHKWEAAHVAEQL RAYLEGTCVEWLRRYLENGKETLQRTDAPKTHMTHHAVS DHEATLRCWALSFYPAEITLTWQRDGEDQTQDTELVETRP AGDGTFQKWAAVVVPSGQEQRYTCHVQHEGLPKPLTLRW E | 75 |
| Human CD3 | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGG LLLLVYYWSKNRKAKAKPVTRGAGAGGRQRGQNKERPPP VPNPDYEPIRKGQRDLYSGLNQRRI | 76 |
| Cynomolgus CD3 | QDGNEEMGSITQTPYQVSISGTTVILTCSQHLGSEAQWQHN GKNKEDSGDRLFLPEFSEMEQSGYYVCYPRGSNPEDASHH LYLKARVCENCMEMDVMAVATIVIVDICITLGLLLLVYYW SKNRKAKAKPVTRGAGAGGRQRGQNKERPPPVPNPDYEPI RKGQQDLYSGLNQRRI | 77 |
| hIgG1 Fc region | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSP | 78 |

III. SEQUENCES

| | Amino Acid Sequence | SEQ ID NO |
|---|---|---|
| Human kappa CL domain | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC | 79 |
| Human lambda CL domain | QPKAAPSVTLFPPSSEELQANKATLVCLISDFYPGAVTVAW KADSSPVKAGVETTTPSKQSNNKYAASSYLSLTPEQWKSH RSYSCQVTHEGSTVEKTVAPTECS | 80 |
| Human IgG1 heavy chain constant region (CH1-CH2-CH3) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 81 |
| linker | GGGGSGGGGS | 82 |
| linker | DGGGGSGGGGS | 83 |
| WT1$_{RMF}$ peptide | RMFPNAPYL | 84 |
| NY-ESO1 $_{p157-165}$ | SLLMWITQC | 85 |

| Peptide ID | Amino Acid Sequence | SEQ ID NO |
|---|---|---|
| PFKA_44 | GLYEGRIKQL | 86 |
| GUTQ_85 | GMIESRDVML | 87 |
| DPYSL4_497 | GLYDGPVHEV | 88 |
| CRMP1_497 | GMYDGPVYEV | 89 |
| DPYSL2_497 | GLYDGPVCEV | 90 |
| TRANK1_1501 | GLFDGPKPTV | 91 |
| C19orf54_5 | GLVDGRYSPV | 92 |
| AGFG2_113 | GLFDARTSLV | 93 |
| DPYSL3_497 | GMYDGPVFDL | 94 |
| UBE2V2_96 | GMVDARSIPV | 95 |
| PIGG_755 | GIIEARFVYV | 96 |
| ZNF624_159 | GLWDSRMEGL | 97 |
| WDFY4_961 | GLAEGPWPAA | 98 |
| BNRF1_1173 | GMFESRWLNI | 99 |
| MSTIR_465 | GTMDGRILQV | 100 |
| EDC3_19 | GVYQGRVSAV | 101 |
| FBXO34_198 | GVYAGRPLSV | 102 |
| KEAP1_419 | GVIDGHIYAV | 103 |
| MAGEA10_254 | GLYDGMEHLI | 104 |
| MAGEB2_231 | GVYDGEEHSV | 105 |
| MAGEB6_315 | GIYDGILHSI | 106 |
| URB1_190 | GVYDVRQAYV | 107 |
| CCS_117 | GTIDGLEPGL | 108 |
| DYNC1H1_3019 | GLFEGDEYAT | 109 |
| SLC45A1_451 | GLLEGREGAL | 110 |
| UNC80_1096 | GLADGVEDLL | 111 |
| VPS13D_3737 | GLFDGAEVVL | 112 |
| ARF1_165 | GLYEGLDWLS | 113 |
| ARF3_165 | GLYEGLDWLA | 114 |
| GAPDHS_241 | GIVEGLMTTV | 115 |
| KDMIA_577 | ALAEGLDIKL | 116 |
| MTOR_2046 | GMFEVLEPLH | 117 |
| PKP1_449 | GLIDSLMAYV | 118 |
| CDHR1_HU[703:712] | GVLAGTMATV | 119 |
| CNT3B_HU[447:456] | GLNDGQWHSV | 120 |
| CNTP2_HU[452:461] | GLNDGQWHEV | 121 |
| CSCL1_HU[44:53] | GVTFGGIPTV | 122 |
| DISP1_HU[634:643] | GVYAGTAILV | 123 |

| Peptide ID | Amino Acid Sequence | SEQ ID NO |
|---|---|---|
| FA8_HU[1257:1266] | GSYDGAYAPV | 124 |
| NCOA1_HU[1310:1319] | GVYNNMSITV | 125 |
| NDST1_HU[218:227] | GVLPGEDWTV | 126 |
| NRAC_HU[119:128] | GLYCGRAKPV | 127 |
| RIOX2_HU[93:102] | GMYYGRDVNV | 128 |
| SAMC_HU[139:148] | GLYRGYKSTV | 129 |
| TEX35_HU[204:213] | GLYKGGEEPV | 130 |
| UBA3_HU[437:446] | GLVDGQELAV | 131 |
| UBN2_HU[504:513] | GVYSHLEAFV | 132 |
| AVIL_HU[573:582] | LLCDGSENTV | 133 |
| CC166_HU[114:123] | SLYHGREDGV | 134 |
| CSMD2_HU[2540:2549] | GMVFGKEYTV | 135 |
| RNF8_HU[31:40] | LLEDGCEVTV | 136 |
| STXB5_HU[695:704] | GLCDISEGTV | 137 |
| AKNA_HU[1217:1226] | GQYTGHEYHV | 138 |
| AMPO_HU[776:785] | GVYLYGELMV | 139 |
| ARFRP_HU[175:184] | GVREGIEWMV | 140 |
| ARHGQ_HU[369:378] | GTFDGEENAV | 141 |
| CDKL4_HU[97:106] | GVADGVIKSV | 142 |
| DUS27_HU[171:180] | GVYTGPEFYT | 143 |
| EWS_HU[96:105] | GAYDTTTATV | 144 |
| HMCN2_HU[4402:4411] | GVINGRKFGV | 145 |
| IIGP5_HU[206:215] | GVADPRIFLV | 146 |
| KIF19_HU[91:100] | GVISGYNATV | 147 |
| KIF4A_HU[75:84] | GVFKGYNATV | 148 |
| LAMA5_HU[3195:3204] | GFADGAPHYV | 149 |
| LPINI_HU[812:821] | GVSLNRIFTV | 150 |
| LYST_HU[3682:3691] | GGSDLRLWTV | 151 |
| MCES_HU[364:373] | GVVDVPEFLV | 152 |
| MOXD2_HU[317:326] | GVYDSSGIRV | 153 |
| NIM1_HU[385:394] | GVYRIILHRV | 154 |
| NKX62_HU[90:99] | GVYFGPAAAV | 155 |
| PFKAL_HU[573:582] | GGYCGYLATV | 156 |
| PHEX_HU[102:111] | GVYPWLRHNV | 157 |
| PRS8_HU[367:376] | GMYALRERRV | 158 |
| RL23_HU[56:65] | GVGDMVMATV | 159 |
| SPT5H_HU[173:182] | GVKDPNLWTV | 160 |
| TIM21_HU[219:228] | GEYDFRYIFV | 161 |
| TMC4_HU[365:374] | GVYWATGCTV | 162 |
| TRIL_HU[663:672] | GVLGGRVCPV | 163 |
| TXTP_HU[179:188] | GTYQGLTATV | 164 |
| VPP3_HU[759:768] | GLGLGREVGV | 165 |
| TSHR_HU-S3[223:232] | GVYSGPSLLV | 166 |
| ACSF2_HU[557:566] | RLKDGEETTV | 167 |
| BICLI_HU[428:437] | SIVDGMEPTV | 168 |
| CE104_HU[621:630] | RVYEVRETAV | 169 |
| CHD8_HU[1721:1730] | SVIDGDEAQV | 170 |
| FCGBP_HU[2792:2801] | GAYYEPEQTV | 171 |
| ITIH3_HU[494:503] | HFYDGSEIVV | 172 |
| LTBP2_HU[1677:1686] | YNYLGPEDTV | 173 |
| NECT3_HU-S3[478:487] | VYIDPREHYV | 174 |
| LEG9B_HU[24:33] | GLQDGFQITV | 175 |
| LEG9_HU[24:33] | GLQDGLQITV | 176 |
| PTPRJ_HU[946:955] | GLIDGAESYV | 177 |
| ZARIL_HU[10:19] | GLYQGYGSTV | 178 |
| IHO1_HU[417:426] | FLCDPREHLV | 179 |
| BTBD7_HU[208:217] | GMEDSRFQNV | 180 |
| ERN2_HU[538:547] | GQFEGRAVAV | 181 |
| HEYL_HU[105:114] | GFFDARALAV | 182 |
| OXSR1_HU[472:481] | GLVDGRDLVI | 183 |
| PEARI_HU[93:102] | GFYESRGFCV | 184 |
| ADCL2_HU[311:320] | GLTDSRALPL | 185 |
| BC11A_HU[253:262] | GLAEGRFPPT | 186 |
| BUB1_HU[729:738] | GTVDAPNFIV | 187 |
| CELR3_HU[1506:1515] | GAFEGPRCEV | 188 |
| GT253_HU[24:33] | GVAESPLPAV | 189 |
| K1755_HU[600:609] | GAWEAPWCTV | 190 |
| K2022_HU[82:91] | GLIEAPEHAA | 191 |
| KMT2C_HU[4411:4420] | GLTDGPARLL | 192 |
| LPIN3_HU[445:454] | GLADSRDISL | 193 |
| MYOM1_HU[573:582] | GLIEGRSYIF | 194 |
| MYOM2_HU[446:455] | GLFEGRSYIF | 195 |
| SCN4A_HU[898:907] | GLADGPPSSL | 196 |
| SHC2_HU[351:360] | GLVDSRLALT | 197 |
| ASNS_HU[289:298] | GMEDSPDLLA | 198 |

| Peptide ID | Amino Acid Sequence | SEQ ID NO |
|---|---|---|
| CAN12_HU[461:470] | GLWDSPRSHA | 199 |
| CENPN_HU[313:322] | GIADAPLSPL | 200 |
| DDHD1_HU[854:863] | GLVESRYWSA | 201 |
| FANCE_HU[304:313] | GLEDAPPVEL | 202 |
| NYNRI_HU[507:516] | GLEEGPAPVL | 203 |
| SC16A_HU[1210:1219] | GSYEAPLPPG | 204 |
| SPTN4_HU[1186:1195] | GLWEARREAL | 205 |
| T4S1_HU[114:123] | GLAEGPLCLD | 206 |
| TB10B_HU[222:231] | GTCEAPVAVV | 207 |
| ACD10_HU-S3[478:487] | GLEDAPGCFL | 208 |
| MELT_HU-S3[201:210] | GLWEARPRVL | 209 |
| PRRC1_HU-S2[443:452] | GLVEARNFPA | 210 |
| CJ071_HU[547:556] | GLEESPPNEL | 211 |
| DHDH_HU[299:308] | GMKESPVIPL | 212 |
| SHRM2_HU[240:249] | GLWEAPRQGG | 213 |
| CELR1_HU[1521:1530] | GVSDGRWHSV | 214 |
| RBBP5_HU[223:232] | RVYDGREILT | 215 |
| RPC2_HU[952:961] | GVLDGRFHYG | 216 |
| SRSF2_HU[78:87] | AVLDGRELRV | 217 |
| TPPP_HU[84:93] | QVIDGRNVTV | 218 |
| CBPZ_HU[215:224] | RSFDGRELLV | 219 |
| CTBP1_HU[31:40] | ALLDGRDCTV | 220 |
| KLDC2_HU[37:46] | AVSDGRHMFV | 221 |
| NEUL4_HU[80:89] | PLRDGRVFTV | 222 |
| SHBG_HU[123:132] | RLDDGRWHQV | 223 |
| AB12B_HU[106:115] | GVMLGIWHTV | 224 |
| CBLN3_HU[122:131] | GVYSFRFHVV | 225 |
| CELR2_HU[1446:1455] | GVSDGQWHTV | 226 |
| CELR3_HU[1594:1603] | GLSDGQWHTV | 227 |
| CNDP2_HU[230:239] | GVYGGSVHEA | 228 |
| FCGBP_HU[1591:1600] | GVYYEPEQTV | 229 |
| IBTK_HU[288:297] | GVAAGRFHTV | 230 |
| LPIN2_HU[823:832] | GVPDCRIFTV | 231 |
| PAPP2_HU[307:316] | GVFDNCSHTV | 232 |
| PIWL2_HU[816:825] | GVSDGQLKTV | 233 |
| AT134_HU[240:249] | TVYDLREQSV | 234 |
| GAS6_HU[611:620] | KVCDGQEHVV | 235 |
| HMGX3_HU[249:258] | ASYDGTEVTV | 236 |
| KLH29_HU[333:342] | IVVEGREFEV | 237 |
| PTN5_HU[417:426] | VAYDGVEITV | 238 |
| TPC_HU[111:120] | SVYDAREFSV | 239 |
| ACAP1_HU[394:403] | GMARGREPGG | 240 |
| ARF5_HU[165:174] | GLYDGLDWLS | 241 |
| ARFG1_HU[117:126] | ALAEGREWSL | 242 |
| CBPE_HU[81:90] | RSFEGRELLV | 243 |
| COCA1_HU[1159:1168] | GMFDGGESSP | 244 |
| COKA1_HU[525:534] | GLEPGRDYEV | 245 |
| DGKA_HU[409:418] | LLKDGPEIGL | 246 |
| DYH6_HU[1555:1564] | FMFEGREIKL | 247 |
| ERN1_HU[589:598] | GMFDNRDVAV | 248 |
| FGD5_HU[551:560] | FSVEGREIPV | 249 |
| HPCA_HU[78:87] | GTIDFREFII | 250 |
| LPCT4_HU[385:394] | GLVDFRDVAL | 251 |
| LRC15_HU[339:348] | GLTELRELSL | 252 |
| MZB1_HU[117:126] | GLSEGPEPSI | 253 |
| NMDE2_HU[588:597] | CLADGREPGG | 254 |
| NP1L1_HU[245:254] | FSFDGPEIMG | 255 |
| ODO2_HU[425:434] | RLIDGREAVT | 256 |
| PCAT2_HU[409:418] | GSIDFREYVI | 257 |
| PTGIS_HU[368:377] | PMADGREFNL | 258 |
| RENT1_HU[944:953] | AMYDAREAII | 259 |
| SI1L3_HU[1622:1631] | SLADGRDRPL | 260 |
| TITIN_HU[20082:20091] | GLVEGLEYSF | 261 |
| TITIN_HU[21166:21175] | GLTEGLEYEF | 262 |
| TRIL_HU[149:158] | GSFEGLESLV | 263 |
| UNC5B_HU[495:504] | GLADGADLLG | 264 |
| ZBT7A_HU[38:47] | ILVEGREFPT | 265 |
| ZER1_HU[641:650] | IMFDGPEAWG | 266 |
| ACOXL_HU-S2[352:361] | GMVVGRELLA | 267 |
| ACPH_HU[621:630] | GSTDIPDWCV | 268 |
| AGRB1_HU[1170:1179] | AVFDSLEGFV | 269 |
| AMPB_HU[193:202] | ALIEVPDGFT | 270 |
| C1QBP_HU[234:243] | ALYDHLMDFL | 271 |
| CAMP1_HU[146:155] | AMVDALMMAY | 272 |
| CLCN2_HU[613:622] | ALVESPESMI | 273 |

-continued

| Peptide ID | Amino Acid Sequence | SEQ ID NO |
|---|---|---|
| E2F6_HU[152:161] | AMEDALDELI | 274 |
| GZF1_HU[176:185] | GLTDSLDYPG | 275 |
| HYOU1_HU[328:337] | AQIEGLMDDV | 276 |
| KCNH8_HU[646:655] | GLFEVLDLYP | 277 |
| LDHB_HU[50:59] | ALVDVLEDKL | 278 |
| LRC30_HU[59:68] | GMTDIPDFLW | 279 |
| MYPT2_HU[293:302] | GLVEHLELLQ | 280 |
| PK3CB_HU[10:19] | AMADILDIWA | 281 |
| RDH12_HU[269:278] | ALAEGLEPLS | 282 |
| RING2_HU[31:40] | AITDGLEIVV | 283 |
| SPTN5_HU[2418:2427] | AQVESLEREV | 284 |
| SUV3_HU[630:639] | AVHDVLDLYL | 285 |
| SYIM_HU[822:831] | ALVEILDVIV | 286 |
| TCAF1_HU[6:15] | AAFEALMNGV | 287 |
| TCAF2_HU[7:16] | AAFEALMDGV | 288 |
| TITIN_HU[28747:28756] | GLVEGLDYQF | 289 |
| ZSC18_HU[126:135] | GLADVLEEPG | 290 |
| MAGA8_HU[232:241] | GLYDGREHSV | 291 |
| DC4L1_HU[148:157] | GITDAPSCAV | 292 |
| HUS1B_HU[48:57] | GLHEARLWCE | 293 |
| IFNA8_HU[128:137] | GVIESPLMYE | 294 |
| MAGAB_HU[342:351] | GVYAGREHFL | 295 |
| MAGB1_HU[228:237] | GAYDGEEHLI | 296 |
| MAGBA_HU[231:240] | GLYDGIEHFM | 297 |
| MAGC2_HU[257:266] | GVYAGREHFV | 298 |
| KRT84_HU[493:502] | GLVCGPEPLV | 299 |
| NAL11_HU[984:993] | SLKEGREIGV | 300 |
| O2AP1_HU[14:23] | GLTDVPELQV | 301 |
| OR5BC_HU[14:23] | GLTDDPELQI | 302 |
| ECT2L_HU[513:522] | ALADGLMELS | 303 |
| IFNL1_HU[109:118] | ALEDVLDQPL | 304 |
| IFNL2_HU[118:127] | ALVDVLDQPL | 305 |
| F173B_HU_96-A105V-114[96:105] | GSGDGRIVIV | 306 |
| K0319_HU_764-S773G-782[765:774] | DVIDGSDHGV | 307 |
| VU8_HHV6Z[204:213] | GLYDGPRFES | 308 |
| CVC1_HHV8P[371:380] | GLWESRPHTL | 309 |
| PB2_INCAA[651:660] | GMFEGRLFFS | 310 |

-continued

| Peptide ID | Amino Acid Sequence | SEQ ID NO |
|---|---|---|
| PB2_INCBE[651:660] | GMFEGRFFFS | 311 |
| POLN_BFV[1885:1894] | GEYLGTEHPV | 312 |
| PHOSP_CHAV[158:167] | GTRDGIEFTV | 313 |
| POLG_DEN1B[3209:3218] | IMKDGREIVV | 314 |
| ENV_SFV1[609:618] | GVYLLRDHVV | 315 |
| ICP4_VZVD[54:63] | GVMVGREHEI | 316 |
| RIAB_CVHN1[6624:6633] | ILFDGRDTGA | 317 |
| RIAB_CVHN2[6594:6603] | VLFDGRDNGA | 318 |
| ORF27_HHV8P[232:241] | GIFDERDYGL | 319 |
| VE4_HPV1[61:70] | GLTDGEDPEV | 320 |
| A16_VACCA[15:24] | GIADIRDKYM | 321 |
| VIF_HV2NZ[206:215] | GLAEVLEILA | 322 |
| L_SABVB[1992:2001] | ALVESLELFA | 323 |
| D13_VACCA[54:63] | ASFEIRDQYI | 324 |
| E2_VACCC[206:215] | AIIEILMAVV | 325 |
| LR75B_HU-S2[79:88] | GVWEARGYGL | 326 |
| EHIL1_HU[857:866] | GMAEARVLMT | 327 |
| CO5A3_HU[141:150] | NLTDGRWHRV | 328 |
| MAGBH_HU[229:238] | GMYKGRKHFI | 329 |
| MBD4_HU[507:516] | GLYDLRAKTI | 330 |
| MUTYH_HU[230:239] | GVVDGNVARV | 331 |
| RNH1_HU[161:170] | GVYWGPGHPL | 332 |
| GH_EBVA8[672:681] | GLYEERAHVV | 333 |
| US23_HCMVA[583:592] | KSFDFREHFV | 334 |
| POLG_HCV6A[2266:2275] | AEYDEREISV | 335 |
| POLG_HCVT5[2266:2275] | AEYDDREISV | 336 |
| GH_HHV7J[377:386] | SLADGRIVTV | 337 |
| HEMA_INCHY[211:220] | GTYECRLHLV | 338 |
| POLG_POL32[1609:1618] | IVIDGKEIEV | 339 |
| VP3_ROTHC[137:146] | ELYAGREYTL | 340 |
| ADA19_HU[69:78] | VMAEGRELIL | 341 |
| ALS_HU[216:225] | GLAELRELDL | 342 |
| RBM33_HU[146:155] | GQYEGHEAEL | 343 |
| S13A2_HU[71:80] | GIVDASEVAV | 344 |
| STK39_HU[490:499] | GLVDGHDVVI | 345 |
| STXB2_HU[270:279] | GLSEAREKAV | 346 |
| TXND6_HU[119:128] | VLAEGRERKV | 347 |
| SRAC1_HU-S2[477:486] | GIVEGLESPL | 348 |

-continued

| Peptide ID | Amino Acid Sequence | SEQ ID NO |
|---|---|---|
| KCNKF_HU[24:33] | AVFDALESEA | 349 |
| ACBG1_HU[72:81] | AQWDAPEEAL | 350 |
| ECT2L_HU[235:244] | GLHEALEKQL | 351 |
| TAF5L_HU[557:566] | GVYTGQMSNV | 352 |
| CDHR3_HU[112:121] | GVTDLQVLTV | 353 |
| GOS2_HU[37:46] | GVVLGLMETV | 354 |
| PLS3_HU[71:80] | GVPSGLEFLV | 355 |
| RN112_HU[599:608] | GVGAGLAATV | 356 |
| ACV1B_HU[57:66] | FNLDGMEHHV | 357 |
| AL4A1_HU[195:204] | TVYRGLEGFV | 358 |
| AT135_HU[241:250] | SVYDLRQQSV | 359 |
| CDR2_HU[163:172] | ELYDLRQHFV | 360 |
| DC111_HU[603:612] | WVYDVGELAV | 361 |
| FINC_HU[1691:1700] | GLRPGSEYTV | 362 |
| GAN_HU[34:43] | LVLDGEEIPV | 363 |
| GLO2_HU[216:225] | RVYCGHEYTI | 364 |
| IGS22_HU[481:490] | QLSDGGEYTV | 365 |
| KLH29_HU[679:688] | LVYDGKIYTL | 366 |
| LRC56_HU[384:393] | GLRAWREHGV | 367 |
| M3K5_HU[133:142] | GKLDFGETTV | 368 |
| MALT1_HU[690:699] | YQYSGLEDTV | 369 |
| NRP2_HU[911:920] | ELYDGLKHKV | 370 |
| PHF20_HU[119:128] | KFYDGVVQTV | 371 |
| PHLD_HU[759:768] | YVYNGKETTL | 372 |
| PI51B_HU[368:377] | LVYDGDTVSV | 373 |
| S22AK_HU[391:400] | MIYVGRRATV | 374 |
| SART3_HU[168:177] | HVYDLFEKAV | 375 |
| SMC2_HU[1063:1072] | TVLDGLEFKV | 376 |
| TBC3A_HU[234:243] | GLQDQQEHVV | 377 |
| TENN_HU[589:598] | GLRPGVEYTV | 378 |
| TENN_HU[854:863] | GLRPGMEYTV | 379 |
| UXS1_HU[108:117] | LMMDGHEVTV | 380 |
| ZN831_HU[1594:1603] | GQYGCGEMTV | 381 |
| CFLAR_HU-S6[430:439] | YMYDSLEHTG | 382 |
| ACAP1_HU[308:317] | VVDDLRLCTV | 383 |
| ACS2L_HU[81:90] | LVWDTPYHTV | 384 |
| ADA2_HU[417:426] | LVSDLRNHPV | 385 |
| AEBP1_HU[656:665] | LVQDTRIHLV | 386 |
| ALPK1_HU[1031:1040] | IVYLGDYLTV | 387 |
| ASB7_HU[21:30] | AVAAGDVHTV | 388 |
| ASPH1_HU[342:351] | LVDDSFLHTV | 389 |
| C3P1_HU[55:64] | CVSDPFELTV | 390 |
| CA112_HU[108:117] | SVYSGCLHLV | 391 |
| CAN5_HU[134:143] | VVIDDRLPTV | 392 |
| CAVI_HU[146:155] | RVYSIYVHTV | 393 |
| CCD61_HU[11:20] | YVFRGVEHAV | 394 |
| CKLF_HU[46:55] | IVITGFEVTV | 395 |
| CO3_HU[816:825] | CVADPFEVTV | 396 |
| CRUM1_HU[1028:1037] | SVNDGTWHEV | 397 |
| CRUM2_HU[950:959] | RVADGAWHRV | 398 |
| ES1_HU[185:194] | KVLRGVEVTV | 399 |
| FA12_HU[605:614] | YLAWIREHTV | 400 |
| FAT3_HU[3911:3920] | AVNDGSWHSV | 401 |
| FAT4_HU[4053:4062] | KVSDGHFHTV | 402 |
| FBLL1_HU[128:137] | SVYGERRVTV | 403 |
| FREM2_HU[1875:1884] | IVDPGDEPTV | 404 |
| GPR98_HU[4032:4041] | GVFGFEEKTV | 405 |
| HAGHL_HU[167:176] | KVFCGHEHTL | 406 |
| IF4G1_HU[1046:1055] | LVDDGGWNTV | 407 |
| IP6K3_HU[30:39] | SVMKYDEHTV | 408 |
| K1C27_HU[433:442] | KVLSSRVHTV | 409 |
| LAMA1_HU[2791:2800] | LLSDGKWHTV | 410 |
| MYOF_HU[286:295] | FVYDEPGHAV | 411 |
| NOL12_HU[96:105] | VQYDHPNHTV | 412 |
| NWD1_HU[1461:1470] | SVLDGTLLTV | 413 |
| ORIL4_HU[268:277] | SVMKGRVATV | 414 |
| PKD1_HU[1251:1260] | TVLSGPEATV | 415 |
| PTC1_HU[1089:1098] | SVGIGVEFTV | 416 |
| RBM47_HU[464:473] | MIEDGKIHTV | 417 |
| S22AB_HU[462:471] | MTADGILHTV | 418 |
| SACS_HU[2563:2572] | FVFDPRQHPV | 419 |
| SIX4_HU[746:755] | YVLDGMVDTV | 420 |
| SLIT1_HU[1240:1249] | TINDGQFHTV | 421 |
| SLIT3_HU[1232:1241] | TVNDGQFHSV | 422 |
| SNX22_HU[31:40] | VLCSGRRHTV | 423 |

| Peptide ID | Amino Acid Sequence | SEQ ID NO |
|---|---|---|
| THADA_HU[767:776] | HVPEGRIYTV | 424 |
| TIGD2_HU[33:42] | VVYGIGESTV | 425 |
| TLN2_HU[1633:1642] | SVLAGHSHTV | 426 |
| TM260_HU[628:637] | IVYLQKEHPV | 427 |
| TRPV4_HU[805:814] | YQYYGFSHTV | 428 |
| UB2J2_HU[189:198] | VVPDGETHLV | 429 |
| USH2A_HU[160:169] | GVMCVIEKTV | 430 |
| ZHX2_HU[789:798] | SVVDYVEVTV | 431 |
| HECD2_HU-S2[192:201] | AVYDTLLNTV | 432 |
| ITB4_HU-S2[1364:1373] | SVSDDTEHLV | 433 |
| OFUT2_HU-S1[411:420] | CVHSGHFHTV | 434 |
| ANR53_HU_422-H431L-440[9:18] | GLGGARLHTV | 435 |
| LAMP3_HU_309-1318V-327[9:18] | TVYQGIKHAV | 436 |
| COBQ_NOCFA[409:418] | GLVDAPEAAV | 437 |
| PMPG_CHLTR[35:44] | GIYDGETLTV | 438 |
| DXS_MYCLB[374:383] | GLAMGRMHPV | 439 |
| RL10_MYCVP[108:117] | GYMDGRALTV | 440 |
| RNZ_NOCFA[183:192] | LLVDGRTVTV | 441 |
| VG69_BPML5[58:67] | ALAEGREMSL | 442 |
| BHUA_BRUA2[194:203] | GLKDGFDWLL | 443 |
| METK_MYCUA[310:319] | GLAEGVEVQV | 444 |
| MNMA_FRAP2[228:237] | GMHDGLMYYT | 445 |
| PROA_NEIGI[32:41] | AMADSLEAAA | 446 |
| SYT_RICAH[118:127] | AMIEARMHEI | 447 |
| PARE_RICBR[140:149] | ALAEHLEIKV | 448 |
| Y1265_RICBR[432:441] | ALWDALDCRV | 449 |
| GLUP_BRUA2[245:254] | FVYVGAEVSV | 450 |
| FTSK_BRUME[508:517] | SVYDGIPHLL | 451 |
| COAX_EHRCJ[193:202] | GVYWGYITMV | 452 |
| COAX_EHRRG[192:201] | GVYWGYIAMV | 453 |
| MIAB_FRAP2[26:35] | EVLDEHFHTV | 454 |
| EFG_FRAT1[577:586] | TLYDGSYHDV | 455 |
| EFG_LISIN[563:572] | KLYDGSYHDV | 456 |
| GCSPA_LISIN[78:87] | GVYSHYIPTV | 457 |
| LP074_MYCA9[95:104] | LVYDGAALAV | 458 |
| GLGX_MYCBO[196:205] | GTYAGLAHPV | 459 |
| MURE_MYCBO[129:138] | GVLGGLAATV | 460 |
| RL10_MYCBO[108:117] | GYMDGHPLTV | 461 |
| RL10_MYCLB[108:117] | GYMDGHPMTV | 462 |
| ILVD_MYCLE[158:167] | KLSDGTEHEV | 463 |
| TRUA_MYCPA[3:12] | GVLDEALTTV | 464 |
| MGLL_MYCS2[250:259] | KVYPGLYHEV | 465 |
| SYM_NEIGI[326:335] | GVYAHGFLTV | 466 |
| FTSZ_NEIGO[3:12] | FVYDVAESAV | 467 |
| FISL_NEIMA[30:39] | GVYDMVLHQV | 468 |
| KAD_NOCFA[81:90] | FVLDGYPRTV | 469 |
| MNMA_ORITB[207:216] | FVADGAYHNV | 470 |
| FAD3_RICFE[238:247] | GLYDLIGHDV | 471 |
| Y381_RICFE[744:753] | AVYDGNLDLV | 472 |
| GCSP_SALA4[925:934] | GVADKYWPTV | 473 |
| HSCA_SALA4[147:156] | GELDGVVITV | 474 |
| METE_SALA4[689:698] | GVYDIHSPNV | 475 |
| YIHY_SALA4[261:270] | IVLLGAEITV | 476 |
| SIRB1_SALTI[33:42] | FVYDELERLV | 477 |
| NUSB_YERE8[125:134] | GVLDKVAPTV | 478 |
| Y868_CHLMU[379:388] | GMAEARAEEL | 479 |
| YIDC_CHLPN[190:199] | GLYDSREEKL | 480 |
| EFG_RICPR[248:257] | GTIEARFYPI | 481 |
| SIGA_CHLMU[506:515] | GLLDGRPKTL | 482 |
| ESPG3_MYCS2[186:195] | SVFDGRRTYV | 483 |
| Y459_NEIMB[262:271] | GVADTADWTV | 484 |
| RL4_RICB8[152:161] | FVIDGNEVDV | 485 |
| PROB_MYCA1[37:46] | GLADAIEARM | 486 |
| END4_CHLMU[25:34] | ALYEGRDIGA | 487 |
| G3P_CHLPN[168:177] | GITEGLMTTV | 488 |
| GSA_CHLT2[410:419] | ALIESLEQVF | 489 |
| Y3359_MYCA1[268:277] | AIAEALMQRL | 490 |
| MSHB_MYCGI[183:192] | ALTDVPDGWV | 491 |
| TSAD_NEIGI[249:258] | AVVEVLEAKV | 492 |
| PROA_NEIMB[32:41] | AMADSLEAAT | 493 |
| MIAA_NOCFA[21:30] | ALAEHLDGEI | 494 |
| DPS_YERP3[72:81] | ALTDHLDTFA | 495 |
| DEGPL_BRUA2[153:162] | VVSDGDAYTV | 496 |
| CLPB_BRUME[698:707] | RLTDGQGHTV | 497 |
| RF3_FRAP2[179:188] | GVYDLYNDEV | 498 |

-continued

| Peptide ID | Amino Acid Sequence | SEQ ID NO |
|---|---|---|
| RLMD_LEGPA[424:433] | GVMDMFPHTA | 499 |
| METE_LISIN[695:704] | GVYDIHSPRV | 500 |
| CYSH_MYCBO[106:115] | SVYDVRVLNV | 501 |
| GCH1L_MYCBO[108:117] | GVSDALAHAV | 502 |
| MMPL8_MYCBO[179:188] | RVADIVEHQV | 503 |
| PSTC1_MYCBO[68:77] | VVTDGVAHPV | 504 |
| RECX_MYCBO[94:103] | GVDDDVITTV | 505 |
| Y2248_MYCBO[483:492] | LTFDGTQHTV | 506 |
| LP816_MYCHT[73:82] | IVIDQRAHPV | 507 |
| HIS6_MYCS2[237:246] | SVFHFRELTV | 508 |
| MPRB_MYCS2[480:489] | FVDDRGGHTV | 509 |
| Y3120_MYCS2[435:444] | AVLRGRLHPV | 510 |
| EGTA_MYCTO[285:294] | VLLDGRRATV | 511 |
| Y492_MYCTO[197:206] | GLYRGAGATV | 512 |
| GLTB_MYCTU[390:399] | GVLDLHPSTV | 513 |
| MOBA_MYCVP[141:150] | GIYRTALHTV | 514 |
| MURA_NEIGI[219:228] | GELYGCEHSV | 515 |
| MUTS_NEIMO[219:228] | FGLDGKEHAV | 516 |
| MNMA_RICPR[198:207] | FVPDGNYKTV | 517 |
| FDHD_SALA4[45:54] | LVYNGISHVV | 518 |
| YIDD_SALEP[49:58] | GVIKGSWLTV | 519 |
| FUCK_SALTI[420:429] | KVLDDAETTV | 520 |
| GLGX_YERE8[646:655] | TVWNGSAHTV | 521 |
| PUR7_MYCGI[62:71] | GLVDSPNHLA | 522 |
| FMT_MYCSJ[183:192] | GIADGRLQAV | 523 |
| GYRB_RICBR[156:165] | GITEAPLAVV | 524 |
| RL31B_CHLCV[35:44] | EVYEGQEYPV | 525 |
| PMPG_CHLMU[33:42] | GIYDGTTLTA | 526 |
| YAJC_CHLMU[81:90] | TIAEIREHTV | 527 |
| Y1617_MYCLE[4:13] | VVVDAVEHVV | 528 |
| DOP_MYCS2[301:310] | ALADGRELTA | 529 |
| DNLI_MYCVP[469:478] | GAADGFTVTV | 530 |
| RIMP_MYCVP[120:129] | GVADGTVGVV | 531 |
| RMUC_NEIMA[346:355] | GLQKGREYVV | 532 |
| GLGC_NOCFA[240:249] | GVYDFADNQV | 533 |
| CYSD_YERP3[71:80] | EMYEFRDHTV | 534 |
| LPXA_YERP3[23:32] | GVYIGPFCIV | 535 |
| MTNK_YERP3[236:245] | FVADGRLKTI | 536 |
| SYL_MYCLB[208:217] | RLVDGRDWAT | 537 |
| SYL_MYCMM[216:225] | SLVDGRDWST | 538 |
| CAS9_NEIM8[230:239] | GLKEGIETLL | 539 |
| TRPD_NOCFA[4:13] | ALADGRDLSA | 540 |
| MIAB_ORITB[89:98] | GQAEGEEIFI | 541 |
| MRAY_PARUW[115:124] | GLIGGRDDYL | 542 |
| PEPB_YERP3[288:297] | GLIDASEQNA | 543 |
| LPXC_CHLAB[75:84] | ATVEHLMAAL | 544 |
| G3P_CHLMU[168:177] | GIEEGLMTTV | 545 |
| CLGR_MYCS2[55:64] | AICDALDVPL | 546 |
| PROA_MYCS2[327:336] | AVVDGLDAAI | 547 |
| RPOC_NOCFA[602:611] | ATADAPEFGV | 548 |
| NFI_PARUW[99:108] | ALIDALESLP | 549 |
| DPOL_BPMD2[453:462] | RVYGGGANTV | 550 |
| PYRG_CHLCV[106:115] | GVYLGSTVQV | 551 |
| RNH3_CHLT2[34:43] | TVFQGRSPTV | 552 |
| IF2_EHRCR[511:520] | AVYDTRASGV | 553 |
| ISPE_EHRCR[37:46] | NVYDILEVDV | 554 |
| RL10_FRAP2[26:35] | AVADYRGLTV | 555 |
| RLMD_FRATI[429:438] | GVMDMFPHTM | 556 |
| LEPA_LEGPA[180:189] | GVNDVLEALV | 557 |
| RL10_LEGPA[26:35] | VVADYRGLTV | 558 |
| INLI_LISMF[1557:1566] | GVFSTVEQTV | 559 |
| MURD_MYCA1[214:223] | RVLDGRVAVV | 560 |
| FRDA_MYCBO[37:46] | KVYPMRSHTV | 561 |
| PPX1_MYCBO[4:13] | GVLDVGSNTV | 562 |
| RELA_MYCBO[359:368] | GVYQSLHTTV | 563 |
| Y2937_MYCBO[39:48] | GIRDGVVATV | 564 |
| Y968_MYCBO[120:129] | RTSDGVEHPV | 565 |
| Y1451_MYCGI[200:209] | MVSRGRVHAV | 566 |
| HIS1_MYCLE[124:133] | LVAKGIEATV | 567 |
| Y358_MYCMM[135:144] | KVLDYKEHTL | 568 |
| AFTD_MYCS2[1070:1079] | TVLDGRGAPV | 569 |
| ECCC3_MYCS2[1126:1135] | TVIDRRLHLV | 570 |
| DAGK_MYCTO[192:201] | LVLDGTEEIV | 571 |
| ECCB2_MYCTO[360:369] | AVYNGRGLPV | 572 |
| ECCC3_MYCTO[1136:1145] | TVLDRRLHLV | 573 |

-continued

| Peptide ID | Amino Acid Sequence | SEQ ID NO |
|---|---|---|
| KSHB_MYCTO[273:282] | VELDGQTHTV | 574 |
| NARG_MYCTO[1159:1168] | FVYHVQERTV | 575 |
| MAK_MYCVP[290:299] | RRLDGRAITV | 576 |
| SYFB_NEIG1[406:415] | GLRLGRLKTV | 577 |
| MURA_NEIMO[219:228] | GELHGCEHSV | 578 |
| ARC_NOCFA[86:95] | GVYDDQTVDV | 579 |
| SYFB_PARUW[317:326] | GVMGGRNSEV | 580 |
| DNAK_RICAH[302:311] | LVDDLIEKTV | 581 |
| SYY_RICCK[325:334] | GEIDENLHTV | 582 |
| GLND_SALA4[24:33] | GVWPRAELTV | 583 |
| YNFA_SALA4[76:85] | RVVDGVRLTV | 584 |
| ASNA_SALTI[204:213] | KLSDGRRHDV | 585 |
| SDHA_SALTY[38:47] | KVFPTRSHTV | 586 |
| DTD_YERE8[109:118] | FVAQCREHGV | 587 |
| RFBJ_YERPU[220:229] | SIYTPTEHTV | 588 |
| MAGEA8 | GLYDGREHSV | 589 |

IV. Examples

The following are examples of methods and compositions of the invention. It is understood that various other aspects may be practiced, given the general description provided above.

Example 1. Generation of HLA-A2/MAGE-A4 Binders

Selection and Screening of Anti-HLA-A2/MAGE-A4 Fabs

Anti-HLA-A2/MAGE-A4 Fabs were selected by phage display from synthetic Fab libraries consisting of VL and VH pairings derived from different V-domain families. These libraries are based on entirely human frameworks with sequence diversity in CDR1, CDR2 and CDR3 of VL and VH domains.

Selection rounds (bio panning) were performed in solution according to the following protocol: 1. pre-clearing of ~$10^{12}$ phagemid particles per library pool on neutravidin coated 96-well plates coated with 500 nM of an unrelated biotinylated HLA-A2/WT1$_{RMF}$ complex (see SEQ ID NO: 84 for the WT1$_{RMF}$ peptide), 2. incubation of the non-HLA-A2/WT1$_{RMF}$-binding phagemid particles with 100 nM biotinylated HLA-A2/MAGEA4$_{p230-239}$ complex for 0.5 h in a total volume of 800 µl, 3. capture of biotinylated HLA-A2/MAGE-A4$_{p230-239}$ and specifically binding phage by adding 80 µl of streptavidin-coated magnetic particles for 20 min on a shaker, 4. washing of respective magnetic particles 5-10× with 1 ml PBS/Tween 20 and 5-10× with 1 ml PBS using a magnetic particle separator, 5. elution of phage particles by addition of 1 ml 100 mM triethylamine (TEA) for 5-10 min and neutralization by addition of an ½ volume of 1 M Tris/HCl pH 7.4, 6. re-infection of log-phase E. coli TG1 cells with the eluted phage particles, incubation on a shaker at 37° C. for 0.5 h, infection with helper phage VCSM13, incubation on a shaker at 30° C. overnight and subsequent PEG/NaCl precipitation of phagemid particles to be used in the next selection round.

Selections were carried out over 3 to 4 rounds using decreasing antigen concentrations of 100 nM, 50 nM, 50 nM and 10 nm, respectively.

HLA-A2/MAGE-A4 Binding Assays: Sandwich ELISA for Characterization of Fabs Obtained by Phage Display Individual clones were bacterially expressed as 1 ml cultures in 96-well format and supernatants (with binders in soluble Fab format, tagged with either a FLAG or a T7 sequence) were subjected to a screening by ELISA. Specific binders were defined as having signals higher than 5×background for HLA-A2/MAGE$_{p230-239}$ and signals lower than 3×background for HLA-A2/WT1$_{RMF}$ (an unrelated HLA-A2/peptide complex). More precisely, neutravidin 96 well strip plates (Thermo Fisher) were coated with 10 nM of HLA-A2/MAGE$_{p230-239}$ or 50 nM HLA-A2/WT1$_{RMF}$ at 37° C. for 30 min, followed by blocking of the plate with 2% (w/v) milk-phosphate buffered saline (MPBS) (200 µl/well) for 1-2 h at room temperature. The plate was washed 3 times with PBS, then Fab containing bacterial supernatants were added and the plate was incubated at room temperature for 1 h. After another 3 washing steps with PBS, anti-FLAG-HRP secondary antibody (1:4000) or anti-T7-HRP secondary antibody (1:10000) was added and the plate was incubated for 1 h at room temperature. The plate was washed 3 times with PBS and developed by adding 100 µl/well BM Blue POD (Roche). The enzymatic reaction was stopped by adding 50 µl/well 1M $H_2SO_4$. The OD was read at 450 nm (reference at 900 nm) for a final read-out of $OD_{450-900}$. ELISA-positive clones were subjected to the kinetic screening experiment described below.

HLA-A2/MAGE-A4 Binding Assays: Surface Plasmon Resonance (SPR) for Kinetic Characterization Fabs Obtained by Phage Display Specific binders were identified by surface plasmon resonance-screening of Fab-containing bacterial culture supernatants using a ProteOn XPR36 biosensor (BioRad). In brief, after infection of log-phase E. coli TG1 cells with the eluted phage particles, single colony forming units (cfu) were plated and picked for inoculation of 1 ml expression cultures in 96-deep well plates.

All experiments were performed at 25° C. using PBST as running buffer (10 mM PBS, pH 7.4 and 0.005% (v/v) Tween 20). A ProteOn XPR36 biosensor equipped with GLM sensor chips and coupling reagents (10 mM sodium acetate, pH 4.5, sulfo-N-hydroxysuccinimide [sulfo-NHS], 1-ethyl-3-(3-dimethylaminopropyl)-carbodiimide hydrochloride [EDC] and ethanolamine) were used (all BioRad).

Immobilizations were performed at 30 µl/min on a GLM chip. pAb (goat) anti human IgG, F(ab)$_2$ specific antibody (Jackson ImmunoResearch) was coupled in vertical direction using a standard amine-coupling procedure: all six ligand channels were activated for 5 min with a mixture of EDC (200 mM) and sulfo-NHS (50 mM). Immediately after the surfaces were activated, pAb (goat) anti human IgG, F(ab)$_2$ specific antibody (50 µg/ml, 10 mM sodium acetate, pH 5) was injected across all six channels for 5 min. Finally, channels were blocked with a 5 min injection of 1 M ethanolamine-HCl (pH 8.5). Final immobilization levels were similar on all channels, ranging from 10000 to 11500 RU. The Fab antibodies were captured from E. coli supernatants by simultaneous injection along five of the separate horizontal channels (30 μl/min) for 5 min and resulted in levels ranging from 200 to 900 RU, depending on the concentration of Fab in supernatant. Conditioned medium was injected along the sixth channel to provide an 'in-line' blank for double referencing purposes. One-shot kinetic measurements were performed by injection of a dilution series of HLA-A2/MAGE$_{p230\text{-}239}$ or HLA-A2/WT1$_{RMF}$ (100, 50, 25, 12.5, 6.25, 0 nM, 50 μl/min) for 2 min along the vertical channels. Dissociation was monitored for 3 min. Kinetic data were analyzed in ProteOn Manager v. 2.1. Processing of the reaction spot data involved applying an interspot-reference and a double-reference step using an inline buffer blank (Myszka, J Mol Recognit (1999) 12, 279-284). The processed data from replicate one-shot injections were fit to a simple 1:1 Langmuir binding model without mass transport (O'Shannessy et al., Anal Biochem (1993) 212, 457-468).

For measurements of IgG from supernatants of HEK productions in 48-well format, the IgG variants were captured from HEK293 supernatants by simultaneous injection along five of the separate whole horizontal channels (30 μl/min) for 5 min and resulted in levels ranging from 200 to 400 RU. Conditioned medium was injected along the sixth channel to provide an 'in-line' blank for double referencing purposes. One-shot kinetic measurements were performed by injection of a dilution series of HLA-A2/MAGE$_{p230\text{-}239}$ or HLA-A2/WT1$_{RMF}$ (100, 50, 25, 12.5, 6.25, 0 nM, 50 μl/min) for 3 min along the vertical channels. Dissociation was monitored for 5 min. Kinetic data were analyzed as described above.

Based on binding profile and measured specificity to bind to the antigen, binders were shortlisted and measured in functional assays.

Sequences of all selected binders (007A09, 007D10, 057B04, 057D03, 032G09, 034F05) are provided in the sequence listing included herein and summarized in Table 1 below.

TABLE 1

Amino acid sequences of selected HLA-A2/MAGE-A4 binders.

| Binder | SEQ ID NO | | | | | | | |
|---|---|---|---|---|---|---|---|---|
| | HCDR1 | HCDR2 | HCDR3 | VH | LCDR1 | LCDR2 | LCDR3 | VL |
| 007A09 | 1 | 2 | 3 | 7 | 4 | 5 | 6 | 8 |
| 007D10 | 9 | 10 | 11 | 15 | 12 | 13 | 14 | 16 |
| 057B04 | 17 | 18 | 19 | 23 | 20 | 21 | 22 | 24 |
| 057D03 | 25 | 26 | 27 | 31 | 28 | 29 | 30 | 32 |
| 032G09 | 33 | 34 | 35 | 39 | 36 | 37 | 38 | 40 |
| 034F05 | 41 | 42 | 43 | 47 | 44 | 45 | 46 | 48 |

Figure 2:
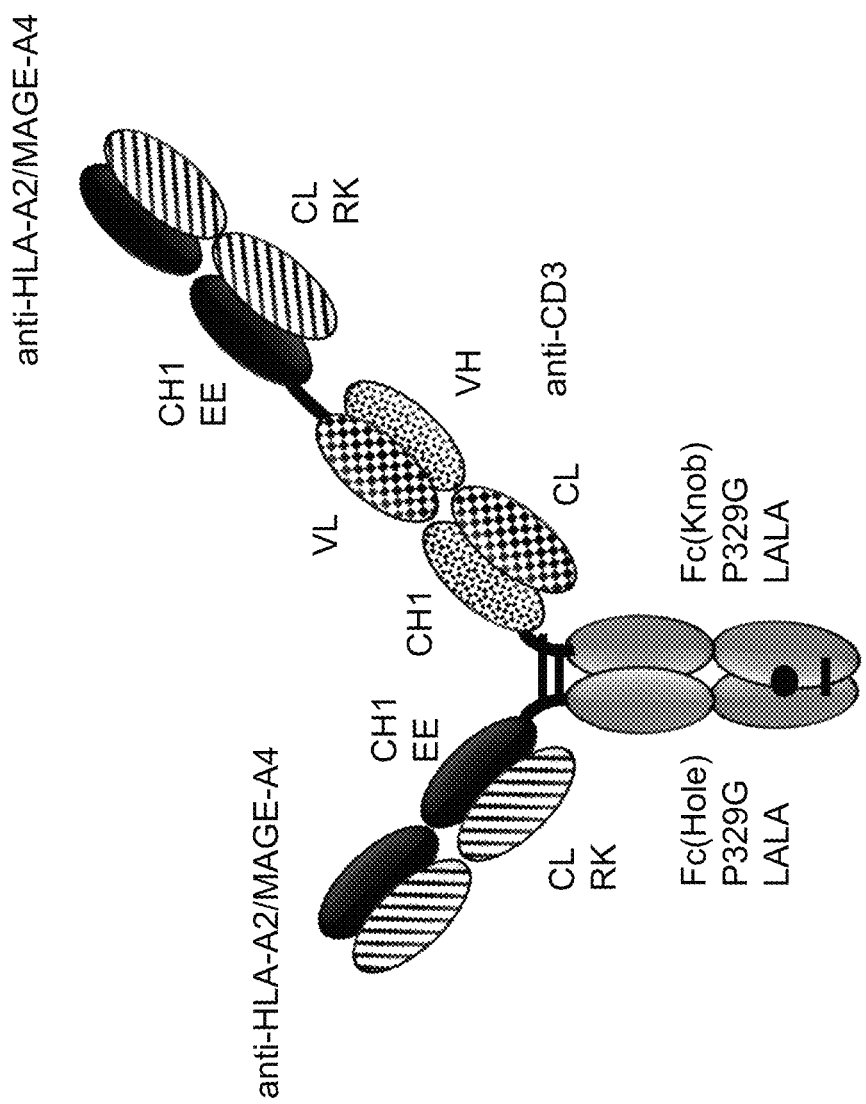
FIG. 2. Illustration of the T-cell bispecific (TCB) antibody molecules prepared in the Examples. All tested TCB antibody molecules were produced as "2+1 IgG CrossFab, inverted" with charge modifications (VH/VL exchange in CD3 binder, charge modifications in MAGE-A4 binders, EE=147E, 213E; RK=123R, 124K).

Example 2. Preparation of HLA-A2/MAGE-A4 IgG and HLA-A2/MAGE-A4 CD3 T-Cell Bispecific (TCB) Antibodies CD3 bispecific antibodies are also referred to herein a "T cell bispecific antibodies", "TCB antibodies", or "TCBs". A schematic illustration of the bispecific antibodies prepared in this Example is given in FIG. 2.

As CD3 binders, either antibody CH2527 or antibody V9 were used. Sequences of these binders are provided in the sequence listing included herein and summarized in Table 2 below.

TABLE 2

Amino acid sequences of CD3 binders.

| Binder | SEQ ID NO | | | | | | | |
|---|---|---|---|---|---|---|---|---|
| | HCDR1 | HCDR2 | HCDR3 | VH | LCDR1 | LCDR2 | LCDR3 | VL |
| CH2527 | 51 | 52 | 53 | 57 | 54 | 55 | 56 | 58 |
| V9 | 59 | 60 | 61 | 65 | 62 | 63 | 64 | 66 |

Exemplary sequences of TCB antibodies are given in SEQ ID NOs 67, 69, 70 and 71 (Molecule D) and SEQ ID NOs 68, 69, 70 and 72 (Molecule R). Other TCB antibodies were constructed in an analogous manner, using the VH and VL sequences of the corresponding HLA-A2/MAGE-A4 binders.

As controls, a HLA-A2/MAGE-A4 IgG antibody and TCB antibody based on the binder "C106B9", described in WO 2016/199141, were prepared. The VH and VL region sequences of this binder are shown in SEQ ID NOs 49 and 50, respectively.

Table 3 below shows the IgG and TCB antibody molecules produced, and the nomenclature used herein for these molecules.

TABLE 3

Overview of IgG and TCB antibody molecules produced and their nomenclature as used herein.

| Binder | IgG antibody | TCB antibody (CD3 binder CH2527) | TCB antibody (CD3 binder V9) |
| --- | --- | --- | --- |
| 007A09 | Molecule H | Molecule A | Molecule O |
| 007D10 | Molecule I | Molecule B | Molecule P |
| 057B04 | Molecule J | Molecule C | Molecule Q |
| 057D03 | Molecule K | Molecule D | Molecule R |
| 032G09 | Molecule L | Molecule E | Molecule S |
| 034F05 | Molecule M | Molecule F | Molecule T |
| C106B9 | Molecule N | Molecule G | Molecule U |

General Methods and Tools

Recombinant DNA Techniques. Standard methods were used to manipulate DNA as described in Sambrook, J. et al, Molecular cloning: A laboratory manual; Cold Spring Harbor Laboratory press, Cold spring Harbor, New York, 1989. The molecular biological reagents were used according to the manufacturer's instructions. General information regarding the nucleotide sequences of human immunoglobulin light and heavy chains is given in: Kabat, E. A. et al. (1991) Sequences of Proteins of Immunological Interest, Fifth Ed., NIH Publication No 91-3242.

DNA sequencing. DNA sequences were determined by double strand sequencing.

Gene Synthesis. Desired gene segments, where required, were either generated by PCR using appropriate templates or were synthesized at Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells.

Production of IgG and TCB Antibodies

The DNA sequences encoding the variable heavy and light chain regions of the HLA-A2/MAGE-A4 binders (and, where applicable, the CD3 binders) were cloned into mammalian expression vectors using conventional cloning techniques.

IgG and TCB antibodies were generated by transient transfection of HEK293 EBNA cells or CHO EBNA cells. Cells were centrifuged and, medium was replaced by prewarmed CD CHO medium (Thermo Fisher, #10743029). Expression vectors were mixed in CD CHO medium, polyethylenimine (PEI, Polysciences, #23966-1) was added, and the solution vortexed and incubated for 10 minutes at room temperature. Afterwards, cells (2 mio/ml) were mixed with the vector/PEI solution, transferred to a flask and incubated for 3 hours at 37° C. in a shaking incubator with a 5% $CO_2$ atmosphere. After the incubation, Excell medium with supplements (80% of total volume) was added (W. Zhou and A. Kantardjieff, Mammalian Cell Cultures for Biologics Manufacturing, DOI: 10.1007/978-3-642-54050-9; 2014). One day after transfection, supplements (Feed, 12% of total volume) were added. Cell supernatants were harvested after 7 days by centrifugation and subsequent filtration (0.2 μm filter), and proteins were purified from the harvested supernatant by standard methods as indicated below.

Alternatively, the IgG and TCB antibodies described herein were prepared by Evitria (Schlieren, Switzerland) using their proprietary vector system with conventional (non-PCR based) cloning techniques and using suspension-adapted CHO K1 cells (originally received from ATCC and adapted to serum-free growth in suspension culture at Evitria). For the production, Evitria used its proprietary, animal-component free and serum-free media (eviGrow and eviMake2) and its proprietary transfection reagent (eviFect). Supernatant was harvested by centrifugation and subsequent filtration (0.2 μm filter) and, proteins were purified from the harvested supernatant by standard methods.

Purification of IgG and TCB Antibodies

Proteins were purified from filtered cell culture supernatants referring to standard protocols. In brief, Fc containing proteins were purified from cell culture supernatants by Protein A-affinity chromatography (equilibration buffer: 20 mM sodium citrate, 20 mM sodium phosphate, pH 7.5; elution buffer: 20 mM sodium citrate, pH 3.0). Elution was achieved at pH 3.0 followed by immediate pH neutralization of the sample. The protein was concentrated by centrifugation (Millipore Amicon® ULTRA-15, #UFC903096), and aggregated protein was separated from monomeric protein by size exclusion chromatography in 20 mM histidine, 140 mM sodium chloride, pH 6.0.

Analytics of IgG and TCB Antibodies

The concentrations of purified proteins were determined by measuring the absorption at 280 nm using the mass extinction coefficient calculated on the basis of the amino acid sequence according to Pace, et al., Protein Science, 1995, 4, 2411-1423. Purity and molecular weight of the proteins were analyzed by CE-SDS in the presence and absence of a reducing agent using a LabChipGXII or LabChip GX Touch (Perkin Elmer). Determination of the aggregate content was performed by HPLC chromatography at 25° C. using analytical size-exclusion column (TSKgel G3000 SW XL or UP-SW3000, Tosoh Bioscience) equilibrated in running buffer (200 mM $KH_2PO_4$, 250 mM KCl pH 6.2, 0.02% $NaN_3$).

The final quality was very good for all molecules with almost 100% monomer content and 100% purity on CE-SDS.

Example 3. Affinity Analysis of HLA-A2/MAGE-A4 Antibodies

For determination of affinity of HLA-A2/MAGE-A4 antibodies to HLA-A2/MAGE-A4$_{p230-239}$, surface plasmon resonance (SPR) experiments were performed at 25° C. on a Biacore T200 with HBS-EP+ as running buffer (0.01 M HEPES pH 7.4, 0.15 M NaCl, 0.005% Surfactant P20 (GE Healthcare, #BR-1006-69)). Anti-human Fc specific antibody (GE Healthcare, #BR-1008-39) was directly immobilized by amine coupling on a CMS chip (GE Healthcare). The HLA-A2/MAGE-A4 antibodies were captured for 60 s at 2.5 nM. A three-fold dilution series of the HLA-A2/MAGE-A4$_{p230-239}$ complex in HBS-EP (6.17 to 1500 nM) was passed over the ligand at 30 μl/min for 240 sec to record the association phase. The dissociation phase was monitored for 240 s and triggered by switching from the sample solution to HBS-EP+. The chip surface was regenerated after every cycle using an injection of 3M MgCl$_2$ at 10 μl/min for 30 sec. Bulk refractive index differences were corrected for by subtracting the response obtained on the reference flow cell which contains the anti-human Fc antibody, but without HLA-A2/MAGE-A4 antibody captured on it. The affinity constants were derived from the kinetic rate constants by fitting to a 1:1 Langmuir binding using the BIAeval software (GE Healthcare). The measurement was performed in triplicate with independent dilution series.

For all tested molecules (Molecules H, I, J, K, L and M (all IgG antibodies) and Molecule R (TCB antibody)), the kinetic constants for a 1:1 Langmuir binding are summarized in Table 4.

All tested HLA-A2/MAGE-A4 antibodies bind to HLA-A2/MAGE-A4$_{p230-239}$ with double-digit nanomolar (monovalent) affinity and keep the same affinity when converted from IgG to bispecific format (as shown for Molecule K and R).

TABLE 4

Summary of affinity data as determined by SPR for selected HLA-A2/MAGE-A4 IgG and HLA-A2/MAGE-A4 CD3 TCB antibodies to HLA-A2/MAGE-A4$_{p230-239}$.

| Molecule | ka [1/Ms] (stdev) | kd [1/s] (stdev) | KD (stdev) | Rmax [RU] (stdev) |
|---|---|---|---|---|
| Molecule H | 2.47E+05 (9.68 E+03) | 4.26E−03 (1.61 E−04) | 1.73E−08 (4.74 E−10) | 96.7 (17.1) |
| Molecule I | 2.55E+04 (6.07 E+02) | 2.46E−03 (5.97 E−05) | 9.64E−08 (4.51 E−09) | 92.1 (3.7) |
| Molecule J | 1.06E+06 (7.57 E+04) | 4.30E−02 (1.39 E−03) | 4.07E−08 (3.86 E−09) | 93.7 (5.2) |
| Molecule K | 2.60E+06 (2.42 E+05) | 4.08E−02 (2.32 E−03) | 1.57E−08 (6.55 E−10) | 117.3 (15.8) |
| Molecule R | 3.33E+06 (2.32 E+05) | 4.36E−02 (1.44 E−03) | 1.31E−08 (4.91 E−10) | 99.3 (19.9) |
| Molecule L | 1.20E+05 (4.12 E+03) | 3.00E−03 (3.52 E−05) | 2.51E−08 (8.63 E−10) | 136.6 (38.2) |
| Molecule M | 4.50E+05 (2.30 E+04) | 1.11E−03 (1.67 E−05) | 2.47E−09 (1.15 E−10) | 102.6 (23.2) |

Example 4. T-Cell Mediated Lysis of Peptide-Pulsed T2 Cells Induced by HLA-A2/MAGE-A4 CD3 T-Cell Bispecific (TCB) Antibodies T-cell killing mediated by different HLA-A2/MAGE-A4 CD3 TCB antibodies was assessed on peptide-pulsed T2 cells. Human PBMCs were used as effectors and the killing was detected at 24 h of incubation with the bispecific antibody.

T2 cells were harvested, washed, and pulsed for 2 h at 37° C. with 0.8 μM of either the MAGE-A4$_{p230-239}$ peptide (GVYDGREHTV, SEQ ID NO: 73) or an irrelevant peptide (NY-ESO1$_{p157-165}$: SLLMWITQC, SEQ ID NO: 85). After one washing step in PBS, peptide-pulsed target cells were plated at a density of 30 000 cells/well using flat-bottom 96-well plates.

Peripheral blood mononuclear cells (PBMCs) were prepared by Histopaque density centrifugation of enriched lymphocyte preparations of heparinized blood obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, #1(0302) at 37° C., 5% CO$_2$ in cell incubator until further use (no longer than 24 h).

For the killing assay, the antibodies were added at the indicated concentrations (range of 0.02 pM-50 nM in triplicates). PBMCs were added to target cells to obtain a final E:T ratio of 10:1. Target cell killing was assessed after 24 h of incubation at 37° C., 5% CO$_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 3:
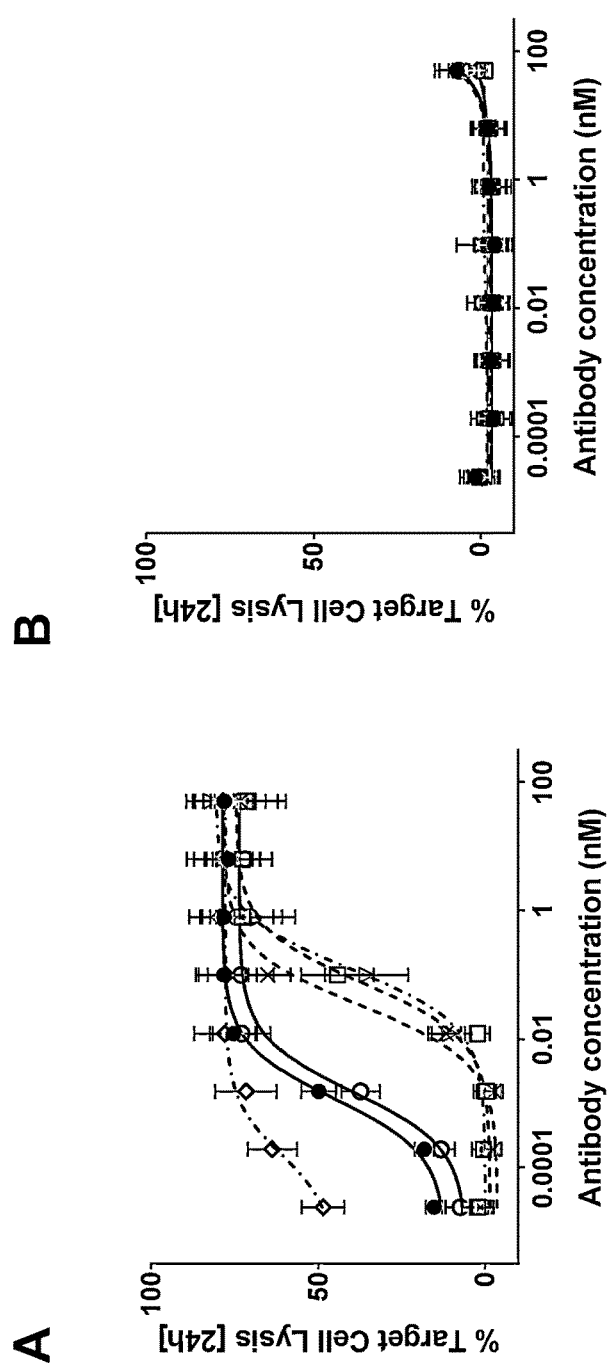
FIG. 3. T-cell mediated lysis of T2 cells pulsed with either the MAGE-A4$_{p230-239}$ peptide (GVYDGREHTV) (A) or an irrelevant peptide (NY-ESO1$_{p157-165}$: (SLLMWITQC)) (B), induced by different MAGE-A4 CD3 TCB molecules (E:T=10:1, human PBMC effector cells). Depicted are triplicates with SD.

As shown in FIG. 3, all evaluated HLA-A2/MAGE-A4 CD3 TCB antibodies induce killing of MAGE-A4 peptide-pulsed T2 cells after 24 h of incubation. The ranking of the HLA-A2/MAGE-A4 CD3 TCB antibodies is the following: Molecule D>Molecule A=Molecule F>Molecule E≥Molecule C=Molecule B.

The corresponding EC50 values for tumor cell lysis were calculated using GraphPadPrism6, and are given in Table 5.

TABLE 5

EC50 values (pM) for T-cell mediated lysis of MAGE-A4 peptide pulsed T2 cells, induced by the indicated HLA-A2/MAGE-A4 CD3 TCB antibodies.

| TCB antibody | EC50 [pM] 24 h |
|---|---|
| Molecule A | 1.2 |
| Molecule B | 72.8 |
| Molecule C | 120.9 |
| Molecule D | 0.2 |
| Molecule E | 32.7 |
| Molecule F | 1.5 |

Example 5. HLA-A2/MAGE-A4 CD3 TCB Antibody-Induced Jurkat Cell Activation on Peptide-Pulsed T2 Cells (Jurkat-NFAT Activation Assay)

The capacity of the HLA-A2/MAGE-A4 CD3 TCB antibodies to induce CD3-mediated activation of Jurkat-NFAT effector cells upon simultaneous binding to CD3 and HLA-A2/MAGE-A4 peptide MHC (pMHC) complex on cells, was assessed using co-cultures of T2 cells pulsed with either the MAGE-A4$_{p230-239}$ peptide (GVYDGREHTV) or an irrelevant peptide (NY-ESO1$_{p157-165}$: (SLLMWITQC)) and Jurkat-NFAT reporter cells (a CD3-expressing human acute lymphatic leukemia reporter cell line with a NFAT promoter, GloResponse Jurkat NFAT-RE-luc2P, Promega #CS176501). Upon simultaneous binding of the TCB antibody to the HLA-A2/MAGE-A4 on MAGE-A4 peptide pulsed T2 cells and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling.

For the assay, T2 cells were harvested, washed, and pulsed with 0.8 µM of either the (MAGE-A4$_{p230\text{-}239}$ peptide (GVYDGREHTV)) or an irrelevant peptide (NY-ESO1$_{p157\text{-}165}$: (SLLMWITQC)). 8000 cells/well were plated in a flat-bottom, white-walled 384-well-plate (Falcon, #353963) and diluted antibodies or medium (for controls) was added (range of 0.1 pM-100 nM) Subsequently, Jurkat-NFAT reporter cells were harvested and viability assessed using ViCell. Cells were re-suspended in cell culture medium and added to tumor cells to obtain a final E:T of 2.5:1, as indicated and a final volume of 30 µl per well. Cells were incubated for 6 h at 37° C. in a humidified incubator. At the end of the incubation time, 10 µl/well of ONE-Glo solution (Promega; 1:4 ONE-Glo and assay medium volume per well) were added to wells and incubated for 10 min at room temperature in the dark. Luminescence was detected using WALLAC Victor3 ELISA reader (PerkinElmer2030), 1 sec/well as detection time.

Figure 4:
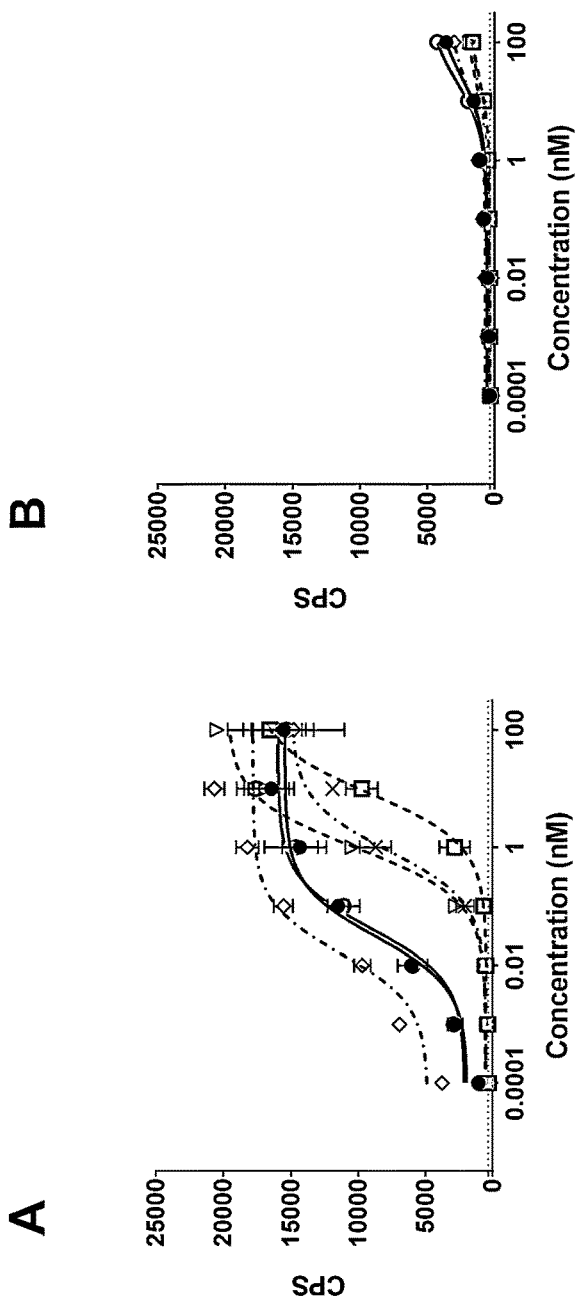
FIG. 4. Jurkat activation, as determined by luminescence, upon simultaneous binding of different MAGE-A4 CD3 TCB molecules to human CD3 on Jurkat-NFAT reporter cells and T2 cells pulsed with either the MAGE-A4$_{p230-239}$ peptide (GVYDGREHTV) (A) or an irrelevant peptide (NY-ESO1$_{p157-165}$: (SLLMWITQC)) (B). Depicted are triplicates with SD.

As shown in FIG. 4, all evaluated HLA-A2/MAGE-A4 CD3 TCB antibodies induce T cell cross-linking via CD3 and subsequently T cell activation when incubated with T2 cells pulsed with the MAGE-A4 peptide. Taking into account both, EC50 as well as the overall level of activation induced, the ranking of the HLA-A2/MAGE-A4 CD3 TCB antibodies is the following: Molecule D>Molecule A=Molecule F>Molecule C>Molecule E>Molecule B.

The corresponding EC50 values for Jurkat activation were calculated using GraphPadPrism6, and are given in Table 6.

TABLE 6

EC50 values (pM) for HLA-A2/MAGE-A4 CD3 TCB antibody-mediated activation of Jurkat-NFAT reporter cells, as measured by luminescence after 6 h of incubation.

| TCB antibody | EC50 [pM] |
|---|---|
| Molecule A | 30.3 |
| Molecule B | n.c. (8309) |
| Molecule C | 975.6 |
| Molecule D | 15.7 |
| Molecule E | 876.6 |
| Molecule F | 41.6 | n.c.: curve fit doesn't allow proper calculation of EC50s

Example 6. T-Cell Mediated Lysis of a Panel of HLA-A2+ MAGE-A4 Expressing Tumor Cell Lines Induced by HLA-A2/MAGE-A4 CD3 TCB Antibodies T-cell killing mediated by different HLA-A2/MAGE-A4 CD3 TCB antibodies was assessed on a panel of HLA-A2+ MAGE-A4 expressing tumor cell lines (NCI-H1755, NCI-H2023, IM-9, U266B1, A-375, UMUC-3, C-33A). The HLA-A2+ MAGE-A4-negative cell line MDA-MB-231 was included as negative control. The assay was performed as described in Example 4.

For the killing assay, the antibodies were added at the indicated concentrations (range of 0.02 pM-50 nM in triplicates).

Figure 5:
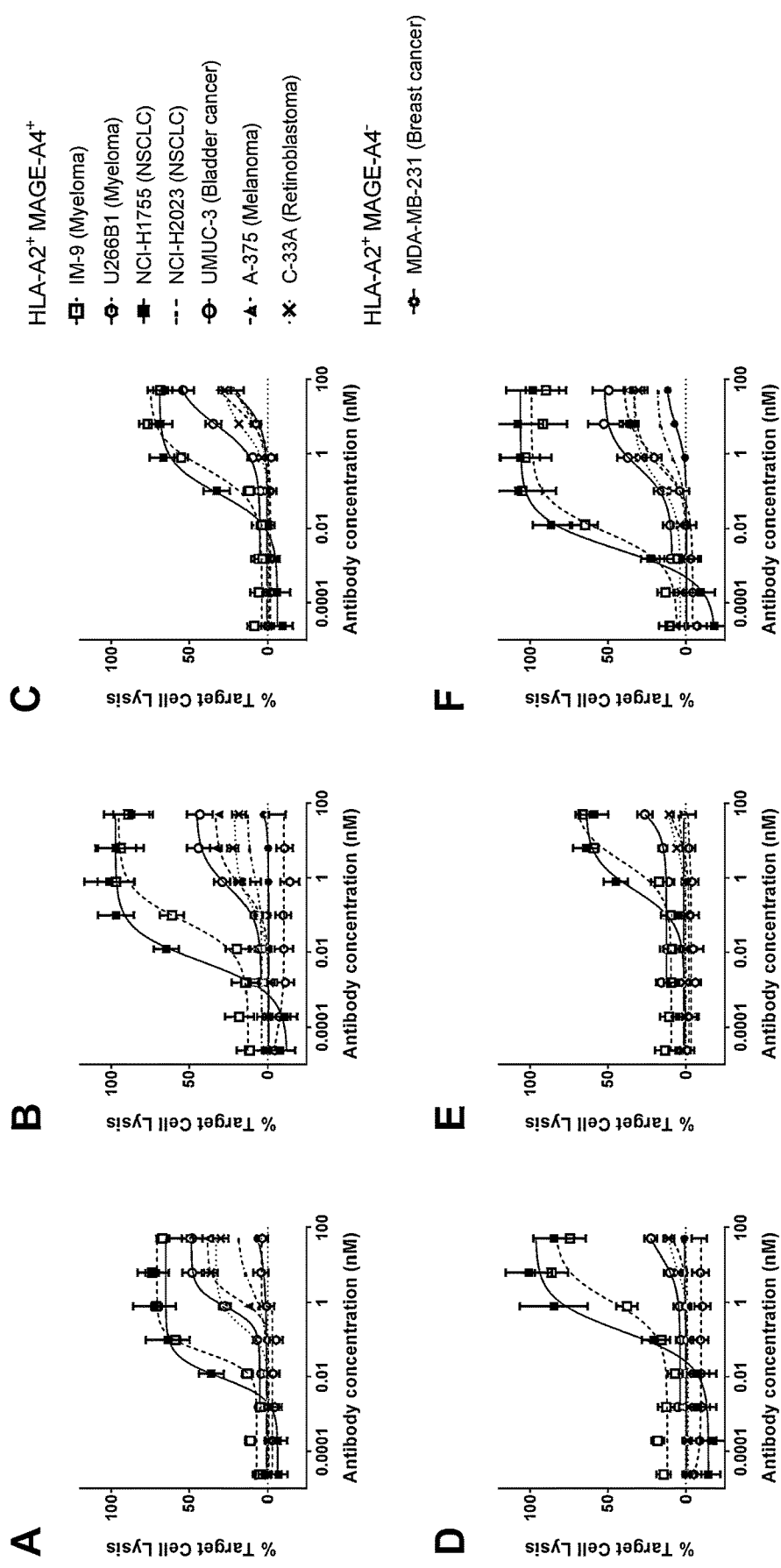
FIG. 5. T-cell mediated lysis of various HLA-A2+/MAGE-A4+ tumor cell lines of different indications versus HLA-A2+/MAGE-A4− MDA-MB-231 cells induced by different MAGE-A4 CD3 TCB molecules (E:T=10:1, human PBMC effector cells). (A) Molecule A, (B) Molecule D, (C) Molecule E, (D) Molecule B, (E) Molecule C, (F) Molecule F. Depicted are triplicates with SD.

The results after 24 h (FIG. 5) show that all HLA-A2/MAGE-A4 CD3 TCB antibodies are able to induce killing of HLA-A2+ MAGE-A4 expressing tumor cell lines. The extent of killing varies between the different TCB antibodies and the different tumor cell lines. NCI-H1755 and IM-9 cells are killed best. HLA-A2/MAGE-A4 CD3 TCB antibody Molecule A, D and F are the most potent amongst the 6 TCB antibodies tested.

The corresponding EC50 values for tumor cell lysis were calculated using GraphPadPrism6, and are given in Table 7.

TABLE 7

EC50 values (pM) for T-cell mediated lysis of various HLA-A2 + MAGE-A4 + tumor cell lines, induced by the indicated HLA-A2/MAGE-A4 CD3 TCB antibodies.

| EC50 [pM] | Molecule A | Molecule B | Molecule C | Molecule D | Molecule E | Molecule F |
|---|---|---|---|---|---|---|
| NCI-H1755 | 9.4 | 168.4 | 459.6 | 5.7 | 84.4 | 2.7 |
| NCI-H2023 | 2092.0 | — | — | 1155.9 | — | 890.3 |
| IM-9 | 43.4 | 1075.5 | 2744.0 | 70.0 | 393.4 | 8.3 |
| U266B1 | — | — | — | — | — | 351.7 |
| A-375 | 1213.6 | — | — | 543.1 | — | 822.2 |
| UMUC-3 | 775.0 | — | — | 563.8 | n.c. (5799.6) | 429.3 |
| C-33A | 225.3 | n.c. | n.c. | 178.3 | 3984.9 | 186.2 |

Example 7. T-Cell Mediated Tumor Lysis of a Panel of HLA-A2+ MAGE-A4-Negative Tumor Cell Lines Induced by HLA-A2/MAGE-A4 CD3 TCB Antibodies T-cell killing mediated by different HLA-A2/MAGE-A4 CD3 TCB antibodies was assessed on a panel of HLA-A2+ MAGE-A4-negative tumor cell lines (MDA-MA-231, SKM-1, SW-480, Colo-205, HCT-116, SW-620, Saos-2, L363). The HLA-A2+ MAGE-A4-positive cell line NCI-H1755 was included as positive control. The assay was performed as described in Example 4.

For the killing assay, the antibodies were added at the indicated concentrations (range of 0.02 pM-50 nM in triplicates).

Figure 6:
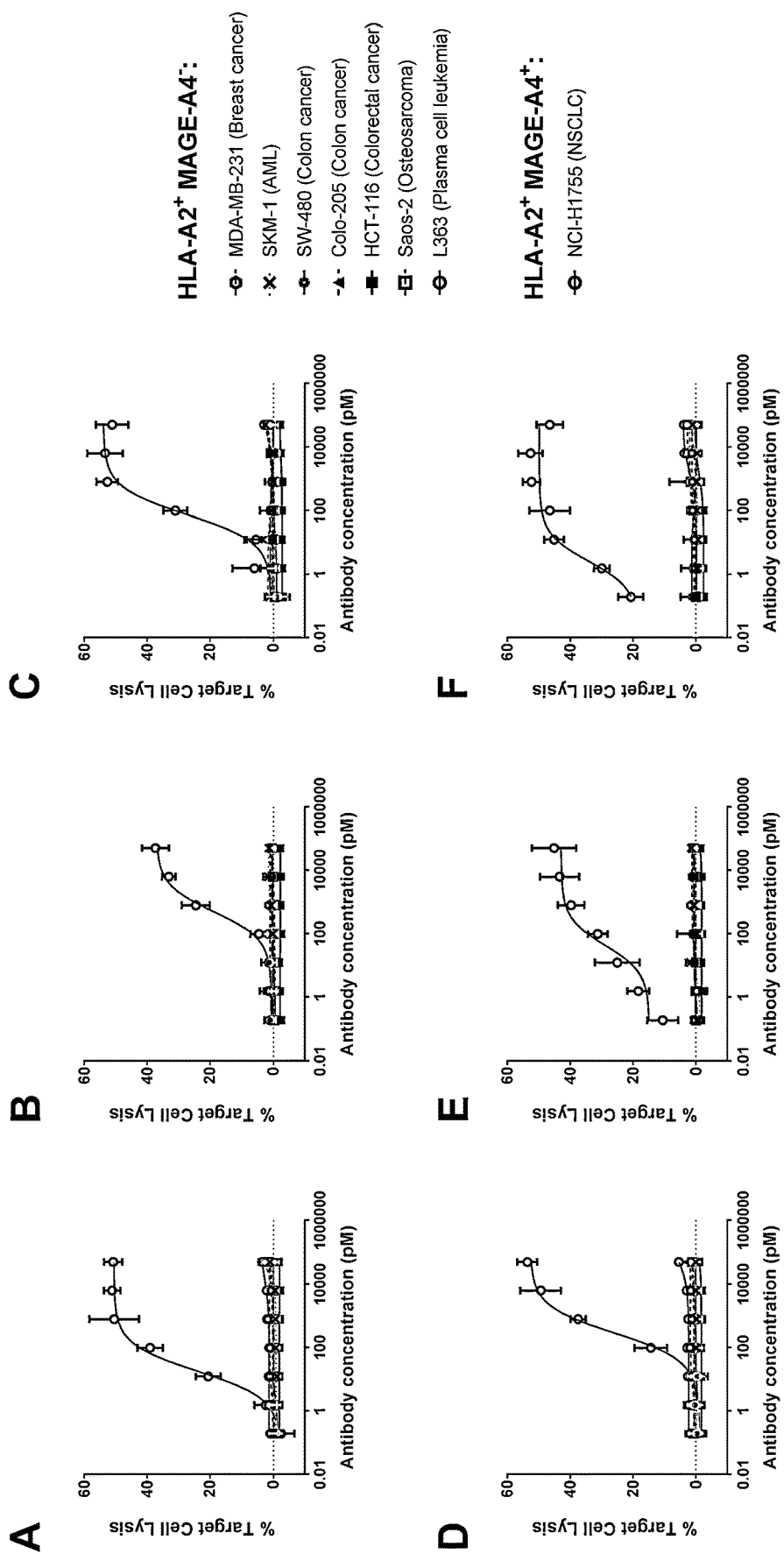
FIG. 6. T-cell mediated lysis of various HLA-A2+/MAGE-A4− tumor cell lines of different indications versus HLA-A2+/MAGE-A4+ NCI-H1755 cells induced by different MAGE-A4 CD3 TCB molecules (E:T=10:1, human PBMC effector cells). (A) Molecule A, (B) Molecule C, (C) Molecule E, (D) Molecule B, (E) Molecule D, (F) Molecule F. Depicted are triplicates with SD.

The results after 24 h (FIG. 6) show that none of the HLA-A2/MAGE-A4 CD3 TCB antibodies induces killing of HLA-A2+ MAGE-A4 negative tumor cells. All tested TCBs show selectivity versus HLA-A2 alone and do not induce target cell killing in absence of MAGE-A4 expression.

Example 8. Definition of Binding Residues of Selected HLA-A2/MAGE-A4 CD3 TCBs by Alanine Scan Assay To characterize the potential binding motifs of the MAGE-A4 peptide by our TCB antibodies, we set up an alanine scan assay using peptides derived from native sequences by individually replacing each amino acid with an alanine, and measured the NFAT-reporter signal by T2 cells pulsed with these peptides For the assay, T2 cells were harvested, washed, and pulsed with 0.8 µM of either the MAGE-A4$_{p230\text{-}239}$ peptide (GVYDGREHTV) or an alanine-replaced peptide. 20 000 cells/well were plated in a flat-bottom, white-walled 96-well-plate (Greiner Bio-One, #655098) and diluted antibodies or medium (for controls) was added. Subsequently, Jurkat-NFAT reporter cells were harvested and viability assessed using ViCell. Cells were re-suspended in cell culture medium and added to tumor cells to obtain a final E:T of 5:1, as indicated and a final volume of 100 µl per well. Cells were incubated for 6 h at 37° C. in a humidified incubator. At the end of the incubation time, 100 µl/well of ONE-Glo solution (Promega; 1:1 ONE-Glo and assay medium volume per well) were added to wells and incubated for 10 min at room temperature in the dark. Luminescence was detected using WALLAC Victor3 ELISA reader (PerkinElmer2030), 5 sec/well as detection time.

The EC50 values for the NFAT-reporter signal were calculated using GraphPadPrism6, and are given in FIG. 7A. Further, the fold change of EC50 relative to the EC50 for the native peptide was calculated, and a fold change of ≥5 was considered as significant (FIG. 7B).

The alanine scan results show different binding motifs of the MAGE-A4 peptide by the TCB antibodies.

Example 9. Predicted Off Target Peptide (POTP) Assessment for Different MAGE-A4 CD3 TCB Antibodies on Peptide-Pulsed T2 Cells (Jurkat-NFAT Activation Assay)

The capacity of the HLA-A2/MAGE-A4 CD3 TCB antibodies to induce CD3-mediated activation of Jurkat-NFAT cells upon simultaneous binding to CD3 and HLA-A2/MAGE-A4 peptide MHC (pMHC) complex on cells was assessed using co-cultures of T2 cells, pulsed with either the MAGE-A4$_{p230\text{-}239}$ peptide (GVYDGREHTV) or one of 33 predicted off target peptides (FIG. 8), and Jurkat-NFAT reporter cells (a CD3-expressing human acute lymphatic leukemia reporter cell line with a NFAT promoter, GloResponse Jurkat NFAT-RE-luc2P, Promega #CS176501). Upon simultaneous binding of the TCB antibody to the HLA-A2/MAGE-A4 complex on MAGE-A4 peptide pulsed T2 cells and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling.

For the assay, T2 cells were harvested, washed, and pulsed at 1 mio cells/ml for 2 h at 37° C. with 10 µM of the MAGE-A4$_{p230\text{-}239}$ peptide (GVYDGREHTV) or a POTP using 96-well plates. Pulsed T2 cells were washed and transferred to a 96-deep-well plate at a concentration of 0.4 mio cells/ml in RPMI1640 medium containing 2% FCS, 1% L-alanyl-L-glutamine (Biochrom, #K0302) and 1% penicillin-streptomycin (Sigma, #P4333) (Automation medium).

Subsequently, Jurkat-NFAT reporter cells were harvested and viability assessed using ViCell. Cells were re-suspended in the Automation medium at a concentration of 1 mio/ml to obtain an E:T ratio of 2.5:1 in the final assay plates.

HLA-A2/MAGE-A4 CD3 TCB antibodies were diluted in Automation medium to obtain a final assay concentration of 10 nM and stored at 4° C. until usage.

The following steps were run in an automated way, using a TECAN EVO 200 platform:

Peptide-pulsed T2 cells, Jurkat-NFAT reporter cells and MAGE-A4 CD3 TCB antibody were added to flat-bottom, white-walled 384-well-plates (Falcon, #353963). and incubated for 16 h at 37° C. in a humidified incubator. At the end of the incubation time, 20 µl/well of ONE-Glo solution (Promega; diluted 1:2 with assay medium) were added and the mixture was incubated for 10 min at room temperature in the dark. Luminescence was detected using a Tecan Spark reader, 0.5 sec/well as detection time.

The resulting Jurkat-NFAT reporter cell activation signals were measured as quantified relative light units as counts per second (CPS signals). The ratio of the POTP signal to the MAGE-A4-induced signal in percent was calculated as follows: (CPS[POTP]−CPS[unpulsed cells])/(CPS[MAGE-A4]−CPS[unpulsed cells])*100. POTPs, which induced a signal of above 2% compared to 100% induced by T2-cells pulsed with the MAGE-A4 peptide were defined as relevant and considered for further evaluation.

As shown in FIG. 8, all evaluated HLA-A2/MAGE-A4 CD3 TCB antibodies except for Molecule C induced T cell activation upon simultaneous binding to CD3 on Jurkat-NFAT reporter cells and to the pMHC on T2-cells pulsed with the indicated POTPs. Molecule C did induce Jurkat-NFAT reporter cell activation only in presence of T2-cells pulsed with the MAGE-A4 peptide, but not in presence of T2-cells pulsed with any of the indicated POTPs, showing a high level of specificity. However, previous tumor cell lysis experiments revealed only rather poor anti-tumor efficacy in vitro (see FIG. 5).

Therefore, Molecule D was selected for further evaluation, based on its favorable potency (see FIG. 5) versus safety profile, showing Jurkat activation only in presence of T2-cells pulsed with peptides with no broad expression on high-risk organs, such as lung and heart.

Next, the panel of POTPs was extended to 503 peptides (SEQ ID NOs 86-589) and Molecule D was assessed in a similar Jurkat-NFAT reporter cell assay in presence of pulsed T2-cells as described above. FIG. 9 sums-up the resulting Jurkat-NFAT reporter cell activation signals as ratio of the POTP signal to the MAGE-A4-induced signal in percent which induced a signal of above 2%.

POTPs that induced signals above 2% were verified in a Jurkat NFAT assay using T2 pulsed with the respective peptide. The assay was performed as described in Example 4. Most of the previously identified peptides could be verified as off-targets (FIG. 10). Nevertheless there is a clear therapeutic window between the MAGE-A4 target peptide and the tested POTPs. The corresponding EC50 values for HLA-A2/MAGE-A4 CD3 TCB antibody-mediated activation of Jurkat-NFAT reporter cells were calculated using GraphPadPrism6, and are given in Table 8.

TABLE 8

EC50 values (nM) for HLA-A2/MAGE-A4 CD3 TCB antibody-mediated activation of Jurkat-NFAT reporter cells, as measured by luminescence.

| Peptide | EC50 [nM] |
|---------|-----------|
| MAGE-A4 | 0.001 |
| MAGE-A8 | 0.012 |
| MAGAB | 1.066 |
| MAGBA | 1.800 |
| MAGC2 | 0.916 |
| TSHR | 5.347 |
| MAGB6 | 2.861 |
| MAGA10 | 3.457 |
| HUS1B | 9.313 |

The MAGE-A8 derived peptide shows only a 10× therapeutic window which can be explained by a strong homology of the MAGE-A8-derived peptide (GLYDGREHSV) and the MAGE-A4 target peptide (GVYDGREHTV). However, none of the identified POTPs is broadly expressed in a high-risk organ. This clearly demonstrates a maintained favorable safety profile of Molecule D.

A similar assay set-up as described above was used to analyze the specificity of Molecule G. The extended panel of 503 POTPs was evaluated in a Jurkat-NFAT reporter cell assay in presence of T2-cells pulsed with 10 µM of either the MAGE-A4$_{p230-239}$ peptide (GVYDGREHTV) or the indicated POTP. FIG. 11 depicts the ratio of the POTP signal to the MAGE-A4-induced signal in percent which induced a signal of above 2% compared to 100% induced by T2-cells pulsed with the MAGE-A4 peptide. A few of the verified POTPs (TPC, RBBP5 and RENT1) show a rather broad expression profile, indicating the need of a more in-depth risk assessment to judge potential associated safety risks. It may therefore be anticipated that a molecule comprising the HLA-A2/MAGE-A4 binder included in Molecule D will have a much better therapeutic window/safety profile than a similar molecule which comprises the HLA-A2/MAGE-A4 binder included in Molecule G.

Example 10. HLA-A2/MAGE-A4 IgG-Induced Jurkat Cell Activation on Peptide-Pulsed T2 Cells (PGLALA-CAR-J Activation Assay)

The capacity of the HLA-A2/MAGE-A4 binders in IgG format to activate PGLALA-CAR-J effector cells was assessed as described in the following. T2 cells were pulsed with the MAGE-A4$_{p230-239}$ peptide (GVYDGREHTV) and co-cultured with anti-PGLALA-CAR-J effector cells (Jurkat-NFAT human acute lymphatic leukemia reporter cell line expressing a chimeric antigen receptor (CAR) directed against the PGLALA (P329G L234A L235A (EU numbering)) mutation in the Fc part of IgG molecules and containing a NFAT promoter, see PCT publication no. WO 2019/122046 (incorporated herein by reference in its entirety). Upon simultaneous binding of the IgG molecule to the HLA-A2/MAGE-A4 complex on MAGE-A4 peptide-pulsed T2 cells and PGLALA-CAR-J cells, the NFAT promoter is activated and leads to expression of active firefly luciferase.

For the assay, T2 cells were harvested, washed, and pulsed with 10 µM of the MAGE-A4$_{p230-239}$ peptide (GVYDGREHTV). Simultaneously, HLA-A2+/MAGE-A4− MDA-MB-231 cells were harvested and seeded. 8000 cells/well were plated in a flat-bottom, white-walled 384-well-plate (Falcon, #353963) and diluted antibodies or medium (for controls) were added (range of 0.01 pM-10 nM).

Subsequently, PGLALA-CAR-J reporter cells were harvested and viability assessed using ViCell. Cells were re-suspended in cell culture medium and added to tumor cells to obtain a final E:T of 2.5:1, as indicated and a final volume of 30 µl per well. Cells were incubated for 16 h at 37° C. in a humidified incubator. At the end of the incubation time, 10 µl/well of ONE-Glo solution (Promega; 1:4 ONE-Glo and assay medium volume per well) were added to wells and incubated for 10 min at room temperature in the dark. Luminescence was detected using a Tecan Spark instrument, 0.5 sec/well as detection time.

As shown in FIG. 12, all evaluated HLA-A2/MAGE-A4 IgGs induce CAR-J activation upon simultaneous binding to the PGLALA-CAR-J and to T2-cells pulsed with the MAGE-A4 peptide. No CAR-J activation can be observed on MAGE-A4-negative MDA-MB231 cells indicating that there is no cross-reactivity of the tested IgGs to HLA-A2 in absence of the MAGE-A4 peptide. In terms of potency, as determined by both EC50 value (Table 9), as well as maximal amplitude of the signal, Molecule H and Molecule K are the most potent ones amongst the tested IgGs.

TABLE 9

EC50 values (pM) for activation of PGLALA-CAR-J cells induced by the indicated IgGs in presence of MAGE-A4 peptide pulsed T2 cells.

| Cell Line\ EC50 (pM) | Molecule H | Molecule I | Molecule J | Molecule K | Molecule L | Molecule M | Molecule N |
|---|---|---|---|---|---|---|---|
| MAGE-A4-pulsed T2 | 8.6 | 181.5 | 208.2 | 18.2 | 83.7 | 19.2 | 19.2 |

Example 11. T-Cell Mediated Tumor Lysis of a Panel of HLA-A2+ MAGE-A4+ Tumor Cell Lines Induced by HLA-A2/MAGE-A4 CD3 TCB Antibodies T-cell killing mediated by HLA-A2/MAGE-A4 CD3 TCB antibodies containing different HLA-A2/MAGE-A4 binders and different CD3 binders was assessed on a panel of HLA-A2+ MAGE-A4+ tumor cell lines (UM-UC3, A375, NCI-H2013). The assay was performed as described in Example 4.

For the killing assay, the antibodies were added at the indicated concentrations (range of 1 pM-50 nM in triplicates).

The results after 48 h (FIG. 13) show that there is no difference in TCB-induced target cell lysis between the two TCB antibodies containing different HLA-A2/MAGE-A4 binders (Molecule D vs G and Molecule R vs U).

Target cell lysis is increased in the two TCB antibodies (Molecule R and U) containing the V9 as CD3 binder in comparison to the TCBs containing CH2527 (Molecule D and G).

The corresponding EC50 values for tumor cell lysis were calculated using GraphPadPrism6, and are given in Table 10.

TABLE 10

EC50 values (nM) for T-cell mediated lysis of various HLA-A2+ MAGE-A4+ tumor cell lines, induced by the indicated HLA-A2/MAGE-A4 CD3 TCB antibodies.

| Molecule\ EC50 (nM) | UMUC-3 | A375 | NCI-H2023 |
|---|---|---|---|
| Molecule D | 1.56 | 4.12 | 1.37 |
| Molecule G | 1.18 | 4.67 | 1.35 |
| Molecule R | 0.57 | 1.47 | 1.06 |
| Molecule U | 0.45 | 1.96 | 1.12 |

Example 12. T-Cell Mediated Tumor Lysis and Cytokine Release Induced by HLA-A2/MAGE-A4 CD3 TCB Antibody (Molecule R) on HLA-A2+ MAGE-A4 Expressing A375 Cells, A375 Cells Engineered to Overexpress HLA-A2 and A375 Cells with MAGE-A4 Knockout T-cell killing mediated by Molecule R was assessed on A375 cells expressing different levels of HLA-A2/MAGE-A4 peptide MHC (pMHC) complexes (A375 cells, A375 cells genetically engineered (with a lentivirus) to overexpress HLA-A2, and A375 cells with a MAGE-A4 knockout (generated via CRISPR-Cas9)).

MAGE-A4/HLA-A2 pMHC copy numbers detected via MHC-Associated Peptide Proteomics (MAPPS) of the different A375 cells are shown in Table 11.

TABLE 11

MAGE-A4/HLA-A2 pMHC copy numbers as detected via MHC-Associated Peptide Proteomics (MAPPS).

| cell line | MAGE-A4/HLA-A2 pMHC copy number |
|---|---|
| A375 | 32 |
| A375 HLA-A2 overexpressing | 495 |
| A375 MAGE-A4 knockout | n.d. |

The assay was performed as described in Example 4. For the killing assay, Molecule R was added at the indicated concentrations (range of 1 pM-50 nM in triplicates).

The results after 24 hours (FIG. 14) show that Molecule R is able to induce killing of A375 cells, but to a much stronger extent of A375 cells with HLA-A2 overexpression. A375 cells with a MAGE-A4 knockout were not killed as they do not present the target pMHC complex due to a lack of MAGE-A4 expression.

The corresponding EC50 values for tumor cell lysis were calculated using GraphPadPrism6, and are given in Table 12.

TABLE 12

EC50 values (pM) for T-cell mediated lysis of A375 and A375 overexpressing HLA-A2, induced by Molecule R.

| Cells | EC50 [pM] |
|---|---|
| A375 | 0.6 |
| A375 HLA-A2 overexpressing | 0.08 |

After 24 and 48 hours, supernatant was collected for subsequent analysis of the cytokines TNFα and IFNγ via Luminex assay (Human Custom ProcartaPlex 7-plex; Thermo Fisher Scientific; #PPX-07-MXFVK4Y). The assay was performed according to manufacturer's instructions.

IFNγ release after 24 hrs and TNFα release after 48 hrs of incubation with 1.4 nM of Molecule R are depicted in FIG. 15. The release of both cytokines upon Molecule R mediated killing is strongly increased on A375 HLA-A2 overexpressing cells, which shows that IFNγ and TNFα release is correlating with MAGE-A4/HLA-A2 pMHC complex expression levels. No cytokine release can be observed on A375 MAGE-A4 knockout cells.

Example 13. Tumor Cell Growth Upon Treatment with HLA-A2/MAGE-A4 CD3 TCB Antibody (Molecule R)

In order to monitor tumor cell growth upon treatment with different concentrations of Molecule R, different HLA-A2$^+$/MAGE-A4$^+$ cell lines (A375, NCI-H1755, ScaBer, UM-UC3, NCI-H2023, NCI-H1703) were transduced with the Essen CellPlayer NucLight Red Lentivirus (Essenbioscience, #4476; EF1α, puromycin) to stably express the NucLight Red fluorescent protein restricted to the nucleus. Quantification per well over time allows thus real-time assessment of tumor cell lysis or proliferation.

Effector cells (PBMC) were isolated out of the blood of healthy volunteers as described in Example 4.

HLA-A2$^+$/MAGE-A4$^+$ NucLight red cells (A375, NCI-H1755, ScaBer, UM-UC3, NCI-H2023, NCI-H1703) were harvested using cell dissociation buffer (Invitrogen, #13151-014) and plated at a density of 15×10$^3$ cells per well (A375, UM-UC3, NCI-H2023, NCI-H1703), 5×10$^3$ cells/well (ScaBer) or 25×10$^3$ cells/well (NCI-H1755) in cell culture media in a sterile 96-well flat bottom adhesion tissue culture plate (TPP, #92096) over night at 37° C. and 5% CO$_2$ in an incubator. Molecule R was added at the indicated concentrations (range of 1 pM-50 nM in triplicates). PBMC were added as effector cells to each well at an E:T ratio of 5:1.

Plates were monitored by fluorescence microscopy high content life imaging using the Incucyte® Zoom System (Essenbioscience, HD phase-contrast, red fluorescence, 10× objective) in a 3 hours interval for up to 96 hrs at 37° C. and 5% CO$_2$. The amount of healthy tumor cells (Count (Per Image)) was quantified using the IncucyteZoom Software to monitor tumor cell growth. Values were plotted for the respective time point and conditions against the used TCB concentration to analyse effects on the cytolytic potential of T cells.

FIG. 16 shows that Molecule R can inhibit tumor growth of HLA-A2$^+$/MAGE-A4$^+$ tumor cell lines. The extent of tumor growth inhibition as well as the effective concentration varies between the different cell lines which can be explained by different HLA-A2/MAGE-A4 pMHC complex expression levels as well as the different origin of the cancer cell lines.

Example 14. Dose Finding Efficacy Study with HLA-A2/MAGE-A4 CD3 TCB Antibody (Molecule R) in IM-9 Xenograft in Humanized Mice The efficacy study described in this Example was aimed to understand dose dependent efficacy of Molecule R in terms of tumor regression and Immuno-PD in fully humanized NSG mice.

Human IM-9 cells (human multiple myeloma) were originally obtained from DMSZ and after expansion deposited in the Roche Glycart internal cell bank. Cells were cultured in RPMI 1640+10% FCS+1% Glutamax+10 mM HEPES+1 mM sodium pyruvate at 37° C. in a water-saturated atmosphere at 5% $CO_2$. In vitro passage 12 was used for subcutaneous injection at a viability of 98%.

50 microliters tumor cell suspension mixed with 50 microliters Matrigel were injected subcutaneously in the flank of anaesthetized mice with a 22G to 30G needle.

Female NSG mice, age 4-5 weeks at start of the experiment (Jackson Laboratory) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Female NSG mice were injected i.p. with 15 mg/kg of busulfan followed one day later by an i.v. injection of $1\times10^5$ human hematopoietic stem cells isolated from cord blood. At week 14-16 after stem cell injection mice were bled sublingual and blood was analyzed by flow cytometry for successful humanization. Efficiently engrafted mice were randomized according to their human T cell frequencies into the different treatment groups. At that time, mice were injected with tumor cells as described above and treated once weekly with different doses of Molecule R or vehicle when tumor size reached approximately 200 $mm^3$ (day 7) (FIG. 17). Application was i.v., with an injection volume of 200 μl. Tumor growth was measured twice weekly using a caliper and tumor volume was calculated as follows:

$$T_v:(W^2/2)\times L (W:\text{Width}, L:\text{Length})$$

At study day 15, four scout mice per group were sacrificed, tumors were removed, weighed, fixed over night with PFA and embedded in paraffin for histological assessment. Slides of the tumors were stained with anti-mouse CD3 antibodies to assess the intra-tumoral T cell frequency in all groups. At study day 28 the study was terminated.

FIG. 18 shows the tumor growth kinetics (mean, +/−SEM) in all groups as well as the individual tumor growth per mouse. All doses of Molecule R as a single agent induced tumor growth inhibition. The lowest dose tested (0.1 mg/kg) showed a more heterogeneous inhibition as two mice escaped from the low dose treatment. The analysis of the human T cell infiltration in the tumors of the scout animals (FIG. 19) revealed a good boosting of the T cell frequency in the tumor in all groups as compared to vehicle, however, no difference was seen between the doses.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antibody that binds to HLA-A2/MAGE-A4, wherein the antibody comprises a first antigen binding domain, comprising a heavy chain variable region (VH) comprising a heavy chain complementarity determining region (HCDR) 1 comprising the amino acid sequence of SEQ ID NO: 25, an HCDR 2 comprising the amino acid sequence of SEQ ID NO: 26, and an HCDR 3 comprising the amino acid sequence of SEQ ID NO: 27, and a light chain variable region (VL) comprising a light chain complementarity determining region (LCDR) 1 comprising the amino acid sequence of SEQ ID NO: 28, an LCDR 2 comprising the amino acid sequence of SEQ ID NO: 29, and an LCDR 3 comprising the amino acid sequence of SEQ ID NO: 30.

2. The antibody of claim 1, wherein the first antigen binding domain comprises: a VH comprising an amino acid sequence that is at least about 95% identical to the amino acid sequence of SEQ ID NO: 31, a VL comprising an amino acid sequence that is at least about 95% identical to the amino acid sequence of SEQ ID NO: 32, or both the VH comprising an amino acid sequence that is at least about 95% identical to the amino acid sequence of SEQ ID NO: 31 and the VL comprising an amino acid sequence that is at least about 95% identical to the amino acid sequence of SEQ ID NO: 32.

3. An antibody that binds to HLA-A2/MAGE-A4, wherein the antibody comprises a first antigen binding domain comprising: a VH comprising the amino acid sequence of SEQ ID NO: 31 and a VL comprising the amino acid sequence of SEQ ID NO: 32.

4. The antibody of claim 1, wherein the antibody is a multispecific antibody.

5. The antibody of claim 4, wherein the antibody is a bispecific antibody.

6. The antibody of claim 1, wherein the antibody comprises a second antigen binding domain which binds to a second antigen.

7. The antibody of claim 6, wherein the second antigen is an activating T cell antigen.

8. The antibody of claim 6, wherein the second antigen is CD3.

9. The antibody of claim 6, wherein the second antigen is CD3ε.

10. The antibody of claim 6, wherein the second antigen binding domain comprises:
   (i) a VH comprising an HCDR 1 comprising the amino acid sequence of SEQ ID NO: 59, an HCDR 2 comprising the amino acid sequence of SEQ ID NO: 60, and an HCDR 3 comprising the amino acid sequence of SEQ ID NO: 61, and a VL comprising an LCDR 1 comprising the amino acid sequence of SEQ ID NO: 62, an LCDR 2 comprising the amino acid sequence of SEQ ID NO: 63 and an LCDR 3 comprising the amino acid sequence of SEQ ID NO: 64; or
   (ii) a VH comprising an HCDR 1 comprising the amino acid sequence of SEQ ID NO: 51, an HCDR 2 comprising the amino acid sequence of SEQ ID NO: 52, and an HCDR 3 comprising the amino acid sequence of SEQ ID NO: 53, and a VL comprising an LCDR 1 comprising the amino acid sequence of SEQ ID NO: 54, an LCDR 2 comprising the amino acid sequence of SEQ ID NO: 55, and an LCDR 3 comprising the amino acid sequence of SEQ ID NO: 56.

11. The antibody of claim 6, wherein the second antigen binding domain comprises:
   (i) a VH comprising an amino acid sequence that is at least about 95% identical to the amino acid sequence of SEQ ID NO: 65, a VL comprising an amino acid sequence that is at least about 95% identical to the amino acid sequence of SEQ ID NO: 66, or both the VH comprising an amino acid sequence that is at least about 95% identical to the amino acid sequence of SEQ ID NO: 65 and the VL comprising an amino acid sequence that is at least about 95% identical to the amino acid sequence of SEQ ID NO: 66; or
   (ii) a VH comprising an amino acid sequence that is at least about 95% identical to the amino acid sequence of SEQ ID NO: 57, a VL comprising an amino acid sequence that is at least about 95% identical to the amino acid sequence of SEQ ID NO: 58, or both the VH comprising an amino acid sequence that is at least about 95% identical to the amino acid sequence of SEQ ID NO: 57 and the VL comprising an amino acid sequence that is at least about 95% identical to the amino acid sequence of SEQ ID NO: 58.

12. The antibody of claim 6, wherein the second antigen binding domain comprises:
   (i) a VH comprising the amino acid sequence of SEQ ID NO: 65, a VL comprising the amino acid sequence of SEQ ID NO: 66, or both the VH comprising the amino acid sequence of SEQ ID NO: 65 and the VL comprising the amino acid sequence of SEQ ID NO: 66; or
   (ii) a VH comprising the amino acid sequence of SEQ ID NO: 57, a VL comprising the amino acid sequence of SEQ ID NO: 58, or both the VH comprising the amino acid sequence of SEQ ID NO: 57 and the VL comprising the amino acid sequence of SEQ ID NO: 58.

13. The antibody of claim 6, wherein the antibody comprises a third antigen binding domain.

14. The antibody of claim 13, wherein the third antigen binding domain binds to HLA-A2/MAGE-A4.

15. The antibody of claim 14, wherein the third antigen binding domain is identical to the first antigen binding domain.

16. The antibody of claim 13, wherein at least the first, the second, or the third antigen binding domain is a Fab molecule.

17. The antibody of claim 6, wherein the second antigen binding domain is a Fab molecule wherein the variable domains VL and VH or the constant domains CL and CH1 of the Fab light chain and the Fab heavy chain are replaced by each other.

18. The antibody of claim 17, wherein the variable domains VL and VH of the Fab light chain and Fab heavy chain are replaced by each other.

19. The antibody of claim 13, wherein the first antigen binding domain is a conventional Fab molecule.

20. The antibody of claim 19, wherein the third antigen binding domain is a conventional Fab molecule.

21. The antibody of claim 20, wherein in the first antigen binding domain in the constant domain CL, the amino acid at position 124 is substituted independently by lysine (K), arginine (R), or histidine (H), with numbering according to Kabat, and the amino acid at position 123 is substituted independently by lysine (K), arginine (R), or histidine (H), with numbering according to Kabat, and in the constant domain CH1 the amino acid at position 147 is substituted independently by glutamic acid (E) or aspartic acid (D), with numbering according to Kabat EU index, and the amino acid at position 213 is substituted independently by glutamic acid (E) or aspartic acid (D), with numbering according to Kabat EU index.

22. The antibody of claim 21, wherein in each of the first and third antigen binding domains in the constant domain CL, the amino acid at position 124 is substituted independently by lysine (K), arginine (R), or histidine (H), with numbering according to Kabat, and the amino acid at position 123 is substituted independently by lysine (K), arginine (R), or histidine (H), with numbering according to Kabat, and in the constant domain CH1 the amino acid at position 147 is substituted independently by glutamic acid (E) or aspartic acid (D), with numbering according to Kabat EU index, and the amino acid at position 213 is substituted independently by glutamic acid (E) or aspartic acid (D), with numbering according to Kabat EU index.

23. The antibody of claim 6, wherein the first and the second antigen binding domains are fused to each other.

24. The antibody of claim 23, wherein the first and the second antigen binding domains are fused to each other via a peptide linker.

25. The antibody of claim 6, wherein the first and the second antigen binding domains are each a Fab molecule and either (i) the first antigen binding domain is fused at the C-terminus of the Fab heavy chain to the N-terminus of the Fab heavy chain of the second antigen binding domain, or (ii) the second antigen binding domain is fused at the C-terminus of the Fab heavy chain to the N-terminus of the Fab heavy chain of the first antigen binding domain.

26. The antibody of claim 1, wherein the antibody comprises an Fc domain composed of a first and a second subunit.

27. The antibody of claim 13, wherein the first, the second, and the third antigen binding domains are each a Fab molecule and the antibody comprises an Fc domain composed of a first and a second subunit; and either (i) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain, or (ii) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain; and the third antigen binding domain is fused at the C-terminus of the Fab heavy chain to the N-terminus of the second subunit of the Fc domain.

28. The antibody of claim 26, wherein the Fc domain is an IgG Fc domain.

29. The antibody of claim 28, wherein the Fc domain is an IgG1 Fc domain.

30. The antibody of claim 26, wherein the Fc domain is a human Fc domain.

31. The antibody of claim 26, wherein the Fc domain comprises a modification promoting the association of the first and the second subunit of the Fc domain.

32. The antibody of claim 26, wherein the Fc domain comprises one or more amino acid substitutions that reduces binding to an Fc receptor and/or effector function.

33. The antibody of claim 1 produced by culturing a host cell comprising an isolated polynucleotide encoding the antibody under conditions suitable for expression of the antibody.

34. A pharmaceutical composition comprising the antibody of claim 1, 3, or 33 and a pharmaceutically acceptable carrier.

35. An antibody that binds to HLA-A2/MAGE-A4, wherein the antibody comprises a first antigen binding domain, comprising
   (i) a VH comprising an HCDR 1 comprising the amino acid sequence of SEQ ID NO: 1, an HCDR 2 comprising the amino acid sequence of SEQ ID NO: 2, and an HCDR 3 comprising the amino acid sequence of SEQ ID NO: 3, and a VL comprising an LCDR 1 comprising the amino acid sequence of SEQ ID NO: 4, an LCDR 2 comprising the amino acid sequence of SEQ ID NO: 5, and an LCDR 3 comprising the amino acid sequence of SEQ ID NO: 6;
   (ii) a VH comprising an HCDR 1 comprising the amino acid sequence of SEQ ID NO: 41, an HCDR 2 comprising the amino acid sequence of SEQ ID NO: 42, and an HCDR 3 comprising the amino acid sequence of SEQ ID NO: 43, and a VL comprising an LCDR 1 comprising the amino acid sequence of SEQ ID NO: 44, an LCDR 2 comprising the amino acid sequence of SEQ ID NO: 45, and an LCDR 3 comprising the amino acid sequence of SEQ ID NO: 46;
   (iii) a VH comprising an HCDR 1 comprising the amino acid sequence of SEQ ID NO: 9, an HCDR 2 comprising the amino acid sequence of SEQ ID NO: 10, and an HCDR 3 comprising the amino acid sequence of SEQ ID NO: 11, and a VL comprising an LCDR 1 comprising the amino acid sequence of SEQ ID NO: 12, an LCDR 2 comprising the amino acid sequence of SEQ ID NO: 13, and an LCDR 3 comprising the amino acid sequence of SEQ ID NO: 14;
   (iv) a VH comprising an HCDR 1 comprising the amino acid sequence of SEQ ID NO: 17, an HCDR 2 comprising the amino acid sequence of SEQ ID NO: 18, and an HCDR 3 comprising the amino acid sequence of SEQ ID NO: 19, and a VL comprising an LCDR 1 comprising the amino acid sequence of SEQ ID NO: 20, an LCDR 2 comprising the amino acid sequence of SEQ ID NO: 21, and an LCDR 3 comprising the amino acid sequence of SEQ ID NO: 22; or
   (v) a VH comprising an HCDR 1 comprising the amino acid sequence of SEQ ID NO: 33, an HCDR 2 comprising the amino acid sequence of SEQ ID NO: 34, and an HCDR 3 comprising the amino acid sequence of SEQ ID NO: 35, and a VL comprising an LCDR 1 comprising the amino acid sequence of SEQ ID NO: 36, an LCDR 2 comprising the amino acid sequence of SEQ ID NO: 37, and an LCDR 3 comprising the amino acid sequence of SEQ ID NO: 38.

36. The antibody of claim 35, wherein the first antigen binding domain comprises:
   (i) a VH comprising an amino acid sequence that is at least about 95% identical to the amino acid sequence of SEQ ID NO: 7, a VL comprising an amino acid sequence that is at least about 95% identical to the amino acid sequence of SEQ ID NO: 8, or both the VH comprising an amino acid sequence that is at least about 95% identical to the amino acid sequence of SEQ ID NO: 7 and the VL comprising an amino acid sequence that is at least about 95% identical to the amino acid sequence of SEQ ID NO: 8;
   (ii) a VH comprising an amino acid sequence that is at least about 95% identical to the amino acid sequence of SEQ ID NO: 47, a VL comprising an amino acid sequence that is at least about 95% identical to the amino acid sequence of SEQ ID NO: 48, or both the VH comprising an amino acid sequence that is at least about 95% identical to the amino acid sequence of SEQ ID NO: 47 and the VL comprising an amino acid sequence that is at least about 95% identical to the amino acid sequence of SEQ ID NO: 48;
   (iii) a VH comprising an amino acid sequence that is at least about 95% identical to the amino acid sequence of SEQ ID NO: 15, a VL comprising an amino acid sequence that is at least about 95% identical to the amino acid sequence of SEQ ID NO: 16, or both the VH comprising an amino acid sequence that is at least about 95% identical to the amino acid sequence of SEQ ID NO: 15 and the VL comprising an amino acid sequence that is at least about 95% identical to the amino acid sequence of SEQ ID NO: 16;
   (iv) a VH comprising an amino acid sequence that is at least about 95% identical to the amino acid sequence of SEQ ID NO: 23, a VL comprising an amino acid sequence that is at least about 95% identical to the amino acid sequence of SEQ ID NO: 24, or both the VH comprising an amino acid sequence that is at least about 95% identical to the amino acid sequence of SEQ ID NO: 23 and the VL comprising an amino acid sequence that is at least about 95% identical to the amino acid sequence of SEQ ID NO: 24; or
   (v) a VH comprising an amino acid sequence that is at least about 95% identical to the amino acid sequence of SEQ ID NO: 39, a VL comprising an amino acid sequence that is at least about 95% identical to the amino acid sequence of SEQ ID NO: 40, or both the VH comprising an amino acid sequence that is at least about 95% identical to the amino acid sequence of SEQ ID NO: 39 and the VL comprising an amino acid sequence that is at least about 95% identical to the amino acid sequence of SEQ ID NO: 40.

37. The antibody of claim 36, wherein the antibody comprises a first antigen binding domain comprising:
- (i) a VH comprising the amino acid sequence of SEQ ID NO: 7, a VL comprising the amino acid sequence of SEQ ID NO: 8, or both the VH comprising the amino acid sequence of SEQ ID NO: 7 and the VL comprising the amino acid sequence of SEQ ID NO: 8;
- (ii) a VH comprising the amino acid sequence of SEQ ID NO: 47, a VL comprising the amino acid sequence of SEQ ID NO: 48, or both the VH comprising the amino acid sequence of SEQ ID NO: 47 and the VL comprising the amino acid sequence of SEQ ID NO: 48;
- (iii) a VH comprising the amino acid sequence of SEQ ID NO: 15, a VL comprising the amino acid sequence of SEQ ID NO: 16, or both the VH comprising the amino acid sequence of SEQ ID NO: 15 and the VL comprising the amino acid sequence of SEQ ID NO: 16;
- (iv) a VH comprising the amino acid sequence of SEQ ID NO: 23, a VL comprising the amino acid sequence of SEQ ID NO: 24, or both the VH comprising the amino acid sequence of SEQ ID NO: 23 and the VL comprising the amino acid sequence of SEQ ID NO: 24; or
- (v) a VH comprising the amino acid sequence of SEQ ID NO: 39, a VL comprising the amino acid sequence of SEQ ID NO: 40, or both the VH comprising the amino acid sequence of SEQ ID NO: 39 and the VL comprising the amino acid sequence of SEQ ID NO: 40.

38. The antibody of claim 35, wherein the antibody is a bispecific antibody that binds to a second antigen.

39. The antibody of claim 38, wherein the second antigen is CD3.

40. The antibody of claim 39, wherein the second antigen binding domain comprises:
- (i) a VH comprising an HCDR 1 comprising the amino acid sequence of SEQ ID NO: 59, an HCDR 2 comprising the amino acid sequence of SEQ ID NO: 60, and an HCDR 3 comprising the amino acid sequence of SEQ ID NO: 61, and a VL comprising an LCDR 1 comprising the amino acid sequence of SEQ ID NO: 62, an LCDR 2 comprising the amino acid sequence of SEQ ID NO: 63, and an LCDR 3 comprising the amino acid sequence of SEQ ID NO: 64; or
- (ii) a VH comprising an HCDR 1 comprising the amino acid sequence of SEQ ID NO: 51, an HCDR 2 comprising the amino acid sequence of SEQ ID NO: 52, and an HCDR 3 comprising the amino acid sequence of SEQ ID NO: 53, and a VL comprising an LCDR 1 comprising the amino acid sequence of SEQ ID NO: 54, an LCDR 2 comprising the amino acid sequence of SEQ ID NO: 55, and an LCDR 3 comprising the amino acid sequence of SEQ ID NO: 56.

41. The antibody of claim 40, wherein the second antigen binding domain comprises:
- (i) a VH comprising the amino acid sequence of SEQ ID NO: 65, a VL comprising the amino acid sequence of SEQ ID NO: 66, or both the VH comprising the amino acid sequence of SEQ ID NO: 65 and the VL comprising the amino acid sequence of SEQ ID NO: 66; or
- (ii) a VH comprising the amino acid sequence of SEQ ID NO: 57, a VL comprising the amino acid sequence of SEQ ID NO: 58, or both the VH comprising the amino acid sequence of SEQ ID NO: 57 and the VL comprising the amino acid sequence of SEQ ID NO: 58.

42. An antibody that binds to HLA-A2/MAGE-A4 and CD3, wherein the antibody comprises:
- (i) a first antigen binding domain that binds to HLA-A2/MAGE-A4, comprising a VH comprising an HCDR 1 comprising the amino acid sequence of SEQ ID NO: 25, an HCDR 2 comprising the amino acid sequence of SEQ ID NO: 26, and an HCDR 3 comprising the amino acid sequence of SEQ ID NO: 27, and a VL comprising an LCDR 1 comprising the amino acid sequence of SEQ ID NO: 28, an LCDR 2 comprising the amino acid sequence of SEQ ID NO: 29, and an LCDR 3 comprising the amino acid sequence of SEQ ID NO: 30;
- (ii) a second antigen binding domain that binds to CD3, comprising a VH comprising an HCDR 1 comprising the amino acid sequence of SEQ ID NO: 59, an HCDR 2 comprising the amino acid sequence of SEQ ID NO: 60, and an HCDR 3 comprising the amino acid sequence of SEQ ID NO: 61, and a VL comprising an LCDR 1 comprising the amino acid sequence of SEQ ID NO: 62, an LCDR 2 comprising the amino acid sequence of SEQ ID NO: 63 and an LCDR 3 comprising the amino acid sequence of SEQ ID NO: 64;
- (iii) a third antigen binding domain that binds to HLA-A2/MAGE-A4, comprising a VH comprising an HCDR 1 comprising the amino acid sequence of SEQ ID NO: 25, an HCDR 2 comprising the amino acid sequence of SEQ ID NO: 26, and an HCDR 3 comprising the amino acid sequence of SEQ ID NO: 27, and a VL comprising an LCDR 1 comprising the amino acid sequence of SEQ ID NO: 28, an LCDR 2 comprising the amino acid sequence of SEQ ID NO: 29, and an LCDR 3 comprising the amino acid sequence of SEQ ID NO: 30; and
- (iv) an IgG Fc domain composed of a first subunit and a second subunit, wherein the first and the third antigen binding domains are each a conventional Fab molecule and the second antigen binding domain is a Fab molecule wherein the variable domains VL and VH or the constant domains CL and CH1 of the Fab light chain and the Fab heavy chain are replaced by each other, wherein in each of the first and third antigen binding domains, in the constant domain CL, the amino acid at position 124 is substituted by lysine (K), with numbering according to Kabat, and the amino acid at position 123 is substituted by arginine (R), with numbering according to Kabat, and in the constant domain CH1 the amino acid at position 147 is substituted independently by glutamic acid (E), with numbering according to Kabat EU index, and the amino acid at position 213 is substituted independently by glutamic acid (E), with numbering according to Kabat EU index, and wherein the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain.

43. An antibody that binds to HLA-A2/MAGE-A4 and CD3, wherein the antibody comprises:
- (i) a first antigen binding domain that binds to HLA-A2/MAGE-A4, comprising a VH comprising the amino acid sequence of SEQ ID NO: 31 and a VL comprising the amino acid sequence of SEQ ID NO: 32;
- (ii) a second antigen binding domain that binds to CD3, comprising a VH comprising the amino acid sequence of SEQ ID NO: 65 and a VL comprising the amino acid sequence of SEQ ID NO: 66;
- (iii) a third antigen binding domain that binds to HLA-A2/MAGE-A4, comprising a VH comprising the amino acid sequence of SEQ ID NO: 31 and a VL comprising the amino acid sequence of SEQ ID NO: 32; and (iv) an IgG Fc domain composed of a first subunit and a second subunit,
wherein the first and the third antigen binding domains are each a conventional Fab molecule and the second antigen binding domain is a Fab molecule wherein the variable domains VL and VH or the constant domains CL and CH1 of the Fab light chain and the Fab heavy chain are replaced by each other,
wherein in each of the first and third antigen binding domains, in the constant domain CL, the amino acid at position 124 is substituted by lysine (K), with numbering according to Kabat, and the amino acid at position 123 is substituted by arginine (R), with numbering according to Kabat, and in the constant domain CH1 the amino acid at position 147 is substituted independently by glutamic acid (E), with numbering according to Kabat EU index, and the amino acid at position 213 is substituted independently by glutamic acid (E), with numbering according to Kabat EU index, and
wherein the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain.

44. The antibody of claim 3, wherein the antibody comprises an Fc domain composed of a first and a second subunit.

45. The antibody of claim 44, wherein the Fc domain is an IgG Fc domain.

46. The antibody of any one of claims 28, 42, 43, and 45, wherein the IgG Fc domain is a human IgG1 Fc domain.

47. The antibody of any one of claims 42-44, wherein the Fc domain comprises a modification promoting the association of the first and the second subunit of the Fc domain.

48. The antibody of any one of claims 31 and 42-44, wherein an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

49. The antibody of any one of claims 31 and 42-44, wherein in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V); and/or in the second subunit of the Fc domain additionally the threonine residue at position 366 is replaced with a serine residue (T366S) and the leucine residue at position 368 is replaced with an alanine residue (L368A), with numbering according to Kabat EU index.

50. The antibody of claim 49, wherein in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C), with numbering according to Kabat EU index.

51. The antibody of any one of claims 42-44, wherein the Fc domain comprises one or more amino acid substitution that reduces binding to an Fc receptor and/or effector function.

52. The antibody of claim 51, wherein the one or more amino acid substitutions is at amino acid position E233, L234, L235, N297, P331, and/or P329, with numbering according to Kabat EU index.

53. The antibody of claim 52, wherein the one or more amino acid substitutions is at amino acid positions L234, L235, and P329, with numbering according to Kabat EU index.

54. The antibody of claim 53, wherein each subunit of the Fc domain comprises the amino acid substitutions L234A, L235A, and P329G, with numbering according to Kabat EU index.

55. The antibody of claim 32, wherein the one or more amino acid substitutions is at amino acid position E233, L234, L235, N297, P331, and/or P329, with numbering according to Kabat EU index.

56. The antibody of claim 55, wherein the one or more amino acid substitutions is at amino acid positions L234, L235, and P329, with numbering according to Kabat EU index.

57. The antibody of claim 56, wherein each subunit of the Fc domain comprises the amino acid substitutions L234A, L235A, and P329G, with numbering according to Kabat EU index.

58. The antibody of any one of claims 1, 3, 41, and 43, wherein the antibody comprises a first polypeptide comprising an amino acid sequence that is at least about 95% identical to the amino acid sequence of SEQ ID NO: 68, a second polypeptide comprising an amino acid sequence that is at least about 95% identical to the amino acid sequence of SEQ ID NO: 69, a third polypeptide and a fourth polypeptide each comprising an amino acid sequence that is at least about 95% identical to the amino acid sequence of SEQ ID NO: 70, and a fifth polypeptide comprising an amino acid sequence that is at least about 95% identical to the amino acid sequence of SEQ ID NO: 72.

59. An antibody that binds to HLA-A2/MAGE-A4 and CD3, wherein the antibody comprises a first polypeptide comprising the amino acid sequence of SEQ ID NO: 68, a second polypeptide comprising the amino acid sequence of SEQ ID NO: 69, a third polypeptide comprising the amino acid sequence of SEQ ID NO: 70, and a fourth polypeptide comprising the amino acid sequence of SEQ ID NO: 72.

60. An antibody that binds to HLA-A2/MAGE-A4 and CD3, wherein the antibody comprises a first polypeptide comprising the amino acid sequence of SEQ ID NO: 68, a second polypeptide comprising the amino acid sequence of SEQ ID NO: 69, a third polypeptide and a fourth polypeptide each comprising the amino acid sequence of SEQ ID NO: 70, and a fifth polypeptide comprising the amino acid sequence of SEQ ID NO: 72.

61. An antibody that binds to HLA-A2/MAGE-A4 and CD3, wherein the antibody comprises:
(i) a first antigen binding domain that binds to HLA-A2/MAGE-A4, comprising a VH comprising an HCDR 1 comprising the amino acid sequence of SEQ ID NO: 25, an HCDR 2 comprising the amino acid sequence of SEQ ID NO: 26, and an HCDR 3 comprising the amino acid sequence of SEQ ID NO: 27, and a VL comprising an LCDR 1 comprising the amino acid sequence of SEQ ID NO: 28, an LCDR 2 comprising the amino acid sequence of SEQ ID NO: 29, and an LCDR 3 comprising the amino acid sequence of SEQ ID NO: 30; and (ii) a second antigen binding domain that binds to CD3, comprising a VH comprising an HCDR 1 comprising the amino acid sequence of SEQ ID NO: 59, an HCDR 2 comprising the amino acid sequence of SEQ ID NO: 60, and an HCDR 3 comprising the amino acid sequence of SEQ ID NO: 61, and a VL comprising an LCDR 1 comprising the amino acid sequence of SEQ ID NO: 62, an LCDR 2 comprising the amino acid sequence of SEQ ID NO: 63 and an LCDR 3 comprising the amino acid sequence of SEQ ID NO: 64.

62. The antibody of claim 61, further comprising a third antigen binding domain that binds to HLA-A2/MAGE-A4, comprising a VH comprising an HCDR 1 comprising the amino acid sequence of SEQ ID NO: 25, an HCDR 2 comprising the amino acid sequence of SEQ ID NO: 26, and an HCDR 3 comprising the amino acid sequence of SEQ ID NO: 27, and a VL comprising an LCDR 1 comprising the amino acid sequence of SEQ ID NO: 28, an LCDR 2 comprising the amino acid sequence of SEQ ID NO: 29, and an LCDR 3 comprising the amino acid sequence of SEQ ID NO: 30.

63. An antibody that binds to HLA-A2/MAGE-A4 and CD3, wherein the antibody comprises:
(i) a first antigen binding domain that binds to HLA-A2/MAGE-A4, comprising a VH comprising the amino acid sequence of SEQ ID NO: 31 and a VL comprising the amino acid sequence of SEQ ID NO: 32; and
(ii) a second antigen binding domain that binds to CD3, comprising a VH comprising the amino acid sequence of SEQ ID NO: 65 and a VL comprising the amino acid sequence of SEQ ID NO: 66.

64. The antibody of claim 63, further comprising a third antigen binding domain that binds to HLA-A2/MAGE-A4, comprising a VH comprising the amino acid sequence of SEQ ID NO: 31 and a VL comprising the amino acid sequence of SEQ ID NO: 32.

65. The antibody of any one of claims 61-64, wherein the antibody further comprises an Fc domain composed of a first and a second subunit.

66. The antibody of claim 65, wherein the antibody comprises an Fc domain is an IgG Fc domain.

67. The antibody of claim 66, wherein the IgG Fc domain is a human IgG1 Fc domain.

68. A pharmaceutical composition comprising the antibody of any one of claims 42, 43, 59, 60, and 61-64 and a pharmaceutically acceptable carrier.

* * * * *